US010160761B2

(12) United States Patent
Grenier et al.

(10) Patent No.: US 10,160,761 B2
(45) Date of Patent: Dec. 25, 2018

(54) SOLID FORMS OF ISOQUINOLINONES, AND PROCESS OF MAKING, COMPOSITION COMPRISING, AND METHODS OF USING THE SAME

(71) Applicant: Infinity Pharmaceuticals, Inc., Cambridge, MA (US)

(72) Inventors: Louis Grenier, Newton, MA (US); Andre Lescarbeau, Somerville, MA (US); Praveen Sharma, Arlington, MA (US); Daniel G. Genov, Boston, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/264,417

(22) Filed: Sep. 13, 2016

(65) Prior Publication Data

US 2017/0088553 A1    Mar. 30, 2017

Related U.S. Application Data

(60) Provisional application No. 62/218,486, filed on Sep. 14, 2015, provisional application No. 62/218,493, filed on Sep. 14, 2015.

(51) Int. Cl.
*C07D 487/04* (2006.01)
*A61K 9/48* (2006.01)
*A61K 31/519* (2006.01)
*C07D 231/12* (2006.01)
*C07D 231/38* (2006.01)
*C07D 401/06* (2006.01)

(52) U.S. Cl.
CPC ............ *C07D 487/04* (2013.01); *A61K 9/485* (2013.01); *A61K 9/4858* (2013.01); *A61K 9/4866* (2013.01); *A61K 31/519* (2013.01); *C07D 231/12* (2013.01); *C07D 231/38* (2013.01); *C07D 401/06* (2013.01); *C07B 2200/13* (2013.01)

(58) Field of Classification Search
CPC ................................................... C07D 487/04
See application file for complete search history.

(56) References Cited

U.S. PATENT DOCUMENTS

| | | | |
|---|---|---|---|
| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 4,981,856 A | 1/1991 | Hughes |
| 5,240,941 A | 8/1993 | Bruneau |
| 5,272,158 A | 12/1993 | Hartman et al. |
| 5,294,612 A | 3/1994 | Bacon et al. |
| 5,310,731 A | 5/1994 | Olsson et al. |
| 5,364,862 A | 11/1994 | Spada et al. |
| 5,409,930 A | 4/1995 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,527,811 A | 6/1996 | Natsugari et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,679,677 A | 10/1997 | Pill et al. |
| 5,686,455 A | 11/1997 | Adams et al. |
| 5,736,554 A | 4/1998 | Spada et al. |
| 5,747,235 A | 5/1998 | Farid et al. |
| 5,756,502 A | 5/1998 | Padia |
| 5,756,711 A | 5/1998 | Zilch et al. |
| 5,763,596 A | 6/1998 | Boyer et al. |
| 5,763,597 A | 6/1998 | Ugarkar et al. |
| 5,763,608 A | 6/1998 | Bhattacharya et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,869,665 A | 2/1999 | Padia |
| 5,872,136 A | 2/1999 | Anthony et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,977,134 A | 11/1999 | Ciccarone et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |

(Continued)

FOREIGN PATENT DOCUMENTS

CA    1338379 C    6/1996
CN    1502608      6/2004

(Continued)

OTHER PUBLICATIONS

Braga "Crystal Polymorphism and Multiple Crystal Forms" Chapter in Structure and Bonding Springer-Verlag Berlin Heidelberg 2009.*

(Continued)

*Primary Examiner* — David K O'Dell
(74) *Attorney, Agent, or Firm* — Jones Day

(57) ABSTRACT

Solid forms of chemical compounds that modulate kinase activity, including PI3 kinase activity, and compounds, pharmaceutical compositions, and methods of treatment of diseases and conditions associated with kinase activity, including PI3 kinase activity, are described herein. Also provided herein are processes for preparing compounds, polymorphic forms, cocrystals, and amorphous forms thereof, and pharmaceutical compositions thereof.

43 Claims, 35 Drawing Sheets

(56) References Cited

U.S. PATENT DOCUMENTS

| | | |
|---|---|---|
| 6,037,474 A | 3/2000 | Drauz et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,184,377 B1 | 2/2001 | Gao |
| 6,191,170 B1 | 2/2001 | Medina |
| 6,207,697 B1 | 3/2001 | Han et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,429,311 B2 | 8/2002 | Gao |
| 6,455,534 B2 | 9/2002 | Bridges et al. |
| 6,469,026 B2 | 10/2002 | Marlowe et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,004 B1 | 4/2003 | Finer et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,562,831 B1 | 5/2003 | Finer et al. |
| 6,583,161 B1 | 6/2003 | Medina |
| 6,596,497 B1 | 7/2003 | Jiang et al. |
| 6,596,718 B1 | 7/2003 | Flohr et al. |
| 6,596,723 B1 | 7/2003 | Watkins et al. |
| 6,613,798 B1 | 9/2003 | Porter et al. |
| 6,630,479 B1 | 10/2003 | Finer et al. |
| 6,630,495 B1 | 10/2003 | Cooke et al. |
| 6,632,789 B1 | 10/2003 | June |
| 6,645,989 B2 | 11/2003 | Adams et al. |
| 6,649,565 B1 | 11/2003 | Feucht et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,683,108 B1 | 1/2004 | Baxter et al. |
| 6,683,192 B2 | 1/2004 | Baxter et al. |
| 6,689,782 B2 | 2/2004 | Watkins et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,753,428 B2 | 6/2004 | Yao et al. |
| 6,770,639 B2 | 8/2004 | Snow et al. |
| 6,777,425 B2 | 8/2004 | Burli et al. |
| 6,777,439 B2 | 8/2004 | Durden |
| 6,794,379 B2 | 8/2004 | Medina et al. |
| 6,790,844 B2 | 9/2004 | Ueno et al. |
| 6,800,620 B2 | 10/2004 | Sadhu et al. |
| 6,831,085 B1 | 12/2004 | Finer et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,870,055 B2 | 3/2005 | Claremon et al. |
| 6,900,219 B2 | 5/2005 | Ibrahim et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 6,964,967 B2 | 11/2005 | Medina et al. |
| 6,995,144 B2 | 2/2006 | Ozaki et al. |
| 7,009,049 B2 | 3/2006 | Bergnes et al. |
| 7,026,461 B1 | 4/2006 | Shokat |
| 7,038,048 B2 | 5/2006 | Dhanak et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,053,215 B2 | 5/2006 | Medina et al. |
| 7,053,216 B2 | 5/2006 | Sun et al. |
| 7,064,218 B2 | 6/2006 | Dyatkina et al. |
| 7,067,662 B2 | 6/2006 | Medina et al. |
| 7,071,355 B2 | 7/2006 | Leban et al. |
| 7,105,668 B1 | 9/2006 | Finer et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,214 B1 | 12/2006 | Janssens et al. |
| 7,157,487 B2 | 1/2007 | Nakayama et al. |
| 7,161,002 B2 | 1/2007 | Bergnes et al. |
| 7,166,293 B2 | 1/2007 | Teng et al. |
| 7,166,595 B2 | 1/2007 | Zhou et al. |
| 7,192,949 B2 | 3/2007 | Fraley et al. |
| 7,208,601 B2 | 4/2007 | Mjalli et al. |
| 7,214,800 B2 | 5/2007 | Feng et al. |
| 7,217,794 B2 | 5/2007 | Abdel-Meguid et al. |
| 7,230,000 B1 | 6/2007 | Finer et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,187 B2 | 8/2007 | Fraley et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,294,634 B2 | 11/2007 | Finer et al. |
| 7,329,765 B2 | 2/2008 | Burli et al. |
| 7,332,497 B2 | 2/2008 | Hirst et al. |
| 7,332,498 B2 | 2/2008 | Dhanak et al. |
| 7,345,046 B2 | 3/2008 | Wang et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,405,235 B2 | 7/2008 | Levy et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,528,137 B2 | 5/2009 | Feng et al. |
| 7,534,797 B2 | 5/2009 | Arnold et al. |
| 7,538,135 B2 | 5/2009 | Vedananda |
| 7,541,373 B2 | 6/2009 | Polisetti et al. |
| 7,550,590 B2 | 6/2009 | Feng et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,589,098 B2 | 9/2009 | Finer et al. |
| 7,608,594 B2 | 10/2009 | Blagg et al. |
| 7,615,552 B2 | 11/2009 | Ono et al. |
| 7,615,554 B2 | 11/2009 | Becklin et al. |
| 7,622,451 B2 | 11/2009 | Blagg et al. |
| 7,632,839 B2 | 12/2009 | Coleman et al. |
| 7,650,848 B2 | 1/2010 | Brennan et al. |
| 7,652,061 B2 | 1/2010 | Ksander et al. |
| 7,671,200 B2 | 3/2010 | Finer et al. |
| 7,678,803 B2 | 3/2010 | Huang et al. |
| 7,700,607 B2 | 4/2010 | Hu et al. |
| 7,705,018 B2 | 4/2010 | Chen et al. |

(56) References Cited

U.S. PATENT DOCUMENTS

| | | |
|---|---|---|
| 7,745,485 B2 | 6/2010 | Durden |
| 7,763,628 B2 | 7/2010 | Finer et al. |
| 7,799,795 B2 | 9/2010 | Bergeron et al. |
| 7,893,260 B2 | 2/2011 | Chong et al. |
| 7,932,260 B2 | 4/2011 | Fowler et al. |
| 7,939,538 B2 | 5/2011 | Fu et al. |
| 7,939,539 B2 | 5/2011 | Wang et al. |
| 8,013,003 B2 | 9/2011 | Sreet et al. |
| 8,030,318 B2 | 10/2011 | Simmen et al. |
| 8,106,146 B2 | 1/2012 | Benz et al. |
| 8,133,998 B2 | 3/2012 | Pajouhesh et al. |
| 8,193,182 B2 | 6/2012 | Ren et al. |
| 8,232,285 B2 | 7/2012 | Liu et al. |
| 8,236,808 B2 | 8/2012 | Collingwood et al. |
| 8,247,436 B2 | 8/2012 | Baettig et al. |
| 8,389,544 B2 | 3/2013 | Wong et al. |
| 8,399,483 B2 | 3/2013 | Allen et al. |
| 8,399,493 B2 | 3/2013 | Bolea et al. |
| 8,569,316 B2 | 10/2013 | Ettmayer et al. |
| 8,569,323 B2 | 10/2013 | Ren et al. |
| 8,586,619 B2 | 11/2013 | Wu et al. |
| 8,604,032 B2 | 12/2013 | Ren et al. |
| 8,637,666 B2 | 1/2014 | Charrier et al. |
| 8,642,609 B2 | 2/2014 | Makings et al. |
| 8,648,084 B2 | 2/2014 | Bunnelle et al. |
| 8,703,777 B2 | 4/2014 | Ren et al. |
| 8,716,297 B2 | 5/2014 | Woods et al. |
| 8,748,440 B2 | 6/2014 | Martin et al. |
| 8,785,470 B2 | 7/2014 | Castro et al. |
| 8,809,349 B2 | 8/2014 | Ren et al. |
| 8,809,530 B1 | 8/2014 | Wu et al. |
| 8,822,453 B2 | 9/2014 | Matsumura et al. |
| 8,901,133 B2 | 12/2014 | Ren et al. |
| 8,940,742 B2 | 1/2015 | Castro et al. |
| 8,969,363 B2 | 3/2015 | Castro et al. |
| 9,056,877 B2 | 6/2015 | Castro et al. |
| 9,115,141 B2 | 8/2015 | Castro et al. |
| 9,359,365 B2 | 6/2016 | Castro et al. |
| 9,388,183 B2 | 7/2016 | Ren et al. |
| 9,255,108 B2 | 9/2016 | Castro et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0198236 A1 | 12/2002 | Baxter et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0144350 A1 | 7/2003 | Stevenson et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0220338 A1 | 11/2003 | Watkins et al. |
| 2003/0229097 A1 | 12/2003 | Watkins et al. |
| 2003/0232832 A1 | 12/2003 | Lombardo et al. |
| 2003/0232849 A1 | 12/2003 | Noe et al. |
| 2003/0235822 A1 | 12/2003 | Lokhov et al. |
| 2004/0023996 A1 | 2/2004 | Finer et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0082567 A1 | 4/2004 | McDonald et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0132732 A1 | 7/2004 | Han et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0242596 A1 | 12/2004 | Kim et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0065169 A1 | 3/2005 | Wang et al. |
| 2005/0070578 A1 | 3/2005 | Baxter et al. |
| 2005/0080138 A1 | 4/2005 | Baxter et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0152940 A1 | 7/2005 | Hezi-Yamit et al. |
| 2005/0153997 A1 | 7/2005 | Simon et al. |
| 2005/0171148 A1 | 8/2005 | Mjalli et al. |
| 2005/0178286 A1 | 8/2005 | Brennan et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0203110 A1 | 9/2005 | Coleman et al. |
| 2005/0209254 A1 | 9/2005 | Wang et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282834 A1 | 12/2005 | Malik et al. |
| 2006/0019988 A1 | 1/2006 | McDonald et al. |
| 2006/0036093 A1 | 2/2006 | Lin et al. |
| 2006/0041128 A1 | 2/2006 | Aquila et al. |
| 2006/0063751 A1 | 3/2006 | Aquila et al. |
| 2006/0069034 A1 | 3/2006 | Burli et al. |
| 2006/0069106 A1 | 3/2006 | Fu et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0270849 A1 | 11/2006 | Nishino et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Baxter et al. |
| 2007/0027193 A1 | 2/2007 | Leban et al. |
| 2007/0032640 A1 | 2/2007 | Varghese et al. |

(56) References Cited

U.S. PATENT DOCUMENTS

| | | |
|---|---|---|
| 2007/0049593 A1 | 3/2007 | Oka et al. |
| 2007/0054915 A1 | 3/2007 | Arora et al. |
| 2007/0066632 A1 | 3/2007 | Hart et al. |
| 2007/0072897 A1 | 3/2007 | Mahaney et al. |
| 2007/0099871 A1 | 5/2007 | Davis et al. |
| 2007/0135454 A1 | 6/2007 | Hollingworth et al. |
| 2007/0142405 A1 | 6/2007 | Dong et al. |
| 2007/0155730 A1 | 7/2007 | Leit et al. |
| 2007/0161644 A1 | 7/2007 | Stockwell |
| 2007/0179151 A1 | 8/2007 | Chen et al. |
| 2007/0207996 A1 | 9/2007 | Auger et al. |
| 2007/0224672 A1 | 9/2007 | Leban et al. |
| 2007/0244133 A1 | 10/2007 | Bower et al. |
| 2007/0249598 A1 | 10/2007 | Wang et al. |
| 2007/0249680 A1 | 10/2007 | Illig et al. |
| 2007/0265231 A1 | 11/2007 | Hofmann et al. |
| 2007/0270452 A1 | 11/2007 | Blagg et al. |
| 2008/0004253 A1 | 1/2008 | Branstetter et al. |
| 2008/0032960 A1 | 2/2008 | Knight et al. |
| 2008/0058521 A1 | 3/2008 | Krishnan et al. |
| 2008/0070864 A1 | 3/2008 | Martin et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0234299 A1 | 9/2008 | Buchstaller et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0030036 A1 | 1/2009 | Dalton et al. |
| 2009/0053192 A1 | 2/2009 | Millan et al. |
| 2009/0088452 A1 | 4/2009 | Coleman et al. |
| 2009/0099210 A1 | 4/2009 | Aquila et al. |
| 2009/0099214 A1 | 4/2009 | Fairhurst et al. |
| 2009/0105233 A1 | 4/2009 | Chua et al. |
| 2009/0118261 A1 | 5/2009 | Aquila et al. |
| 2009/0118283 A1 | 5/2009 | Defert et al. |
| 2009/0124638 A1 | 5/2009 | Shokat et al. |
| 2009/0124641 A1 | 5/2009 | Coleman et al. |
| 2009/0124654 A1 | 5/2009 | Mjalli et al. |
| 2009/0130097 A1 | 5/2009 | Liu et al. |
| 2009/0137581 A1 | 5/2009 | Chen et al. |
| 2009/0149484 A1 | 6/2009 | Aquila et al. |
| 2009/0163481 A1 | 6/2009 | Murphy et al. |
| 2009/0163525 A1 | 6/2009 | Aquila et al. |
| 2009/0163545 A1 | 6/2009 | Goldfarb |
| 2009/0163709 A1 | 6/2009 | Blagg |
| 2009/0170834 A1 | 7/2009 | Venkat et al. |
| 2009/0170849 A1 | 7/2009 | Aquila et al. |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0214465 A1 | 8/2009 | Becklin et al. |
| 2009/0221488 A1 | 9/2009 | Wood et al. |
| 2009/0232768 A1 | 9/2009 | Birkus et al. |
| 2009/0233907 A1 | 9/2009 | Austin et al. |
| 2009/0233947 A1 | 9/2009 | Bayliss et al. |
| 2009/0247513 A1 | 10/2009 | Burli et al. |
| 2009/0247567 A1 | 10/2009 | Do et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0280153 A1 | 11/2009 | Hunter et al. |
| 2009/0291442 A1 | 11/2009 | Hegde et al. |
| 2009/0298856 A1 | 12/2009 | Brown et al. |
| 2009/0306069 A1 | 12/2009 | Rueckle et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0046780 A1 | 2/2010 | Song |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0099871 A1 | 4/2010 | Miller et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0189685 A1 | 7/2010 | Byrd et al. |
| 2010/0190749 A1 | 7/2010 | Ren et al. |
| 2010/0226943 A1 | 9/2010 | Brennan et al. |
| 2010/0249030 A1 | 9/2010 | Basso |
| 2010/0280010 A1 | 11/2010 | Gudmundsson et al. |
| 2010/0292188 A1 | 11/2010 | Denonne et al. |
| 2010/0310503 A1 | 12/2010 | Li et al. |
| 2010/0323973 A1 | 12/2010 | Leamon et al. |
| 2011/0014186 A1 | 1/2011 | Ehrhardt et al. |
| 2011/0046165 A1 | 2/2011 | Ren et al. |
| 2011/0059953 A1 | 3/2011 | Fersht et al. |
| 2011/0071148 A1 | 3/2011 | Ding et al. |
| 2011/0123486 A1 | 5/2011 | Robbins et al. |
| 2011/0124641 A1 | 5/2011 | Ren et al. |
| 2011/0144134 A1 | 6/2011 | Shokat et al. |
| 2011/0152242 A1 | 6/2011 | Bayliss et al. |
| 2011/0172228 A1 | 7/2011 | Ren et al. |
| 2011/0217300 A1 | 9/2011 | Liu et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2011/0313156 A1 | 12/2011 | Engelhardt et al. |
| 2012/0041683 A1 | 2/2012 | Vaske et al. |
| 2012/0059000 A1 | 3/2012 | Ren et al. |
| 2012/0065154 A1 | 3/2012 | Tanaka et al. |
| 2012/0065205 A1 | 3/2012 | Mercer et al. |
| 2012/0094997 A1 | 4/2012 | Alexandra et al. |
| 2012/0122838 A1 | 5/2012 | Ren et al. |
| 2012/0149701 A1 | 6/2012 | Ren et al. |
| 2012/0157306 A1 | 6/2012 | Frankenpohl et al. |
| 2012/0184568 A1 | 7/2012 | Ren et al. |
| 2012/0202784 A1 | 8/2012 | Aronov et al. |
| 2012/0220575 A1 | 8/2012 | Chang et al. |
| 2012/0225866 A1 | 9/2012 | Oshima et al. |
| 2012/0245136 A1 | 9/2012 | Hadida-Ruah et al. |
| 2012/0245166 A1 | 9/2012 | Grimaldi et al. |
| 2012/0245169 A1 | 9/2012 | Ren et al. |
| 2012/0270863 A1 | 10/2012 | Williams et al. |
| 2012/0289493 A1 | 11/2012 | Corkey et al. |
| 2012/0329776 A1 | 12/2012 | Ren et al. |
| 2013/0005802 A1 | 1/2013 | Chen et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2013/0116277 A1 | 5/2013 | Dalton et al. |
| 2013/0190308 A1 | 7/2013 | Jain et al. |
| 2013/0267521 A1 | 10/2013 | Castro et al. |
| 2013/0267542 A1 | 10/2013 | Chern et al. |
| 2013/0289033 A1 | 10/2013 | Griffioen et al. |
| 2013/0344061 A1 | 12/2013 | Palombella et al. |
| 2013/0345216 A1 | 12/2013 | Ren et al. |
| 2014/0045825 A1 | 2/2014 | Leahy |
| 2014/0088099 A1 | 3/2014 | Ren et al. |
| 2014/0100214 A1 | 4/2014 | Castro et al. |
| 2014/0120060 A1 | 5/2014 | Palombella et al. |
| 2014/0120083 A1 | 5/2014 | Stern et al. |
| 2014/0155387 A1 | 6/2014 | No et al. |
| 2014/0194417 A1 | 7/2014 | Greenwood et al. |
| 2014/0227321 A1 | 8/2014 | Iadonato et al. |

(56) References Cited

U.S. PATENT DOCUMENTS

| | | | |
|---|---|---|---|
| 2014/0249145 A1 | 9/2014 | Marugan et al. | |
| 2015/0225410 A1* | 8/2015 | Castro | C07D 403/12 514/210.21 |
| 2015/0290207 A1 | 10/2015 | Kutok et al. | |
| 2016/0122365 A1 | 5/2016 | Castro et al. | |

FOREIGN PATENT DOCUMENTS

| | | |
|---|---|---|
| CN | 101602768 A | 12/2009 |
| DE | 2139107 A1 | 2/1973 |
| DE | 19940859 | 3/2001 |
| DE | 102010013716 | 10/2011 |
| EP | 773023 A1 | 5/1997 |
| EP | 1020445 B1 | 8/2008 |
| EP | 2070932 | 6/2009 |
| GB | 812366 A | 4/1959 |
| GB | 937725 A | 9/1963 |
| GB | 2373186 | 9/2002 |
| JP | 61-109797 A | 5/1986 |
| JP | H05239036 | 9/1993 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2001250689 | 9/2001 |
| JP | 2002131859 A | 5/2002 |
| JP | 2003073357 A | 3/2003 |
| JP | 2004161716 A | 6/2004 |
| JP | 2005035933 | 2/2005 |
| JP | 2006265107 | 10/2006 |
| JP | 2012184225 | 9/2012 |
| JP | 5569437 | 10/2012 |
| WO | WO 1983/001446 A1 | 4/1983 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/040706 A1 | 12/1996 |
| WO | WO 1997/010221 | 3/1997 |
| WO | WO 1997/028133 A1 | 8/1997 |
| WO | WO 1997/028161 A1 | 8/1997 |
| WO | WO 1997/036901 | 10/1997 |
| WO | WO 1998/002162 | 1/1998 |
| WO | WO 1998/041525 A1 | 9/1998 |
| WO | WO 1998/052611 A1 | 11/1998 |
| WO | WO 1998/057952 A1 | 12/1998 |
| WO | WO 1999/024416 | 5/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019829 A2 | 3/2001 |
| WO | WO 2001/025238 A2 | 4/2001 |
| WO | WO 2001/031063 A1 | 5/2001 |
| WO | WO 2001/038584 A2 | 5/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/081346 A2 | 11/2001 |
| WO | WO 2001/098278 | 12/2001 |
| WO | WO 2002/006192 A1 | 1/2002 |
| WO | WO 2001/081346 A3 | 3/2002 |
| WO | WO 2002/024655 A1 | 3/2002 |
| WO | WO 2001/002369 A3 | 4/2002 |
| WO | WO 2002/030944 A2 | 4/2002 |
| WO | WO 2002/050091 | 6/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/083884 | 10/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/016275 A1 | 2/2003 |
| WO | WO 2003/020279 | 3/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/045385 | 6/2003 |
| WO | WO 2003/059884 A1 | 7/2003 |
| WO | WO 2003/076418 | 9/2003 |
| WO | WO 2003/020880 A3 | 10/2003 |
| WO | WO 2003/082341 A1 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/069145 | 8/2004 |
| WO | WO 2004/087053 A2 | 10/2004 |
| WO | WO 2004/092123 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/061707 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/121522 | 11/2006 |

(56) References Cited

FOREIGN PATENT DOCUMENTS

| | | |
|---|---|---|
| WO | WO 2006/068760 A3 | 12/2006 |
| WO | WO 2006/089106 A3 | 12/2006 |
| WO | WO 2006/135479 | 12/2006 |
| WO | WO 2007/002293 A2 | 1/2007 |
| WO | WO 2007/006547 A1 | 1/2007 |
| WO | WO 2007/008541 | 1/2007 |
| WO | WO 2007/015877 | 2/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/056155 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/076055 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2008/013840 | 1/2008 |
| WO | WO 2008/013987 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/054252 | 5/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2008/094909 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/120098 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2008/153701 | 12/2008 |
| WO | WO 2009/000412 A1 | 12/2008 |
| WO | WO 2009/002808 | 12/2008 |
| WO | WO 2009/004621 A1 | 1/2009 |
| WO | WO 2009/010925 A2 | 1/2009 |
| WO | WO 2009/018811 | 2/2009 |
| WO | WO 2009/021163 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/065919 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/097233 | 8/2009 |
| WO | WO 2009/100406 A2 | 8/2009 |
| WO | WO 2009/114826 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/118207 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/046780 | 4/2010 |
| WO | WO 2010/019210 A3 | 5/2010 |
| WO | WO 2010/051391 | 5/2010 |
| WO | WO 2010/056758 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/096680 | 8/2010 |
| WO | WO 2010/127208 | 11/2010 |
| WO | WO 2010/133836 A1 | 11/2010 |
| WO | WO 2011/008302 A1 | 1/2011 |
| WO | WO 2011/020849 | 2/2011 |
| WO | WO 2011/025774 A1 | 3/2011 |
| WO | WO 2011/048111 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/146882 A1 | 11/2011 |
| WO | WO 2011/150201 | 12/2011 |
| WO | WO 2012/009097 A1 | 1/2012 |
| WO | WO 2012/032334 A1 | 3/2012 |
| WO | WO 2012/037204 | 3/2012 |
| WO | WO 2012/040634 | 3/2012 |
| WO | WO 2012/052753 | 4/2012 |
| WO | WO 2012/061696 A1 | 5/2012 |
| WO | WO 2012/064973 A2 | 5/2012 |
| WO | WO 2012/065019 A2 | 5/2012 |
| WO | WO 2012/065057 A2 | 5/2012 |
| WO | WO 2012/165606 | 6/2012 |
| WO | WO 2012/097000 A1 | 7/2012 |
| WO | WO 2012/177997 | 12/2012 |
| WO | WO 2013/012915 | 1/2013 |
| WO | WO 2013/012918 A1 | 1/2013 |
| WO | WO 2013/032591 | 3/2013 |
| WO | WO 2013/038381 | 3/2013 |
| WO | WO 2013/065725 | 5/2013 |
| WO | WO 2013/136076 | 9/2013 |
| WO | WO 2013/154878 A1 | 10/2013 |
| WO | WO 2013/188432 | 12/2013 |
| WO | WO 2014/034750 | 3/2014 |
| WO | WO 2014/158528 | 10/2014 |
| WO | WO 2015/010641 | 1/2015 |
| WO | WO 2015/048318 | 4/2015 |
| WO | WO 2015/051241 | 4/2015 |
| WO | WO 2015/051244 | 4/2015 |
| WO | WO 2015/091685 | 6/2015 |

(56) References Cited

FOREIGN PATENT DOCUMENTS

| WO | WO 2015/143012 | 9/2015 |
|---|---|---|
| WO | WO 2016/054491 | 4/2016 |

OTHER PUBLICATIONS

Zell et. al. "Investigation of Polymorphism in Aspartame and Neotame Using Solid-State NMR Spectroscopy." Tetrahedron 2000, 56, 6603-6616.*
Pirrung, "Handbook of Synthetic Organic Chemistry" 2nd Ed. 2017, p. 178.*
Bernstein, Joel "Polymorphism in Molecular Crystals" 2002, Oxford: New York, p. 46.*
Guillory, J. K. "Generation of Polymorphs, Hydrates, Solvates, and Amorphous Solids" Chapter 5 in Polymorphism is Pharmaceutical Solids, Ed. By Harry G. Brittain Dekker: New York, 1999 pp. 183-226.*
Brittain "Effects of Pharmaceutical Processing on Drug Polymorphs and Solvates" Chapter 8 in Polymorphism is Pharmaceutical Solids, Ed. By Harry G. Brittain Dekker: New York, 1999 pp. 331-360.*
Golub, T.R., et al., "Molecular classification of Cancer: Class Discover and Class Predication by Expression Monitoring," Science, 286:531-537, 1999.
Pomel et al, "Furan-2-ylmethylene Thiazolidinediones as Novel, Potent, and Selective Inhibitors of Phosphoinositide 3-Kinase γ," J. Med. Chem. 49:3857-3871, 2006.
Abdel-Mohsen, "Synthesis, Reactions and Antimicrobial Activity of 2-Amino-4-(8-quinolino1-5-yl)-1-(p-tolyl)-pyrrole-3-carbonitrile," Bull. Korean Chem. Soc. 26(5):719-728.
Abe et al., "T cell receptor-mediated recognition of self-ligand induces signaling in immature thymocytes before negative selection," J. Exp. Med. 176(2):459-468 (1992).
Abrahamian et al., "Immunological and Clinical Profile of Adult Patients with Selective Immunoglobulin Subclass deficiency: response to intravenous immunoglobulin therapy," Clin. Exp. Immunol. 159(3):344-350 (2010).
Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," J.C.S. Perkin I 1390-1395 (1975).
Anderson et al., "Paradoxical inhibition of T-cell function in response to CTLA-4 blockade; heterogeneity within the human T-cell population," Nat. Med. 6(2):211-214 (2000).
Andrews et al., "Effects of the 11β-hydroxysteroid dehydrogenase inhibitor carbenoxolone on insulin sensitive in men with type 2 diabetes," J. Clin. Endocrinol. Metab. 88(1):285-291 (2003).
Arcaro et al., "Wortmannin is a potent phosphatidylinositol 3-kinase inhibitor: the role of phosphatidylinositol 3,4,5-triphosphate in neutrophil responses," Biochem. J., 296(Pt 2):297-301 (1993).
Arnold et al., "Pyrrolo[2,3-d]pyrimidines containing an extended 5-substituent as potent and selective inhibitors of Ick I," Bioorg. Med. Chem. Lett. 10(19):2167-2170 (2000).
Augustine et al., "Interleukin 2- and polyomavirus middle T antigen-induced modification of phosphatidylinositol 3-kinase activity in activated T lymphocytes," Mol. Cell. Biol. 11(9):4431-440 (1991).
Baggiolini et al., "Inhibition of the phagocytosis-inducted respirator busrt by the fungal metabolite wortmannin and some analogues," Exp. Cell. Res. 169(2): 408-418 (1987).
Ballell et al. "New Thiopyrazolo[3,4-d] pyrimidine derivatives as anti-mycobacterial agents," Bioorg. Med. Chem. Lett. 17(6):1736-1740 (2007).
Banker et al., Modern Pharmaceutics, pp. 451, 596, $3^{rd}$ ed, Marcel Dekker, New York (1996).

Bansal et al., "The Molecular Biology of Endometrial Cancers and the Implications for Pathogenesis, Classification, and Targeted Therapies," Cancer Control 16(1):8-13 (2009).
Barber et al., "PI3Kgamma inhibition blocks glomerulonephritis and extends lifespan in a mouse model of systemic lupus," Nat. Med. 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," Discovery J. Med. Chem. 45(18):3813-3815 (2002).
Barnes et al., "Efficacy and Safety of Inhaled Corticosteroids in Asthma—Report of A Workshop Held in Eze, France Oct. 1992," Am. Rev. Respir. Dis. 148:S1-S26 (1993).
Bartholomeusz et al., "Targeting the PI3K Signaling Pathway in Cancer Therapy," Expert. Opin. Ther. Targets 16(1):121-130 (2012).
Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," Ann Oncol. 18(8):1323-1328 (2007).
Bell et al., "Glucokinase mutations insulin secretion, and diabetes mellitus", Annu. Rev. Physiol. 58:171-186 (1996).
Berndt et al., "The p110δ crystal structure uncovers mechanisms for selectivity and potency of novel PI3K inhibitors," Nat. Chem. Biol. 6(2):117-124 (2010).
Bhat et al., "Pyrazolopyrimidine nucleosides. 12. Synthesis and biological activity of certain pyrazolo[3,4-d]pyrimidine nucleosides related to adenosine," J. Med. Chem. 24(10):1165-1172 (1981).
Bhatt et al., "Dual inhibition of PI3K and mTOR inhibits autocrine and paracrine proliferative loops in PI3K/Akt/mTOR-addicted lymphomas," Blood 115(22):4455-4463 (2010).
Bi et al., "Proliferative defect and embryonic lethality in mice homozygous for a deletion in the p110α subunit of phosphoinositide 3-kinase," J. Biol. Chem. 274:10963-10968 (1999).
Billot'Iet et al., "A selective inhibitor of the p110δ isoform of PI 3-kinase inhibits AML cell proliferation and survival and increases the cytotoxic effects of VP16," Oncogene 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," Cancer Res. 69(3):1027-1036 (2009).
Bishop et al., "Generation of monospecific nanomolar tyrosine kinase inhibitors via a chemical genetic approach," J. Am. Chem. Soc. 121(4):627-631 (1999).
Blunden et al., "Mycotoxins in food," Med. Lab. Sci. 48(4):271-282 (1991).
Bochner et al., "Immunological aspects of allergic asthma," Annu. Rev. Immunol. 12:295-335 (1994).
Bohren et al., "Expression, crystallization and preliminary crystallographic analysis of human carbonyl reductase," J. Mol. Biol. 224:659-664 (1994).
Bone et al., "Phosphoinositide 3-kinase signalling regulates early development and developmental haemopoiesis," J. Cell. Sci. 120(Pt 10):1752-1762 (2007).
Bowers et al., "A platelet biomarker for assessing phosphoinositide 3-kinase inhibition during cancer chemotherapy," Mol. Cancer Ther. 6(9):2600-2607 (2007).
Brzezianska et al., "A Minireview: The Role of MAPK/ERK and PI3K/Akt Pathways in Thyroid Follicular Cell-Derived Neoplasm," Front. Biosci. 16:422-439 (2011).
Buitenhuis et al., "The role of the PI3k-PKB signaling module in regulation of hematopoiesis," Cell Cycle 8(4):560-566 (2009).
Burger et al., "High-level expression of the T-cell chemokines CCL3 and CCL4 by chronic lymphocytic leukemia B cells in nurselike cell cocultures and after BCR stimulation," Blood 113(13):3050-3058 (2009).
Burger et al., "Phosphoinositide 3'-kinase delta: turning off BCR signaling in Chronic Lymphocytic Leukemia," Oncotarget 2(10):737-738 (2011).

(56) References Cited

OTHER PUBLICATIONS

Burger, "Inhibiting B-Cell Receptor Signaling Pathways in Chronic Lymphocytic Leukemia," *Curr. Mematol. Malig. Rep.* 7:26-33 (2012).

Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).

Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).

Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).

Camps et al., "Blockade of PI3Kγ suppresses joint inflammation and damage in mouse models of rheumatoid arthritis," *Nat. Med.* 11(9):936-943 (2005).

Chaisuparat et al., "Dual inhibition of PI3Kα and mTOR as an alternative treatment for Kaposi's Sarcoma," *Cancer Res.* 68:8361-8368 (2008).

Chang et al., "The Bruton tyrosine kinase inhibitor PCI-32765 ameliorates autoimmune arthritis by inhibition of multiple effector cells," *Arthritis Research & Therapy* 13:R115 (2011).

Chappelow et al., "Neovascular age-related macular degeneration: potential therapies," *Drugs* 68(8):1029-1036 (2008).

Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).

Chawla et. al., "Challenges in Polymorphism of Pharmaceuticals," *Current Research & Information on Pharmaceutical Science* 5(1):9-12 (2004).

Chen et al., "Characterization of Structurally Distinct, Isoform-Selective Phosphoinositide 3'-Kinase Inhibitors in Combination with Radiation in the Treatment of Glioblastoma," *Mol. Cancer. Ther.* 7(4):841-850 (2008).

Cheson et al., "Bendamustine: Rebirth of an Old Drug," *J. Clin. Oncol.* 27(9):1492-1501 (2009).

Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).

Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).

Cho et al., "A novel synthesis of benzo[c]phenanthridine skeleton and biological evaluation of isoquinoline derivatives," *Chem. Pharm. Bull.(Tokyo)* 47(6):900-902 (1999).

Clayton et al., "A crucial role for the p110delta subunit of phosphatidylinositol 3-kinase in B cell development and activation," *J. Exp. Med.* 196:753-763 (2002).

Closse et al., "2,3-dihydrobenzofuran-2-ones: a new class of highly potent antiinflammatory agents," *J. Med. Chem.* 24:1465-1471 (1981).

Courtney et al., "The PI3K Pathway as Drug Target in Human Cancer," *J. Clin. Oncol.* 28(6):1075-1083 (2010).

Cox et al., "Human colorectal cancer cells efficiently conjugate the cyclopentenone prostaglandin, prostaglandin $J_2$, to glutathjone," *Biochem. Biophys. Acta.* 1584:37-45 (2002).

Cushing et al., "PI3Kδ and PI3Kγ as Targets for Autoimmune and Inflammatory Diseases," *J. Med. Chem.* 55:8559-8581 (2012).

Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).

Davids et al., "Decreased mitochondrial apoptotic priming underlies stroma-mediated treatment resistance in chronic lymphocytic leukemia," *Blood* 120(17):3501-3509 (2012).

Davies et al., "The Human T3 γ Chain is Phospholylated at Serine 126 in Response to T Lymphocyte Activation," *J. Biol. Chem.* 262(23):10918-10921 (1987).

Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).

Davis et al., "Chronic active B-cell-receptor signaling in diffuse large B-cell lymphoma," *Nature* 463:88-92 (2010).

De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).

Diederich et al., "In search for specific inhibitors of human IIβ-hydroxysteroid-dehydrogenases (11βHSDs): chenodeoxycholic acid selectively inhibits IIβ-HSD-I," *Eur. J. Endocrinol.* 142(2):200-207 (2000).

Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).

Ding et al., "A combinatorial scaffold approach toward kinase-directed heterocycle libraries," *J. Am. Chem. Soc.* 124(8):1594-1596 (2002).

Ding et al., "A concise and traceless linker strategy toward combinatorial libraries of 2,6,9-substituted purines," *J. Org. Chem.* 66(24):8273-8276 (2001).

Ding et al., "Resin-capture and release strategy toward combinatorial libraries of 2,6,9-substituted purines," *J. Comb. Chem.* 4(2):183-186 (2002).

Donati, G., "Emerging therapies for neovascular age-related macular degeneration: state of the art," *Ophthalmologica* 221(6):366-377 (2007).

European Examination Report for EP Application No. 07873406.8 dated Sep. 14, 2011.

European Search Report for EP Application No. 05857011.0 dated Feb. 4, 2011.

European Search Report for EP Application No. 09700784.3 dated Oct. 28, 2011.

European Search Report and Search Opinion for EP Application No. 09700424.6 dated Oct. 26, 2011.

European Search Report for EP Application No. 07873406.8 dated Mar. 1, 2010.

European Search Report for EP Application No. 07754845.1 dated Sep. 20, 2011.

Examination Report for GB Application No. GB 0819947.3 dated Oct. 27, 2010.

Extended European Search Report for EP Application No. 09816603.6 dated Mar. 19, 2012.

Extended European Search Report from European Application No. 09700784.3 dated Oct. 28, 2011.

Fajans et al., "Maturity onset diabetes of the young (MODY)," *Diabet. Med.* 13(9 Suppl 6):S90-S95 (1996).

Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).

Feldman et al., "Active-Site Inhibitors of mTOR Target Rapamycin-Resistant Outputs of mTORC1 and mTORC2," *PLoS Biol.* 7(2):371-383 (2009).

Fingl et al., "Chapter 1—General Principles," The Pharmacological Basis of Therapeutics, 5th edition, Goodman and Gilman editors, MacMillan Publishings Co., Inc., New York, pp. 1-46, (1975).

Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).

Forrest et al., "Carbonyl Reductase," *Chem. Biol. Interact.* 129(1-2): 21-40 (2000).

Forrest et al., "Induction of a human carbonyl reductase gene located on chromosome 21," *Biochem. Biophys. Acta.* 1048(2-3):149-155 (1990).

(56) References Cited

OTHER PUBLICATIONS

Franzen, "The Suzuki, the Heck, and the Stille reaction—three versatile methods for the introduction of new C-C bonds on solid support," Can. J. Chem. 78:957-962 (2000).
Funder et al., "Mineralocorticoid action: target tissue specificity is enzyme, not receptor, mediated," Science 242:583-585 (1998).
Fung-Leung, W. P., "Phosphoinositide 3-kinase delta (PI3Kδ) in leukocyte signaling and function," Cell Signal 23:603-608 (2011).
Furukawa, T., "Molecular Targeting Therapy for Pancreatic Cancer: Current Knowledge and Perspectives from Bench to Bedside," J. Gastroenterol. 43(12):905-911 (2008).
Garber et al., "Diversity of gene expression in adenocarcinoma of the lung," Proc. Natl. Acad. Sci. U.S.A. 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," Bioorg. Med. Chem. Lett. 18(9):2924-2929 (2008).
Gonzalez et al., "Protection against daunorubicin cytotoxicity by expression of a cloned human carbonyl reductase cDNA in K562 leukemia cells," Cancer Res. 55(20):4646-4650 (1995).
Graber et al., "The protein tyrosine kinase inhibitor herbirnycin A, but not genistein, specifically inhibits signal transduction by the T cell antigen receptor," Int. Immunol. 4(1): 1201-1210 (1992).
Graupera et al., "Angiogenesis selectively requires the p110α isoform of PI3K to control endothelial cell migration," Nature 453(7195):662-666 (2008).
Gunther et al., "Acute pathological effects on rats of orally administered wortmannin-containing preparations and purified wortmannin from Fusarium oxysporum," Food Chem. Toxicol. 27(3): 173-179 (1989).
Gunther et al., "Immunosuppressive effects of dietary wortmannin on rats and mice," Immunopharmacol. Immunotoxicol. 11(4):559-570 (1989).
Haase et al., "Detection of viral nucleic acids by in situ hybridization," Methods in Virology 7:189-226 (1984).
Haluska et al., "The RTK/RAS/BRAF/P13K Pathways in Melanoma: Biology, Small Molecule Inhibitors, and Potential Applications," Semin. Oncol. 34(6):546-554 (2007).
Hanefeld et al., "One-pot synthesis of tetrasubstituted pyrazoles proof of regiochemistry," J. Chem. Soc. Perkin 1 1545-1552 (1996).
Harada et al., "Novel role of phosphatidylinositol 3-kinase in CD28-mediated costimulation," J. Biol. Chem. 276(12):9003-9008 (2001).
Harding et al., "CD28-mediated signalling co-stimulates murine T cells and prevents induction of anergy in T-cell clones," Nature 356(6370):607-609 (1992).
Hasselblom et al., "High immunohistochemical expression of p-AKT predicts inferior survival in patients with diffuse large B-cell lymphoma treated with immunochemotherapy," Brit. J. Haematol. 149:560-568 (2010).
Haylock-Jacobs et al., "PI3Kδ drives the pathogenesis of experimental autoimmune encephalomyelitis by inhibiting effector T cell apoptosis and promoting Th17 differentiation," J. Autoimmun. 36:278-287 (2011).
Hellwinkel et al., "Heterocyclensynthesen mit MF/Al2O3-basensystemen; 2-arylbenzofurane and 2,3-diarylisochinolin-1(2H)-one," Synthesis 1995(9):1135-1141 (1995).
Herishanu et al., "The lymph node microenvironment promotes B-cell receptor signaling, NF-κB activation, and tumor proliferation in chronic lymphocytic leukemia," Blood 117(2):563- 574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," Blood 116(12):2078-2088 (2010).
Herman et al., "The role of phosphatidylinositol 3-kinase-δ in the immunomodulatory effects of lenalidomide in chronic lymphocytic leukemia," Blood 117(16):4323-4327 (2011).
Herrera et al., "The dual P13K/mTOR inhibitor BEZ235 is effective in lung cancer cell lines," Anticancer Res. 31:849-854 (2011).
Hickey et al., "BCR-ABL Regulates Phosphatidylinositol 3-Kinase-p110γ Transcription and Activation and Is Required for Proliferation and Drug Resistance," J. Biol. Chem. 281(5):2441-2450 (2006).
Hirsch et al., "CALming Down T Cell Acute Leukemia," Cancer Cell 21:449-450 (2012).
Hirsch et al., "Central Role for G Protein-Coupled Phosphoinositide 3-Kinase γ in Inflammation," Science 287:1049-1053 (2000).
Hoellenriegel and Burger, "Phosphoinositide 3'-kinase delta: turning off BCR signaling in Chronic Lymphocytic Leukemia," Oncotarget 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," Blood 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," PNAS 107(29):13075-13080 (2010).
Ikeda et al., "PI3K/p110δ is a novel therapeutic target in multiple myeloma," Blood 116(9):1460-l468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.

(56) References Cited

OTHER PUBLICATIONS

International Search Report for PCT/US2010/002020 dated Nov. 2, 2010.
Ishiyama et al., "A stoichiometric aromatic C-H borylation catalyzed by iridium(I)/2,2'-bipyridme complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391(2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1): 153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347 :169-188 (2010).
Kim et al., "Activation and Function of the mTORC1 Pathway in Mast Cells," *J. Immunol.* 180(7):4586-4595 (2008).
Knight et al., "A Pharmacological Map of the P13-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio-and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al, "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent pro state intraepithelial neoplasia through regulation of apoptotic and HIF-1-dependent pathways," *Nat. Med.* 10(6):594-601 (2004).
Markman et al., "Status of PIBK inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al, "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "P13K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironrnent in Cellular Models of Hodgkin Lymphoma," Blood (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J. Chem.* 18B:304-306 (1979).

(56) References Cited

OTHER PUBLICATIONS

Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, A Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al, "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et 211., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," (1989). *Pulm. Pharmacol.* 2(3):163-166.
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2): 141-153 (2011).
Polak et al., "The PBK/PKB signaling module as key regulator of hematopoiesis: implications for therapeutic strategies in leukemia," *Blood* 119(4):911-923 (2012).

Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Sic-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d] pyrimidines," *J. Med. Chem.* 33(7): 1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2(Suppl. 1):S5-S19 (1992).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 11b-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Rott et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, A PI3K Inhibitor Administered Orally to Patients with Solid Tumors," *J. Clin. Oncol.* 27: 146x (Suppl Abstr 3500) (2009).
Shibasaki et al., "Different properties of monomer and heterodimer forms of phosphatidylinositol 3-kinases," *Biochem. J.* 289 (Pt 1):227-231 (1993).

(56) References Cited

OTHER PUBLICATIONS

Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).
Soond et al., "PBK p110δ regulates T-cell cytokine production during primary and secondary immune responses in mice and humans," *Blood* 115(11):2203-2213 (2010).
Srinivasan et al., "P13 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7 (4):719-725 (1992).
Torbett et al, "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecalboxylic Acids into N-Amino Pyrazolopyridinones," *Journal of Heterocyclic Chemistry* 39(6):1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo[4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27: 146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation Via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White, et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines—potent inhibitors of the tyrosine kinase c-Src," *Bioorg. Med. Chem. Lett.* 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, $5^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al, "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4): 1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).

(56) References Cited

OTHER PUBLICATIONS

Yoshida et al, "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27 (41):5486-5496 (2008).
Abdel-Rahman et al., "Synthesis of heterobicyclic quinazolinones derived from N-[2-(2-chloro-phenyl)-1-(6,8-dibromo-4-oxo-4H-benzo[d][1,3]oxazin-2-yl)-vinyl]-benzamide as antimicrobial agents," Egyptian Journal of Chemistry (2006), 49(4), 461-474.
Abdel-Rahman et al., "Synthesis, reactions and antifungal agents of 2-[benzoylamino-2-(naphthyl- and/or 2'-furyl)]vinyl-4-H-3,1-benzoxazin-4-ones derivatives," Egyptian Journal of Chemistry (2006), 49(2), 169-184.
Abdel-Rahman, T., "Reactivity of 3-amino-3H-quinazolin-4-one derivatives towards some electrophilic and nucleophilic reagents and using of the products in the building of some interesting heterocycles as anticancer agent," Journal of Heterocyclic Chemistry (2006), 43(3), 527-534.
Abdel-Rahman, T., "Reactivity of 3-arnino-3H-quinazolin-4-one derivatives towards some electrophilic and nucleophilic reagents and using of the products in the building of some interesting heterocycles as anticancer agent," Bollettino Chimico Farmaceutico (2005), 144(3), 124-138.
Afantitis et al., "A combined LS-SVM & MLR QSAR workflow for predicting the inhibition of CXCR3 receptor by guinazolinone analogs," Molecular Diversity (2010), 14(2), 225-235.
Afify, A.A. et al., "Synthesis and reactions of substituted benzoxazinones bearing a bulky group at position-2," Indian Journal of Chemistry, Section B: Organic Chemistry Including Medicinal Chemistry (1988), 27B(10), 920-25.
Afify, A.A. et al., Synthesis and reactions of substituted benzoxazinones bearing a bulky group at position-2. Part I, Revue Roumaine de Chimie (1990), 35(4), 567-75.
Ahmad, S. et al., "Monoamine oxidase inhibitory activity of 4(3H)-quinazolinones of dopamine," Indian Journal of Pharmaceutical Sciences (1979), 41(3), 126-7.
Avila, M.A. et al., "New therapies for hepatocellular carcinoma," Oncogene (2006), 25(27), 3866-3884.
Barili, P.L. et al., "A facile one pot synthesis of 2,9-disubstituted 8-azapurin-6-ones (3,5-disubstituted 7-hydroxy-3H-1,2,3-triazolo[4,5-d]pyrimidines)," Journal of Heterocyclic Chemistry (1985), 22(6), 1607-9.
Basso et al., "SCH 1473759, a novel Aurora inhibitor, demonstrates enhanced anti-tumor activity in combination with taxanes and KSP inhibitors", Cancer Chemotherapy and Pharmacology (2011), 68(4), 923-933.
Beer, T. et al., "Southwest oncology group phase II study of ispinesib in androgen-independent prostate cancer previously treated with taxanes," Clinical Genitourinary Cancer (2008), 6(2), 103-109.
Birk et al., "Cell cycle-dependent cytotoxicity and mitotic spindle checkpoint dependency of investigational and approved antimitotic agents", International Journal of Cancer (2012), 130(4), 798-807.
Blagden, S.P. et al., "A phase I trial of ispinesib, a kinesin spindle protein inhibitor, with docetaxel in patients with advanced solid tumours," British Journal of Cancer (2008), 98(5), 894-899.
Bol'but, A.V. et al., "Condensed pyrimidine systems. 5.6-methyl-functionalized in pyrazolo[3,4-d]pyrimidin-4(5H)-ones," Zhurnal Organichnoi to Farmatsevtichnoi Khimii (2006), 4(3), 57-61.
Brunton, S. et al., "Potent Inhibitors of the Hedgehog Signaling Pathway," Journal of Medicinal Chemistry (2008), 51(5), 1108-1110.
Burris et al., "A phase I study of ispinesib, a kinesin spindle protein inhibitor, administered weekly for three consecutive weeks of a 28-day cycle in patients with solid tumors", Investigational New Drugs (2011), 29(3), 467-472.
Chau et al., "The association between EGFR variant III, HPV, p16, c-MET, EGFR gene copy number and response to EGFR inhibitors in patients with recurrent or metastatic squamous cell carcinoma of the head and neck", Head & Neck Oncology (2011), 3(11), 1-11.

Davis et al., "Increased therapeutic potential of an experimental anti-mitotic inhibitor SB715992 by genistein in PC-3 human prostate cancer cell line," BMC Cancer (2006), 6, 22.
Debnath, A. et al., "Structure-Based Identification of Small Molecule Antiviral Compounds Targeted to the gp41 Core Structure of the Human Immunodeficiency Virus Type 1," Journal of Medicinal Chemistry (1999), 42(17), 3203-3209.
El-Bassiouny et al., "Synthesis and some reactions of 2-[a-benzoylamino-b-2-furylvinyl]-6,8-dibromobenzoxazin-4(3H)-one and 3-aminoquinazolin-4(3H)-one derivatives," Asian Journal of Chemistry (1990), 2(1), 67-72.
El-Farargy et al., "Study on the reactivity of 2-[benzamido-(a-naphthylidene)]-4H-3,1-benzoxazin-4 one towards different carbon and nitrogen nucleophiles," Egyptian Journal of Chemistry (1993), Volume Date 1992, 35(5), 603-9.
El-Farargy, A.F., "Study on the stability and behavior of 2-[benzamido(naphthylidene)methyl]-4(3H)-quinazolinone," Egyptian Journal of Pharmaceutical Sciences (1991), 32(3-4), 565-74.
Elkafrawy, et al., "Steric and polar factors involving heteroring opening of 2-(a-benzoylamino-p-methoxystyryl)-6,8-dibromo-3,1-benzoxazin-4(H)-one," Indian Journal of Chemistry, Section B: Organic Chemistry Including Medicinal Chemistry (1992), 31B(1), 19-23.
El-Khamry et al., "Synthesis and reactions of 2-(a-benzoylamino-p-chlorostyry1)-3,1(4H)-benzoxazin-4-one with some nucleophilic reagents: synthesis of quinazolinone, tetrazole and benzimidazole derivatives," Egyptian Journal of Chemistry (1990), Volume Date 1988, 31(2), 261-9.
El-Nagdy, S. et al., "Behavior of benzoxazinone derivatives bearing a bulky group at position 2 toward some nitrogen and carbon nucleophiles. Part 2," Revue Roumaine de Chimie (1990), 35(1), 55-62.
El-Nagdy, S. et al., "Behavior of benzoxazinone derivatives bearing a bulky group at position-2 towards some nitrogen and carbon nucleophiles," Indian Journal of Chemistry, Section B: Organic Chemistry Including Medicinal Chemistry (1989), 28B(2), 126-30.
El-Nagdy, S. et al., "Synthesis and some reactions of 2-(a-benzoylaminostyryl)-3,1(4H)-benzoxazin-4-one and 3-amino-2-(a-benzoylaminostyrylquinazolin-4(3H)-one," Revue Roumaine de Chimie (1988), 33(8), 827-32.
El-Nagdy, S. et al., "Synthesis and some reactions of 2-(a-benzoylaminostyryl)-3,1(4H)-benzoxazin-4-one and 3-amino-2-(a-benzoylaminostyryl)quinazolin-4(3H)-one," Egyptian Journal of Chemistry (1990), Volume Date 1988, 31(5), 599-606.
El-Nagdy, S., "Synthesis and some reactions of 2-[a-(benzoylamino)styryl]-6,8-dibromo-3,1-benzoxazin-4(H)-one, quinazolin-4(3H)-one, and chloroquinazoline derivatives with some nucleophilic reagents," Asian Journal of Chemistry (1990), 2(4), 368-78.
El-Sharief et al., "Oxidation of 3-aminoquinazolinones with lead tetraacetate. A novel synthesis of naphtho-fused azirino-pyrazolo- and 1,4,5-oxadiazepinoquinazolinones," Journal of Chemical Research, Synopses (2002), (5), 205-208.
Essawy et al., "Behavior of 2-(a-phenylimido-b-p-nitrophenyl) vinyl-(4H)-3,1-benzoxazin-4-one towards some nucleophiles," Journal of Pure and Applied Sciences (1990), 9(2), 29-35 (abstract only).
Gao, H. et al., "A Dramatic Substituent Effect in Silver(I)-Catalyzed Regioselective Cyclization of ortho-Aikynylaryl Aldehyde Oxime Derivatives," Advanced Synthesis & Catalysis (2009), 351 (1-2), 85-88.
Garg, P. et al., "Synthesis and anti-implantation activity of 2-[2-[2-aryl-4(3H)-oxoquinazolin-3-yl]ethyl]-5-benzylidenecyclohexanone thiosemicarbazones," Biological Memoirs (1988), 14(2), 180-6.
Ghosh, T., "Quinazolines. I," Journal of the Indian Chemical Society (1937), 14, 411-13.
Guirguis, D., "The behaviour of some nucleophiles towards 2-[a-(benzoylamino)-b-(2-thienyl)vinyl]benzoxazin-4(3H)-one," Indian Journal of Chemistry, Section B: Organic Chemistry Including Medicinal Chemistry (2000), 39B(4), 264-269.

(56) References Cited

OTHER PUBLICATIONS

Hassanein et al, "Synthesis of 2-substituted-10H-[1,2,4]triazino[,1-b]quinazoline-10-ones and 8,13,14,16-tetrahydronaphtho[2',3':3,4][1,2,5]triazepino[7,1-b]quinazoline-8,13,16-triones with biological interest," Al-Azhar Bulletin of Science (1997), 8(2), 417-434.

Heiser et al., "Subtype and pathway specific responses to anticancer compounds in breast cancer", Proceedings of the National Academy of Sciences of the United States of America (2012), 109(8), 2724-2729.

Huang, W. et al., "Synthesis and evaluation of quinazolin-4-ones as hypoxia-inducible factor-1 inhibitors," Bioorganic & Medicinal Chemistry Letters (2011), 21(18), 5239-5243.

Jackson, J. et al., "Targeted anti-mitotic therapies: can we improve on tubulin agents?" Nature Reviews Cancer (2007), 7(2), 107-117.

Jankowski, F. et al., "Efficient microwave-assisted two-step procedure for the synthesis of 1,3-disubstituted-imidazo[1,5-a]quinazolin-5(4H)-ones," Tetrahedron (2010), 66(1), 128-133.

Jiang, C. et al., "De novo design, synthesis and biological evaluation of 1,4-dihydroquinolin-4-ones and 1,2,3,4-tetrahydroquinazolin-4-ones as potent kinesin spindle protein (KSP) inhibitors", Bioorganic & Medicinal Chemistry (2011), 19(18), 5612-5627.

Jiang, C. et al., "Docking studies on kinesin spindle protein inhibitors: an important cooperative 'minor binding pocket' which increases the binding affinity significantly," Journal of Molecular Modeling (2007), 13(9), 987-992.

Johnson, M. et al., "Discovery and optimization of a series of quinazolinone-derived antagonists of CXCR3," Bioorganic & Medicinal Chemistry Letters (2007), 17(12), 3339-3343.

Karanov et al., "Cytokinin and anticytokinin activity of some 4-substituted 1H-pyrazoles and 8-aza analogs of adenine," Plant Growth Regulation (1993), 13(1), 7-11.

Kathman, S. et al., "A Bayesian population PK-PD model for ispinesib/docetaxel combination-induced myelosuppression," Cancer Chemotherapy and Pharmacology (2009), 63(3), 469-476.

Kathman, S. et al., "A bayesian population PK-PD model of ispinesib-induced myelosuppression," Clinical Pharmacology & Therapeutics (New York, NY, United States) (2007), 81(1), 88-94.

Kirmani et al., "Studies on the reactivity of 2-methyl-3-phenyl-4(3H)-quinazolinone," Indian Journal of Chemistry, Section B: Organic Chernistly Including Medicinal Chemistry (1979), 17B(5), 445-9.

Knox, J. et al., "A phase II and pharmacokinetic study of SB-715992, in patients with metastatic hepatocellular carcinoma: a study of the National Cancer Institute of Canada Clinical Trials Group (NCIC CTG IND.168)," Investigational New Drugs (2008), 26(3), 265-272.

Lad, L. et al., "Mechanism of Inhibition of Human KSP by Ispinesib," Biochemistry (2008), 47(11), 3576-3585.

Lee, C. et al., "A phase II study of ispinesib (SB-715992) in patients with metastatic or recurrent malignant melanoma: a National Cancer Institute of Canada Clinical Trials Group trial," Investigational New Drugs (2008), 26(3), 249-255.

Lee, R. et al., "A University of Chicago consortium phase II trial of SB-715992 in advanced renal cell cancer," Clinical Genitourinary Cancer (2008), 6(1), 21-24.

Liu F. et al., "Discovery of tetrahydro-b-carbolines as inhibitors of the mitotic kinesin KSP," Bioorganic & Medicinal Chemistry (2010), 18(12), 4167-4177.

Liu F. et al., "Pharmacophore identification of KSP inhibitors," Bioorganic & Medicinal Chemistry Letters (2007), 17(3), 722-726.

Liu, D. et al., "Impurity identification in process chemistry by mass spectrometry", Characterization of Impurities and Degradants Using Mass Spectrometry, First Edition, John Wiley & Sons, Inc., Hoboken, NJ, (2011), pp. 251-277.

Mahmoud et al., "Heteroannulated quinazoline and quinazolinone derivatives from (Z)-2-[1-benzamido-2-(3,4,5-trimethoxyphenyl)vinyl]-3,1-benzoxazin-4(3H)-one," Synthetic Communications (2010), 40(10), 1516-1529.

Mahmoud et al., "Synthesis of new thiadiazoles, 1,2,4-triazolo[3,4-b]-1,3,4-thiadiazoles, and 1,2,4-triazolo[2,3-c]quinazoline derivatives from 4H-3,1-benzoxazin-4-one derivative," Phosphorus, Sulfur and Silicon and the Related Elements (2007), 182(6), 1275-1289.

Mahmoud et al., "Synthesis of novel quinazolinone and fused quinazolinones", European Journal of Chemistry (2011), 2(3), 404-409.

Marone et al., "Targeting phosphoinositide 3-kinase—Moving towards therapy," Biochimica et Biophysica Acta. 1784 (2008) 159-185.

Mealy, et al., "Drugs under development for the treatment of head and neck cancer," Drugs of the Future (2006), 31(7), 627-639.

Morsy, J.M., "Use of 2-(substituted vinyl)-4(3H)-quinazolinone and -4H-3,1-benzoxazinone in synthesis of heterocycles," Bulgarian Chemical Communications (2007), 39(2), 146-151.

Mossetti et al., "Imides: forgotten players in the Ugi reaction. One-pot multicomponent synthesis of quinazolinones", Chemical Communications, (2011), 47(24), 6966-6968.

Natsugari, H. et al., "Novel, Potent, and Orally Active Substance P Antagonists: Synthesis and Antagonist Activity of N-Benzylcarboxamide Derivatives of Pyrido[3,4-b]pyridine," Journal of Medicinal Chemistry (1995), 38(16), 3106-20.

Pandey, V.K. et al., "Quinazolylthiazoles as CNS acting agents," Acta Phannaceutica (Zagreb) (1996), 46(1), 51-9.

Pandey, V.K. et al., "Synthesis and antiviral activity of quinazolinyl sydnones," Indian Journal of Heterocyclic Chemistry (2006), 15(4), 399-400.

Pandey, V.K. et al., "Synthesis of 1-(2'-aryl-4'-oxo(3H)quinazoly1)-3-aryl-5-phenyl-formazans as potential anti-viral agents," Indian Drugs (1999), 36(1), 37-40.

Pandey, V.K., "Antiparkinsonism and CNS activities of (±)-2-aryl/alkyl-3-{b-(3',4'-dihydroxyphenyl)ethyl}quinazolin-4(3H)-ones," Biological Memoirs (1985), 11(2), 213-15.

Pandey, V.K., "Possible antiparkinsonian compounds. Part XI. Synthesis of 2-aryl/alkyl-3-[b-(3':4'-dihydroxyphenyl)ethyl]-quinazoline(3H)-4-one and 2-aryl/alkyl-3-[(7'-(phenothiazinyl)-ethyl]quinazoline(3H)-4-one," Acta Ciencia Indica (1978), 4(3), 230-5.

Parrish, C. et al., "Novel ATP-Competitive Kinesin Spindle Protein Inhibitors," Journal of Medicinal Chemistry (2007), 50(20), 4939-4952.

Pattan, S. et al., "Synthesis and microbiological evaluation of N'-3-(4-(4-chlorophenyl)thiazol-2-yl)quinazolin-4(3H)-ones," Indian Journal of Heterocyclic Chemistry (2005), 15(1), 79-80.

Pattan, S. et al., "Synthesis of N-3(4-(4-chlorophenyl thiazole-2-yl)-(2-(amino)methyl)-quinazoline-4(3H)-one and their derivatives for antitubercular activity," Indian Journal of Chemistry, Section B: Organic Chemistry Including Medicinal Chemistry (2006), 45B(7), 1778-1781.

Pinkerton, A. et al., "Synthesis and SAR of thiophene containing kinesin spindle protein (KSP) inhibitors," Bioorganic & Medicinal Chemistry Letters (2007), 17(13), 3562-3569.

Poupert, J.H., "Drug Design: Basic Principles and Applications", 2 Encyclopedia of Pharmaceutical Technology, 1362-1369, (James Swarbrick ed., 3rd ed., 2007).

Purcell, J. et al., "Activity of the kinesin spindle protein inhibitor ispinesib (SB-715992) in models of breast cancer," Clinical Cancer Research (2010), 16(2), 566-576.

Rodriguez et al., "Synthesis and characterization tritylthioethanamine derivatives with potent KSP inhibitory activity", Bioorganic & Medicinal Chemistry (2011), 19(18), 5446-5453.

Sakowicz, R. et al., "Antitumor Activity of a Kinesin Inhibitor," Cancer Research (2004), 64(9), 3276-3280.

Saleh, R.M. et al., "Synthesis and reactions of 2-[1-benzamido-2-(o-chlorophenyl)vinyl]-4H-3,1-benzoxazin-4-one," Revue Roumaine de Chimie (1994), 39(5), 567-76.

Saleh, R.M. et al., "Synthesis and some reactions of 2-(a-benzamido-p-chlorostyryl)-3,1-benzoxazin-4-one," Pakistan Journal of Scientific and Industrial Research (1991), 34(11), 417-21.

Sheth, P. et al., "Novel Benzimidazole Inhibitors Bind to a Unique Site in the Kinesin Spindle Protein Motor Domain," Biochemistry (2010), 49(38), 8350-8358.

(56) References Cited

OTHER PUBLICATIONS

Sheth, P. et al., "Thermodynamics of Nucleotide and Inhibitor Binding to Wild-Type and Ispinesib-Resistant Forms of Human Kinesin Spindle Protein," Biochemistry (2009), 48(46), 11045-11055.
Singh, B. et al., "4-Quinazolones. II. Synthesis of some imidazo[1,5-a]quinazolin-5(4H)ones," Journal of the indian Chemical Society (1969), 46(1), 21-5.
Singh, R. et al., "Synthesis and pharmacological screening of some 2-aryl-3-(phenyl-aryl-hydrazonyl)quinazolin-(3H)4-ones," Indian Drugs (1990), 28(2), 70-4.
Soliman et al., "Synthesis and reactions of substituted benzoxazinones bearing a bulky group at position 2," Revue Roumaine de Chimie (1992), 37(10), 1153-8.
Soliman et al., "Synthesis and reactions of substituted benzoxazinones bearing a bulky group at position 2," Delta Journal of Science (1990), 14(1), 166-80.
Sorbera, L.A. et al., "Ispinesib mesilate," Drugs of the Future (2006), 31(9), 778-787.
Storelli, S. et al., "Synthesis and structure-activity relationship of 3-phenyl-3H-quinazolin-4-one derivatives as CXCR3 chemokine receptor antagonists," Bioorganic & Medicinal Chemistry Letters (2005), 15(11), 2910-2913.
Storelli, S. et al., "Synthesis and structure-activity relationships of 3H-quinazolin-4-ones and 3H-pyrido[2,3-d]pyrimidin-4-ones as CXCR3 receptor antagonists," Archiv der Pharmazie (Weinheim, Germany) (2007), 340(6), 281-291.
Tang, P. et al., "Phase II study of ispinesib in recurrent or metastatic squamous cell carcinoma of the head and neck," Investigational New Drugs (2008), 26(3), 257-264.
Theoclitou et al., "Discovery of(+)-N-(3-Aminopropyl)-N-[1-(5-benzyl-3-methyl-4-oxo-[1,2]thiazolo [5,4-d]pyrimidin-6-yl)-2-methylpropyl]-4-methylbenzamide (AZD4877), a Kinesin Spindle Protein Inhibitor and Potential Anticancer Agent," Journal of Medicinal Chemistry (2011), 54(19), 6734-6750.
Tiwari, A. et al., "Synthesis and biological properties of 4-(3H)-quinazolone derivatives," European Journal of Medicinal Chemistry (2007), 42(9), 1234-1238.
Tiwari, S. et al., "Possible antifertility compounds—Part III: Synthesis of 2-hippuryl-3-arylquinazolinones," Journal of the Chemical Society of Pakistan (1981), 3(4), 215-17.
Tiwari, S. et al., "Synthesis and central nervous systems activity of 2-aryl-3(3',4'-dihydroxyphenylethyl)-6,8-substituted 4(3H)-quinazolinones," Indian Journal of Pharmaceutical Sciences (1978), 40(2), 40-3.
Tiwari, S. et al., "Synthesis of possible antiparkinsonian compounds. X. Synthesis of 2,6,8-trisubstituted benzoxazinones and their corresponding 3-hydroxyquinazolinones," Journal of the Indian Chemical Society (1975), 52(8), 736-7.
Valensin S., et al., "KIF11 inhibition for glioblastoma treatment: reason to hope or a struggle with the brain?" BMC Cancer (2009), 9.
Voultsiadou et al., "Recent advances of kinesin motor inhibitors and their clinical progress", Reviews on Recent Clinical Trials (2011), 6(3), 271-277.
Wang, F. et al., "Triphenylbutanamines: Kinesin Spindle Protein Inhibitors with in Vivo Antitumor Activity," Journal of Medicinal Chemistry (2012), 55 (4), 1511-1525.
Watkins, W. et al., "Quinazolinone fungal efflux pump inhibitors. Part 2: In Vitro structure-activity relationships of (N-methylpiperazinyl)-containing derivatives," Bioorganic & Medicinal Chemistry Letters (2004), 14(20), 5133-5137.
White, M., "Targeting mitotic fragility in cancer," Future Oncology (2009), 5(5), 613-615.
Zhang, B. et al., "Crystal structure of HsEg5 in complex with clinical candidate CK0238273 provides insight into inhibitory mechanism, potency, and specificity," Biochemical and Biophysical Research Communications (2008), 72(4), 565-570.
Zhang, B. et al., "Development of a high-throughput robotic fluorescence-based assay for HsEg5 inhibitor screening," Analytical Biochemistry (2005), 345(2), 326-335.
Aksoy et al., "The p110d isoform of the kinase PI(3)K controls the subcellular compartmentalization of TLR4 signaling and protects from endotoxic shock", Nature Immunology, 2012, vol. 13(11), pp. 1045-1054.
Ali et al., "Leukocyte Extravasation: An Immunoregulatory Role for-L-Fucosidase?", J Immunol 2008, vol. 181, pp. 2407-2413.
Balla et al. (Eds), Phosphoinositides I: Enzymes of Synthesis and Degradation, Chapter 5: P13Ks—Drug Targets in Inflammation and Cancer Series: Subcellular Biochemistry, vol. 58, 2012, XVI, 356 p.
Burger et al, "CXCR4: a key receptor in the crosstalk between tumor cells and their microenvironment", Blood, Mar. 1, 2006;107(5), pp. 1761-1767.
Burger et al., "The microenvironrnent in chronic lymphocytic leukemia (CLL) and other B cell malignancies: insight into disease biology and new targeted therapies", Semin Cancer Biol, Feb. 2014; vol. 24:pp. 71-81
Curran et al., "PD-1 and CTLA-4 combination blockade expands infiltrating T cells and reduces regulatory T and myeloid cells within B16 melanoma tumors," PNAS, Mar. 2, 2010, vol. 107(9), pp. 4275-4280.
De Palma and Lewis, "Macrophage Regulation of Tumor Responses to Anticancer Therapies", Cancer Cell, vol. 23, Issue 3, Mar. 18, 2013, pp. 277-286.
Denardo et al., "Leukocyte Complexity Predicts Breast Cancer Survival and Functionally Regulates Response to Chemotherapy", Cancer Discovery, Jun. 2011, vol. 1, pp. 54-67.
Duraiswamy et al., "Dual Blockade of PD-1 and CTLA-4 Combined with Tumor Vaccine Effectively Restores T-Cell Rejection Function in Tumors," Cancer Research, Jun. 5, 2013;73(12):3591-603.
Feig et al., "Targeting CXCL12 from FAP-expressing carcinoma associated fibroblasts synergizes with anti-PD-L1 immunotherapy in pancreatic cancer," PNAS, Dec. 10, 2013, vol. 110, No. 50, pp. 20212-20217.
Ferrandi et al., "Phosphoinositide 3-Kinase Inhibition Plays a Crucial Role in Early Steps of Inflammation by Blocking Neutrophil Recruitment", J Pharmacol Exp Ther, Sep. 2007, vol. 322, pp. 923-930.
Fruman, D., "Phosphoinositide 3-kinase and its targets in B-cell and T-cell signaling", Current Opinion in Immunology, vol. 16, Issue 3, Jun. 2004, pp. 314-320.
Ghia et al., "Chronic lymphocytic leukemia B cells are endowed with the capacity to attract CD4+, CD40L+ T cells by producing CCL22", Eur J Immunol., May 2002; vol. 32(5): pp. 1403-1413.
Hardamon et al., "Inhibition of myeloid cell PI3K is a potential therapeutic approach to treat pancreatic cancer", Cancer Research, Apr. 15, 2012; vol. 72, Issue 8, Supplement 1, Abstract 5228.
Herman et al., "Molecular pathways: targeting phosphoinositide 3-kinase p110-delta in chronic lymphocytic leukemia", Clin Cancer Res., Aug. 1, 2012; vol. 18(15): pp. 4013-4018.
Hirsch et al., "Phosphoinositide 3-kinases as a common platform for multi-hormone signaling", J Endocrinol, 2007, vol. 194 (2), pp. 243-256.
Kaneda et al., "PI3-kinase gamma controls the macrophage M1-M2 switch, thereby promoting tumor immunosuppression and progression", AACR; Cancer Res 2014, vol. 74 (19 Suppl), Abstract 3650.
Lewis and Pollard, "Distinct Role of Macrophages in Different Tumor Microenvironments", Cancer Res 2006, vol. 66 (2), pp. 605-612.
Monjazeb et al., "Immunoediting and antigen loss: overcoming the Achilles heel of immunotherapy with antigen non-specific therapies", Front. Oncol., 2013, vol. 3, Article 197, pp. 1-10.
Mraz et al., "miR-34a, miR-29c and miR-17-5p are downregulated in CLL patients with TP53 abnormalities", Leukemia (2009), vol. 23(6), pp. 1159-1163.
Ni et al., "Functional Characterization of an Isoform-Selective Inhibitor of PI3K-p110b as a Potential Anticancer Agent", Cancer Discovery, May 2012, vol. 2, pp. 425-433.

(56) References Cited

OTHER PUBLICATIONS

Okkenhaug, K., "Signaling by the Phosphoinositide 3-Kinase Family in Immune Cells", Annu. Rev. Immunol., 2013, vol. 31, pp. 675-704.
Ries, et al., "Targeting Tumor-Associated Macrophages with Anti-CSF-1R Antibody Reveals a Strategy for Cancer Therapy", Cancer Cell, vol. 25, Issue 6, Jun. 16, 2014, pp. 846-859.
Rommel et al., Taking PI3Kδ and PI3Kγ One Step Ahead: Dual Active PI3Kδ/γ Inhibitors for the Treatment of Immune-Mediated Inflammatory Diseases, Phosphoinositide 3-Kinase in Health and Disease, 2011, vol. 1, pp. 279-299.
Roy et al., "DDB2 Suppresses Epithelial-to-Mesenchymal Transition in Colon Cancer", Cancer Res Jun. 15, 2013, 73(12), pp. 3771-3782.
Schmid et al., "PI3 Kinase gamma control of Arginase-1 expression promotes tumor immunosuppression", Cancer Research, Apr. 15, 2012, vol. 72, Issue 8, Supplement 1, Abstract 411.
Schmid et al., "ReceptorTyrosineKinasesandTLR/IL1Rs Unexpectedly Activate Myeloid Cell PI3Kg, A Single Convergent Point Promoting Tumor Inflammation and Progression", Cancer Cell, vol. 19, Issue 6, Jun. 14, 2011, pp. 715-727.
Topalian et al., "Safety, Activity, and Immune Correlates of Anti-PD-1 Antibody in Cancer", N Engl J Med 2012, 366(26), pp. 2443-2454.
Wolchok et al., "Antitumor response and new lesions in advanced melanoma patients on ipilimumab treatment", Wolchok et al., J. Clin. Oncology, 2008 ASCO (Post-Meeting Edition), vol. 26, No. 15S (May 20 Suppl), Abstract 3020.
Wolchok et al., "Nivolumab plus Ipilimumab in Advanced Melanoma", NEJM, 2013, vol. 369, pp. 122-133.
Wurth et al., "CXCL12 modulation of CXCR4 and CXCR7 activity in human glioblastoma stem-like cells and regulation of the tumor microenvironment," Frontiers in Cellular Neuroscience, May 2014, vol. 8, Article 144, pp. 1-19.
Brachman et al., "PI3K and mTOR inhibitors—a new generation of targeted anticancer agents", Current Opinion in Cell Biology (2009), vol. 21, pp. 194-198.
Dagia et al., "A preferential p110α/γ PI3K inhibitor attenuates experimental inflammation by suppressing the production of proinflammatory mediators in a NF-κB-dependent manner", American Journal of Physiology—Cell Physiology (2010), vol. 298, pp. 929-941.
Dushianthan et al., "Acute respiratory distress syndrome and acute lung injury", Post Graduate Medical Journal (2011), vol. 87, pp. 612-622.
Engelman, J. "Targeting PI3K signalling in cancer: opportunities, challenges and limitations", Nature Reviews: Cancer. vol. 9 (2009), pp. 550-562.
Ghigo et al., "PI3K Inhibition in Inflammation: Toward tailored therapies for specific diseases," BioEssays 32 (2010), pp. 185-196.
Hirsch, E. et al., "Taming the PI3K team to hold inflammation and cancer at bay", Pharmacology & Therapeutics (2008), vol. 118, pp. 192-205.
Kolliputi, N. et al., "IL-6 cytoprotection in hyperoxic acute lung injury occurs via PI3K/Akt-mediated Bax phosphorylation", American Journal of Physiology, Lung Cellular and Molecular Physiology (2009), vol. 297, pp. L6-L16.
Kong, D. et al., "Phosphatidylinositol 3-kinase inhibitors: promising drug candidates for cancer therapy", Cancer Science (2008), vol. 9, pp. 1734-1740.
Liu, Q. et al. "mTOR mediated anti-cancer drug discovery ", Drug Discovery Today: Therapeutic Strategies, (2009), vol. 6, pp. 47-55.
Shuttleworth et al., "Progress in the Preclinical Discovery and Clinical Development of Class I and Dual Class I/IV Phosphoinositide 3-Kinase (PI3K) Inhibitors ", Current Medicinal Chemistry (2011), vol. 18, pp. 2686-2714.
Evans, "Principles of Radiopharmacology", Colombett, L.G editor, CRC Press, 1979, pp. 11-13 and 24.
Banham-Hall et al., "The therapeutic potential for PI3K inhibitors in autoimmune and rheumatic diseases", Open Rheumatol. J. 2012, 6, 245-258.

Bell et al., "SAR studies around a series of triazolopyridines as potent and selective PI3Kc inhibitors", Bioorg. Med. Chem. Lett. 2012, 22, 5257-5263.
Bergamini et al., "A selective inhibitor reveals PI3Kγ dependence of TH17 cell differentiation", Nat. Chem. Biol. 2012, 8, 576-582.
Bruce et al., "Development of isoform selective PI3K-kinase inhibitors as pharmacological tools for elucidating the PI3K pathway", Bioorg. Med. Chem. Lett. 2012, 22, 5445-5450.
Cantley, L.C., "The phosphoinositide 3-kinase pathway", Science, 2002, 296, 1655-1657.
Collier et al., "Discovery of highly isoform selective thiazolopiperidine inhibitors of phosphoinositide 3-kinase γ", J. Med. Chem. 2015, 58, 5684-5688.
Collier et al., "Structural basis for isoform selectivity in a class of benzothiazole inhibitors of phosphoinositide 3-kinase γ", J. Med Chem. 2015, 58, 517-521.
DeHenau et al., "Checkpoint Blockade Therapy is Improved by Altering the Immune-Suppressive Microenvironment with IPI-549, a Potent and Selective Inhibitor of PI3K-γ, in Preclinical Models," AACR Annual Meeeting 2016, Apr. 17, 2016, New Orleans, Poster 554.
Gunderson et al., "Bruton tryrosine kinase-dependent immune cell cross-talk drives pancreas cancer", Cancer Discovery 2016, 6, 270-285.
Hawkins et al., PI3K signalling in inflammation. Biochim. Biophys. Acta, Mol. Cell Biol. Lipids 2015, 1851, 882-897.
Joshi et al., "A macrophage-dominant PI3K isoform controls hypoxia-induced HIF1alpha nad HIF2alpha stability and tumor growth, angiogenesis, and metastasis", Mol. Cancer. Res. 2014, 12, 1520-1531.
Kutok et al., "The Potent and Selective Phosphoinositide-3 -Kinase (PI3K)-γ Inhibitor, IPI-549, Inhibits Tumor Growth in Murine Syngeneic Solid Tumor Models through Alterations in the Immune Suppressive Microenvironment", CRI-CIMT-EATI-AACR—The Inaugural International Cancer Immunotherapy Conference, Sep. 18, 2015, New York, NY, Poster.
Leahy et al., "Discovery of a novel series of potent and orally bioavailable phosphoinositide 3-kinase γ inhibitiors", J. Med. Chem. 2012, 55, 5467-5482.
NCT02637531: A dose-escalation study to evaluate the safety, tolerability, pharmacokinetics, and pharmacodynamics of IPI-549. www.clinicaltrials.gov, May 19, 2016.
Oka et al., "Discovery of N-{5[3-(3-hydroxypiperdin-1-yl)-1,2,4-oxadiazol-5-yl]-4-methyl-1,3-thiazol-2-yl}acetamide (TASP0415914) as an orally potent phosphoinosititide 3-kinase γ inhibitor for the treatment of inflammatory diseases", Bioorg. Med. Chem. 2013, 21, 7578-7583.
Reif et al., "Cutting Edge: Differential Roles for Phosphoinositide 3-Kinases, p110γ and p110δ, in Lymphocyte Chemotaxis and Homing," J. Immunol. 173:2236-2240 (2004).
Rivera et al., "Intratumoral myeloid cells regulate repsoniveness and resistance to antiangiogenic therapy", Cell Rep. 2015, 11, 577-591.
Sunose et al., "Discovery of 5-(2-amino-[1,2,4]triazolo[1,5-a]pyridin-7-yl)-N-(tert-butyl)pyridine-3-sulfonamide (CZC24758), as a potent, orally bioavailable and selective inhibitor of PI3K for the treatment of inflammatory disease", Bioorg. Med. Chem. Lett. 2012, 22, 4613-4618.
Thorpe et al., "PI3K in cancer: divergent rols of isoforms, modes of activation and therapeutic targeting", Nat. Rev. Cancer 2015, 15, 7-24.
Tolcher et al., "A Phase 1/1b First-In-Human Study of IPI-549, a PI3K-g Inhibitor, as Monotherapy and in Combination with an Anti-PD1 Antibody in Subjects with Advanced Solid Tumors", ASCO Annual Meeting 2016, Jun. 3-7, Chicago, IL, Poster.
Vanhaesebroeck et al., "Molecules in medicine mini-review: isoforms of PI3K in biology and disease", J. Mol. Med. 2016, 94, 5-11.
Winkler et al., "PI3K-d and PI3K-g Inhibition by Ipi-145 Abrogates Immune Responses and Suppresses Activity in Autoimmune and Inflammatory Disease Models," Chem. Biol. 2013, 20, 1364-1374.
Brunk et al., "Anti-PD-L1 therapy yielded durable responses in early NSCLC trials, Oncology Practice Digital Network", Feb. 2014, pp. 1-3.

(56) References Cited

OTHER PUBLICATIONS

Tomasini et al., "Ipilimumab: its potential in non-small cell lung cancer", Ther Ad Med Oncol, 2012, Issue 4, No. 2, pp. 43-50.
Evans et al., "Discovery of a Selective Phosphoinositide-3-Kinase {P13K}-γ inhibitor (IP1-549) as an Immuno-Oncology Clinical Candidate," ACS Med. Chem. Lett., 2016, 7, 862-867.
Braga et al., "Crystal polymorphism and multiple crystal forms," Struct. Bond. 132:25-50 (2009).
Zell et al., "Investigation of polymorphism in aspartame and neotame using solid-state NMR spectroscopy," Tetrahedron, 56:6603-6616 (2000).
Bernstein, "Polymorphism in Molecular Crystals," Oxford, 2002, p. 46.

* cited by examiner

SOLID FORMS OF ISOQUINOLINONES, AND PROCESS OF MAKING, COMPOSITION COMPRISING, AND METHODS OF USING THE SAME

This application claims priority to U.S. Provisional Application Nos. 62/218,486, filed Sep. 14, 2015, and 62/218,493, filed Sep. 14, 2015, the entireties of which are incorporated herein by reference.

1. BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-Kinases), diacylglycerol kinases, and sphingosine kinases.

Phosphoinositide 3-kinases (PI3Ks) constitute a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate a lipid product termed $PIP_3$, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2.

The PI3K signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

Many inhibitors of PI3Ks have been generated. While such compounds are often initially evaluated for their activity when dissolved in solution, solid state characteristics such as polymorphism play an important role. Polymorphic forms of a drug substance, such as an inhibitor of PI3K, can have different chemical and physical properties, including crystallinity, melting point, chemical reactivity, solubility, dissolution rate, optical and mechanical properties, vapor pressure, and density. These properties can have a direct effect on the ability to process or manufacture a drug substance and the drug product. Moreover, polymorphism is often a factor under regulatory review of the "sameness" of drug products from various manufacturers. For example, polymorphism has been evaluated in compounds such as warfarin sodium, famotidine, and ranitidine. Polymorphism can affect the quality, safety, and/or efficacy of a drug product, such as a kinase inhibitor. Thus, research directed towards polymorphs of PI3K inhibitors and processes for preparing polymorphs of PI3K inhibitors represents a significantly useful field of investigation in the development of active pharmaceutical ingredients (APIs).

In addition, PI3K inhibitors have been used to treat various diseases and disorders in humans (e.g., in clinical trials). For the production of a drug substance intended for use in humans, current Good Manufacturing Practices (GMP) are applicable. Procedures need to be in place that can control the levels of impurities and ensure that API products are produced, which consistently meet their predetermined specifications. Thus, a significant need exists for a process to prepare PI3K inhibitors suitable for human use, particularly on a commercial scale, that is, inter alia, safe, scalable, efficient, economically viable, and/or having other desirable properties. Among other entities, disclosed herein are polymorphic forms of PI3K inhibitors which address these needs and provide exemplary advantages.

2. SUMMARY

Provided herein are solid forms comprising a compound of formula (I) (also referred as Compound 1 herein):

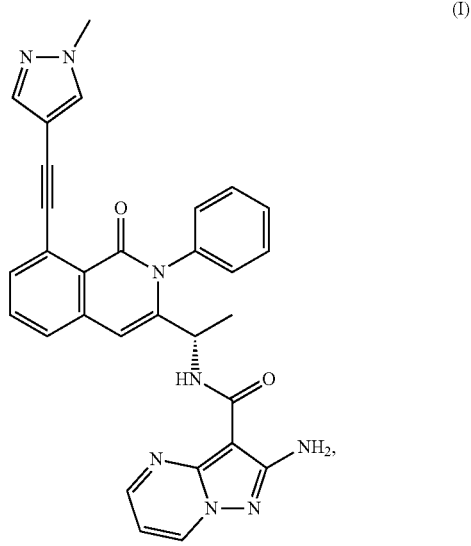 [SMILES: C[C@H](NC(=O)c1c(N)nn2cccnc12)c1cc2cccc(C#Cc3cnn(C)c3)c2c(=O)n1-c1ccccc1]

or a salt, or solvate (e.g., hydrate), or solvate of a salt thereof, or a mixture thereof. Also provided herein are methods of synthesizing the solid forms.

The solid forms provided herein include, but are not limited to, hydrates, anhydrates, solvates of Compound 1 and salts and cocrystals thereof. The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, and/or a multiple-component crystal form comprising the compound of formula (I) and a pharmaceutically acceptable diluent, excipient or carrier.

In one embodiment, the solid form is a crystalline form. In one embodiment, the solid form further comprises a coformer. In one embodiment, the solid form comprising Compound 1 and a coformer is a cocrystal. In another embodiment, the solid form is an amorphous form.

Also provided herein are pharmaceutical compositions, single unit dosage forms, dosing regimens and kits comprising the amorphous form provided herein.

Also provided herein are methods for treating, preventing, and managing various disorders using the compositions and amorphous form provided herein. The methods comprise administering to a patient in need of such treatment or management a therapeutically effective amount of a compound provided herein. Further provided are methods of preventing various diseases and disorders, which comprise administering to a patient in need of such prevention a prophylactically effective amount of a compound provided herein.

Further provided herein are processes of preparing a compound of formula (I), or a salt, or solvate (e.g., hydrate), or solvate of a salt thereof, or a mixture thereof.

Further provided herein are methods for analyzing a material for the presence or amount of a solid form provided herein, comprising providing a material comprising a compound of formula (I), or a salt, solvate (e.g., hydrate), or solvate of a salt thereof, or a mixture thereof; and using a characterization method to determine whether a signatory characteristic associated with the solid form is present in the material by comparing the characteristic obtained from the material with a reference signatory characteristic; wherein the existence of a characteristic substantially identical to the reference signatory characteristic indicates the presence of the solid form in the material.

3. INCORPORATION BY REFERENCE

All publications, patents, and patent applications mentioned in this specification are herein incorporated by reference in their entireties and to the same extent as if each individual publication, patent, or patent application was specifically and individually indicated to be incorporated by reference.

4. BRIEF DESCRIPTION OF FIGURES

FIG. 33 is a representative TGA analysis of spray dried Compound 1 and HPMC-AS.

Figure 34A:
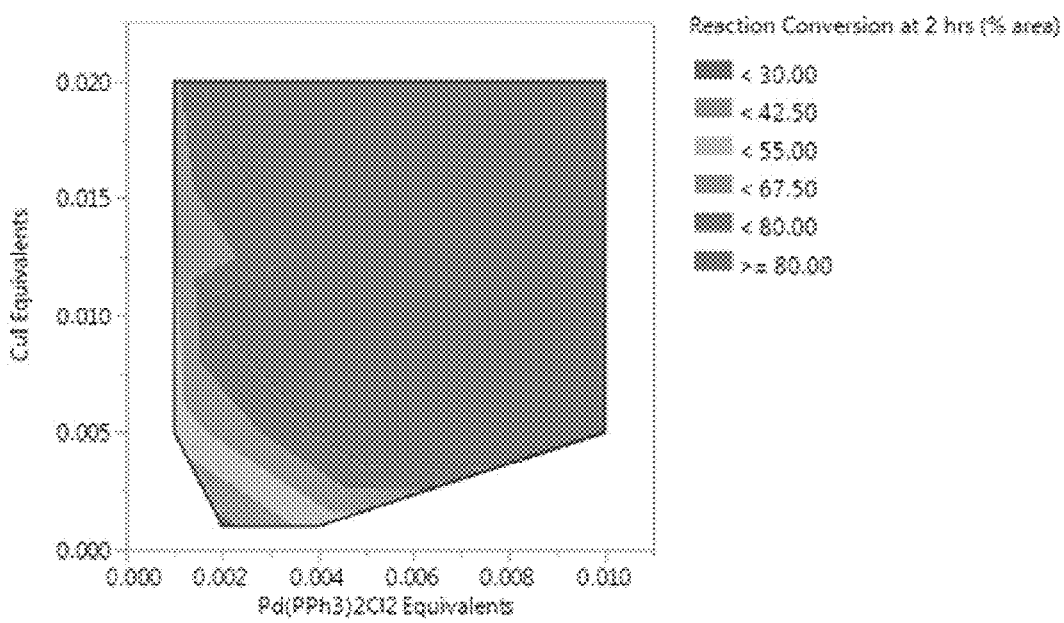
Figure 34B:
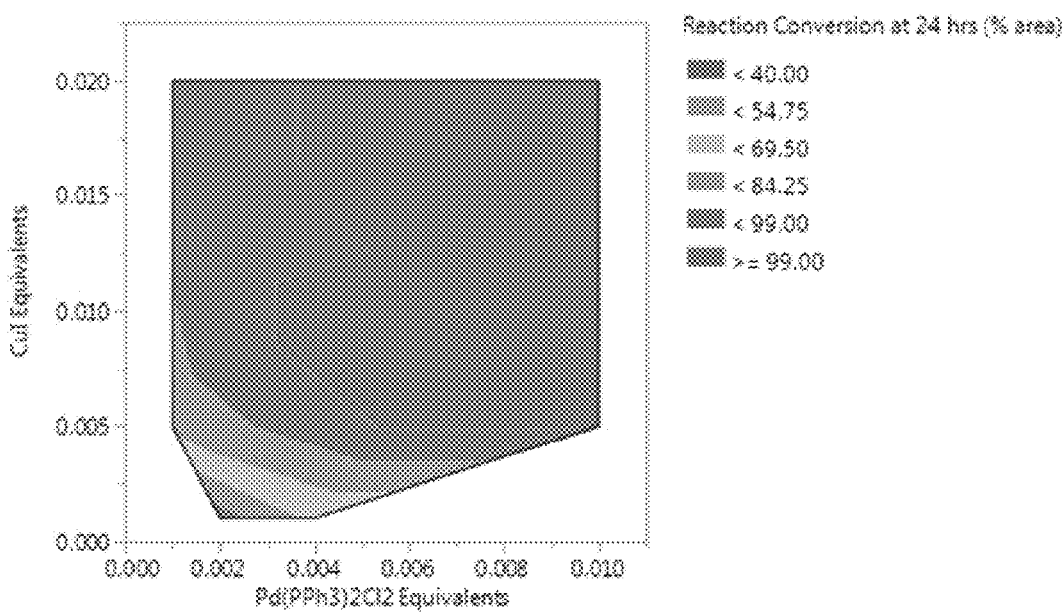
Figure 34C:
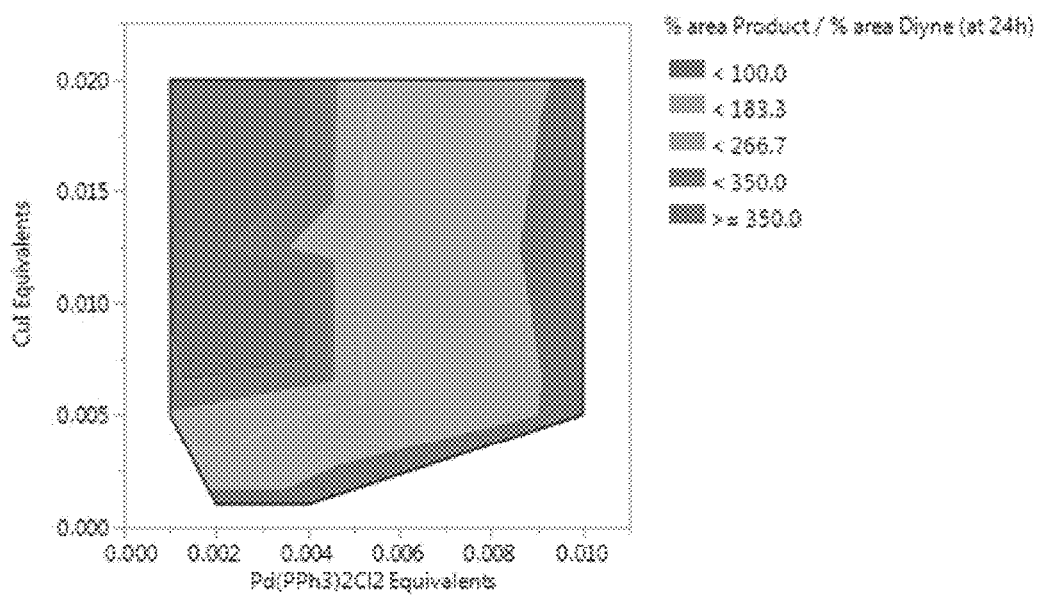
Figure 34D:
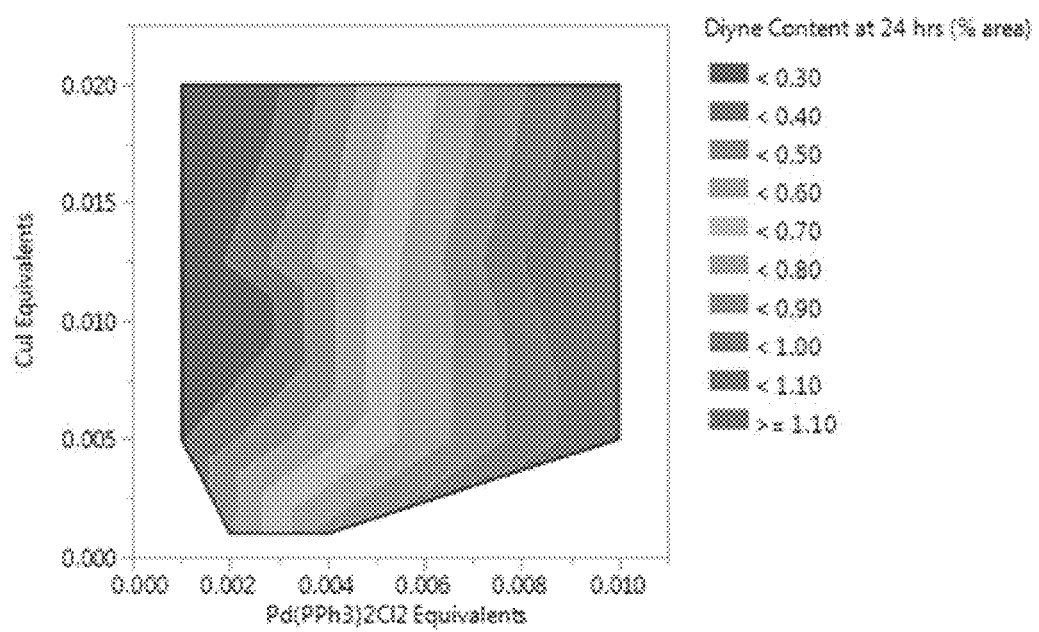

FIG. 34A shows the conversion at 2 hours (% area) for the coupling reaction of 4-iodo-1-methyl-1H-pyrazole with trimethylsilylacetylene; FIG. 34B shows the reaction conversion at 24 hours (% area); FIG. 34C shows the product/diyne ratio (% area) at 24 hours; and FIG. 34D shows the diyne content at 24 hours (% area).

5. DETAILED DESCRIPTION

5.1 Definitions

Unless defined otherwise, all technical and scientific terms used herein have the same meaning as is commonly understood by one of skill in the art.

As used in the specification and claims, the singular form "a", "an" and "the" includes plural references unless the context clearly dictates otherwise.

When ranges are used herein for physical properties, such as molecular weight, or chemical properties, such as chemical formulae, all combinations and subcombinations of ranges and specific embodiments therein are intended to be included. As used herein, the terms "about" and "approximately" when used in combination with a numeric value or range of values mean that the value or range of values may deviate to an extent deemed reasonable to one of ordinary skill in the art, e.g., within experimental variability (or within statistical experimental error), and thus the numeric value or range of values can vary from, for example, between 1% and 15%, between 1% and 10%, between 1% and 5%, between 0.5% and 5%, and between 0.5% and 1%, of the stated numeric value or range of values. As disclosed herein, every instance where a numeric value or range of values preceded by the term "about" also includes the embodiment of the given value(s). For example, "about 3° C." discloses the embodiment of the temperature being "3° C.". The terms "about" and "approximately" are used completely interchangeable throughout the disclosure. The term "between" includes the endpoint numbers on both limits of the range. For example, the range described by "between 3 and 5" is inclusive of the numbers "3" and "5". As used herein, a tilde (i.e., "~") preceding a numerical value or range of values indicates "about" or "approximately."

As used herein, and unless otherwise specified, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

As used herein, and unless otherwise specified, the term "agonist" refers to a compound having the ability to initiate or enhance a biological function of a target protein, whether by enhancing or initiating the activity or expression of the target protein. Accordingly, the term "agonist" is defined in the context of the biological role of the target protein. While agonists provided herein can specifically interact with (e.g., bind to) the target, compounds that initiate or enhance a biological activity of the target protein by interacting with other members of the signal transduction pathway of which the target protein is a member are also specifically included within this definition.

As used herein, and unless otherwise specified, the terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While antagonists provided herein can specifically interact with (e.g., bind to) the target, compounds that inhibit a biological activity of the target protein by interacting with other members of the signal transduction pathway of which the target protein is a member are also specifically included within this definition. In one embodiment, a biological activity inhibited by an antagonist is associated with the development, growth, or spread of a tumor, or an undesired immune response, e.g., as manifested in autoimmune disease.

As used herein, and unless otherwise specified, an "anti-cancer agent", "anti-tumor agent" or "chemotherapeutic agent" refers to any agent useful in the treatment of a neoplastic condition. One class of anti-cancer agents comprises chemotherapeutic agents. As used herein, and unless otherwise specified, "chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, and unless otherwise specified, the term "cell proliferation" refers to a phenomenon by which the cell number has changed as a result of division. In one embodiment, this term also encompasses cell growth by which the cell morphology has changed (e.g., increased in size) consistent with a proliferative signal.

As used herein, and unless otherwise specified, the term "co-administration," "administered in combination with," and their grammatical equivalents, encompasses administration of two or more agents to an animal either simultaneously or sequentially. In one embodiment, both agents and/or their metabolites are present in the animal at the same time. In one embodiment, co-administration includes simultaneous administration in separate compositions, administration at different times in separate compositions, or administration in a composition in which both agents are present.

As used herein, and unless otherwise specified, the term "effective amount" or "therapeutically effective amount" refers to an amount of a compound described herein that is sufficient to effect an intended application or effect, including, but not limited to, disease treatment, as defined herein. The therapeutically effective amount can vary depending upon the intended application (in vitro or in vivo), or the subject and disease condition being treated, e.g., the weight and age of the subject, the severity of the disease condition, the manner of administration, and the like, which can be determined by one of ordinary skill in the art. The term can also apply to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, and unless otherwise specified, the terms "treatment", "treating", "palliating" and "ameliorating" are used interchangeably herein, and refer to an approach for obtaining beneficial or desired results, including, but not limited to, a therapeutic benefit. In one embodiment, therapeutic benefit means eradication or amelioration of the underlying disorder being treated. In one embodiment, a therapeutic benefit is achieved with the eradication or amelioration of one or more of the physiological symptoms associated with the underlying disorder, such that an improvement is observed in the patient, notwithstanding that the patient can still be afflicted with the underlying disorder.

As used herein, and unless otherwise specified, the terms "prevention" and "preventing" refer to an approach for obtaining beneficial or desired results including, but not limited to, prophylactic benefit. In one embodiment, prophylactic benefit includes delaying or eliminating the appearance of a disease or condition, delaying or eliminating the onset of symptoms of a disease or condition, slowing, halting, or reversing the progression of a disease or condition, or any combination thereof. To obtain prophylactic benefit, the compositions can be administered to a patient at risk of developing a particular disease, or to a patient reporting one or more of the physiological symptoms of a disease, even though a diagnosis of this disease can or cannot have been made.

As used herein, and unless otherwise specified, "signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator can augment (agonist) or suppress (antagonist) the activity of a signaling molecule.

As used herein, and unless otherwise specified, the term "selective inhibition" or "selectively inhibit" as applied to a biologically active agent refers to the agent's ability to selectively reduce the target signaling activity as compared to off-target signaling activity, via direct or interact interaction with the target.

As used herein, and unless otherwise specified, the term "in vivo" refers to an event that takes place in a subject's body.

As used herein, and unless otherwise specified, the term "in vitro" refers to an event that takes places outside of a subject's body. For example, an in vitro assay encompasses any assay run outside of a subject assay. In vitro assays encompass cell-based assays in which cells alive or dead are employed. In one embodiment, in vitro assays also encompass a cell-free assay in which no intact cells are employed.

"Subject" to which administration is contemplated includes, but is not limited to, humans (i.e., a male or female of any age group, e.g., a pediatric subject (e g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, and unless otherwise specified, "radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation, x-rays, gamma rays, and neutrons.

As used herein, the term "combining" refers to bringing one or more chemical entities into association with another one or more chemical entities. Combining includes the processes of adding one or more compounds to a solid, liquid or gaseous mixture of one or more compounds (the same or other chemical entities), or a liquid solution or multiphasic liquid mixture. The act of combining includes the process or processes of one or more compounds reacting (e.g., bond formation or cleavage; salt formation, solvate formation, chelation, or other non-bond altering association) with one or more compounds (the same or other chemical entities). The act of combining can include alteration of one or more compounds, such as by isomerization (e.g., tautomerization, resolution of one isomer from another, or racemization).

As used herein, and unless otherwise specified, a "one-pot" process refers to a process of preparing a desired product, wherein all reactants are added simultaneously or successively, and wherein no separation, isolation, and/or purification of any intermediate formed is conducted before the formation of the desired product is substantially complete. A "one-pot" process is preferably conducted in a single container, but may be conducted in more than one container.

As used herein, the term "recovering" includes, but is not limited to, the action of obtaining one or more compounds by collection during and/or after a process step as disclosed herein, and the action of obtaining one or more compounds by separation of one or more compounds from one or more other chemical entities during and/or after a process step as disclosed herein. The term "collection" refers to any action(s) known in the art for this purpose, including, but not limited to, filtration, decanting a mother liquor from a solid to obtain one or more compounds, and evaporation of liquid media in a solution or other mixture to afford a solid, oil, or other residue that includes one or more compounds. The solid can be crystalline, acrystalline, partially crystalline, amorphous, containing one or more polymorphs, a powder, granular, of varying particle sizes, of uniform particle size, among other characteristics known in the art. An oil can vary in color and viscosity, and include one or more solid forms as a heterogeneous mixture, among other characteristics known in the art. The term "separation" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques. Recovering one or more compounds can involve preparation of a salt, solvate, hydrate, chelate or other complexes of the same, then collecting or separating as described above.

As used herein, a "pharmaceutically acceptable form" of a disclosed Formula (I) includes, but is not limited to, pharmaceutically acceptable salts, hydrates, solvates, chelates, non-covalent complexes, isomers, prodrugs, and isotopically labeled derivatives thereof, and mixtures thereof. Hence, the terms "chemical entity" and "chemical entities" also encompass pharmaceutically acceptable salts, hydrates, solvates, chelates, non-covalent complexes, isomers, prodrugs, and isotopically labeled derivatives, and mixtures thereof. In some embodiments, a pharmaceutically acceptable form of a disclosed Formula (I) includes a salt, a solvate, or a hydrate thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)^4$-salts. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines, including naturally occurring substituted amines, cyclic amines, basic ion exchange resins, and the like, examples include, but are not limited to, isopropylamine, trimethylamine, diethylamine, triethylamine, tripropylamine, and ethanolamine. In some embodiments, the pharmaceutically acceptable base addition salt is ammonium, potassium, sodium, calcium, or magnesium salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e., two counterions) and higher salts (e.g., three or more counterions) are encompassed within the meaning of pharmaceutically acceptable salts.

In addition, if a compound of the present disclosure is obtained as an acid addition salt, the free base can be obtained by basifying a solution of the acid salt. Conversely, if a product is a free base, an acid addition salt, particularly a pharmaceutically acceptable addition salt, can be produced by dissolving the free base in a suitable organic solvent and treating the solution with an acid, in accordance with conventional procedures for preparing acid addition salts from base compounds. Those skilled in the art will recognize various synthetic methodologies that can be used to prepare non-toxic pharmaceutically acceptable addition salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. In some embodiments, the solvate can be a channel solvate. It will be understood that the term "compound" as used herein encompasses the compound and solvates of the compound, as well as mixtures thereof.

As used herein, and unless otherwise specified, "prodrug" is meant to indicate a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. In some embodiments, the prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active Formula (I) in vivo when such prodrug is administered to a mammalian subject. Prodrugs of an active compound, as described herein, can be prepared by modifying functional groups present in the active Formula (I) in such a way that the modifications are cleaved, either in routine manipulation or in vivo, to the parent active compound. Prodrugs include compounds wherein a hydroxy, amino or mercapto group is bonded to any group that, when the prodrug of the active Formula (I) is administered to a mammalian subject, cleaves to form a free hydroxy, free amino or free mercapto group, respectively. Examples of prodrugs include, but are not limited to, acetate, formate, and benzoate derivatives of an alcohol; or acetamide, formamide, and benzamide derivatives of an amine functional group in the active compound, and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1-(($C_1$-$C_6$)alkanoyloxy)ethyl($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the Formula (I) incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$) alkyl or mono-N—or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a Formula (I) is an enantiomer, the stereochemistry at each chirogenic carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, optically substantially pure forms and intermediate mixtures. Optically active (R)— and (S)— isomers can be prepared, for example, using chiral synthons or chiral reagents, or resolved using conventional techniques.

As used herein, and unless otherwise specified, the term "stereomerically pure" means a composition or substance that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other stereoisomers (e.g., diastereoisomers or enantiomers, or syn or anti isomers, or cis or trans isomers) of the compound. A typical stereomerically pure compound comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, or greater than about 97 percent by weight of one stereoisomer of the compound and less than about 3 percent by weight of the other stereoisomers of the compound.

As used herein, and unless otherwise specified, the term "enantiomerically pure" means a stereomerically pure composition of a compound having one or more chiral center(s).

As used herein, and unless otherwise specified, the terms "enantiomeric excess" and "diastereomeric excess" are used interchangeably herein. In some embodiments, compounds with a single stereocenter can be referred to as being present in "enantiomeric excess," and those with at least two stereocenters can be referred to as being present in "diastereomeric excess." For example, the term "enantiomeric excess" is well known in the art and is defined as:

$$ee_a = \left(\frac{\text{conc. of } a - \text{conc. of } b}{\text{conc. of } a + \text{conc. of } b}\right) \times 100$$

Thus, the term "enantiomeric excess" is related to the term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than about 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the Formula (I) is made up of at least about 95%, 98%, or 99% by weight of one enantiomer.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N Y, 1962); and *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. An example of keto-enol tautomerization is the interconversion of pentane-2,4-dione and 4-hydroxypent-3-en-2-one tautomers. Another example of tautomerization is phenol-keto tautomerization. Another example of phenol-keto tautomerization is the interconversion of pyridin-4-ol and pyridin-4(1H)-one tautomers.

As used herein, and unless otherwise specified, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C-$ or $^{14}C$-enriched carbon, or the replacement of a nitrogen by $^{13}N-$ or $^{15}N$-enriched nitrogen, or the replacement of an oxygen by $^{14}O-$, $^{15}O-$, $^{17}O-$, or $^{18}O$-enriched oxygen, or the replacement of a chlorine by $^{35}Cl-$, $^{36}Cl-$, or $^{37}Cl$-enriched chlorine, are within the scope of this disclosure.

In one embodiment, the compounds of the present disclosure can also contain unnatural proportions of atomic isotopes at one or more of atoms that constitute such compounds. For example, the compounds can be radiolabeled with radioactive isotopes, such as, for example, tritium ($^3H$), iodine-125 ($^{125}I$), or carbon-14 ($^{14}C$). Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of compounds of the present disclosure, whether radioactive or not, are encompassed within the scope of the present disclosure.

As used herein, and unless otherwise specified, the terms "solvent," "organic solvent," or "inert solvent" each mean a solvent inert under the conditions of the reaction being described in conjunction therewith, including, without limitation, benzene, toluene, acetonitrile ("MeCN"), ethyl acetate ("EtOAc"), isopropyl acetate ("IPAc"), hexanes, heptanes, dioxane, tetrahydrofuran ("THF"), dimethylformamide ("DMF"), dimethylacetamide ("DMA"), chloroform, methylene chloride ("DCM"), diethyl ether, methanol ("MeOH"), butanol ("1-BuOH"), methyl t-butyl ether ("MTBE", or "TBME"), 2-butanone ("MEK"), N-methylpyrrolidone ("NMP"), pyridine, and the like. Unless specified to the contrary, the solvents used in reactions described herein are inert organic solvents. Unless specified to the contrary, for each gram of a limiting reagent, one cc (or mL) of solvent constitutes a volume equivalent.

As used herein, and unless otherwise specified, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is known in the art. Except insofar as any conventional media or agent is incompatible with the active ingredient, its use in the therapeutic compositions of the present disclosure is contemplated. Supplementary active ingredients can also be incorporated into the compositions.

As used herein and unless otherwise specified, the term "solid form" and related terms refer to a physical form which is not predominantly in a liquid or a gaseous state. Solid forms may be crystalline, amorphous or mixtures thereof. In particular embodiments, solid forms may be liquid crystals.

In some embodiments, a solid form provided herein is a single component or multiple component solid form. A "single-component" solid form comprising a compound of a formula consists essentially of the compound of the formula. A "multiple-component" solid form comprising a compound of a formula comprises a significant quantity of one or more additional species, such as ions and/or molecules, within the solid form. For example, a crystalline multiple-component solid form comprising a compound of a formula further comprises one or more species non-covalently bonded at regular positions in the crystal lattice. A multiple component solid form provided herein may be a co-crystal.

As used herein and unless otherwise specified, the term "crystalline" and related terms, when used to describe a substance, modification, material, component or product mean that the substance, modification, material, component or product is substantially crystalline as determined by X-ray diffraction. See, e.g., Remington: The Science and Practice of Pharmacy, 21$^{st}$ edition, Lippincott, Williams and Wilkins, Baltimore, Md. (2005); The United States Pharmacopeia, 23$^{rd}$ edition, 1843-1844 (1995).

As used herein and unless otherwise specified, the term "crystal forms" and related terms refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

As used herein and unless otherwise specified, the term "solvate" and "solvated," refer to a crystal form of a substance which contains solvent. The term "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure.

Techniques for characterizing solid forms include, but are not limited to, thermal gravimetric analysis (TGA), differential scanning calorimetry (DSC), X-ray powder diffractometry (XRPD), gravimetric vapor sorption (GVS), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

In some embodiments, the solid forms, e.g., crystal forms, described herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis.

The solid forms provided herein may be crystalline or an intermediate form (e.g., a mixture of crystalline and amorphous forms). The crystal forms described herein, therefore, may have varying degrees of crystallinity or lattice order. The solid forms described herein are not limited by any particular degree of crystallinity or lattice order, and may be 0-100% crystalline. Methods of determining the degree of crystallinity are known to those of ordinary skill in the art, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Definitions of specific functional groups and chemical terms are described in more detail below. For purposes of this application, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987.

The term "alkyl," as used herein, refers to saturated, straight- or branched-chain optionally substituted hydrocarbon radicals derived from an aliphatic moiety containing between one and six carbon atoms (e.g., $C_{1-6}$ alkyl) by removal of a single hydrogen atom. In some embodiments, the alkyl group employed contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain optionally substituted aliphatic moiety having at least one carbon-carbon double bond by the removal of a single hydrogen atom. In certain embodiments, the alkenyl group contains 2-6 carbon atoms (e.g., $C_{2-6}$ alkenyl). In certain embodiments, the alkenyl group contains 2-5 carbon atoms. In some embodiments, the alkenyl group contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain optionally substituted aliphatic moiety having at least one carbon-carbon triple bond by the removal of a single hydrogen atom. In certain embodiments, the alkynyl group contains 2-6 carbon atoms (e.g., $C_{2-6}$ alkynyl). In certain embodiments, the alkynyl group contains 2-5 carbon atoms. In some embodiments, the alkynyl group contains 2-4 carbon atoms. In another embodiment, the alkynyl group contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and bicyclic optionally substituted ring systems having a total of five to twelve ring members, wherein at least one ring in the system is aromatic and wherein each ring in the system contains three to seven ring members. In some embodiments, "aryl" refers to monocyclic and bicyclic optionally substituted ring systems having a total of six to twelve ring members (e.g., $C_{6-12}$ aryl), wherein at least one ring in the system is aromatic and wherein each ring in the system contains three to seven ring members. The term "aryl" may be used interchangeably with the term "aryl ring". In certain embodiments, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" used alone or as part of a larger moiety, e.g., "heteroaralkyl", or "heteroaralkoxy", refer to optionally substituted groups having 5 to 10 ring atoms, preferably 5, 6, or 9 ring atoms; having 6, 10, or 14 π electrons shared in a cyclic array; and having, in addition to carbon atoms, from one to five heteroatoms. In some embodiments, the term "heteroaryl" refers to optionally substituted groups as defined above having 6 to 10 ring atoms (e.g., $C_{6-12}$ heteroaryl). The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As described herein, compounds provided herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this application are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —$NH_2$, —NHR$^●$, —NR$^●_2$, or —$NO_2$, wherein each R$^●$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

5.2 Solid Forms

Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42). A change in solid form may affect a variety of physical and chemical properties, which may provide benefits or drawbacks in processing, formulation, stability and bioavailability, among other important pharmaceutical characteristics.

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Provided herein are also cocrystals of Compound 1 and polymorphs thereof. Multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, and/or a multiple-component crystal form comprising the compound of formula (I) and a pharmaceutically acceptable diluent, excipient or carrier.

Solid form and related terms refer to a physical form which is not predominantly in a liquid or a gaseous state. Solid forms may be crystalline or mixtures of crystalline and amorphous forms. A "single-component" solid form comprising a particular compound consists essentially of that compound. A "multiple-component" solid form comprising a particular compound comprises that compound and a significant quantity of one or more additional species, such as ions and/or molecules, within the solid form. The solid forms provided herein may be crystalline or an intermediate form (e.g., a mixture of crystalline and amorphous forms). The crystal forms described herein, therefore, may have varying degrees of crystallinity or lattice order. The solid forms described herein are not limited to any particular degree of crystallinity or lattice order, and may be 0-100% crystalline. Methods of determining the degree of crystallinity are known to those of ordinary skill in the art, such as those described in Suryanarayanan, R., *X-Ray Powder Diffractometry*, Physical Characterization of Pharmaceutical Solids, H. G. Brittain, Editor, Marcel Dekker, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data is "substantially similar" to the reference data provided herein, which is identified as being characteristic of a particular solid form. Characterization data that is "substantially similar" to those of a reference solid form is understood by those skilled in the art to correspond to the same solid form as the reference solid form. In analyzing whether data is "substantially similar," a person of ordinary skill in the art understands that particular characterization data points may vary to a reasonable extent while still describing a given solid form, due to, for example, experimental error and routine sample-to-sample analysis.

In some embodiments, provided herein are solid forms comprising a compound of formula (I):

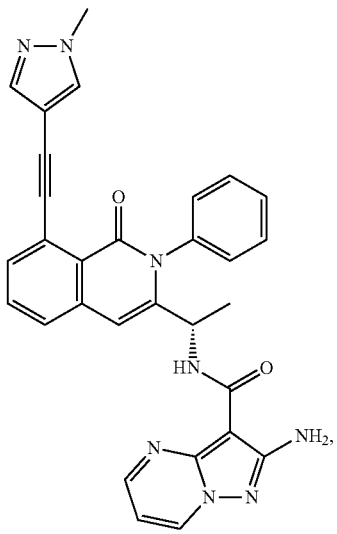

(I)

or a salt, solvate (e.g., hydrate), or solvate of a salt thereof, or a mixture thereof. In one embodiment, the solid form comprising a compound of formula (I) can be a crystalline form, a partially crystalline form, or a mixture of crystalline form(s) and amorphous form(s). In one embodiment, provided herein is a solid form comprising a crystalline form of a compound of formula (I), or a salt, solvate (e.g., hydrate), or solvate of a salt thereof, or a mixture thereof. In one embodiment, the solid form further comprises a coformer. In one embodiment, the solid form comprising Compound 1 and a coformer is a cocrystal. In another embodiment, the solid form is an amorphous form. In one embodiment, the solid form is substantially pure. The compound of formula (I) has a chemical name of (S)-2-amino-N-(1-(8-((1-methyl-1H-pyrazol-4-yl)ethynyl)-1-oxo-2-phenyl-1,2-dihydroisoquinolin-3-yl)ethyl)pyrazolo[1,5-a]pyrimidine-3-carboxamide. The compound of formula (I) is described in US2015/011874, the entirety of which is incorporated herein by reference.

In some embodiments, the Formula (I) is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

5.2.1. Solid Forms of Compound 1

Provided herein is a solid form comprising a compound of Formula (I):

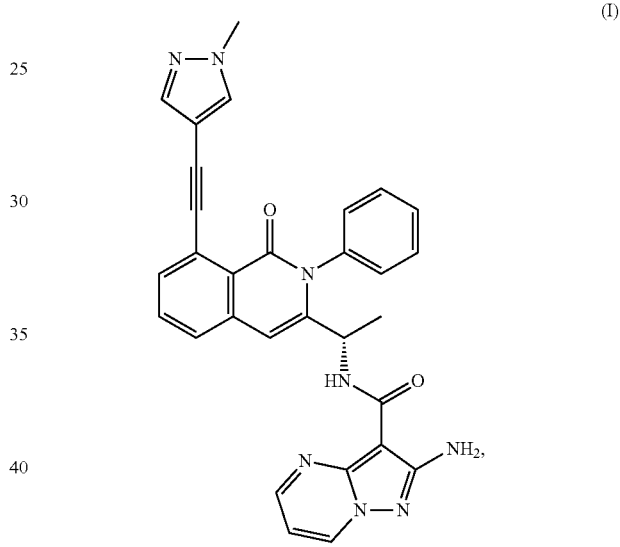

(I)

or a salt, or solvate (e.g., hydrate), or solvate of a salt thereof, or a mixture thereof.

In one embodiment, provided herein a solid form comprising a free base of Compound 1, or a solvate (e.g., hydrate) thereof. In one embodiment, provided herein is a solid form comprising an anhydrous free base of Compound 1. In one embodiment, provided herein is a solid form comprising a solvate of a free base of Compound 1. In one embodiment, provided herein is a solid form comprising a hydrate of a free base of Compound 1.

It is contemplated that Compound 1, or a salt, or solvate (e.g., hydrate), or solvate of a salt thereof, or a mixture thereof, can exist in a variety of solid forms. Such solid forms include crystalline solids (e.g., polymorphs of anhydride Compound 1, polymorphs of hydrates of Compound 1, and polymorphs of solvates of Compound 1), amorphous solids, or mixtures of crystalline and amorphous solids. In one embodiment, the solid form is substantially crystalline. In one embodiment, the solid form is crystalline.

In some embodiments, the molar ratio of Compound 1 to the solvent/water in the solid form ranges from about 10:1 to about 1:10. In some embodiments, the molar ratio of Compound 1 to the solvent/water in the solid form ranges from about 5:1 to about 1:5. In some embodiments, the molar ratio of Compound 1 to the solvent/water in the solid form ranges from about 3:1 to about 1:3. In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

5.2.1.1 Form 1 of Compound 1

In some embodiments, provided herein is Form 1 of a compound of formula (I). In one embodiment, Form 1 of Compound 1 is a crystalline non-solvated anhydrous free base of Compound 1. In some embodiments, Form 1 of Compound 1 is substantially free of amorphous Compound 1. In some embodiments, Form 1 of Compound 1 is substantially free of other crystalline forms (i.e., polymorphs) of Compound 1. In some embodiments, Form 1 of Compound 1 is substantially free of salts of Compound 1. In some embodiments, Form 1 of Compound 1 is provided as substantially pure Form 1 of Compound 1. In some embodiments, one or more residual solvent (e.g., small amount of EtOH or $^i$PrOH) may be present in Form 1 of Compound 1, but the residual solvent does not form a solvate of Compound 1.

Figure 1:
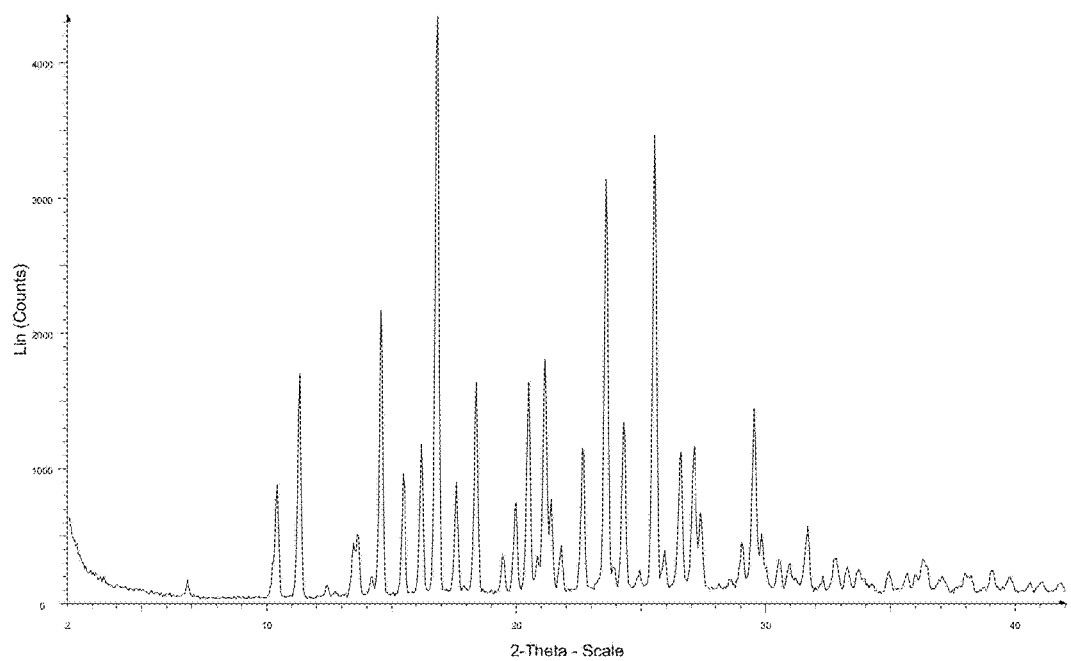
FIG. 1 is a representative X-ray powder diffraction (XRPD) pattern of Form 1 of Compound 1.

A representative XRPD pattern of Form 1 of Compound 1 is provided in FIG. 1.

In one embodiment, Form 1 has an X-ray powder diffraction (XRPD) pattern comprising peaks at 16.8, 23.6, and 25.6 degrees 2θ, plus or minus 0.2. In one embodiment, Form 1 has an XRPD pattern further comprising at least one peak selected from 14.6 and 21.2 degrees 2θ, plus or minus 0.2. In one embodiment, Form 1 has an XRPD pattern comprising peaks at 14.6, 16.8, 21.2, 23.6, and 25.6 degrees 2θ, in combination with at least one peak selected from 11.3, 15.4, 16.2, 18.4, 20.5, 22.6, 24.3, 26.6, 27.1, and 29.5 degrees 2θ, plus or minus 0.2.

In one embodiment, Form 1 is characterized by XRPD peaks located at 1, 2, 3, 4, 5, 6, 7, 8, 9, 10, 11, 12, 13, 14, or all of the following positions: 11.3, 14.6, 15.4, 16.2, 16.8, 18.4, 20.5, 21.2, 22.6, 23.6, 24.3, 25.6, 26.6, 27.1, and 29.5 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 1 has an XRPD pattern substantially as shown in FIG. 1.

Figure 2:
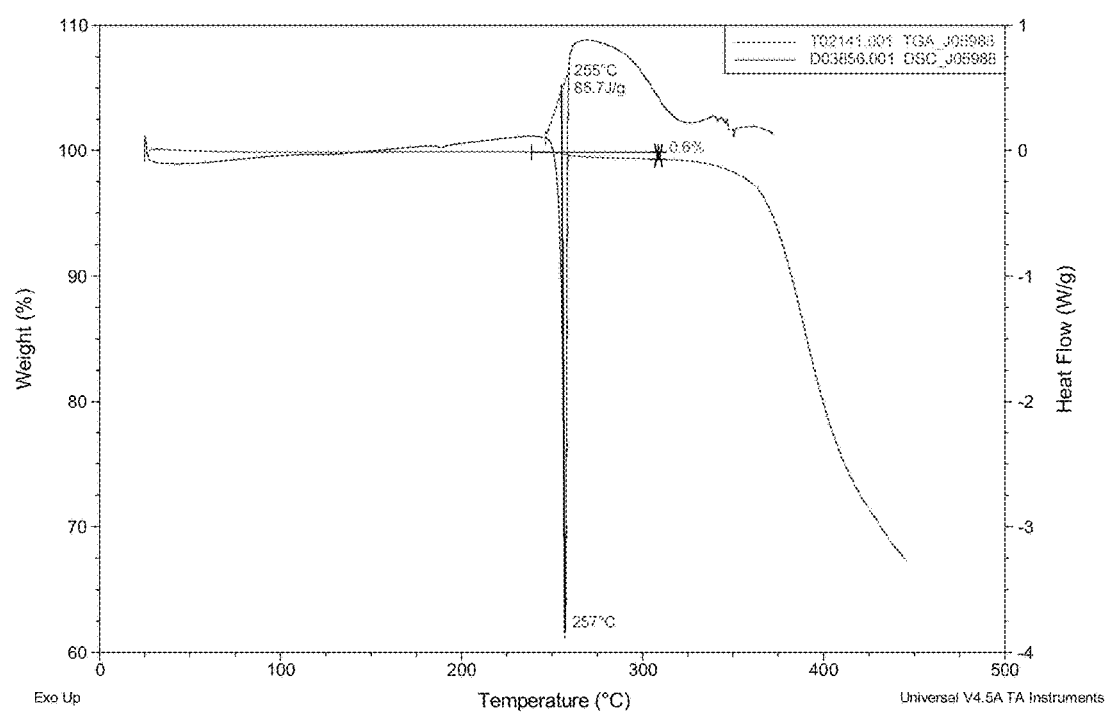
FIG. 2 is a representative overlay of thermal gravimetric analysis (TGA) and differential scanning calorimetry (DSC) thermograms for Form 1 of Compound 1.

A representative overlay of thermal gravimetric analysis (TGA) and differential scanning calorimetry (DSC) thermograms for Form 1 of Compound 1 is provided in FIG. 2.

In one embodiment, Form 1 exhibits an endothermic event, as characterized by DSC, with an onset temperature at about 255° C. and/or a peak temperature at about 257° C. In one embodiment, Form 1 is characterized by a DSC thermogram substantially as shown in the DSC thermogram presented in FIG. 2. In another embodiment, Form 1 exhibits an endothermic event, as characterized by DSC, with an onset temperature at about 242° C. and/or a peak temperature at about 251° C. In yet another embodiment, Form 1 exhibits an endothermic event, as characterized by DSC, with an onset temperature at from about 242° C. to about 255° C.

In one embodiment, Form 1 exhibits a weight loss of about 0.6% upon heating from about 230° C. to about 310° C. In one embodiment, Form 1 is characterized by a TGA thermogram substantially as shown in the TGA thermogram presented in FIG. 2. In another embodiment, Form 1 exhibits a weight loss of about 0.4% upon heating from about 25° C. to about 70° C., and a weight loss of about 1.1% upon heating from about 200° C. to about 280° C.

Figure 3:
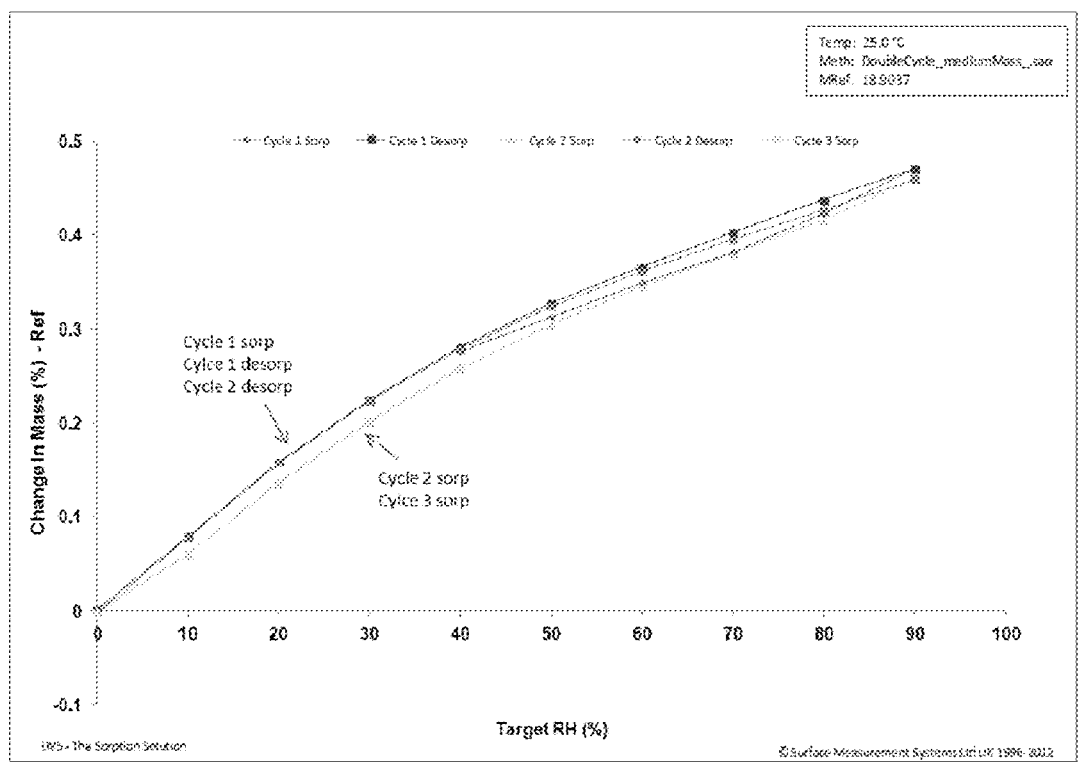
FIG. 3 is a representative gravimetric vapour sorption (GVS) isotherm plot of Form 1 of Compound 1.

A representative gravimetric vapor sorption (GVS) isotherm of Form 1 is presented in FIG. 3. In one embodiment, Form 1 exhibits a weight increase of about 0.5% when subjected to an increase in relative humidity from about 0 to about 90% relative humidity. In one embodiment, Form 1 is characterized by a GVS thermogram substantially as shown in the GVS thermogram presented in FIG. 3.

In one embodiment, Form 1 has approximately unit cell dimensions of: a=11.1 Å, b=12.8 Å, c=16.1 Å, α=90°, β=90°, and γ=90°. In one embodiment, Form 1 has approximately unit cell dimensions of: a=11.14 Å, b=12.76 Å, c=16.13 Å, α=90°, β=90°, and γ=90°. In one embodiment, Form 1 has approximately unit cell dimensions of: a=11.140 Å, b=12.758 Å, c=16.131 Å, α=90°, β=90°, and γ=90°. In one embodiment, Form 1 has a unit cell of a space group of $P2_12_12_1$. In one embodiment, Form 1 has a volume of about 2292.5 Å$^3$/cell. In one embodiment, Form 1 has a Z value of 4. In one embodiment, Form 1 has a density of about 1.279 g/cm$^3$.

In one embodiment, Form 1 is anhydrous. In one embodiment, Form 1 is non-hygroscopic. In one embodiment, Form 1 is stable after storage at 40° C./75% RH or 25° C./96% RH for more than 9 months.

All of the combinations of the above embodiments are encompassed by this application.

5.2.1.2 Form 2 of Compound 1

In some embodiments, provided herein is Form 2 of a compound of formula (I). In one embodiment, Form 2 of Compound 1 is a crystalline solvate of free base of Compound 1. In some embodiments, Form 2 of Compound 1 is substantially free of amorphous Compound 1. In some embodiments, Form 2 of Compound 1 is substantially free of other crystalline forms (i.e., polymorphs) of Compound 1. In some embodiments, Form 2 of Compound 1 is substantially free of salts of Compound 1. In some embodiments, Form 2 of Compound 1 is provided as substantially pure Form 2 of Compound 1.

In one embodiment, the molar ratio of Compound 1 to the solvent in Form 2 ranges from about 1:0.5 to about 1:2. In one embodiment, the molar ratio of Compound 1 to the solvent in Form 2 ranges from about 1:0.75 to about 1:1.25. In one embodiment, the molar ratio of Compound 1 to the solvent in Form 2 ranges from about 1:0.75 to about 1:1. In one embodiment, the molar ratio of Compound 1 to the solvent in Form 2 is about 1:0.85. In one embodiment, the molar ratio of Compound 1 to the solvent in Form 2 is about 1:1.

In one embodiment, Form 2 is an acetone/DCM solvate of free base of Compound 1. In one embodiment, the molar ratio of Compound 1:acetone:DCM in Form 2 is about 1:0.1:0.75. In another embodiment, Form 2 is an 1-propanol solvate of free base of Compound 1. In one embodiment, the molar ratio of Compound 1 to 1-propanol in Form 2 is about 1:0.85. In another embodiment, Form 2 is an DCM solvate of free base of Compound 1. In one embodiment, the molar ratio of Compound 1 to DCM in Form 2 is about 1:1.

Figure 4:
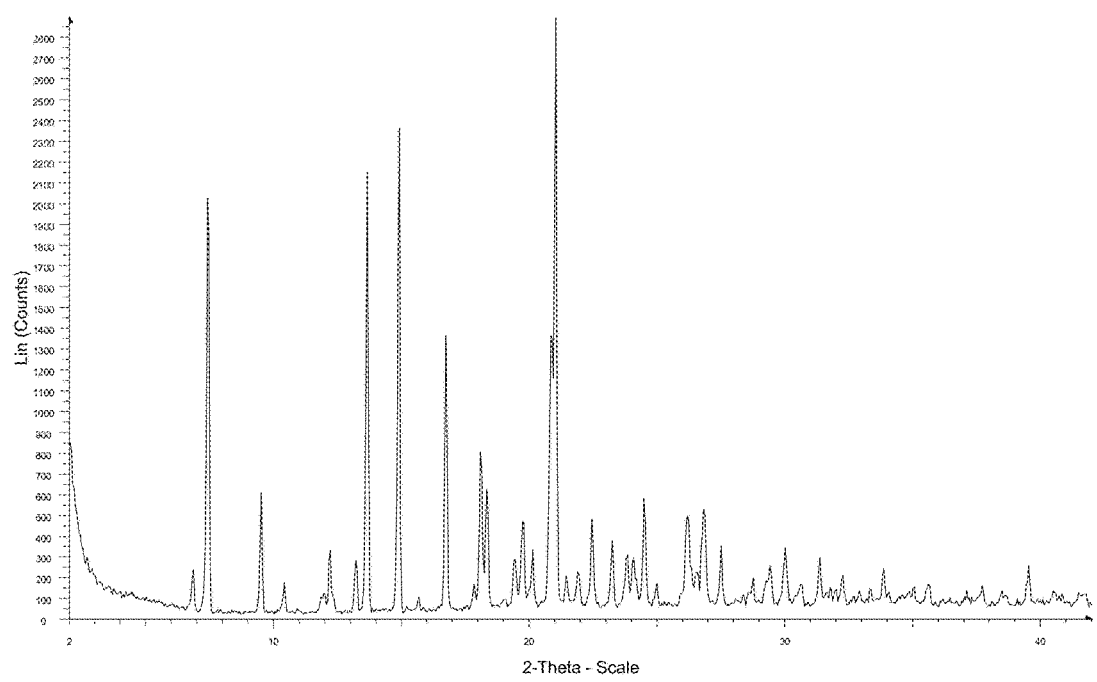
FIG. 4 is a representative XRPD pattern of Form 2 of Compound 1.

A representative XRPD pattern of Form 2 of Compound 1 is provided in FIG. 4. Another representative XRPD pattern of Form 2 of Compound 1 is provided in FIG. 8.

In one embodiment, Form 2 has an XRPD pattern comprising peaks at 13.6, 14.9, and 21.0 degrees 2θ, plus or minus 0.2. In one embodiment, Form 2 has an XRPD pattern further comprising at least one peak selected from 7.4 and 16.7 degrees 2θ, plus or minus 0.2. In one embodiment, Form 2 has an XRPD pattern comprising peaks at 7.4, 13.6, 14.9, 16.7, and 21.0 degrees 2θ, in combination with at least one peak selected from 9.5, 18.1, 18.4, 19.7, 20.8, 22.4, 23.2, 24.5, 26.2, and 26.8 degrees 2θ, plus or minus 0.2.

In one embodiment, Form 2 is characterized by XRPD peaks located at 1, 2, 3, 4, 5, 6, 7, 8, 9, 10, 11, 12, 13, 14, or all of the following positions: 7.4, 9.5, 13.6, 14.9, 16.7, 18.1, 18.4, 19.7, 20.8, 21.0, 22.4, 23.2, 24.5, 26.2, and 26.8 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

Figure 8:
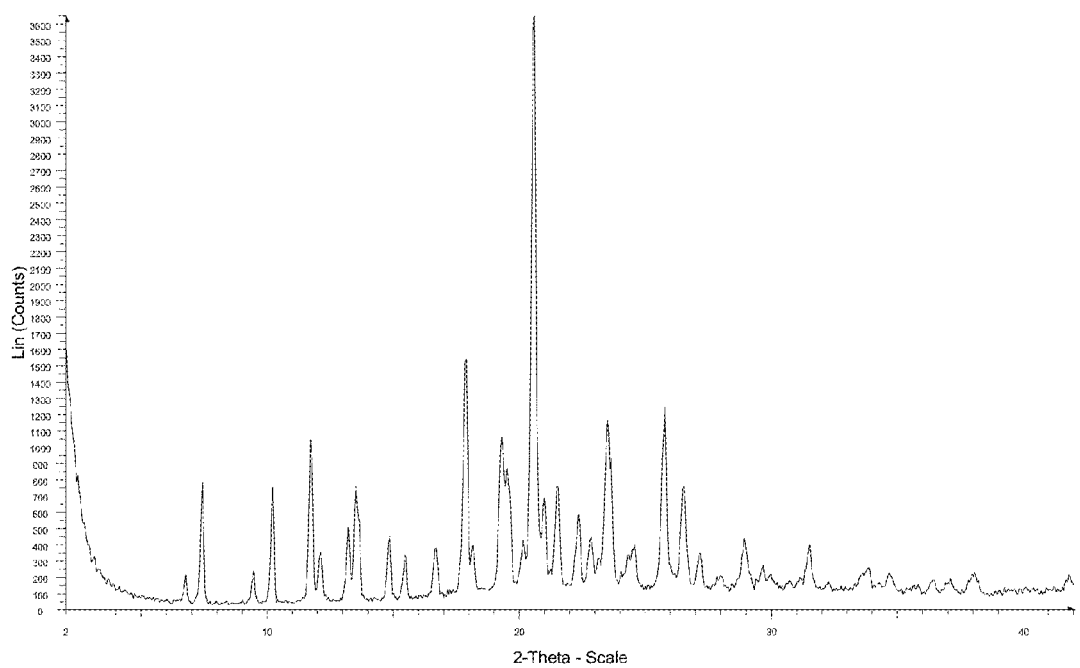
FIG. 8 is another representative XRPD pattern of form 2 of Compound 1.

In one embodiment, Form 2 has an XRPD pattern substantially as shown in FIG. 4. In another embodiment, Form 2 has an XRPD pattern substantially as shown in FIG. 8.

Figure 5:
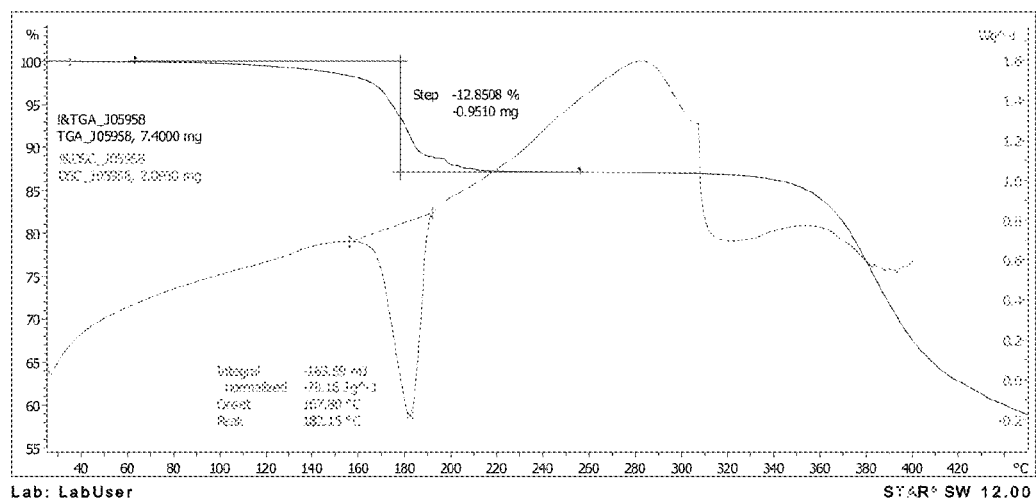
FIG. 5 is a representative overlay of TGA and DSC thermograms for Form 2 of Compound 1.

A representative overlay of thermal gravimetric analysis (TGA) and differential scanning calorimetry (DSC) thermograms for Form 2 of Compound 1 is provided in FIG. 5.

In one embodiment, Form 2 exhibits an endothermic event, as characterized by DSC, with an onset temperature at about 168° C. and/or a peak temperature at about 182° C. In one embodiment, Form 2 is characterized by a DSC thermogram substantially as shown in the DSC thermogram presented in FIG. 5.

In one embodiment, Form 2 exhibits a weight loss of about 12.9% upon heating from about 80° C. to about 240° C. In one embodiment, Form 2 is characterized by a TGA thermogram substantially as shown in the TGA thermogram presented in FIG. 5.

Figure 7:
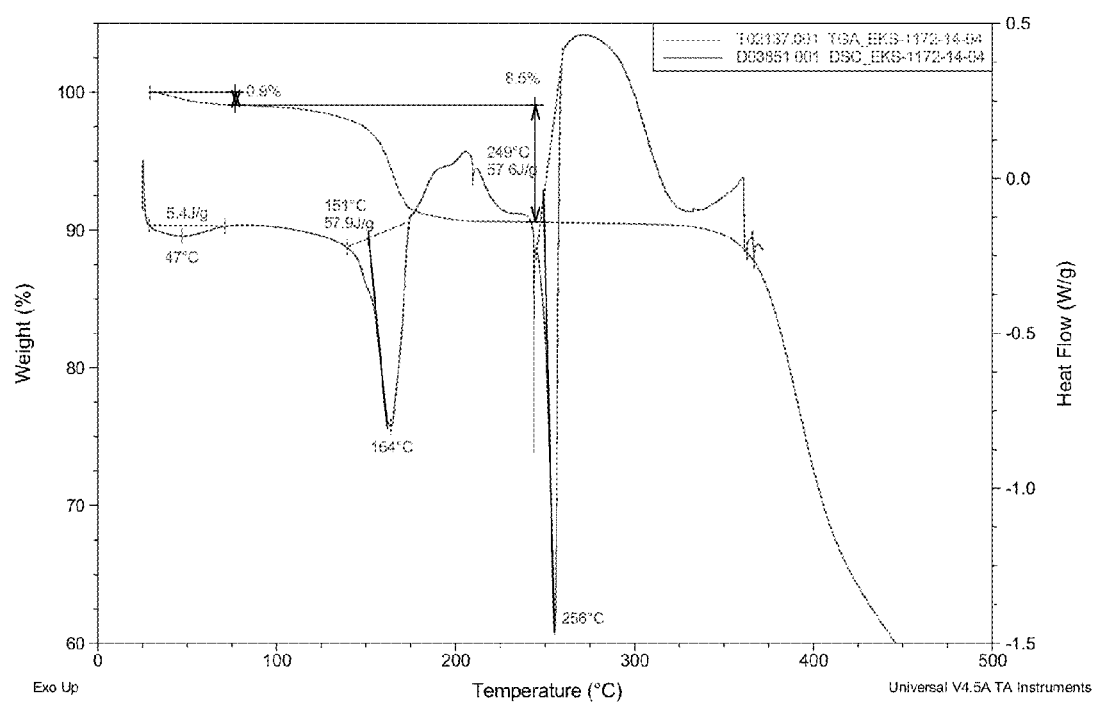
FIG. 7 is another representative overlay of TGA and DSC thermograms for Form 2 of Compound 1.

Another representative overlay of thermal gravimetric analysis (TGA) and differential scanning calorimetry (DSC) thermograms for Form 2 of Compound 1 is provided in FIG. 7.

In one embodiment, Form 2 exhibits, as characterized by DSC, an endothermic event with an onset temperature at about 25° C., an endothermic event with an onset temperature at about 151° C., an exothermic event with an onset temperature at about 179° C., or an endothermic event with an onset temperature at about 244° C. In one embodiment, Form 2 exhibits, as characterized by DSC, an endothermic event with an onset temperature at about 25° C., an endothermic event with an onset temperature at about 151° C., an exothermic event with an onset temperature at about 179° C., and an endothermic event with an onset temperature at about 244° C. In one embodiment, Form 2 is characterized by a DSC thermogram substantially as shown in the DSC thermogram presented in FIG. 7.

In one embodiment, Form 2 exhibits a weight loss of about 0.9% upon heating from about 25° C. to about 75° C., and a weight loss of about 8.5% upon heating from about 75° C. to about 250° C. In one embodiment, Form 2 is characterized by a TGA thermogram substantially as shown in the TGA thermogram presented in FIG. 7.

Figure 6:
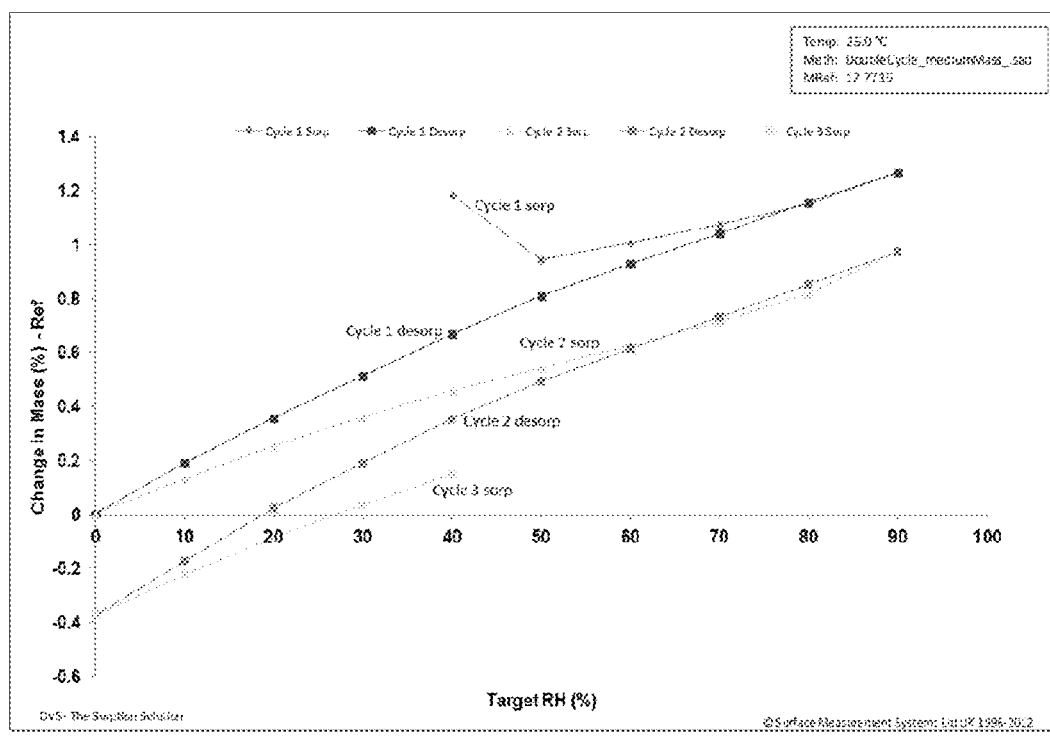
FIG. 6 is a representative GVS isotherm plot of Form 2 of Compound 1.

A representative gravimetric vapor sorption (GVS) isotherm of Form 2 is presented in FIG. 6. In one embodiment, Form 2 exhibits a weight increase of about 1.3% when subjected to an increase in relative humidity from about 0 to about 90% relative humidity. In one embodiment, Form 2 is characterized by a GVS thermogram substantially as shown in the GVS thermogram presented in FIG. 6.

In one embodiment, Form 2 is non-hygroscopic.

In one embodiment, Form 2 has approximately unit cell dimensions of: a=8.7 Å, b=13.2 Å, c=26.0 Å, α=90°, β=90°, and γ=90°. In one embodiment, Form 2 has approximately unit cell dimensions of: a=8.73 Å, b=13.22 Å, c=25.96 Å, α=90°, β=90°, and γ=90°. In one embodiment, Form 2 has approximately unit cell dimensions of: a=8.729 Å, b=13.222 Å, c=25.955 Å, α=90°, β=90°, and γ=90°. In one embodiment, Form 2 has a unit cell of a space group of $P2_12_12_1$. In one embodiment, Form 2 has a volume of about 2995.6 Å$^3$/cell. In one embodiment, Form 2 has a Z value of 4. In one embodiment, Form 2 has a density of about 1.360 Mg/m$^3$.

All of the combinations of the above embodiments are encompassed by this application.

5.2.1.3 Form 3 of Compound 1

In some embodiments, provided herein is Form 3 of a compound of formula (I). In one embodiment, Form 3 of Compound 1 is a crystalline solvate of free base of Compound 1. In some embodiments, Form 3 of Compound 1 is substantially free of amorphous Compound 1. In some embodiments, Form 3 of Compound 1 is substantially free of other crystalline forms (i.e., polymorphs) of Compound 1. In some embodiments, Form 3 of Compound 1 is substantially free of salts of Compound 1. In some embodiments, Form 3 of Compound 1 is provided as substantially pure Form 3 of Compound 1.

In one embodiment, the molar ratio of Compound 1 to the solvent in Form 3 ranges from about 1:0.2 to about 1:1. In one embodiment, Form 3 is a 2-methyl-1-propanol solvate of free base of Compound 1. In one embodiment, the molar ratio of Compound 1 to 2-methyl-1-propanol in Form 3 is about 1:0.79. In another embodiment, Form 3 is a MEK solvate of free base of Compound 1. In one embodiment, the molar ratio of Compound 1 to MEK in Form 3 is about 1:0.25.

Figure 9:
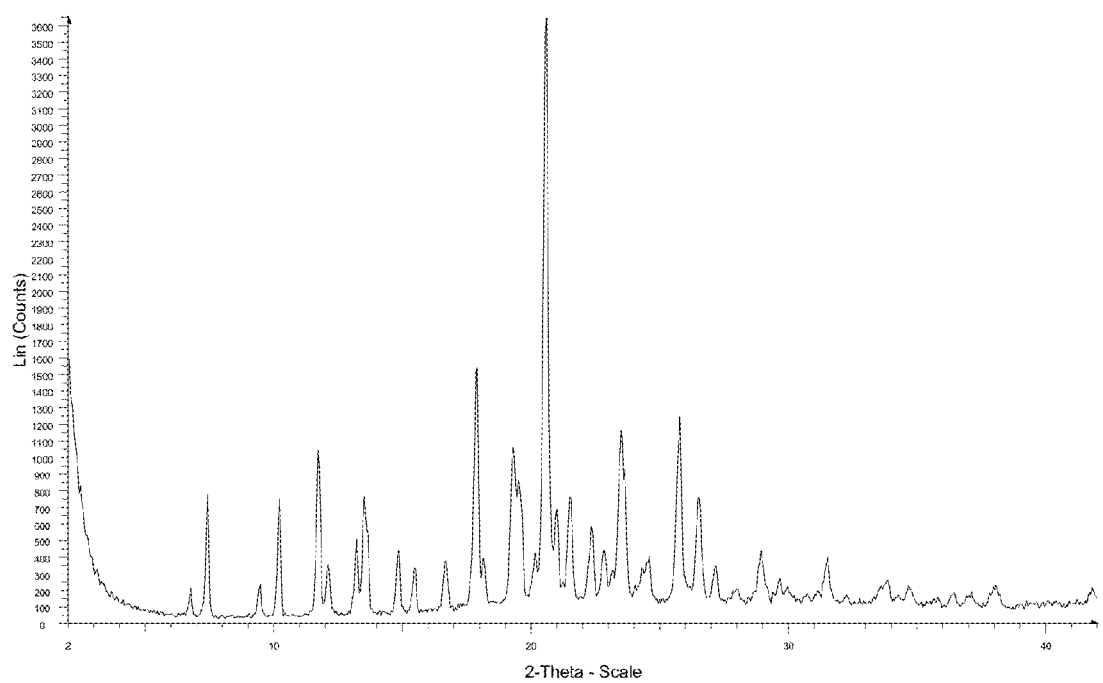
FIG. 9 is a representative XRPD pattern of Form 3 of Compound 1.

A representative XRPD pattern of Form 3 of Compound 1 is provided in FIG. 9.

In one embodiment, Form 3 has an XRPD pattern comprising peaks at 17.9, 20.6, and 25.8 degrees 2θ, plus or minus 0.2. In one embodiment, Form 3 has an XRPD pattern further comprising at least one peak selected from 11.7 and 23.5 degrees 2θ, plus or minus 0.2. In one embodiment, Form 3 has an XRPD pattern comprising peaks at 11.7, 17.9, 20.6, 23.5, and 25.8 degrees 2θ, in combination with at least one peak selected from 7.4, 10.2, 13.5, 19.3, 19.5, 21.0, 21.5, 22.4, 23.7, and 26.5 degrees 2θ, plus or minus 0.2.

In one embodiment, Form 3 is characterized by XRPD peaks located at 1, 2, 3, 4, 5, 6, 7, 8, 9, 10, 11, 12, 13, 14, or all of the following positions: 7.4, 10.2, 11.7, 13.5, 17.9, 19.3, 19.5, 20.6, 21.0, 21.5, 22.4, 23.5, 23.7, 25.8, and 26.5 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 3 has an XRPD pattern substantially as shown in FIG. 9.

Figure 10:
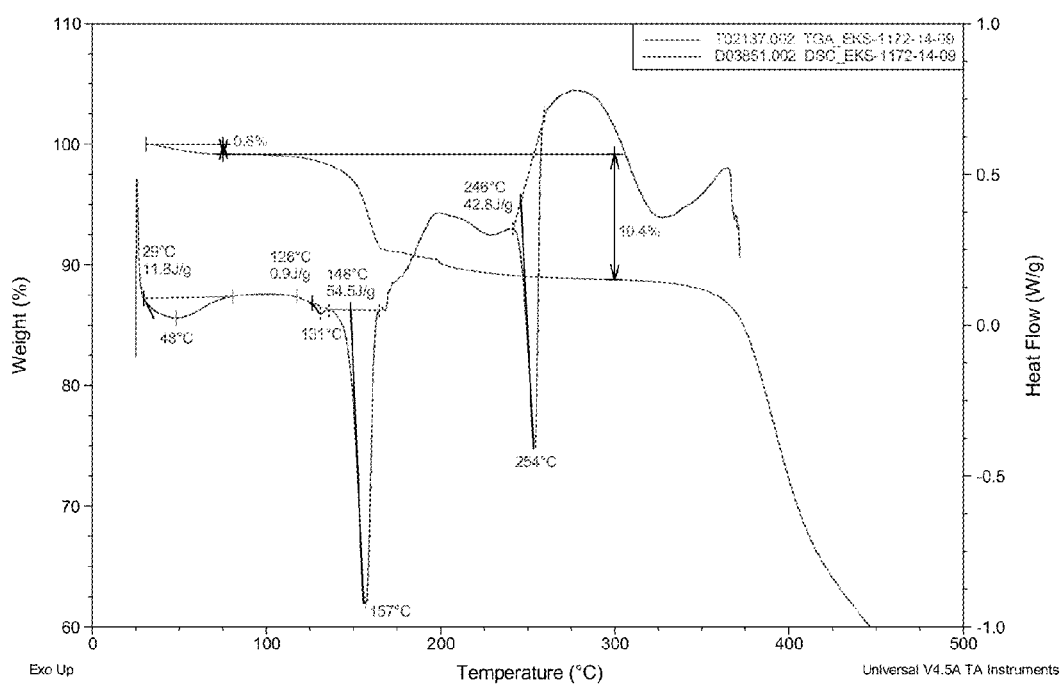
FIG. 10 is a representative overlay of TGA and DSC thermograms for Form 3 of Compound 1.

A representative overlay of thermal gravimetric analysis (TGA) and differential scanning calorimetry (DSC) thermograms for Form 3 of Compound 1 is provided in FIG. 10.

In one embodiment, Form 3 exhibits, as characterized by DSC, an endothermic event with an onset temperature at about 29° C., an endothermic event with an onset temperature at about 126° C., an endothermic event with an onset temperature at about 148° C., an exothermic event with an onset temperature at about 181° C., or an endothermic event with an onset temperature at about 246° C. In one embodiment, Form 3 exhibits, as characterized by DSC, an endothermic event with an onset temperature at about 29° C., an endothermic event with an onset temperature at about 126° C., an endothermic event with an onset temperature at about 148° C., an exothermic event with an onset temperature at about 181° C., and an endothermic event with an onset temperature at about 246° C. In one embodiment, Form 3 is characterized by a DSC thermogram substantially as shown in the DSC thermogram presented in FIG. 10.

In one embodiment, Form 3 exhibits, as characterized by DSC, an endothermic event with an onset temperature at about 30° C., an endothermic event with an onset temperature at about 127° C., an endothermic event with an onset temperature at about 137° C., an exothermic event with an onset temperature at about 169° C., an endothermic event with an onset temperature at about 207° C., or an endothermic event with an onset temperature at about 250° C. In one embodiment, Form 3 exhibits, as characterized by DSC, an endothermic event with an onset temperature at about 30° C., an endothermic event with an onset temperature at about 127° C., an endothermic event with an onset temperature at about 137° C., an exothermic event with an onset temperature at about 169° C., an endothermic event with an onset temperature at about 207° C., and an endothermic event with an onset temperature at about 250° C.

In one embodiment, Form 3 exhibits a weight loss of about 0.8% upon heating from about 25° C. to about 75° C., and a weight loss of about 10.4% upon heating from about 75° C. to about 300° C. In one embodiment, Form 3 is characterized by a TGA thermogram substantially as shown in the TGA thermogram presented in FIG. 10.

In one embodiment, Form 3 exhibits a weight loss of about 2.0% upon heating from about 25° C. to about 80° C., and a weight loss of about 3.4% upon heating from about 80° C. to about 175° C.

All of the combinations of the above embodiments are encompassed by this application.

5.2.1.4 Form 4 of Compound 1

In some embodiments, provided herein is Form 4 of a compound of formula (I). In one embodiment, Form 4 of Compound 1 is a crystalline solvate of free base of Compound 1. In some embodiments, Form 4 of Compound 1 is substantially free of amorphous Compound 1. In some embodiments, Form 4 of Compound 1 is substantially free of other crystalline forms (i.e., polymorphs) of Compound 1.

In some embodiments, Form 4 of Compound 1 is substantially free of salts of Compound 1. In some embodiments, Form 4 of Compound 1 is provided as substantially pure Form 4 of Compound 1.

In one embodiment, the molar ratio of Compound 1 to the solvent in Form 4 ranges from about 1:0.75 to about 1:1. In one embodiment, the molar ratio of Compound 1 to the solvent in Form 4 ranges from about 1:0.83 to about 1:0.9. In one embodiment, Form 4 is an isopropyl alcohol solvate of free base of Compound 1. In one embodiment, the molar ratio of Compound 1 to isopropyl alcohol in Form 4 is about 1:0.9. In another embodiment, the molar ratio of Compound 1 to isopropyl alcohol in Form 4 is about 1:0.83.

Figure 11:
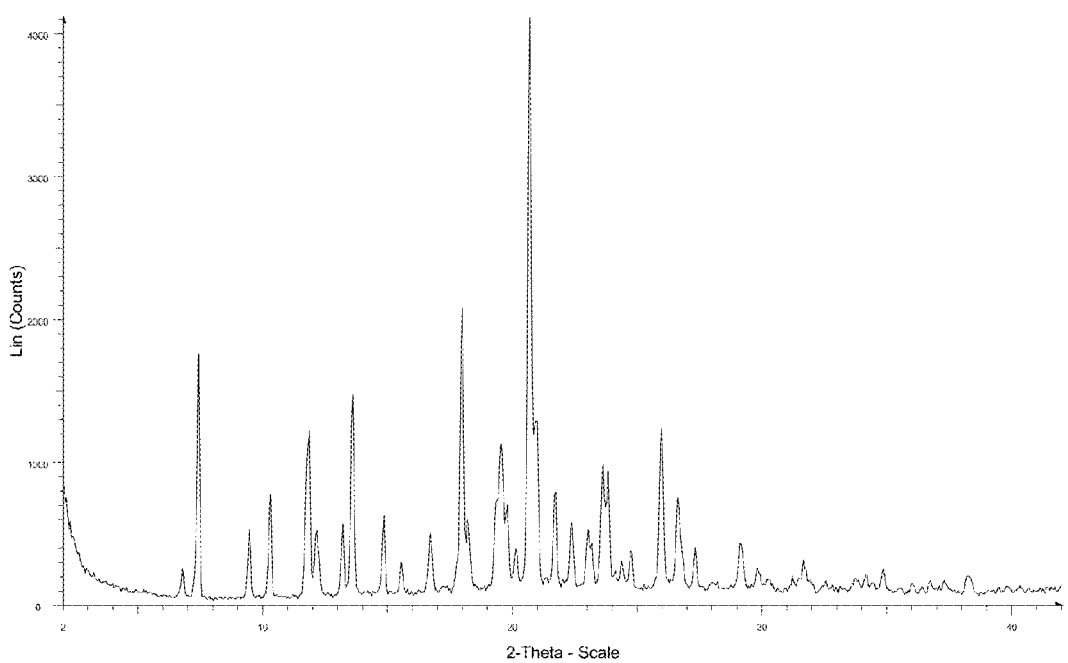
FIG. 11 is a representative XRPD pattern of Form 4 of Compound 1.

A representative XRPD pattern of Form 4 of Compound 1 is provided in FIG. 11.

In one embodiment, Form 4 has an XRPD pattern comprising peaks at 7.4, 18.0, and 20.7 degrees 2θ, plus or minus 0.2. In one embodiment, Form 4 has an XRPD pattern further comprising at least one peak selected from 11.9 and 13.6 degrees 2θ, plus or minus 0.2. In one embodiment, Form 4 has an XRPD pattern comprising peaks at 7.4, 11.9, 13.6, 18.0, and 20.7 degrees 2θ, in combination with at least one peak selected from 10.3, 19.3, 19.6, 19.8, 21.0, 21.8, 23.6, 23.8, 26.0, and 26.6 degrees 2θ, plus or minus 0.2.

In one embodiment, Form 4 is characterized by XRPD peaks located at 1, 2, 3, 4, 5, 6, 7, 8, 9, 10, 11, 12, 13, 14, or all of the following positions: 7.4, 10.3, 11.9, 13.6, 18.0, 19.3, 19.6, 19.8, 20.7, 21.0, 21.8, 23.6, 23.8, 26.0, and 26.6 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 4 has an XRPD pattern substantially as shown in FIG. 11.

Figure 12:
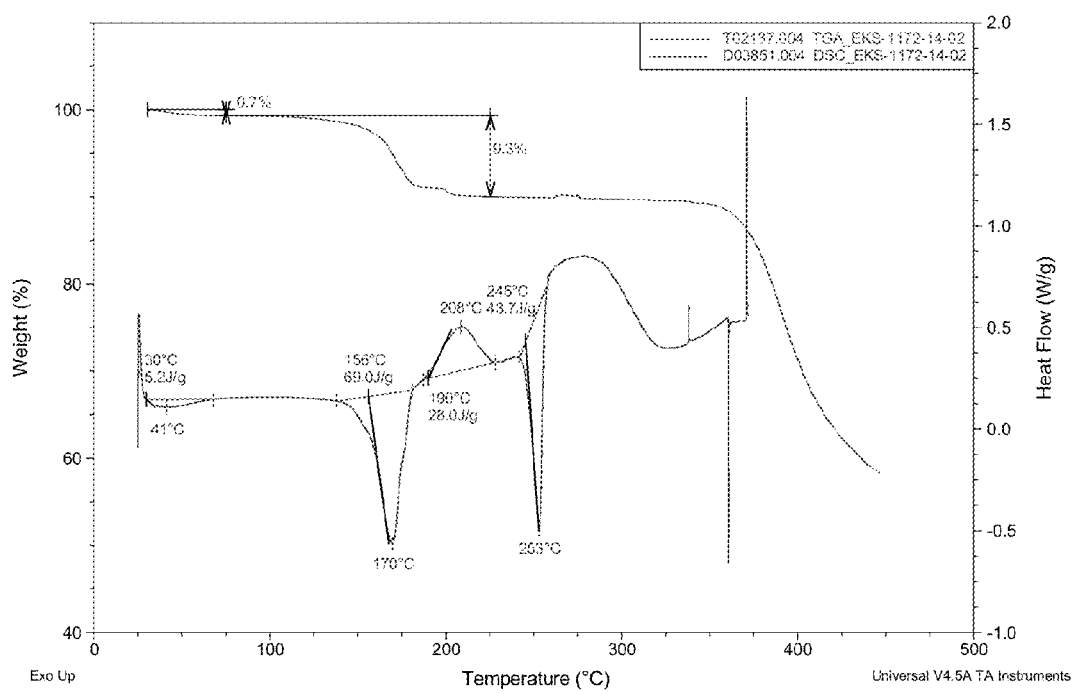
FIG. 12 is a representative overlay of TGA and DSC thermograms for Form 4 of Compound 1.

A representative overlay of thermal gravimetric analysis (TGA) and differential scanning calorimetry (DSC) thermograms for Form 4 of Compound 1 is provided in FIG. 12.

In one embodiment, Form 4 exhibits, as characterized by DSC, an endothermic event with an onset temperature at about 30° C., an endothermic event with an onset temperature at about 156° C., an exothermic event with an onset temperature at about 190° C., or an endothermic event with an onset temperature at about 245° C. In one embodiment, Form 4 exhibits, as characterized by DSC, an endothermic event with an onset temperature at about 30° C., an endothermic event with an onset temperature at about 156° C., an exothermic event with an onset temperature at about 190° C., and an endothermic event with an onset temperature at about 245° C. In one embodiment, Form 4 is characterized by a DSC thermogram substantially as shown in the DSC thermogram presented in FIG. 12.

In one embodiment, Form 4 exhibits, as characterized by DSC, an endothermic event with an onset temperature at about 28° C., an endothermic event with an onset temperature at about 156° C., an exothermic event with an onset temperature at about 201° C., or an endothermic event with an onset temperature at about 247° C. In one embodiment, Form 4 exhibits, as characterized by DSC, an endothermic event with an onset temperature at about 28° C., an endothermic event with an onset temperature at about 156° C., an exothermic event with an onset temperature at about 201° C., and an endothermic event with an onset temperature at about 247° C.

In one embodiment, Form 4 exhibits a weight loss of about 0.7% upon heating from about 25° C. to about 75° C., and a weight loss of about 9.3% upon heating from about 75° C. to about 225° C. In one embodiment, Form 4 is characterized by a TGA thermogram substantially as shown in the TGA thermogram presented in FIG. 12.

In one embodiment, Form 4 exhibits a weight loss of about 0.8% upon heating from about 25° C. to about 75° C., and a weight loss of about 8.6% upon heating from about 75° C. to about 250° C.

All of the combinations of the above embodiments are encompassed by this application.

5.2.1.5 Form 5 of Compound 1

In some embodiments, provided herein is Form 5 of a compound of formula (I). In one embodiment, Form 5 of Compound 1 is a crystalline solvate of free base of Compound 1. In some embodiments, Form 5 of Compound 1 is substantially free of amorphous Compound 1. In some embodiments, Form 5 of Compound 1 is substantially free of other crystalline forms (i.e., polymorphs) of Compound 1. In some embodiments, Form 5 of Compound 1 is substantially free of salts of Compound 1. In some embodiments, Form 5 of Compound 1 is provided as substantially pure Form 5 of Compound 1.

In one embodiment, the molar ratio of Compound 1 to the solvent in Form 5 ranges from about 1:0.1 to about 1:0.2. In one embodiment, Form 5 is an anisole solvate of free base of Compound 1. In one embodiment, the molar ratio of Compound 1 to anisole in Form 5 is about 1:0.12.

Figure 13:
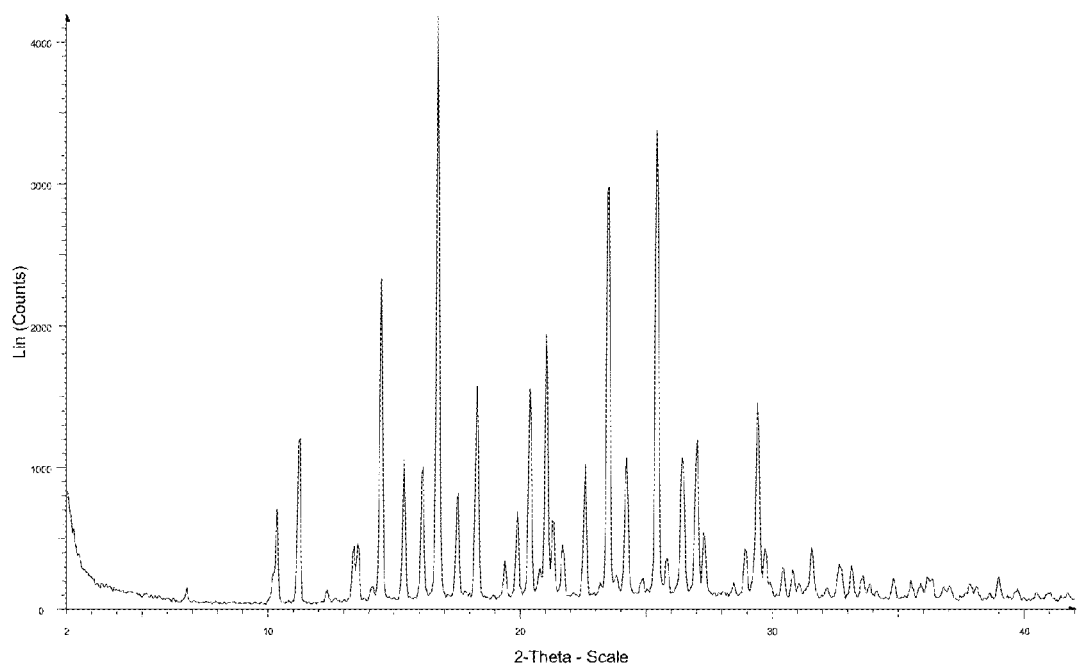
FIG. 13 is a representative XRPD pattern of Form 5 of Compound 1.

A representative XRPD pattern of Form 5 of Compound 1 is provided in FIG. 13.

In one embodiment, Form 5 has an XRPD pattern comprising peaks at 21.0, 22.1, and 25.2 degrees 2θ, plus or minus 0.2. In one embodiment, Form 5 has an XRPD pattern further comprising at least one peak selected from 14.5 and 19.2 degrees 2θ, plus or minus 0.2. In one embodiment, Form 5 has an XRPD pattern comprising peaks at 14.5, 19.2, 21.0, 22.1, and 25.2 degrees 2θ, in combination with at least one peak selected from 7.9, 11.0, 12.7, 16.6, 18.0, 23.3, 27.7, 28.5, 29.1, and 29.2 degrees 2θ, plus or minus 0.2.

In one embodiment, Form 5 is characterized by XRPD peaks located at 1, 2, 3, 4, 5, 6, 7, 8, 9, 10, 11, 12, 13, 14, or all of the following positions: 7.9, 11.0, 12.7, 14.5, 16.6, 18.0, 19.2, 21.0, 22.1, 23.3, 25.2, 27.7, 28.5, 29.1, and 29.2 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 5 has an XRPD pattern substantially as shown in FIG. 13.

Figure 14:
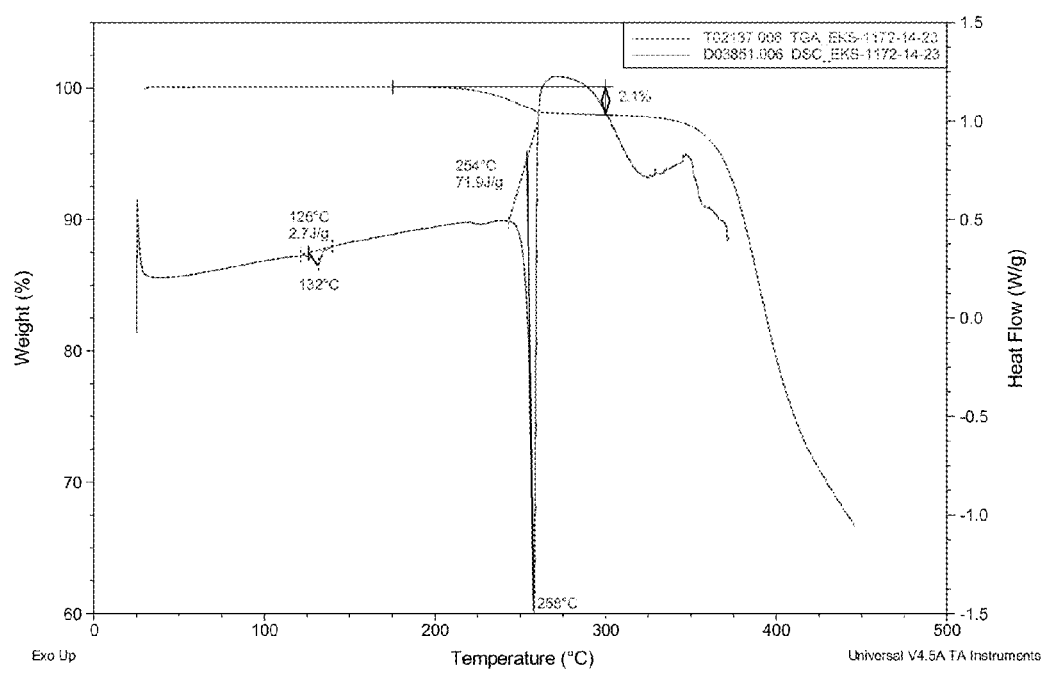
FIG. 14 is a representative overlay of TGA and DSC thermograms for Form 5 of Compound 1.

A representative overlay of thermal gravimetric analysis (TGA) and differential scanning calorimetry (DSC) thermograms for Form 5 of Compound 1 is provided in FIG. 14.

In one embodiment, Form 5 exhibits, as characterized by DSC, an endothermic event with an onset temperature at about 126° C., or an endothermic event with an onset temperature at about 254° C. In one embodiment, Form 5 exhibits, as characterized by DSC, an endothermic event with an onset temperature at about 126° C., and an endothermic event with an onset temperature at about 254° C. In one embodiment, Form 5 is characterized by a DSC thermogram substantially as shown in the DSC thermogram presented in FIG. 14.

In one embodiment, Form 5 exhibits a weight loss of about 2.1% upon heating from about 175° C. to about 300° C. In one embodiment, Form 5 is characterized by a TGA thermogram substantially as shown in the TGA thermogram presented in FIG. 14.

All of the combinations of the above embodiments are encompassed by this application.

5.2.1.6 Form 6 of Compound 1

In some embodiments, provided herein is Form 6 of a compound of formula (I). In one embodiment, Form 6 of Compound 1 is a crystalline hydrate of free base of Compound 1. In some embodiments, Form 6 of Compound 1 is substantially free of amorphous Compound 1. In some embodiments, Form 6 of Compound 1 is substantially free of other crystalline forms (i.e., polymorphs) of Compound 1. In some embodiments, Form 6 of Compound 1 is substantially free of salts of Compound 1. In some embodiments, Form 6 of Compound 1 is provided as substantially pure Form 6 of Compound 1.

In one embodiment, the molar ratio of Compound 1 to the water in Form 6 ranges from about 1:2 to about 1:4. In one embodiment, the molar ratio of Compound 1 to the water in Form 6 is about 1:3.3.

Figure 15:
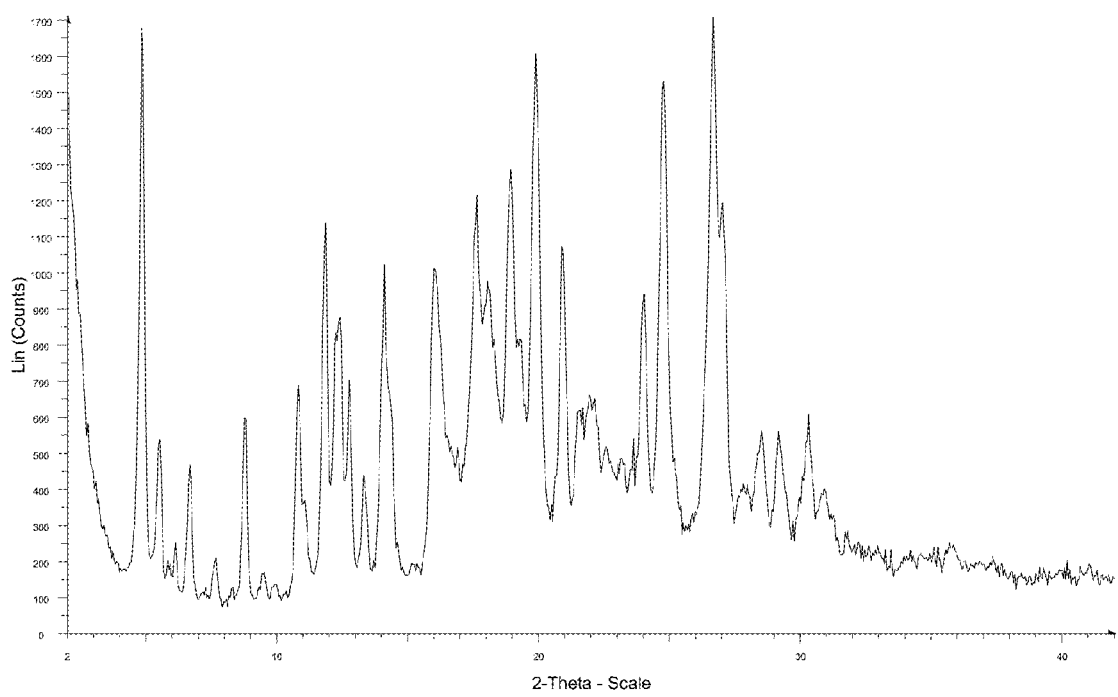
FIG. 15 is a representative XRPD pattern of Form 6 of Compound 1.

A representative XRPD pattern of Form 6 of Compound 1 is provided in FIG. 15.

In one embodiment, Form 6 has an XRPD pattern comprising peaks at 4.8, 19.9, and 26.7 degrees 2θ, plus or minus 0.2. In one embodiment, Form 6 has an XRPD pattern further comprising at least one peak selected from 11.9 and 24.8 degrees 2θ, plus or minus 0.2. In one embodiment, Form 6 has an XRPD pattern comprising peaks at 4.8, 11.9, 19.9, 24.8, and 26.7 degrees 2θ, in combination with at least one peak selected from 12.2, 12.4, 14.1, 16.0, 17.7, 18.1, 18.9, 20.9, 24.0, and 27.1 degrees 2θ, plus or minus 0.2.

In one embodiment, Form 6 is characterized by XRPD peaks located at 1, 2, 3, 4, 5, 6, 7, 8, 9, 10, 11, 12, 13, 14, or all of the following positions: 4.8, 11.9, 12.2, 12.4, 14.1, 16.0, 17.7, 18.1, 18.9, 19.9, 20.9, 24.0, 24.8, 26.7, and 27.1 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 6 has an XRPD pattern substantially as shown in FIG. 15.

Figure 16:
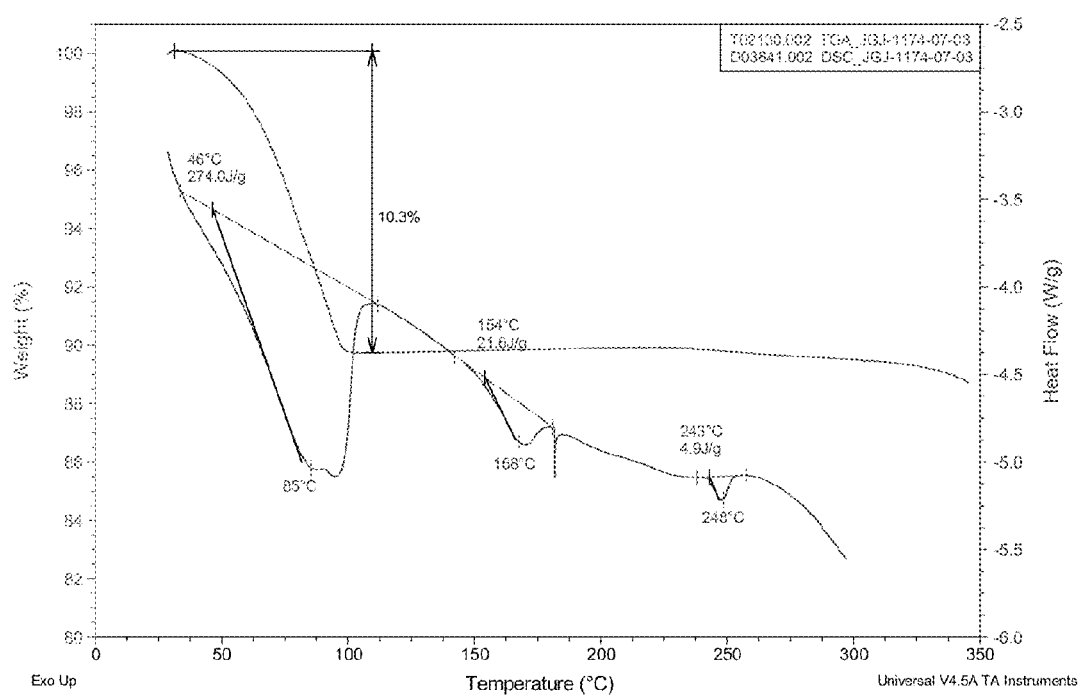
FIG. 16 is a representative overlay of TGA and DSC thermograms for Form 6 of Compound 1.

A representative overlay of thermal gravimetric analysis (TGA) and differential scanning calorimetry (DSC) thermograms for Form 6 of Compound 1 is provided in FIG. 16.

In one embodiment, Form 6 exhibits, as characterized by DSC, an endothermic event with an onset temperature at about 46° C., an endothermic event with an onset temperature at about 154° C., or an endothermic event with an onset temperature at about 243° C. In one embodiment, Form 6 exhibits, as characterized by DSC, an endothermic event with an onset temperature at about 46° C., an endothermic event with an onset temperature at about 154° C., and an endothermic event with an onset temperature at about 243° C. In one embodiment, Form 6 is characterized by a DSC thermogram substantially as shown in the DSC thermogram presented in FIG. 16.

In one embodiment, Form 6 exhibits a weight loss of about 10.3% upon heating from about 30° C. to about 100° C. In one embodiment, Form 6 is characterized by a TGA thermogram substantially as shown in the TGA thermogram presented in FIG. 16.

Figure 17:
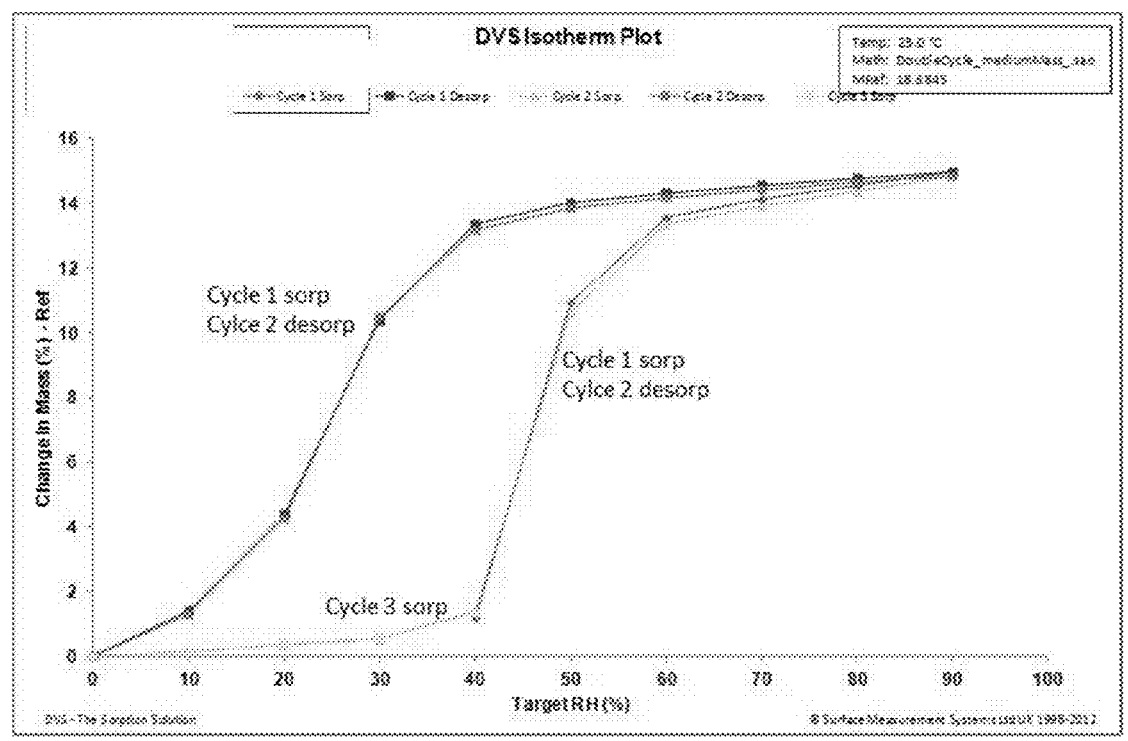
FIG. 17 is a representative GVS isotherm plot of Form 6 of Compound 1.

A representative gravimetric vapor sorption (GVS) isotherm of Form 6 is presented in FIG. 17. In one embodiment, Form 6 exhibits a weight increase of about 14% when subjected to an increase in relative humidity from about 0 to about 90% relative humidity. In one embodiment, Form 6 is characterized by a GVS thermogram substantially as shown in the GVS thermogram presented in FIG. 17.

All of the combinations of the above embodiments are encompassed by this application.

5.2.1.7 Form 7 of Compound 1

In some embodiments, provided herein is Form 7 of a compound of formula (I). In some embodiments, Form 7 of Compound 1 is substantially free of amorphous Compound 1. In some embodiments, Form 7 of Compound 1 is substantially free of other crystalline forms (i.e., polymorphs) of Compound 1. In some embodiments, Form 7 of Compound 1 is substantially free of salts of Compound 1. In some embodiments, Form 7 of Compound 1 is provided as substantially pure Form 7 of Compound 1.

Figure 18:
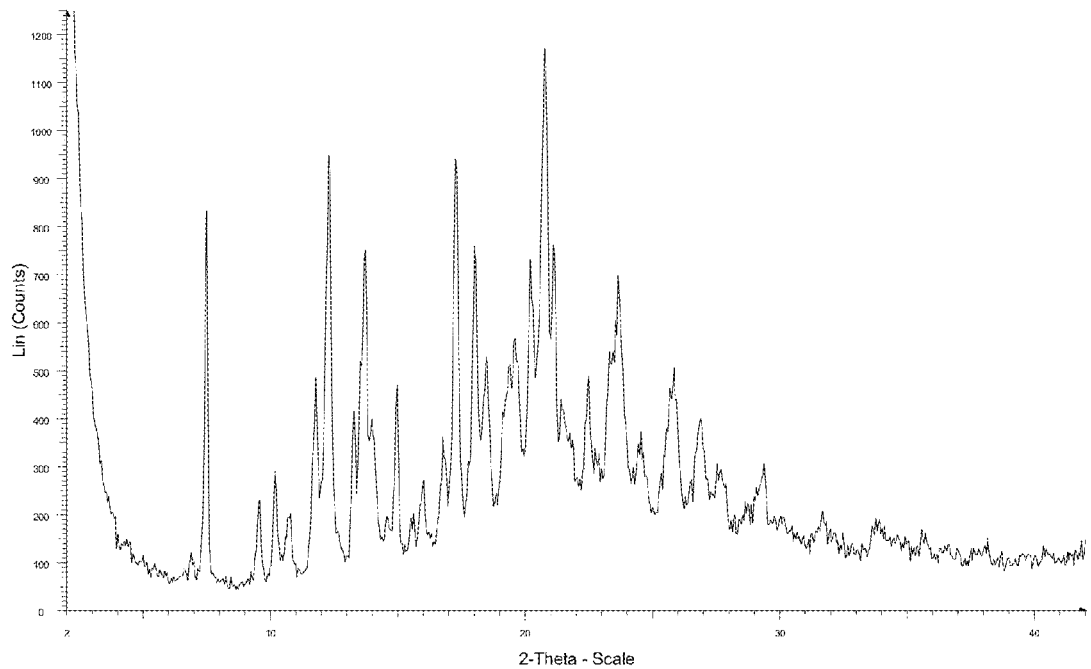
FIG. 18 is a representative XRPD pattern of Form 7 of Compound 1.

A representative XRPD pattern of Form 7 of Compound 1 is provided in FIG. 18.

In one embodiment, Form 7 has an XRPD pattern comprising peaks at 7.5, 12.3, and 20.7 degrees 2θ, plus or minus 0.2. In one embodiment, Form 7 has an XRPD pattern further comprising at least one peak selected from 13.7 and 17.2 degrees 2θ, plus or minus 0.2. In one embodiment, Form 7 has an XRPD pattern comprising peaks at 7.5, 12.3, 13.7, 17.2, and 20.7 degrees 2θ, in combination with at least one peak selected from 11.8, 14.9, 18.0, 18.4, 19.6, 20.2, 21.1, 23.5, 23.6, and 25.9 degrees 2θ, plus or minus 0.2.

In one embodiment, Form 7 is characterized by XRPD peaks located at 1, 2, 3, 4, 5, 6, 7, 8, 9, 10, 11, 12, 13, 14, or all of the following positions: 7.5, 11.8, 12.3, 13.7, 14.9, 17.2, 18.0, 18.4, 19.6, 20.2, 20.7, 21.1, 23.5, 23.6, and 25.9 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 7 has an XRPD pattern substantially as shown in FIG. 18.

Figure 19:
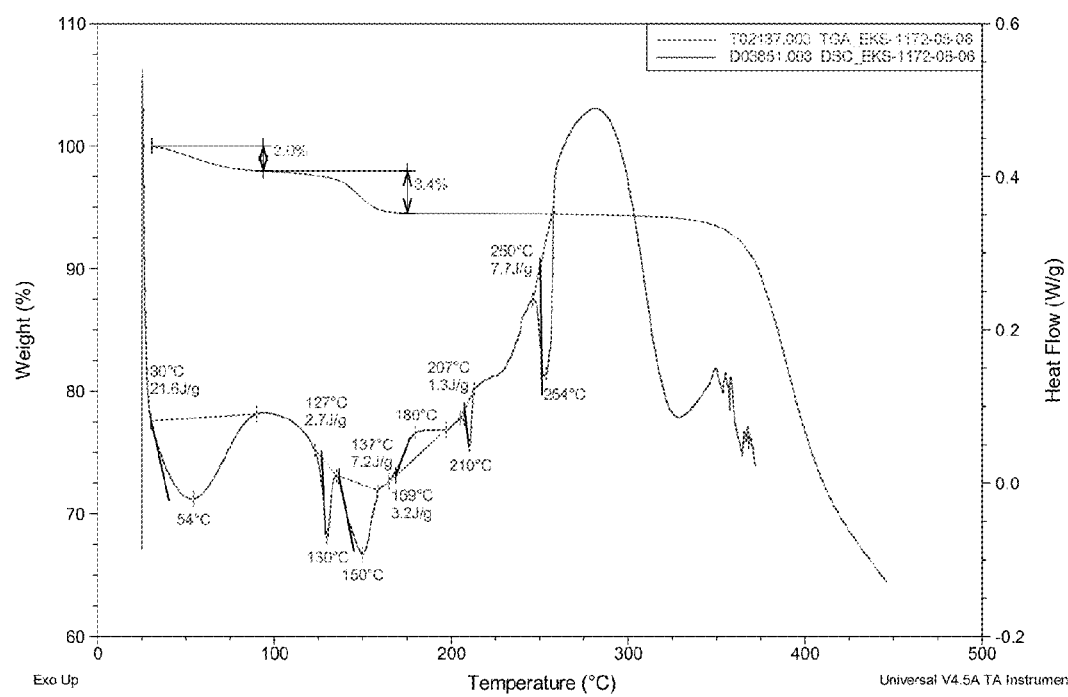
FIG. 19 is a representative overlay of TGA and DSC thermograms for Form 7 of Compound 1.

A representative overlay of thermal gravimetric analysis (TGA) and differential scanning calorimetry (DSC) thermograms for Form 7 of Compound 1 is provided in FIG. 19.

In one embodiment, Form 7 exhibits, as characterized by DSC, an endothermic event with an onset temperature at about 30° C., an endothermic event with an onset temperature at about 127° C., an endothermic event with an onset temperature at about 137° C., an exothermic event with an onset temperature at about 169° C., an endothermic event with an onset temperature at about 207° C., or an endothermic event with an onset temperature at about 250° C. In one embodiment, Form 7 exhibits, as characterized by DSC, an endothermic event with an onset temperature at about 30° C., an endothermic event with an onset temperature at about 127° C., an endothermic event with an onset temperature at about 137° C., an exothermic event with an onset temperature at about 169° C., an endothermic event with an onset temperature at about 207° C., and an endothermic event with an onset temperature at about 250° C. In one embodiment, Form 7 is characterized by a DSC thermogram substantially as shown in the DSC thermogram presented in FIG. 19.

In one embodiment, Form 7 exhibits a weight loss of about 2.0% upon heating from about 10° C. to about 90° C., and a weight loss of about 3.4% upon heating from about 90° C. to about 190° C. In one embodiment, Form 7 is characterized by a TGA thermogram substantially as shown in the TGA thermogram presented in FIG. 19.

All of the combinations of the above embodiments are encompassed by this application.

5.2.1.8 Form 8 of Compound 1

In some embodiments, provided herein is Form 8 of a compound of formula (I). In some embodiments, Form 8 of Compound 1 is substantially free of amorphous Compound 1. In some embodiments, Form 8 of Compound 1 is substantially free of other crystalline forms (i.e., polymorphs) of Compound 1. In some embodiments, Form 8 of Compound 1 is substantially free of salts of Compound 1. In some embodiments, Form 8 of Compound 1 is provided as substantially pure Form 8 of Compound 1.

Figure 20:
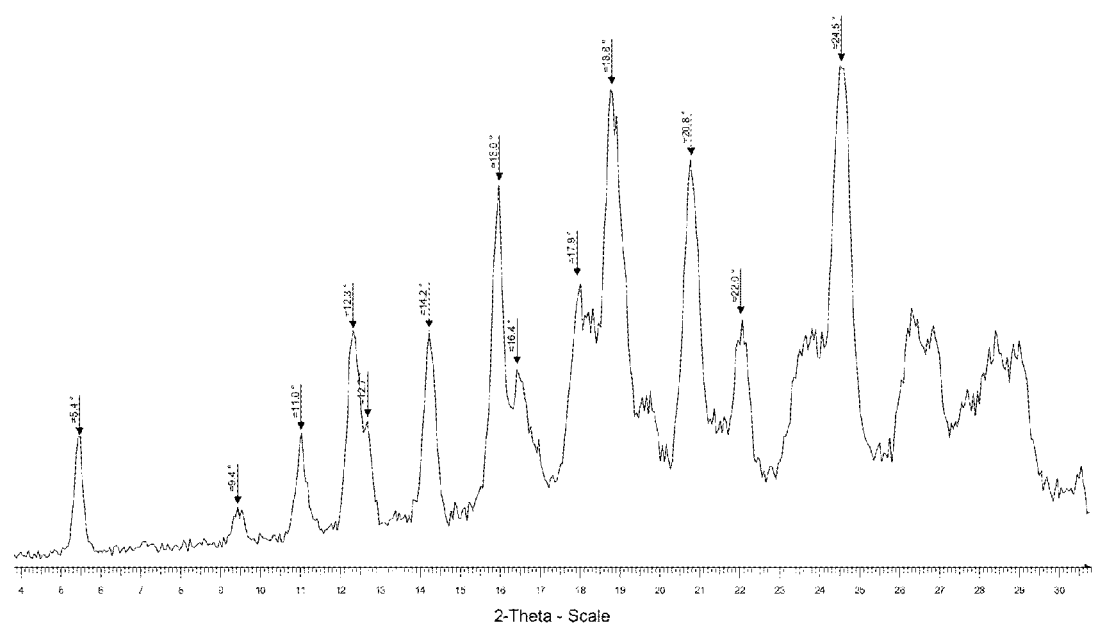
FIG. 20 is a representative XRPD pattern of Form 8 of Compound 1.

A representative XRPD pattern of Form 8 of Compound 1 is provided in FIG. 20.

In one embodiment, Form 8 has an XRPD pattern comprising peaks at 18.8, 20.8, and 24.5 degrees 2θ, plus or minus 0.2. In one embodiment, Form 8 has an XRPD pattern further comprising at least one peak selected from 16.0 and 17.9 degrees 2θ, plus or minus 0.2. In one embodiment, Form 8 has an XRPD pattern comprising peaks at 16.0, 17.9, 18.8, 20.8, and 24.5 degrees 2θ, in combination with at least one peak selected from 5.4, 9.4, 11.0, 12.3, 12.7, 14.2, 16.4, and 22.0 degrees 2θ, plus or minus 0.2.

In one embodiment, Form 8 is characterized by XRPD peaks located at 1, 2, 3, 4, 5, 6, 7, 8, 9, 10, 11, 12, 13, 14, or all of the following positions: 5.4, 9.4, 11.0, 12.3, 12.7, 14.2, 16.0, 16.4, 17.9, 18.8, 20.8, 22.0, and 24.5 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form 8 has an XRPD pattern substantially as shown in FIG. 20.

In one embodiment, Form 8 is an unsolvated solid form of Compound 1.

In one embodiment, Form 8 exhibits an endothermic event, as characterized by DSC, with an onset temperature at about 156° C.

All of the combinations of the above embodiments are encompassed by this application.

In one embodiment, the diameter of the particle of the solid forms provided herein (e.g., Form 1, Form 2, Form 3, Form 4, Form 5, Form 6, Form 7, or Form 8) is from about 0.1 μm to about 150 μm, from about 0.1 μm to about 125 μm, from about 0.1 μm to about 100 μm, from about 0.1 μm to about 75 μm, from about 0.1 μm to about 50 μm, from about 1 μm to about 50 μm, from about 0.1 μm to about 10 μm, from about 0.1 μm to about 7 μm, or from about 0.5 μm to about 5 μm. In one embodiment, the diameter is from about 0.5 μm to about 5 μm. In another embodiment, the diameter is from about 0.6 μm to about 4.8 μm.

In one embodiment, provided herein is a composition comprising a solid form of a compound of formula (I), or a salt, or solvate, or solvate of a salt thereof, or a mixture thereof, wherein the compound has a purity greater than about 98.0% as determined by HPLC. In one embodiment, the compound of formula (I) has a purity of about 98.5%, about 99.0%, about 99.5%, about 99.6%, about 99.9%, or about 99.91%.

5.2.2. Process of Preparing Solid Forms of Compound 1

Provided herein is a process of preparing a compound of Formula (I), wherein the compound is polymorph Form 1 of a compound of Formula (I), or a salt, or solvate, or solvate of a salt thereof, or a mixture thereof; and the process comprises:

(i) exposing a composition comprising at least one non-Form 1 polymorph of a compound of Formula (I), or a salt, or solvate, or solvate of a salt thereof, or a mixture thereof, to one or more solvent for a period of time sufficient to convert at least about 50% of the total amount of non-Form 1 polymorph(s) into Form 1 of a compound of Formula (I); and (ii) recovering said polymorph Form 1.

In one embodiment, the non-Form 1 polymorph of a compound of Formula (I) is exposed to one solvent. In one embodiment, the non-Form 1 polymorph of a compound of Formula (I) is exposed to a mixture of two solvents. In one embodiment, the non-Form 1 polymorph of a compound of Formula (I) is exposed to one or more solvents. In one embodiment, the solvent is an organic solvent. In one embodiment, the solvent is an alcohol. In one embodiment, the solvent is ethanol, 2-methoxyethanol, methanol, ethyleneglycol, or isopropyl alcohol. In one embodiment, the solvent is ethyl acetate, methyl isobutyl ketone, toluene, 1,2-dimethoxyethane, N,N-dimethylformamide, acetonitrile, ethyleneglycol, anisole, or water. In one embodiment, the solvent is ethanol In one embodiment, the solvent system comprises a mixture of two solvents. In one embodiment, the solvent system is a mixture of two solvents. In one embodiment, the mixture of two solvents is a mixture of anisole and isopropyl alcohol, a mixture of anisole and ethanol, a mixture of anisole and toluene, a mixture of acetonitrile and water, a mixture of toluene and ethanol, a mixture of acetone and water, a mixture of isopropyl alcohol and water, a mixture of ethanol and water, a mixture of N,N-dimethylformamide and water, a mixture of N,N-acetamide and water, a mixture of dimethylsulfoxide and water, or a mixture of anisole and methanol In one embodiment, the mixture of two solvents is a mixture of isopropyl alcohol and water. In one embodiment, the volume ratio of isopropyl alcohol to water is from about 1:4 to about 4:1. In one embodiment, the volume ratio of isopropyl alcohol to water is about 1:1 or about 3:2. In one embodiment, the volume ratio of isopropyl alcohol to water is about 1:2. In one embodiment, the mixture of two solvents is a mixture of acetone and water. In one embodiment, the mixture of two solvents is a mixture of ethanol and water. In one embodiment, the mixture of two solvents is a mixture of acetonitrile and water. In one embodiment, the volume ratio of acetonitrile to water is from about 1:4 to about 8:1. In one embodiment, the volume ratio of acetonitrile to water is about 4:1. In one embodiment, the volume ratio of acetonitrile to water is about 2:3. In one embodiment, the solvent system comprises a mixture of three solvents. In one embodiment, the mixture of three solvents is a mixture of ethanol, water, and DCM.

In one embodiment, the non-Form 1 polymorph is amorphous compound of Formula (I). In one embodiment, the non-Form 1 polymorph is Form 2 of a compound of Formula (I). In one embodiment, the period of time sufficient to convert at least about 50% of the total amount of non-Form 1 polymorph(s) into Form 1 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, the non-form 1 polymorph of a compound of Formula (I) is exposed to isopropyl alcohol and water, e.g., at a 1:1 volume ratio. Another volume of water is added at about 60° C., such that the final volume ratio of isopropyl alcohol to water is 1:2. The mixture is aged at about 60° C. for about 30 mins, 1 hr, about 2 hr, about 5 hr, about 10 hr, about 12 hr, about 20 hr, about 24 hr, about 30 hr, about 40 hr, about 48 hr, or about 72 hr.

In one embodiment, the non-form 1 polymorph of a compound of Formula (I) is exposed to acetone and water, e.g., at a 4:1 volume ratio, at about 50° C. to about 60° C. The solvent is exchanged from acetone/water to isopropyl alcohol to a final volume of about 30 volumes. The mixture is aged at about 60° C. for about 30 mins, 1 hr, about 2 hr, about 5 hr, about 10 hr, about 12 hr, about 14 hours, about 20 hr, about 24 hr, about 30 hr, about 40 hr, about 48 hr, or about 72 hr.

In one embodiment, Form 1 is prepared by crystallization or recrystallization of a compound of Formula (I) from one or more solvents. In one embodiment, the solvent is ethanol, 2-methoxyethanol, methanol, ethyleneglycol, or isopropyl alcohol. In one embodiment, the solvent is ethyl acetate, methyl isobutyl ketone, toluene, 1,2-dimethoxyethane, N,N-dimethylformamide, acetonitrile, ethyleneglycol, anisole, or water. In one embodiment, the solvent is ethanol.

In one embodiment, Form 1 is prepared by crystallization or recrystallization of a compound of Formula (I) from a solvent comprising an alcohol. In one embodiment, the solvent is isopropyl alcohol. In one embodiment, the solvent is ethanol.

In one embodiment, Form 1 is prepared by crystallization or recrystallization of a compound of Formula (I) from a solvent comprising a mixture of two solvents. In one embodiment, the mixture of two solvents is a mixture of anisole and isopropyl alcohol, a mixture of anisole and ethanol, a mixture of anisole and toluene, a mixture of acetonitrile and water, a mixture of toluene and ethanol, a mixture of acetone and water, a mixture of isopropyl alcohol and water, a mixture of ethanol and water, a mixture of N,N-dimethylformamide and water, a mixture of N,N-acetamide and water, a mixture of dimethylsulfoxide and water, or a mixture of anisole and methanol In one embodiment, the mixture of two solvents is a mixture of isopropyl alcohol and water. In one embodiment, the volume ratio of isopropyl alcohol to water is from about 1:4 to about 4:1. In one embodiment, the volume ratio of isopropyl alcohol to water is about 1:1 or about 3:2. In one embodiment, the volume ratio of isopropyl alcohol to water is about 1:2. In one embodiment, the mixture of two solvents is a mixture of acetone and water. In one embodiment, the mixture of two solvents is a mixture of ethanol and water. In one embodiment, the mixture of two solvents is a mixture of acetonitrile and water.

In one embodiment, Form 1 is prepared by crystallization or recrystallization of a compound of Formula (I) from a solvent comprising a mixture of an alcohol and water. In one embodiment, the solvent is a mixture of from about 30% to about 90% alcohol in water. In one embodiment, the solvent is a mixture of from about 40% to about 80% alcohol in water. In one embodiment, the solvent is a mixture of isopropyl alcohol and water. In one embodiment, the solvent is a mixture of about 3:2 isopropyl alcohol and water. In one embodiment, the solvent is a mixture of ethanol and water. In one embodiment, the solvent is a mixture of from about 20% to about 90% ethanol in water. In one embodiment, the solvent is a mixture of from about 40% to about 80% ethanol in water. In one embodiment, the solvent is a mixture of about 40% ethanol in water. In one embodiment, the solvent is a mixture of about 60% ethanol in water. In one embodiment, the solvent is a mixture of about 80% ethanol in water. In one embodiment, the solvent further comprises DCM. In one embodiment, the crystallization or recrystallization comprises one or more (e.g., 1, 2, 3, 4, 5 or 6) heating and cooling cycles. In one embodiment, the crystallization or recrystallization comprises 3 heating and cooling cycles. In one embodiment, the crystallization or recrystallization comprises 4 heating and cooling cycles. In one embodiment, the heating phase comprises heating at from about 50° C. to about 60° C. for a period of time (e.g., from about 1 hour to about 6 hours, e.g., about 3 hours). In one embodiment, the cooling phase comprising holding at room temperature for a period of time (e.g., from about 1 hour to about 6 hours, e.g., about 2 hours).

In one embodiment, Form 1 is prepared by crystallization or recrystallization of a compound of Formula (I) from a solvent comprising a mixture of acetonitrile and water. In one embodiment, the volume ratio of acetonitrile to water is from about 1:4 to about 8:1. In one embodiment, the volume ratio of acetonitrile to water is about 4:1. In one embodiment, the volume ratio of acetonitrile to water is about 2:3.

Provided herein is a process of preparing a compound of Formula (I), wherein the compound is polymorph Form 2 of a compound of Formula (I), or a salt, or solvate, or solvate of a salt thereof, or a mixture thereof; and the process comprises:

(i) exposing a composition comprising at least one non-Form 2 polymorph of a compound of Formula (I), or a salt, or solvate, or solvate of a salt thereof, or a mixture thereof, to one or more solvent for a period of time sufficient to convert at least about 50% of the total amount of non-Form 2 polymorph(s) into Form 2 of a compound of Formula (I); and (ii) recovering said polymorph Form 2.

In one embodiment, the non-Form 2 polymorph of a compound of Formula (I) is exposed to one solvent. In one embodiment, the non-Form 2 polymorph of a compound of Formula (I) is exposed to a mixture of two solvents. In one embodiment, the non-Form 2 polymorph of a compound of Formula (I) is exposed to one or more solvents. In one embodiment, the solvent is an organic solvent. In one embodiment, the solvent is dichloromethane, acetone, tetrahydrofuran, water, 1-propanol, or chloroform. In one embodiment, the mixture of two solvents is a mixture of dichloromethane and acetone, a mixture of tetrahydrofuran and water, a mixture of dichloromethane and ethanol, or a mixture of dichloromethane and methanol In one embodiment, the mixture of two solvents is a mixture of dichloromethane and acetone. In one embodiment, the non-Form 2 polymorph of a compound of Formula (I) is exposed to a mixture of three solvents. In one embodiment, the mixture of three solvents is a mixture of dichloromethane, ethanol, and water. In one embodiment, the non-Form 2 polymorph is amorphous compound of Formula (I). In one embodiment, the period of time sufficient to convert at least about 50% of the total amount of non-Form 2 polymorph(s) into Form 2 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, Form 2 is obtained from maturation e.g., in 1-propanol, acetone or dichloromethane, or a mixture of dichloromethane and acetone or a mixture of tetrahydrofuran and water. In one embodiment, Form 2 is obtained from dichloromethane at about 5° C.

Provided herein is a process of preparing a compound of Formula (I), wherein the compound is polymorph Form 3 of a compound of Formula (I), or a salt, or solvate, or solvate of a salt thereof, or a mixture thereof; and the process comprises:

(i) exposing a composition comprising at least one non-Form 3 polymorph of a compound of Formula (I), or a salt, or solvate, or solvate of a salt thereof, or a mixture thereof, to one or more solvent for a period of time sufficient to convert at least about 50% of the total amount of non-Form 3 polymorph(s) into Form 3 of a compound of Formula (I); and (ii) recovering said polymorph Form 3.

In one embodiment, the non-Form 3 polymorph of a compound of Formula (I) is exposed to one solvent. In one embodiment, the non-Form 3 polymorph of a compound of Formula (I) is exposed to a mixture of two solvents. In one embodiment, the non-Form 3 polymorph of a compound of Formula (I) is exposed to one or more solvents. In one embodiment, the solvent is an organic solvent. In one embodiment, the solvent is methyl ethyl ketone, tert-butylmethyl ether, 2-methyl-1-propanol, 2-methyltetrahydrofuran, isopropyl alcohol, ethanol, toluene, 1-propanol, acetone, or acetonitrile. In one embodiment, the mixture of two solvents is a mixture of 2-methyltetrahydrofuran and isopropyl alcohol, a mixture of 2-methyltetrahydrofuran and ethanol, a mixture of 2-methyltetrahydrofuran and toluene, or a mixture of acetonitrile and water. In one embodiment, the non-Form 3 polymorph is amorphous compound of Formula (I). In one embodiment, the period of time sufficient to convert at least about 50% of the total amount of non-Form 3 polymorph(s) into Form 3 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, Form 3 is obtained from maturation in one solvent or a mixture of one or more solvents. In one embodiment, Form 3 is obtained at about 5° C.

Provided herein is a process of preparing a compound of Formula (I), wherein the compound is polymorph Form 4 of a compound of Formula (I), or a salt, or solvate, or solvate of a salt thereof, or a mixture thereof; and the process comprises:

(i) exposing a composition comprising at least one non-Form 4 polymorph of a compound of Formula (I), or a salt, or solvate, or solvate of a salt thereof, or a mixture thereof, to one or more solvent for a period of time sufficient to convert at least about 50% of the total amount of non-Form 4 polymorph(s) into Form 4 of a compound of Formula (I); and (ii) recovering said polymorph Form 4.

In one embodiment, the non-Form 4 polymorph of a compound of Formula (I) is exposed to one solvent. In one embodiment, the non-Form 4 polymorph of a compound of Formula (I) is exposed to a mixture of two solvents. In one embodiment, the non-Form 4 polymorph of a compound of Formula (I) is exposed to one or more solvents. In one embodiment, the solvent is an organic solvent. In one embodiment, the solvent is 1-propanol, acetone, 2-methyl-1-propanol, 1,4-dioxane, chloroform, tetrahydrofuran, 2-methoxyethanol, isopropyl alcohol, water, anisole, toluene, or dimethylsulfoxide. In one embodiment, the mixture of two solvents is a mixture of anisole and tetrahydrofuran, a mixture of toluene and tetrahydrofuran, a mixture of toluene and isopropyl alcohol, or a mixture of isopropyl alcohol and water. In one embodiment, the non-Form 4 polymorph is amorphous compound of Formula (I). In one embodiment, the period of time sufficient to convert at least about 50% of the total amount of non-Form 4 polymorph(s) into Form 4 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, Form 4 is obtained from maturation in one solvent or a mixture of one or more solvents. In one embodiment, Form 4 is obtained at about 5° C.

Provided herein is a process of preparing a compound of Formula (I), wherein the compound is polymorph Form 5 of a compound of Formula (I), or a salt, or solvate, or solvate of a salt thereof, or a mixture thereof; and the process comprises:

(i) exposing a composition comprising at least one non-Form 5 polymorph of a compound of Formula (I), or a salt, or solvate, or solvate of a salt thereof, or a mixture thereof, to one or more solvent for a period of time sufficient to convert at least about 50% of the total amount of non-Form 5 polymorph(s) into Form 5 of a compound of Formula (I); and (ii) recovering said polymorph Form 5.

In one embodiment, the non-Form 5 polymorph of a compound of Formula (I) is exposed to one or more solvents. In one embodiment, the solvent is an organic solvent. In one embodiment, the solvent is anisole. In one embodiment, the non-Form 5 polymorph is amorphous compound of Formula (I). In one embodiment, the period of time sufficient to convert at least about 50% of the total amount of non-Form 5 polymorph(s) into Form 5 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, Form 5 is obtained from maturation in one solvent or a mixture of one or more solvents. In one embodiment, Form 5 is obtained at about 5° C.

Provided herein is a process of preparing compound of Formula (I), wherein the compound is polymorph Form 6 of a compound of Formula (I), or a salt, or solvate, or solvate of a salt thereof, or a mixture thereof; and the process comprises:

(i) exposing a composition comprising at least one non-Form 6 polymorph of a compound of Formula (I), or a salt, or solvate, or solvate of a salt thereof, or a mixture thereof, to one or more solvent for a period of time sufficient to convert at least about 50% of the total amount of non-Form 6 polymorph(s) into Form 6 of a compound of Formula (I); and (ii) recovering said polymorph Form 6.

In one embodiment, the non-Form 6 polymorph of a compound of Formula (I) is exposed to one solvent. In one embodiment, the non-Form 6 polymorph of a compound of Formula (I) is exposed to a mixture of two solvents. In one embodiment, the non-Form 6 polymorph of a compound of Formula (I) is exposed to one or more solvents. In one embodiment, the solvent is an organic solvent. In one embodiment, the solvent is nitromethane, acetonitrile, or water. In one embodiment, the solvent is nitromethane In one embodiment, the mixture of two solvents is a mixture of nitromethane and water or a mixture of acetonitrile and water. In one embodiment, the mixture of two solvents is a mixture of acetonitrile and water. In one embodiment, the volume ratio of acetonitrile to water is 1:1. In one embodiment, the non-Form 6 polymorph is amorphous compound of Formula (I). In one embodiment, the period of time sufficient to convert at least about 50% of the total amount of non-Form 6 polymorph(s) into Form 6 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, Form 6 is obtained from maturation in one solvent or a mixture of one or more solvents. In one embodiment, Form 6 is obtained at about 5° C.

Provided herein is a process of preparing compound of Formula (I), wherein the compound is polymorph Form 7 of a compound of Formula (I), or a salt, or solvate, or solvate of a salt thereof, or a mixture thereof; and the process comprises:

(i) exposing a composition comprising at least one non-Form 7 polymorph of a compound of Formula (I), or a salt, or solvate, or solvate of a salt thereof, or a mixture thereof, to one or more solvent for a period of time sufficient to convert at least about 50% of the total amount of non-Form 7 polymorph(s) into Form 7 of a compound of Formula (I); and (ii) recovering said polymorph Form 7.

In one embodiment, the non-Form 7 polymorph of a compound of Formula (I) is exposed to one solvent. In one embodiment, the non-Form 7 polymorph of a compound of Formula (I) is exposed to a mixture of two solvents. In one embodiment, the non-Form 7 polymorph of a compound of Formula (I) is exposed to one or more solvents. In one embodiment, the solvent is an organic solvent. In one embodiment, the solvent is methyl ethyl ketone, 1-propanol, acetone, or tert-butyl methyl ether. In one embodiment, the non-Form 7 polymorph is amorphous compound of Formula (I). In one embodiment, the period of time sufficient to convert at least about 50% of the total amount of non-Form 7 polymorph(s) into Form 7 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

Provided herein is a process of preparing compound of Formula (I), wherein the compound is polymorph Form 8 of a compound of Formula (I), or a salt, or solvate, or solvate of a salt thereof, or a mixture thereof; and the process comprises:

(i) exposing a composition comprising at least one non-Form 8 polymorph of a compound of Formula (I), or a salt, or solvate, or solvate of a salt thereof, or a mixture thereof, to heat for a period of time sufficient to convert at least about 50% of the total amount of non-Form 8 polymorph(s) into Form 7 of a compound of Formula (I); and (ii) recovering said polymorph Form 8.

In one embodiment, the non-Form 8 polymorph is Form 6 compound of Formula (I). In one embodiment, the period of time sufficient to convert at least about 50% of the total amount of non-Form 8 polymorph(s) into Form 8 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

5.2.3. Solid Forms Comprising Compound 1 and a Coformer

In certain embodiments, the solid forms provided herein further comprise a coformer. In certain embodiments, provided herein is a solid form comprising a compound of Formula (I):

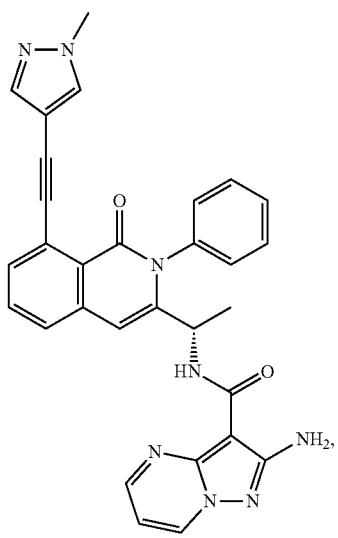

or a salt, or solvate (e.g., hydrate), or solvate of a salt thereof, or a mixture thereof, and a coformer.

In one embodiment, provided herein a solid form comprising a free base of Compound 1, or a solvate (e.g., hydrate) thereof, and a coformer. In one embodiment, provided herein is an unsolvated solid form comprising Compound 1 and a coformer. In one embodiment, provided herein is an anhydrous solid form comprising Compound 1 and a coformer. In one embodiment, provided herein is a solvated solid form comprising Compound 1 and a coformer. In one embodiment, provided herein is a hydrate solid form comprising Compound 1 and a coformer.

It is contemplated that Compound 1, or a salt, or solvate (e.g., hydrate), or solvate of a salt thereof, or a mixture thereof, and a coformer can exist in a variety of solid forms. Such solid forms include crystalline solids or mixtures of crystalline and amorphous solids. In one embodiment, the solid form is substantially crystalline. In one embodiment, the solid form is crystalline. In one embodiment, the solid form is a cocrystal.

In some embodiments, the molar ratio of Compound 1 to the solvent/water in the solid form ranges from about 10:1 to about 1:10. In some embodiments, the molar ratio of Compound 1 to the solvent/water in the solid form ranges from about 5:1 to about 1:5. In some embodiments, the molar ratio of Compound 1 to the solvent/water in the solid form ranges from about 3:1 to about 1:3. In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

The ratio of Compound 1 to coformer may be stoichiometric or non-stoichiometric. In one embodiment, the ratio of Compound 1 to coformer ranges from about 5:1 to about 1:5. In one embodiment, the ratio of Compound 1 to coformer is about 5:1, 4:1, 3:1, 2.5:1, 2:1, 1.5:1, 1:1, 1:1.5, 1:2, 1:2.5, 1:3, 1:4, or 1:5. In one embodiment, the ratio of Compound 1 to coformer is about 1:1. In one embodiment, the co-crystal comprises more than one coformers. In one embodiment, the co-crystal comprises two coformers.

In one embodiment, the coformer is one or more of citric acid, L-malic acid, L-tartaric acid, fumaric acid, succinic acid, maleic acid, sorbic acid, ketoglutaric acid, salicylic acid, benzoic acid, 3-hydroxybenzoic acid, 2,4-dihydroxybenzoic acid, 4-aminobenzoic acid, orotic acid, urea, nicotinic acid, isonicotinic acid, nicotinamide, isonicotinamide, saccharin, L-lactic acid, L-serine, L-proline, glycine, maltol, succinimide, sulfacetamide, and p-toluenesulfonic acid monohydrate.

In one embodiment, the coformer is L-tartaric acid. In another embodiment, the coformer is salicylic acid.

5.2.3.1 Form P1C3 of a Solid Form Comprising Compound 1 and L-tartaric Acid

In some embodiments, provided herein is Form P1C3 of a solid form comprising Compound 1 and L-tartaric acid. In one embodiment, Form P1C3 is a crystalline hydrate solid form comprising Compound 1 and L-tartaric acid. In some embodiments, Form P1C3 is substantially free of amorphous Compound 1. In some embodiments, Form P1C3 of Compound 1 is substantially free of other crystalline forms (i.e., polymorphs) of Compound 1. In some embodiments, Form P1C3 is provided as substantially pure Form P1C3.

In one embodiment, the molar ratio of Compound 1 to L-tartaric acid in Form P1C3 ranges from about 1:2 to 2:1. In one embodiment, the molar ratio of Compound 1 to L-tartaric acid in Form P1C3 is about 1:1. In one embodiment, Form P1C3 further comprises water. In one embodiment, the molar ratio of Compound 1 to water in Form P1C3 ranges from about 1:2 to 2:1. In one embodiment, the molar ratio of Compound 1 to water in Form P1C3 is about 1:1. In one embodiment, the molar ratio of Compound 1:L-tartaric acid:water in Form P1C3 is about 1:1:1.

Figure 22:
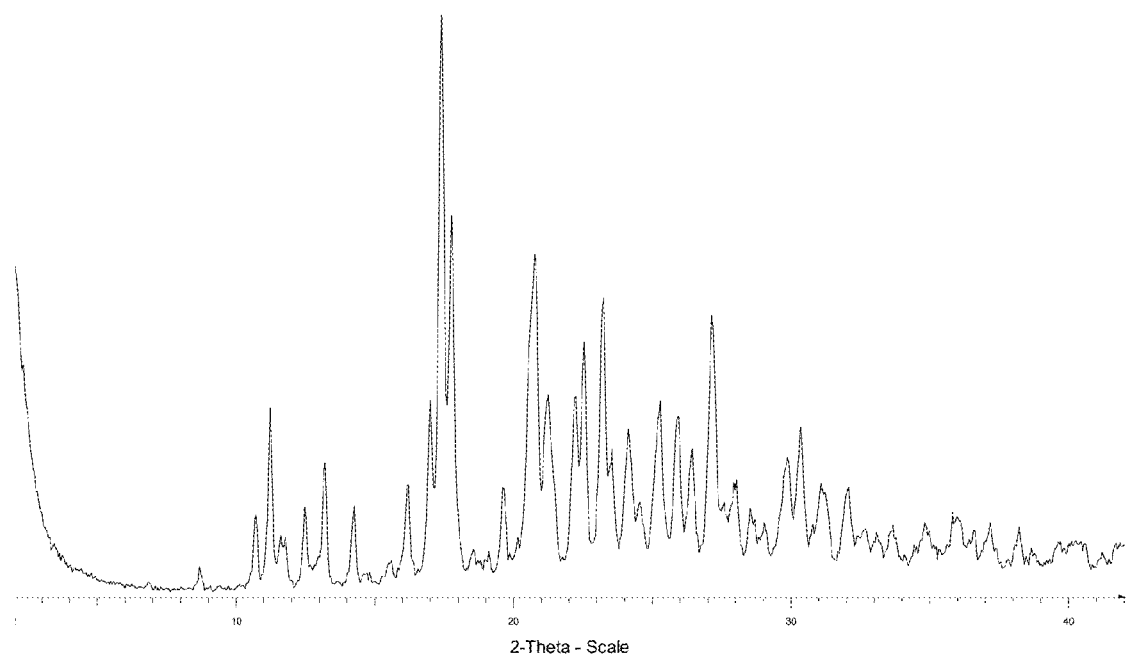
FIG. 22 is a representative XRPD pattern of Form P1C3 of a cocrystal of Compound 1 and L-tartaric acid.

A representative XRPD pattern of Form P1C3 is provided in FIG. 22.

In one embodiment, Form P1C3 has an XRPD pattern comprising peaks at 11.2, 17.4, and 17.7 degrees 2θ, plus or minus 0.2. In one embodiment, Form P1C3 has an XRPD pattern further comprising at least one peak selected from 21.2 and 22.5 degrees 2θ, plus or minus 0.2. In one embodiment, Form P1C3 has an XRPD pattern comprising peaks at 11.2, 17.4, 17.7, 21.2, and 22.5 degrees 2θ, in combination with at least one peak selected from 10.7, 11.6, 17.0, 20.6, 20.8, 21.4, 22.2, 23.2, 23.6, and 24.2 degrees 2θ, plus or minus 0.2.

In one embodiment, Form P1C3 is characterized by XRPD peaks located at 1, 2, 3, 4, 5, 6, 7, 8, 9, 10, 11, 12, 13, 14, or all of the following positions: 10.7, 11.2, 11.6, 17.0, 17.4, 17.7, 20.6, 20.8, 21.2, 21.4, 22.2, 22.5, 23.2, 23.6, and 24.2 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form P1C3 has an XRPD pattern substantially as shown in FIG. 22.

Figure 23:
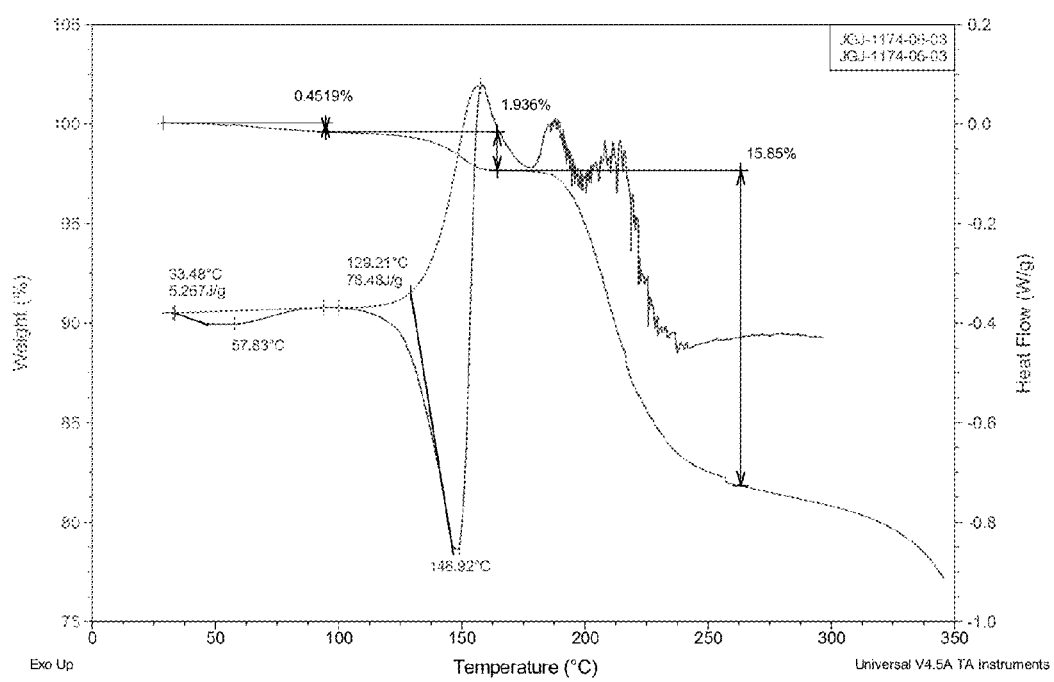
FIG. 23 is a representative TGA and DSC analysis of Form P1C3 of a cocrystal of Compound 1 and L-tartaric acid.

A representative overlay of thermal gravimetric analysis (TGA) and differential scanning calorimetry (DSC) thermograms for Form P1C3 of Compound 1 is provided in FIG. 23.

In one embodiment, Form P1C3 exhibits an endothermic event, as characterized by DSC, with an onset temperature at about 129° C. and/or a peak temperature at about 149° C. In one embodiment, Form P1C3 is characterized by a DSC thermogram substantially as shown in the DSC thermogram presented in FIG. 23.

In one embodiment, Form P1C3 exhibits a weight loss of about 0.5% upon heating from about 30° C. to about 100° C., a weight loss of about 1.9% upon heating from about 100° C. to about 160° C., and a weight loss of about 15.9% upon heating from about 170° C. to about 260° C. In one embodiment, Form P1C3 is characterized by a TGA thermogram substantially as shown in the TGA thermogram presented in FIG. 23.

Figure 28:
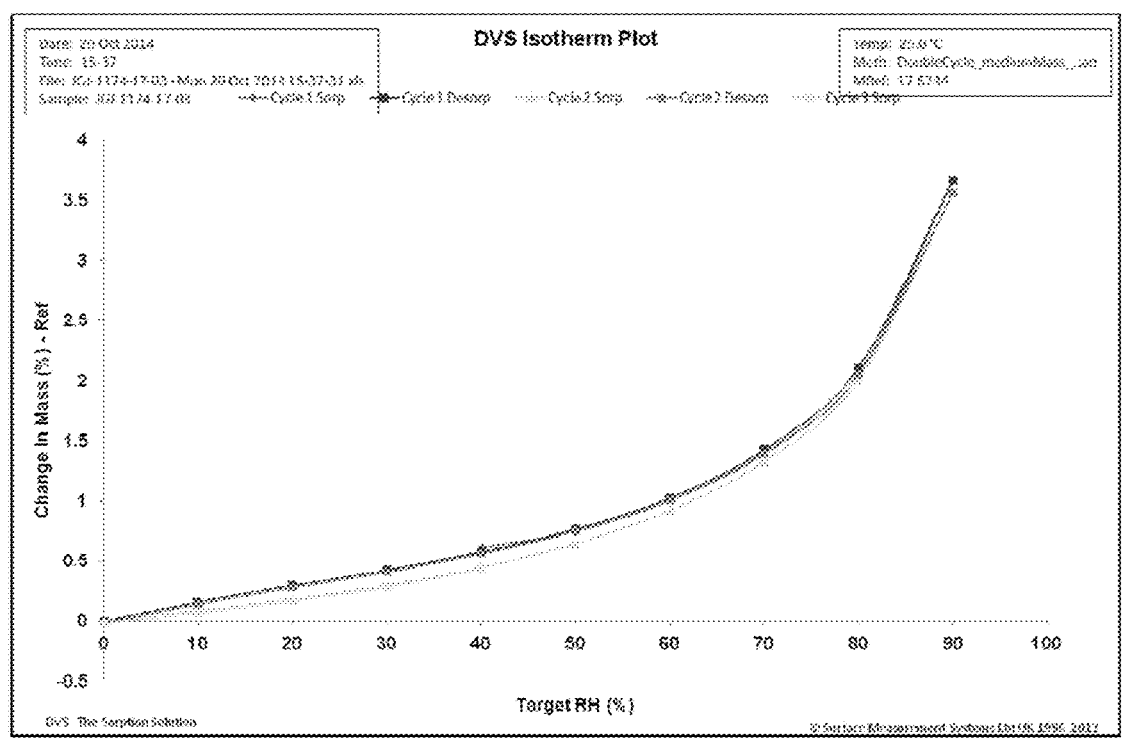
FIG. 28 is a representative GVS analysis of Form P1C3 of a cocrystal of Compound 1 and L-tartaric acid.

A representative gravimetric vapor sorption (GVS) isotherm of Form P1C3 is presented in FIG. 28. In one embodiment, Form P1C3 exhibits a weight increase of about 3.7% when subjected to an increase in relative humidity from about 0 to about 90% relative humidity. In one embodiment, Form P1C3 is characterized by a GVS thermogram substantially as shown in the GVS thermogram presented in FIG. 28.

In one embodiment, preparation of Form P1C3 comprises grinding a mixture of Compound 1 and L-tartaric acid in the presence of a solvent. In one embodiment, the solvent is nitromethane In one embodiment, the nitromethane is not anhydrous, i.e., contains certain amount (e.g., about 5%) of water. In one embodiment, preparation of Form P1C3 comprises grinding a 1:1 mixture of Compound 1 and L-tartaric acid in the presence of nitromethane.

In one embodiment, preparation of Form P1C3 comprises slow cooling a solution of Compound 1 and L-tartaric acid in a solvent. In one embodiment, the solvent is nitromethane In one embodiment, the nitromethane is not anhydrous, i.e., contains certain amount (e.g., about 5%) of water. In one embodiment, preparation of Form P1C3 comprises slow cooling a solution of 1:1 Compound 1 and L-tartaric acid in nitromethane with about 5% water. In one embodiment, the solution is cooled from about 50° C. to about 5° C. at a rate of from about 0.1 to about 0.25° C./min.

All of the combinations of the above embodiments are encompassed by this application.

5.2.3.2 Form P1C9 of a Solid Form Comprising Compound 1 and Salicylic Acid

In some embodiments, provided herein is Form P1C9 of a solid form comprising Compound 1 and salicylic acid. In one embodiment, Form P1C9 is a crystalline hydrate solid form comprising Compound 1 and salicylic acid. In some embodiments, Form P1C9 is substantially free of amorphous Compound 1. In some embodiments, Form P1C9 of Compound 1 is substantially free of other crystalline forms (i.e., polymorphs) of Compound 1. In some embodiments, Form P1C9 is provided as substantially pure Form P1C9.

In one embodiment, the molar ratio of Compound 1 to salicylic acid in Form P1C9 ranges from about 1:1 to 3:1. In one embodiment, the molar ratio of Compound 1 to salicylic acid in Form P1C9 is about 2:1. In one embodiment, Form P1C9 further comprises water. In one embodiment, the molar ratio of Compound 1 to water in Form P1C9 ranges from about 1:3 to 1:5. In one embodiment, the molar ratio of Compound 1 to water in Form P1C9 is about 1:4. In one embodiment, the molar ratio of Compound 1:salicylic acid: water in Form P1C9 is about 1:0.5:4.

Figure 24:
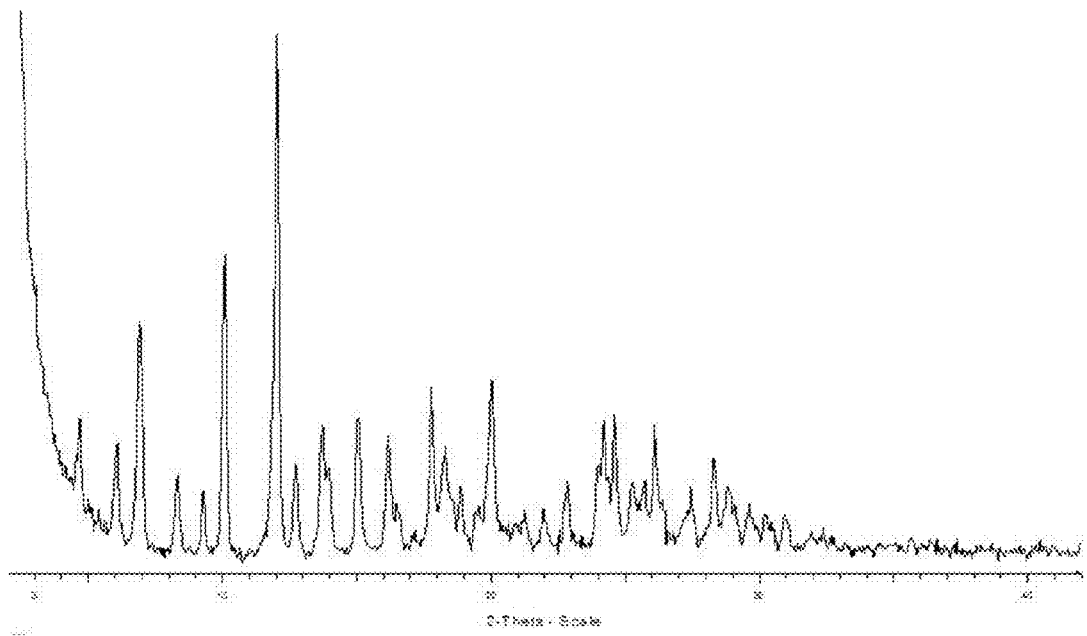
FIG. 24 is a representative XRPD of Form P1C9 of a cocrystal of Compound 1 and salicylic acid.

A representative XRPD pattern of Form P1C9 is provided in FIG. 24.

In one embodiment, Form P1C9 has an XRPD pattern comprising peaks at 6.9, 10.1, and 12.0 degrees 2θ, plus or minus 0.2. In one embodiment, Form P1C9 has an XRPD pattern further comprising at least one peak selected from 17.8 and 20.0 degrees 2θ, plus or minus 0.2. In one embodiment, Form P1C9 has an XRPD pattern comprising peaks at 6.9, 10.1, 12.0, 17.8, and 20.0 degrees 2θ, in combination with at least one peak selected from 4.7, 6.0, 12.7, 13.7, 15.0, 16.2, 24.2, 24.6, 26.1, and 28.3 degrees 2θ, plus or minus 0.2.

In one embodiment, Form P1C9 is characterized by XRPD peaks located at 1, 2, 3, 4, 5, 6, 7, 8, 9, 10, 11, 12, 13, 14, or all of the following positions: 4.7, 6.0, 6.9, 10.1, 12.0, 12.7, 13.7, 15.0, 16.2, 17.8, 20.0, 24.2, 24.6, 26.1, and 28.3 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form P1C9 has an XRPD pattern substantially as shown in FIG. 24.

Figure 25:
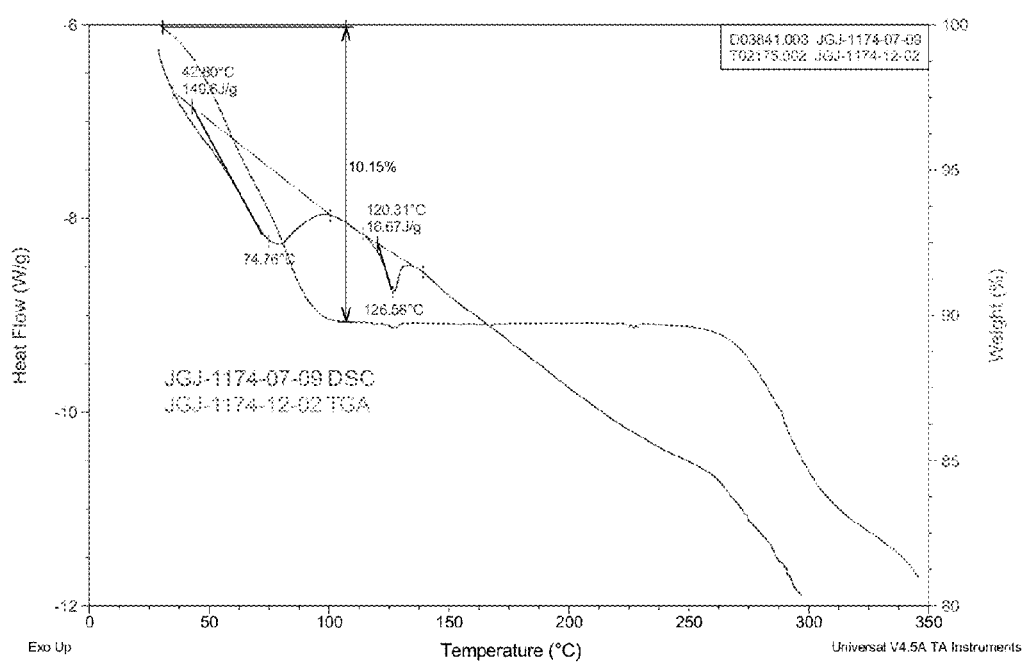
FIG. 25 is a representative TGA vs. DSC analysis of Form P1C9 of a cocrystal of Compound 1 and salicylic acid.

A representative overlay of thermal gravimetric analysis (TGA) and differential scanning calorimetry (DSC) thermograms for Form P1C9 of Compound 1 is provided in FIG. 25.

In one embodiment, Form P1C9 exhibits, as characterized by DSC, an endothermic event with an onset temperature at about 43° C. and/or a peak temperature at about 75° C., or an endothermic event with an onset temperature at about 120° C. and/or a peak temperature at about 127° C. In one embodiment, Form P1C9 exhibits, as characterized by DSC, an endothermic event with an onset temperature at about 43° C. and/or a peak temperature at about 75° C., and an endothermic event with an onset temperature at about 120° C. and/or a peak temperature at about 127° C. In one embodiment, Form P1C9 is characterized by a DSC thermogram substantially as shown in the DSC thermogram presented in FIG. 25.

In one embodiment, Form P1C9 exhibits a weight loss of about 10.15% upon heating from about 30° C. to about 100° C. In one embodiment, Form P1C9 is characterized by a TGA thermogram substantially as shown in the TGA thermogram presented in FIG. 25.

In one embodiment, preparation of Form P1C9 comprises sonicating a mixture of Compound 1 and salicylic acid in the presence of a solvent. In one embodiment, the solvent is a mixture of acetonitrile and water. In one embodiment, the solvent is a 1:1 mixture of acetonitrile and water. In one embodiment, preparation of Form P1C9 comprises sonicating a 1:1 mixture of Compound 1 and salicylic acid in the presence of a 1:1 mixture of acetonitrile and water. In one embodiment, the preparation further comprises settling the material from sonicating step for a period of time. In one embodiment, the settling period is less than about 2 hours. In one embodiment, the settling period is about 30 minutes.

All of the combinations of the above embodiments are encompassed by this application.

5.2.3.3 Form P2C9 of a Solid Form Comprising Compound 1 and Salicylic Acid

In some embodiments, provided herein is Form P2C9 of a solid form comprising Compound 1 and salicylic acid. In one embodiment, Form P2C9 is a crystalline solvate solid form comprising Compound 1 and salicylic acid. In one embodiment, Form P2C9 is a crystalline acetonitrile solvate solid form comprising Compound 1 and salicylic acid. In some embodiments, Form P2C9 is substantially free of amorphous Compound 1. In some embodiments, Form P2C9 of Compound 1 is substantially free of other crystalline forms (i.e., polymorphs) of Compound 1. In some embodiments, Form P2C9 is provided as substantially pure Form P2C9.

In one embodiment, the molar ratio of Compound 1 to salicylic acid in Form P2C9 ranges from about 1:2 to 2:1. In one embodiment, the molar ratio of Compound 1 to salicylic acid in Form P2C9 is about 1:1. In one embodiment, Form P2C9 further comprises acetonitrile. In one embodiment, the molar ratio of Compound 1 to acetonitrile in Form P2C9 ranges from about 1:1 to 3:1. In one embodiment, the molar ratio of Compound 1 to acetonitrle in Form P2C9 is about 1:0.5. In one embodiment, the molar ratio of Compound 1:salicylic acid:acetonitrile in Form P2C9 is about 1:1:0.5.

Figure 26:
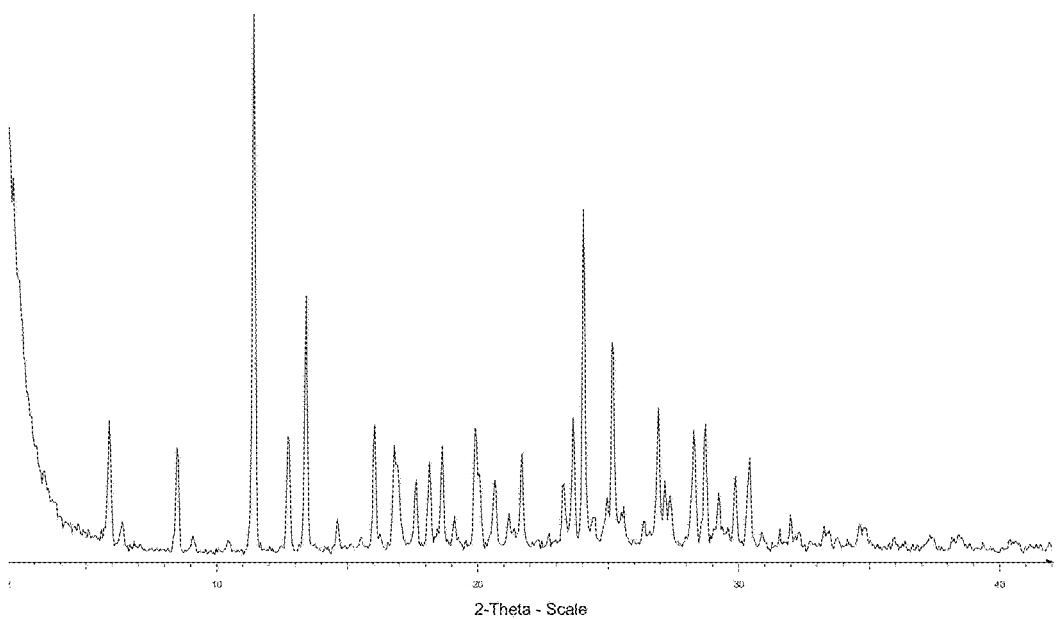
FIG. 26 is a representative XRPD analysis of Form P2C9 of a cocrystal of Compound 1 and salicylic acid.

A representative XRPD pattern of Form P2C9 is provided in FIG. 26.

In one embodiment, Form P2C9 has an XRPD pattern comprising peaks at 11.4, 13.4, and 24.0 degrees 2θ, plus or minus 0.2. In one embodiment, Form P2C9 has an XRPD pattern further comprising at least one peak selected from 25.1 and 26.9 degrees 2θ, plus or minus 0.2. In one embodiment, Form P2C9 has an XRPD pattern comprising peaks at 11.4, 13.4, 24.0, 25.1, and 26.9 degrees 2θ, in combination with at least one peak selected from 8.5, 12.7, 16.0, 16.8, 18.7, 19.9, 21.7, 23.6, 28.3, and 28.7 degrees 2θ, plus or minus 0.2.

In one embodiment, Form P2C9 is characterized by XRPD peaks located at 1, 2, 3, 4, 5, 6, 7, 8, 9, 10, 11, 12, 13, 14, or all of the following positions: 8.5, 11.4, 12.7, 13.4, 16.0, 16.8, 18.7, 19.9, 21.7, 23.6, 24.0, 25.1, 26.9, 28.3, and 28.7 degrees 2θ, plus or minus 0.2. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by 13 of the peaks. In one embodiment, the solid form is characterized by all of the peaks.

In some embodiments, the XRPD peaks above (degrees 2θ peaks) are observed when analyzed using copper Kα radiation.

In one embodiment, Form P2C9 has an XRPD pattern substantially as shown in FIG. 26.

Figure 27:
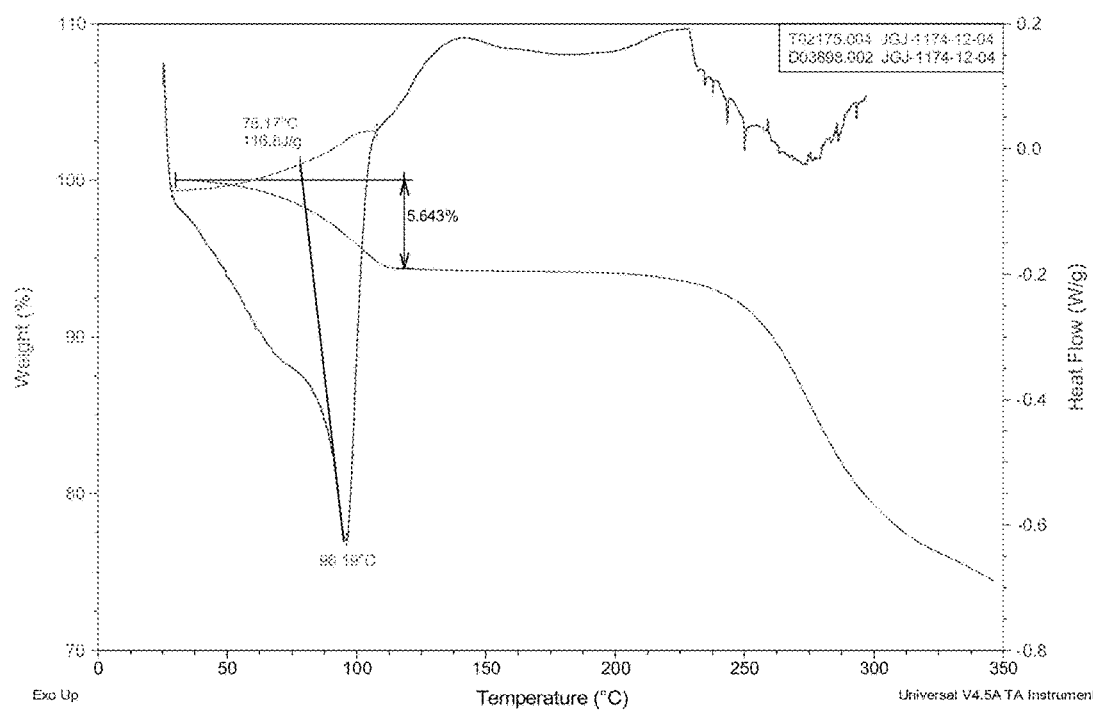
FIG. 27 is a representative TGA and DSC analysis of Form P2C9 of a cocrystal of Compound 1 and salicylic acid.

A representative overlay of thermal gravimetric analysis (TGA) and differential scanning calorimetry (DSC) thermograms for Form P2C9 of Compound 1 is provided in FIG. 27.

In one embodiment, Form P2C9 exhibits an endothermic event, as characterized by DSC, with an onset temperature at about 78° C. and/or a peak temperature at about 96° C. In one embodiment, Form P2C9 is characterized by a DSC thermogram substantially as shown in the DSC thermogram presented in FIG. 27.

In one embodiment, Form P2C9 exhibits a weight loss of about 5.6% upon heating from about 30° C. to about 130° C. In one embodiment, Form P2C9 is characterized by a TGA thermogram substantially as shown in the TGA thermogram presented in FIG. 27.

In one embodiment, preparation of Form P2C9 comprises sonicating a mixture of Compound 1 and salicylic acid in the presence of a solvent. In one embodiment, the solvent is a mixture of acetonitrile and water. In one embodiment, the solvent is a 1:1 mixture of acetonitrile and water. In one embodiment, preparation of Form P2C9 comprises sonicating a 1:1 mixture of Compound 1 and salicylic acid in the presence of a 1:1 mixture of acetonitrile and water. In one embodiment, the preparation further comprises settling the material from sonicating step for a period of time. In one embodiment, the settling period is at least about 2 hours.

All of the combinations of the above embodiments are encompassed by this application.

In one embodiment, the diameter of the particle of the solid forms provided herein (e.g., Form P1C9, Form P1C9, or Form P2C9), wherein the diameter of the particle of the compound is from about 0.1 µm to about 150 µm, from about 0.1 µm to about 125 µm, from about 0.1 µm to about 100 µm, from about 0.1 µm to about 75 µm, from about 0.1 µm to about 50 µm, from about 1 µm to about 50 µm, from about 1 µm to about 50 µm, from about 0.1 µm to about 10 µm, from about 0.1 µm to about 7 µm, or from about 0.5 µm to about 5 µm. In one embodiment, the diameter is from about 0.5 µm to about 5 µm. In one embodiment, the diameter is from about 0.6 µm to about 4.8 µm.

In one embodiment, provided herein is a composition comprising a solid form of a compound of formula (I), or a salt, or solvate, or solvate of a salt thereof, or a mixture thereof, wherein the compound has a purity greater than about 98.0% as determined by HPLC. In one embodiment, the compound of formula (I) has a purity of about 98.5%, about 99.0%, about 99.5%, about 99.6%, about 99.9%, or about 99.91%.

5.2.4 Methods for Analyzing Material

In some embodiments, provided herein are also methods for analyzing a material for the presence or amount of a solid form provided herein, comprising providing a material comprising a compound of formula (I), or a salt, solvate (e.g., hydrate), or solvate of a salt thereof, or a mixture thereof; and using a characterization method to determine whether a signatory characteristic associated with the solid form is present in the material by comparing the characteristic obtained from the material with a reference signatory characteristic; wherein the existence of a characteristic substantially identical to the reference signatory characteristic indicates the presence of the solid form in the material.

In one embodiment, the method further comprises selecting a batch as a result of the determination based upon comparison to the reference standard. In one embodiment, the method further comprises making a determination regarding the quality of the material. In one embodiment, the method further comprises making a determination whether to use the material in the manufacturing of a pharmaceutical composition. In one embodiment, the method further comprises making a determination whether to use the material for treating a PI3K mediated disorder.

In one embodiment, the characterization method is one or more of XRPD, TGA, DSC, GVS, FT-IR, or NMR.

5.2.5. Process for Preparation of Amorphous Form of Compound 1

Provided herein is a process of preparing amorphous form of a compound of Formula (I), wherein the amorphous form is made via a crystalline form. In one embodiment, provided herein is a process of preparing amorphous form of compound of Formula (I), wherein the amorphous form is made via polymorph Form 1 of a compound of Formula (I), or a salt, or solvate, or solvate of a salt thereof, or a mixture thereof.

In one embodiment, the process comprises:
(i) dissolving a solid form comprising a polymorphic form of the compound of formula (I), or a salt, or solvate, or solvate of a salt thereof, or a mixture thereof, in one or more solvents to form a solution; and
(ii) removing the solvent of the solution to provide the amorphous form of the compound of formula (I).

In one embodiment, the polymorphic form is polymorph Form 1.

In one embodiment, the solid form further comprising amorphous form of the compound of formula (I).

In one embodiment, the process comprises:
(i) dissolving a solid form comprising polymorph Form 1 of the compound of formula (I), or a salt, or solvate, or solvate of a salt thereof, or a mixture thereof, in one or more solvents to form a solution; and
(ii) removing the solvent of the solution to provide the amorphous form of the compound of formula (I).

In one embodiment, the process comprises:
(i) exposing a composition comprising at least one non-Form 1 polymorph or amorphous form of a compound of Formula (I), or a salt, or solvate, or solvate of a salt thereof, or a mixture thereof, to one or more solvent for a period of time sufficient to convert at least about 50% of the total amount of non-Form 1 polymorph(s) into Form 1 of a compound of Formula (I);
(ii) recovering said polymorph Form 1;
(iii) dissolving said polymorph Form 1 in one or more solvents to form a solution; and
(iv) removing the solvent of the solution to provide the amorphous form of the compound of formula (I).

In one embodiment, the solvent of the solution is removed by lyophilization. In another embodiment, the solvent of the solution is removed by spray drying.

In one embodiment, the non-Form 1 polymorph of a compound of Formula (I) is exposed to one solvent. In one embodiment, the non-Form 1 polymorph of a compound of Formula (I) is exposed to a mixture of two solvents. In one embodiment, the non-Form 1 polymorph of a compound of Formula (I) is exposed to a one or more solvents. In one embodiment, the solvent is an organic solvent. In one embodiment, the solvent is an alcohol. In one embodiment, the solvent is ethanol, 2-methoxyethanol, methanol, ethyleneglycol, or isopropyl alcohol. In one embodiment, the solvent is ethyl acetate, methyl isobutyl ketone, toluene, 1,2-dimethoxyethane, N,N-dimethylformamide, acetonitrile, ethyleneglycol, anisole, or water. In one embodiment, the solvent is ethanol In one embodiment, the mixture of two solvents is a mixture of anisole and isopropyl alcohol, a mixture of anisole and ethanol, a mixture of anisole and toluene, a mixture of acetonitrile and water, a mixture of toluene and ethanol, a mixture of acetone and water, or a mixture of isopropyl alcohol and water. In one embodiment, the mixture of two solvents is a mixture of isopropyl alcohol and water. In one embodiment, the volume ratio of isopropyl alcohol to water is 1:1 or 3:2. In one embodiment, the volume ratio of isopropyl alcohol to water is 1:2. In one embodiment, the mixture of two solvents is a mixture of acetone and water. In one embodiment, the non-Form 1 polymorph is amorphous compound of Formula (I). In one embodiment, the period of time sufficient to convert at least about 50% of the total amount of non-Form 1 polymorph(s) into Form 1 of a compound of Formula (I) is about 1 hr, about 2 hr, about 5 hr, about 10 hr, about 12 hr, about 20 hr, about 24 hr, about 30 hr, about 40 hr, about 48 hr, or about 72 hr.

In one embodiment, the non-form 1 polymorph of a compound of Formula (I) is exposed to isopropyl alcohol and water, e.g., at a 1:1 volume ratio. Another volume of water is added at about 60° C., such that the final volume ratio of isopropyl alcohol to water is 1:2. The mixture is aged at about 60° C. for about 30 mins, 1 hr, about 2 hr, about 5 hr, about 10 hr, about 12 hr, about 20 hr, about 24 hr, about 30 hr, about 40 hr, about 48 hr, or about 72 hr.

In one embodiment, the non-form 1 polymorph of a compound of Formula (I) is exposed to acetone and water, e.g., at a 4:1 volume ratio, at about 50° C. to about 60° C. The solvent is exchanged from acetone/water to isopropyl alcohol to a final volume of about 30 volumes. The mixture is aged at about 60° C. for about 30 mins, 1 hr, about 2 hr, about 5 hr, about 10 hr, about 12 hr, about 14 hours, about 20 hr, about 24 hr, about 30 hr, about 40 hr, about 48 hr, or about 72 hr.

In one embodiment, the solvent in which compound of Formula (I) is dissolved in is DCM, an alcohol, or a mixture thereof. In one embodiment, the alcohol is MeOH. In one embodiment, the alcohol is 2-propanol. In another embodiment, a polymer is added prior to spray drying. In another embodiment, the polymer is PVP/VA 64. In another embodiment, the polymer is HPMC-AS.

5.3 Process for Preparation

In certain embodiments, provided herein is a process of preparing a compound of Formula (I):

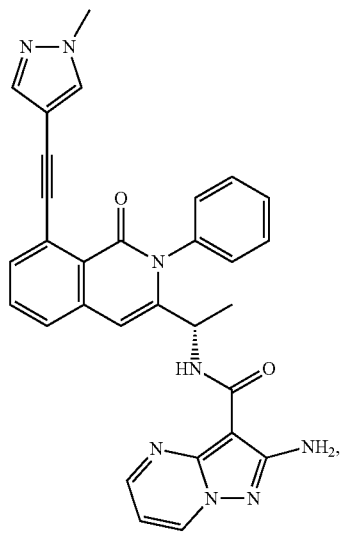

or a salt, or solvate, or solvate of a salt thereof, or a mixture thereof, comprising coupling compound C of formula:

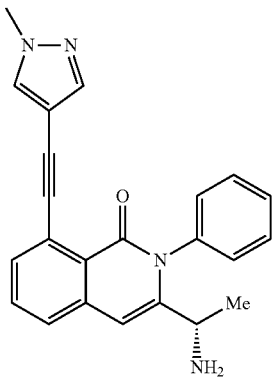

with a carboxylic acid of Formula G:

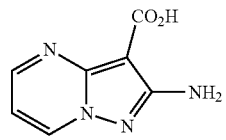

to provide the compound of Formula (I).

In one embodiment, the coupling occurs in the presence of a coupling reagent. In one embodiment, the coupling reagent is a carbodiimide, a triazine, a phosphonium, an uronium, or a mixed anhydride, or a mixture thereof. In one embodiment, the coupling reagent is N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), 2-propanephosphonic acid anhydride (T3P), 1-[(dimethylamino)(morpholino)methylene]-1H-[1,2,3]triazolo[4,5-b]pyridine-1-ium 3-oxide hexafluorophosphate (HDMA), N,N,N',N'-tetramethyl-O-(1H-benzotriazol-1-yl) uronium hexafluorophosphate (HBTU), (1-cyano-2-ethoxy-2-oxoethylidenaminooxy)dimethylamino-morpholino-carbenium hexafluorophosphate (COMU), benzotriazol-1-yloxy-tris(dimethylamino)phosphonium hexafluorophosphate (BOP), (benzotriazol-1-yloxy)tripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), diethyl phosphorocyanidate (DECP), diethyl phosphorochloridate (DEPC), diphenyl phosphorazidate (DPPA) phosphoric acid bis(2-oxazolidide) chloride (BOPCl), chlorodimethoxytriazine or its N-methylmopholinium adduct, 3-(diethoxyphosphoryloxy)-1,2,3-benzotriazin-4(3H)-one (DEPBT), bromo tris(dimethylamino)phosphonium hexafluorophosphate) (BroP), $(EtO)_2P(O)$—Cl, $(EtO)_2P(O)$-Oxyma, pivaloyl chloride, iso-butyl chloroformate, 2-chloro-4,6-dimethoxy-1,3,5-triazine (CDMT), or 4-(4,6-dimethoxy-1,3,5-triazin-2-yl)-4-methylmorpholinium chloride (DMTMM) or its $BF_4$ analog, or a mixture thereof. In one embodiment, the coupling reagent is EDCI. In one embodiment, the coupling reagent is DMTMM.

In one embodiment, the coupling occurs in the presence of an activator. In one embodiment, the activator is HOBt, HBTriazinone, ethyl 2-cyano-2-(hydroxyimino)acetate (Oxyma), NHS, or ethyl (hydroxyimino)cyanoacetate potassium salt (K-Oxyma). In one embodiment, the activator is HOBt.

In one embodiment, the coupling occurs in the presence of a base. In one embodiment, the base is $Et_3N$, DIPEA, pyridine, NMM, DBU, NaOH, or DMAP. In one embodiment, the base is $Et_3N$. In one embodiment, the base is DIPEA.

In one embodiment, the coupling occurs in the presence of a solvent. In one embodiment, the solvent is DMF, NMP, acetonitrile, EtOH, acetone, DCM, MeOH, or water, or a mixture thereof.

In one embodiment, the coupling occurs in the presence of a carbodiimide coupling reagent. In one embodiment, the carbodiimide is 1-ethyl-3-(3-dimethylaminopropyl)carbodiimide. In one embodiment, the coupling occurs in the presence of hydroxybenzotriazole (HOBt). In one embodiment, the coupling occurs in the presence of a base. In one embodiment, the base is DIPEA. In one embodiment, the DIPEA is in DMF. In one embodiment, the coupling occurs under an inert atmosphere.

In one embodiment, the coupling occurs in the presence of a triazine coupling reagent. In one embodiment, the triazine is DMTMM. In one embodiment, the coupling occurs in the presence of a base. In one embodiment, the base is $Et_3N$, DIPEA, pyridine, NMM, DBU, NaOH, or DMAP. In one embodiment, the base is $Et_3N$. In one embodiment, the coupling occurs in a solvent of acetonitrile, EtOH, acetone, DCM, MeOH, or water, or a mixture thereof. In one embodiment, the solvent is a mixture of acetonitrile and water (e.g., 4:1 v/v), a mixture of EtOH and water (e.g., 3:1 v/v), a mixture of EtOH, water, and DCM (e.g., 14.4:4.8:1 v/v/v), a mixture of acetone and water (e.g., 4:1 v/v), a mixture of DCM and MeOH (e.g., 4:1 v/v), a mixture of DCM and EtOH (e.g., 4:1 v/v), or DCM. In one embodiment, the solvent is a mixture of acetonitrile and water. In one embodiment, the volume ratio of acetonitrile to water is about 4:1.

In one embodiment, the coupling occurs in the presence of T3P and DIPEA in DMF.

In certain embodiments, provided herein is a process of preparing a compound of Formula (I):

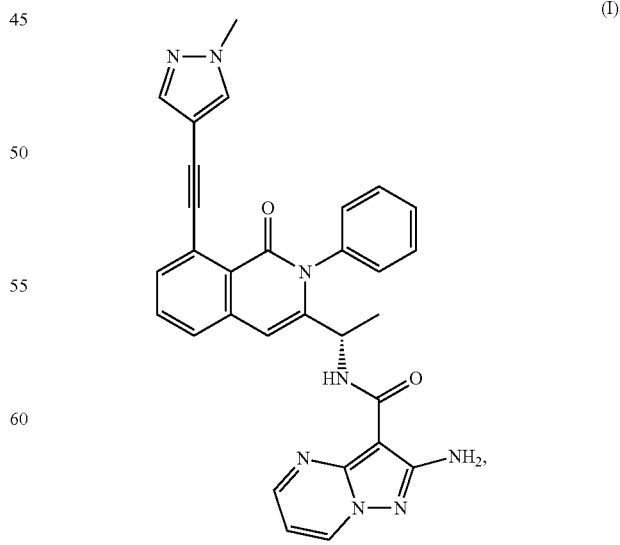

or a salt, or solvate, or solvate of a salt thereof, or a mixture thereof, comprising coupling compound C of formula:

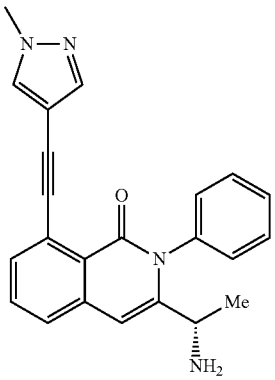

with an ester of Formula D:

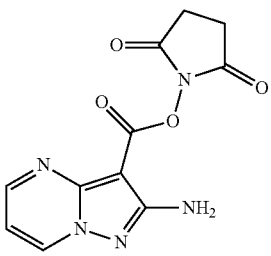

to provide the compound of Formula (I).

In one embodiment, the coupling occurs in the presence of one or more solvents. In another embodiment, the coupling occurs in the presence of a base and one or more solvents. In one embodiment, the base is an amine. In one embodiment, the amine is N,N-diisopropylethylamine (DIPEA). In one embodiment, the solvent is an organic solvent. In one embodiment, the organic solvent is selected from acetonitrile, dimethylformamide, tetrahydrofuran, 2-methyltetrahydrofuran, and dichloromethane, or a mixture thereof. In one embodiment, the organic solvent is acetonitrile. In one embodiment, the organic solvent is a mixture of DCM and ethanol In one embodiment, the volume ratio of DCM to ethanol is from about 8:1 to about 2:1. In one embodiment, the volume ratio of DCM to ethanol is about 4:1. In one embodiment, the coupling occurs in the presence of a mixture of two solvents. In another embodiment, the mixture of solvents is water and acetonitrile. In one embodiment, the volume ratio of water to acetonitrile is about 1:4. In one embodiment, the coupling occurs at a temperature from about 30° C. to about 80° C., from about 40° C. to about 70° C., or from about 55° C. to about 65° C. In one embodiment, the temperature is about 60° C.

In certain embodiments, provided herein is a process of preparing compound C of formula:

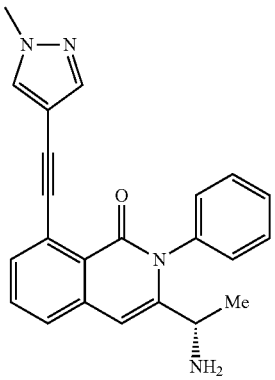

comprising coupling compound A of formula:

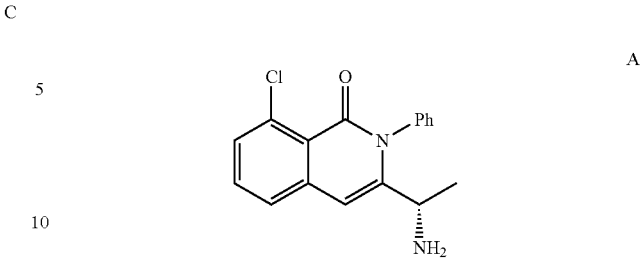

with an alkyne of Formula E:

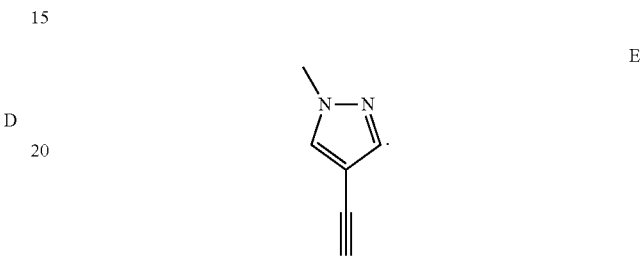

In one embodiment, the coupling occurs in the presence of a catalyst, a ligand, or a catalyst/ligand complex; a base; and a solvent.

In one embodiment, the catalyst is a palladium (Pd) catalyst, a nickel (Ni) catalyst, a copper (Cu) catalyst, or a mixture thereof. In one embodiment, the catalyst is a Pd catalyst. In one embodiment, the Pd catalyst is Pd-G3, $Pd_2(dba)_3$, $PdCl_2(MeCN)_2$, $Pd(OAc)_2$, $Pd(PPh_3)_4$, or $PdCl_2(PPh_3)_2$. In one embodiment, the palladium catalyst is $PdCl_2(MeCN)_2$. In one embodiment, the palladium catalyst is $Pd_2(dba)_3$.

In one embodiment, the catalyst is a Ni catalyst. In one embodiment, the Ni catalyst is $(Ph_3P)_2NiCl_2$.

In one embodiment, the catalyst is a Cu catalyst. In one embodiment, the Cu catalyst is CuI.

In one embodiment, the ligand is a phosphine ligand or bisphosphine ligand. In one embodiment, the ligand is XPhos, $PCy_3$, $PCy_2Ph$, $P^iPr_3$, $PCy_2^tBu$, CataCXium A, $P(MeOC_6H_4)_3$, $PPh_2(C_6H_4CO_2H)$, $PPh_2(C_6H_4SO_3H)$, SPhos, JohnPhos, DavePhos, MePhos, cBRIDP, Cy-vBRIDP, Cy-cBRIDP, $^t$Bu Triplecage, $P^tBu_2Cy$, $P^tBu_3$, CataCXium PICy, $P^tBu_2(PhNMe_2)$, $PPh_3$, dppp, dppe, dppb, BINAP, DPEPhos, dppf, dbpf, XantPhos, N-$^t$Bu$_2$P azetine, dppm, dmpe, dippe, DIPAMP, Chiraphos, SPANphos, SEGPHOS, Me-DuPhos, or Josiphos. In one embodiment, the ligand is XPhos, CataCXium A, JohnPhos, DavePhos, MePhos, cBRIDP, CataCXium PICy, or dbpf. In one embodiment, wherein the ligand is XPhos (2-dicyclohexylphosphino-2',4',6'-triisopropylbiphenyl). In one embodiment, the ligand is cBRIDP.

In one embodiment, the molar ratio of the ligand to the catalyst is from about 5:1 to about 1:5. In one embodiment, the molar ratio of the ligand to the catalyst is from about 2:1 to about 1:2. In one embodiment, the molar ratio of the ligand to the catalyst is from about 2:1 to about 1:1. In one embodiment, the ligand is a monodentate ligand and the molar ratio of the ligand to the catalyst is about 2:1. In one embodiment, the ligand is a monodentate ligand and the molar ratio of the ligand to the catalyst is about 1:1. In one embodiment, the ligand is a bidentate ligand and the molar ratio of the ligand to the catalyst is about 1:1. In one embodiment, the ligand is a bidentate ligand and the molar ratio of the ligand to the catalyst is about 1:2.

In one embodiment, the loading of the catalyst is from about 0.5% to about 10%, from about 1% to about 10%, or from about 1% to about 5%. In one embodiment, the loading of the catalyst is about 5%. In one embodiment, the loading of the catalyst is about 4%. In one embodiment, the loading of the catalyst is about 3%. In one embodiment, the loading of the catalyst is about 2%. In one embodiment, the loading of the catalyst is about 1%.

In one embodiment, the loading of the ligand is from about 0.5% to about 20%, from about 0.5% to about 15%, from about 0.5% to about 10%, from about 1% to about 10%, from about 1% to about 5%, or from about 1% to about 3%. In one embodiment, the loading of the catalyst is about 10%. In one embodiment, the loading of the catalyst is about 5%. In one embodiment, the loading of the catalyst is about 4%. In one embodiment, the loading of the catalyst is about 3%. In one embodiment, the loading of the catalyst is about 2%. In one embodiment, the loading of the catalyst is about 1%.

In one embodiment, the base is an inorganic base. In one embodiment, the base is an alkali metal salt. In one embodiment, the base is an alkaline earth metal salt. In one embodiment, the base is $Cs_2CO_3$, $K_2CO_3$, or $K_3PO_4$. In one embodiment, the base is $Cs_2CO_3$. In one embodiment, the base is $K_2CO_3$. In one embodiment, the base is $K_3PO_4$.

In one embodiment, the base is an organic base.

In one embodiment, the Pd catalyst is $Pd_2(dba)_3$, the ligand is Xphos, and the base is $K_2CO_3$. In one embodiment, the Pd catalyst is $Pd_2(dba)_3$, the ligand is Xphos, and the base is $K_3PO_4$. In one embodiment, the Pd catalyst is $PdCl_2(MeCN)_2$, the ligand is Xphos, and the base is $K_2CO_3$. In one embodiment, the Pd catalyst is $Pd(OAc)_2$, the ligand is Xphos, and the base is $K_2CO_3$.

In one embodiment, the solvent is MeCN, $^i$PrOAc, n-propyl acetate, 2-MeTHF, EtCN, MEK, or toluene. In one embodiment, the solvent is MeCN.

In one embodiment, the coupling occurs in the presence of $PdCl_2(MeCN)_2$. In one embodiment, the coupling occurs further in the presence of XPhos. In one embodiment, the coupling occurs further in the presence of a base. In one embodiment, the base is $Cs_2CO_3$. In one embodiment, the coupling occurs in the presence of a solvent. In one embodiment, the solvent is an organic solvent. In one embodiment, the organic solvent is acetonitrile.

In one embodiment, the coupling occurs in the presence of $Pd_2(dba)_3$. In one embodiment, the coupling occurs further in the presence of XPhos. In one embodiment, the coupling occurs further in the presence of a base. In one embodiment, the base is $K_3PO_4$. In one embodiment, the coupling occurs in the presence of a solvent. In one embodiment, the solvent is an organic solvent. In one embodiment, the organic solvent is acetonitrile.

In certain embodiments, provided herein is a process of preparing an alkyne of Formula E:

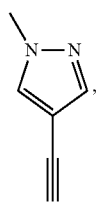

comprising deprotecting a compound of Formula F:

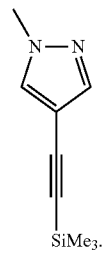

In one embodiment, the deprotection occurs in the presence of a base and a solvent.

In one embodiment, the base is an inorganic base. In one embodiment, the base is an alkali metal salt. In one embodiment, the base is KOH, NaOH, $NaHCO_3$, $K_3PO_4$, or $K_2CO_3$. In one embodiment, the base is an organic base. In one embodiment, the base is pyridine.

In one embodiment, the deprotection occurs in the presence of an acid. In one embodiment, the acid is HCl, AcOH, p-TsOH, or camphorsulfonic acid.

In one embodiment, the deprotection occurs in the presence of a fluoride source. In one embodiment, the fluoride source is tetra-n-butylammonium fluoride (TBAF). In one embodiment, the fluoride source is pyridine-HF.

In one embodiment, the deprotection occurs in the presence of a phase-transfer catalyst. In one embodiment, the phase-transfer catalyst is tetrabutylammonium hydroxide.

In one embodiment, the solvent is an organic solvent. In one embodiment, the organic solvent is MeOH. In one embodiment, the solvent is a mixture of water and a water immiscible solvent. In one embodiment, the water immiscible solvent is MTBE or DCM. In one embodiment, the deprotection occurs in the presence of a mixture of about 10 wt % KOH aqueous solution and MTBE. In one embodiment, the solvent is acetonitrile.

In certain embodiments, provided herein is a process of preparing a compound of Formula F:

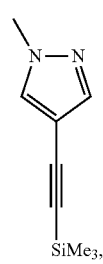

comprising coupling 4-iodo-1-methyl-1H-pyrazole with trimethylsilylacetylene.

In one embodiment, the coupling occurs in the presence of a Cu catalyst, a Pd catalyst, and a base.

In one embodiment, the Cu catalyst is CuI.

In one embodiment, the Pd catalyst is Pd-G3, $Pd_2(dba)_3$, $PdCl_2(MeCN)_2$, $Pd(OAc)_2$, $Pd(PPh_3)_4$, or $PdCl_2(PPh_3)_2$. In one embodiment, the Pd catalyst is $PdCl_2(PPh_3)_2$.

In one embodiment, the molar ratio of the Pd catalyst to the Cu catalyst is from about 1:20 to about 10:1, from about 1:10 to about 5:1, from about 1:7.5 to about 1:1, from about 1:6 to about 1:2. In one embodiment, the molar ratio of the Pd catalyst to the Cu catalyst is about 1:10, about 1:9, about 1:8, about 1:7, about 1:6, about 1:5, about 1:4, about 1:3, about 1:2, about 1:1, or about 2:1. In one embodiment, the molar ratio of the Pd catalyst to the Cu catalyst is about 1:6. In one embodiment, the molar ratio of the Pd catalyst to the Cu catalyst is about 1:2.

In one embodiment, the loading of the Pd catalyst is from about 0.0005 equivalent to about 0.1 equivalent, from about 0.001 equivalent to about 0.05 equivalent, from about 0.002 equivalent to about 0.02 equivalent, or from about 0.003 equivalent to about 0.01 equivalent. In one embodiment, the loading of the Pd catalyst is about 0.003 equivalent. In one embodiment, the loading of the Pd catalyst is about 0.01 equivalent.

In one embodiment, the loading of the Cu catalyst is from about 0.001 equivalent to about 0.2 equivalent, from about 0.005 equivalent to about 0.1 equivalent, from about 0.01 equivalent to about 0.05 equivalent, or from about 0.0175 equivalent to about 0.02 equivalent. In one embodiment, the loading of the Cu catalyst is about 0.0175 equivalent. In one embodiment, the loading of the Cu catalyst is about 0.02 equivalent.

In one embodiment, the loading of the Pd catalyst is about 0.01 equivalent and the loading of the Cu catalyst if about 0.02 equivalent. In one embodiment, the loading of the Pd catalyst is about 0.003 equivalent and the loading of the Cu catalyst if about 0.0175 equivalent.

In one embodiment, the base is DIPA, DIPEA, or N-methylmorpholine (NMM). In one embodiment, the base is DIPA. In one embodiment, the base is DIPEA. In one embodiment, the base is NMM. In one embodiment, the base (e.g., DIPA) is also used as the solvent.

In one embodiment, the coupling occurs in a solvent of DCM, toluene, 2-methyl-tetrahydrofuran, or DIPA, or a mixture thereof. In one embodiment, the coupling occurs in a solvent of DCM. In one embodiment, the coupling occurs in a solvent of toluene. In one embodiment, the coupling occurs in a solvent of 2-methyl-tetrahydrofuran.

In one embodiment, the compound of Formula F is used in the preparation of the alkyne compound of Formula E without purification. In one embodiment, the compound of Formula F is purified before being used in the preparation of the alkyne compound of Formula E.

In one embodiment, the coupling produces less than about 5%, less than about 4%, less than about 3%, less than about 2%, less than about 1%, less than about 0.5%, less than about 0.3%, less than about 0.2%, or less than about 0.1% of a side-product of the formula

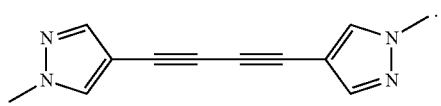

In certain embodiments, the carboxylic acid of Formula G is prepared according to the process as described in PCT publication Nos. WO 2011/003065 and WO 2015/073267. An exemplary synthetic scheme is shown below. The overall average yield is from about 10% to about 25%.

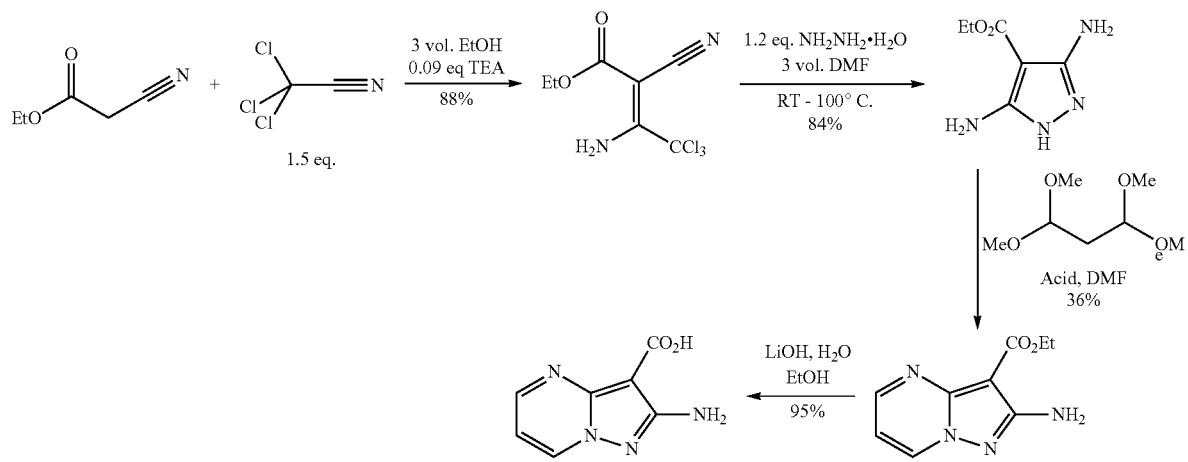

In certain embodiments, provided herein is an alternative approach for the preparation of the carboxylic acid of Formula G. An exemplary synthetic scheme is shown below. This alternative approach results an overall yield of about 40-45% and the product is obtained in an off white color.

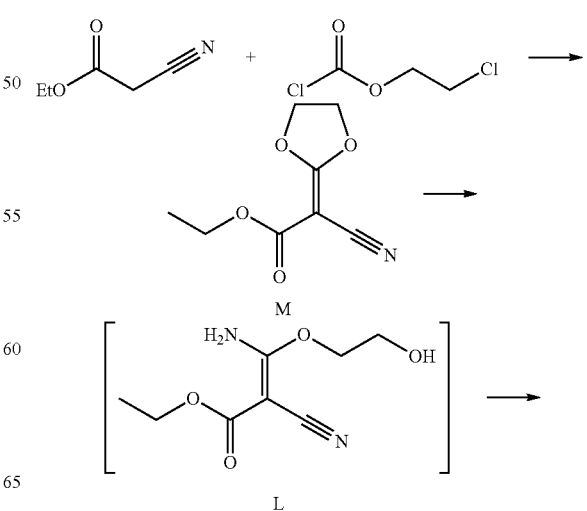

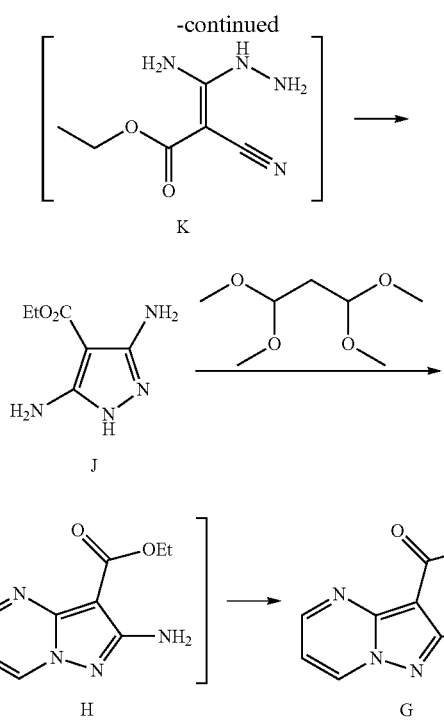

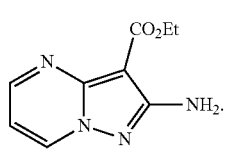

In certain embodiments, the carboxylic acid of Formula G is prepared by a process comprising hydrolyzing a compound of Formula H:

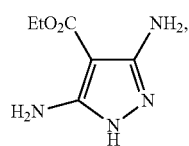

In one embodiment, the hydrolysis occurs in the presence of a base. In one embodiment, the base is LiOH, NaOH, or KOH. In one embodiment, the base is LiOH.

In certain embodiments, the compound of Formula H is prepared by a process comprising reacting a compound of Formula J:

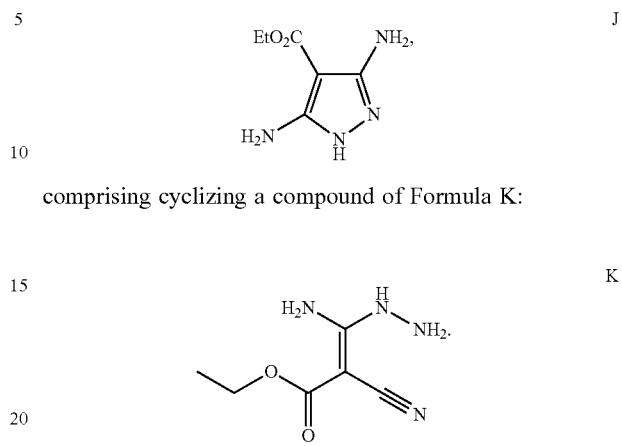

with 1,1,3,3-tetramethoxypropane.

In one embodiment, the reaction between the compound of Formula J and 1,1,3,3-tetramethoxypropane occurs in a solvent of AcOH. In one embodiment, the compound of Formula H is used in the preparation of the compound of Formula G without further purification after the removal of the solvent of AcOH.

In one embodiment, the reaction between the compound of Formula J and 1,1,3,3-tetramethoxypropane occurs in the presence of HCl.

In certain embodiment, provided herein is a process of preparing a compound of Formula J:

comprising cyclizing a compound of Formula K:

In one embodiment, the cyclization occurs by refluxing in a solvent of 1-propanol for from about 2 days to about 4 days. In one embodiment, the cyclization occurs by refluxing in a solvent of 1-propanol for about days.

In one embodiment, the cyclization occurs by refluxing in a solvent of 1-butanol for from about 24 hours to about 48 hours. In one embodiment, the cyclization occurs by refluxing in a solvent of 1-butanol for about 36 hours.

In one embodiment, the compound of Formula K is prepared by a process comprising reacting a compound of Formula L:

with hydrazine or hydrazine hydrate.

In one embodiment, the reaction between the compound of Formula L and hydrazine or hydrazine hydrate occurs by refluxing in a solvent of 1-propanol.

In one embodiment, the reaction between the compound of Formula L and hydrazine or hydrazine hydrate occurs by heating at from about 60° C. to about 80° C. in a solvent of 1-butanol.

In one embodiment, the compound of Formula L is prepared by a process comprising reacting a compound of Formula M:

with $NH_3$ or $NH_4OH$.

In one embodiment, the reaction between the compound of Formula M and $NH_3$ or $NH_4OH$ occurs at room temperature.

In one embodiment, the preparations of the compound of Formula L, the compound of Formula K, and the compound of Formula J occur in one-pot.

In one embodiment, the compound of Formula M is prepared by a process comprising reacting ethyl 2-cyanoacetate with 2-chloroethyl chloroformate.

In one embodiment, the reaction between 2-cyanoacetate and 2-chloroethyl chloroformate occurs in the presence of a base. In one embodiment, the base is an inorganic base. In one embodiment, the base is an alkali metal salt. In one embodiment, the base is an alkaline earth metal salt. In one embodiment, the base is LiOH, NaOH, or KOH. In one embodiment, the base is NaOH.

In one embodiment, the reaction between 2-cyanoacetate and 2-chloroethyl chloroformate occurs in a solvent of MeCN.

In one embodiment, the compound of Formula M is purified by recrystalllization from MeOH. In one embodiment, the compound of Formula M is purified by re-slurrying in 1-propanol. In one embodiment, the compound of Formula M is purified by crystallization from 1-butanol.

5.4. Pharmaceutical Compositions

In some embodiments, provided herein are pharmaceutical compositions comprising a solid form comprising a compound of Formula (I), or a salt, or solvate, or solvate of a salt thereof, or a mixture thereof, and a bulking agent (filler or carrier), and optionally a disintegrant and a lubricant. In some embodiments, provided herein are pharmaceutical compositions comprising a solid form provided herein, or a salt, or solvate, or solvate of a salt thereof, or a mixture thereof, and a pharmaceutically acceptable excipient, diluent, or carrier, including inert solid diluents and fillers, sterile aqueous solution and various organic solvents, permeation enhancers, solubilizers and adjuvants. In one embodiment, provided herein is a pharmaceutical composition comprising a solid form provided herein and a pharmaceutical acceptable excipient thereof. In one embodiment, provided herein is a pharmaceutical composition consisting essentially of a solid form provided herein. In one embodiment, the solid form is present in said composition in an amount of at least about 80% by weight. In one embodiment, the solid form is present in said composition in an amount of at least about 90% by weight.

In one embodiment, the solid form in the pharmaceutical composition is a polymorphic or cocrystal form provided herein. In one embodiment, the solid form is Form 1, Form 2, Form 3, Form 4, Form 5, Form 6, Form 7, Form 8, Form P1C3, Form P1C9, or Form P2C9 of Compound 1. In one embodiment, the solid form is Form 1.

In one embodiment, the solid form in the pharmaceutical composition is an amorphous form of Compound 1. In one embodiment, the amorphous form of Compound 1 is prepared by a process provided herein. In one embodiment, the amorphous form of Compound 1 is prepared by dissolving Form 1 of Compound 1 one or more solvents to form a solution; and removing the solvent of the solution to provide the amorphous form of Compound 1. In one embodiment, the solvent is removed by spray drying.

In one embodiment, the pharmaceutical composition comprises one or more excipients selected from bulking agents (or fillers), disintegrants, lubricants, and capsule shell. In one embodiment, the bulking agent is mannitol or pre-gelatinized starch. In another embodiment, the disintegrant is croscarmellose sodium. In another embodiment, the lubricant is magnesium stearate. In one embodiment, the capsule shell is HPMC capsule shell. In one embodiment, the pharmaceutical composition comprises one or more excipients selected from mannitol, pre-gelatinized starch, croscarmellose sodium, magnesium stearate, and HPMC capsule shell.

In one embodiment, the amount of Compound 1 in the pharmaceutical composition is about 1 mg to about 100 mg, about 1 mg to about 75 mg, about 1 mg to about 50 mg, about 1 mg to about 40 mg, about 5 mg to about 50 mg, about 5 mg to about 30 mg, about 5 mg to about 10 mg, about 5 mg, or about 30 mg. In one embodiment, the amount is about 5 mg, 10 mg, 15 mg, 20 mg, 30 mg, 40 mg, 50 mg, 75 mg, or 100 mg. In one embodiment, the amount is about 5 mg or 30 mg. In one embodiment, the amount of Compound 1 in the pharmaceutical composition is about 1.5% to about 25% w/w, about 1.5% to about 15% w/w, about 1.5% to about 10% w/w, about 1% to about 25% w/w, about 1% to about 15% w/w, or about 1% to about 10% w/w. In one embodiment, the amount of Compound 1 in the pharmaceutical composition is about 1% to about 10% w/w. In one embodiment, the amount of Compound 1 in the pharmaceutical composition is about 1, 1.5, 2, 2.5, 3, 3.5, 4, 4.5, 5, 5.5, 6, 6.5, 7, 7.5, 8, 8.5, 9, 9.5, or 10% w/w. In one embodiment, the amount of Compound 1 in the pharmaceutical composition is about 1.9%, or about 9.4%. In one embodiment, the amount of Compound 1 is about 1.92% or about 9.38%.

In one embodiment, the bulking agent (or filler) (e.g., starch and mannitol) in a pharmaceutical composition is about 80% to about 95% w/w, about 85% to about 95% w/w, or about 90% to about 95% w/w. In one embodiment, the bulking agent (or filler) (e.g., starch and mannitol) in a pharmaceutical composition is about 80%, about 85%, about 90%, or about 95% w/w. In one embodiment, the bulking agent (or filler) (e.g., starch and mannitol) in a pharmaceutical composition is about 93% w/w, about 86% w/w, about 92.3% w/w, or about 85.1% w/w. In one embodiment, the bulking agent is about 93% w/w. In one embodiment, the bulking agent is about 85% w/w. In one embodiment, the bulking agent is starch, mannitol, or a mixture thereof. In one embodiment, the bulking agent is a mixture of starch and mannitol. In one embodiment, the weight ratio of starch to mannitol is from about 1:3 to about 3:1. In one embodiment, the bulking agent is an about 1:1 mixture of starch and mannitol. In one embodiment, the starch is pre-gelatinized starch.

In one embodiment, the disintegrant (e.g., croscarmellose sodium) in a pharmaceutical composition is about 1% to about 20% w/w, about 1% to about 15% w/w, about 1% to about 10% w/w, about 2.5% to about 7.5% w/w, about 1% to about 5% w/w, or about 5% w/w. In one embodiment, the disintegrant is about 1%, about 2%, about 3%, about 4%, about 5%, about 6%, about 7%, about 8%, about 9%, or about 10% w/w. In one embodiment, the disintegrant is about 5% w/w.

In one embodiment, the lubricant (e.g., magnesium stearate) in a pharmaceutical composition is about 0.1% to about 10% w/w, about 0.1% to about 5% w/w, or about 0.1% to about 1% w/w. In one embodiment, the lubricant is about 0.1%, about 0.2%, about 0.3%, about 0.4%, about 0.5%, about 0.6%, about 0.7%, about 0.8%, about 0.9%, or about 1% w/w. In one embodiment, the lubricant is about 0.5% w/w.

In one embodiment, provided herein is a process of preparing a pharmaceutical composition provided herein comprising mixing a solid form comprising a compound of Formula (I) with a pharmaceutically acceptable excipient or carrier; wherein the solid form is Form 1, Form 2, Form 3, Form 4, Form 5, Form 6, Form 7, Form 8, Form P1C3, Form P1C9, or Form P2C9. In one embodiment, provided herein is a pharmaceutical composition prepared by the process above.

In one embodiment, provided herein is a pharmaceutical composition comprising an amorphous form of a compound of Formula (I), or a salt, or solvate, or solvate of a salt thereof, or a mixture thereof, and a bulking agent (filler or carrier), and optionally a disintegrant and a lubricant. In one embodiment, provided herein is a pharmaceutical composition comprising about 1% to about 10% w/w of an amorphous form of a compound of Formula (I), or a salt, or solvate, or solvate of a salt thereof, or a mixture thereof, about 80% to about 95% w/w of a bulking agent, about 2.5% to about 7.5% w/w of a disintegrant, and about 0.1% to about 1% w/w of a lubricant.

In one embodiment, provided herein is a pharmaceutical composition comprising about 5 to 30 mg Compound 1 (e.g., amorphous), pre-gelatinized starch, and mannitol. In one embodiment, the pharmaceutical composition further comprises croscarmellose sodium and magnesium stearate.

In one embodiment, the pharmaceutical composition is formulated as follows: about 5 mg of Compound 1 (e.g., amorphous), about 120 mg of pre-gelatinized starch, about 120 mg of mannitol, about 13 mg of croscarmellose sodium, and about 1.3 mg of magnesium stearate. In embodiment, the pharmaceutical composition is formulated as a capsule. In one embodiment, the pharmaceutical composition is formulated as follows: about 5 mg of Compound 1 (e.g., amorphous), about 120.35 mg of pre-gelatinized starch, about 120.35 mg of mannitol, about 13.00 mg of croscarmellose sodium, and about 1.3 mg of magnesium stearate. In embodiment, the pharmaceutical composition is formulated as a capsule.

In one embodiment, the pharmaceutical composition is formulated as follows: about 30 mg of Compound 1 (e.g., amorphous), about 136 mg of pre-gelatinized starch, about 136 mg of mannitol, about 16 mg of croscarmellose sodium, and about 1.6 mg of magnesium stearate. In one embodiment, the pharmaceutical composition is formulated as follows: about 30 mg of Compound 1 (e.g., amorphous), about 136.20 mg of pre-gelatinized starch, about 136.20 mg of mannitol, about 16.00 mg of croscarmellose sodium, and about 1.60 mg of magnesium stearate. In embodiment, the pharmaceutical composition formulated as a capsule.

In some embodiments, a pharmaceutical composition described herein includes a second active agent such as an additional therapeutic agent, (e.g., a chemotherapeutic agent).

In some embodiments, provided herein is a pharmaceutical composition for oral administration (e.g., capsule) comprising: (a) about 5 mg of amorphous Compound 1; (b) about 120.35 mg of pre-gelatinized starch; (c) about 120.35 mg of maanitol; (d) about 13 mg of croscarmellose sodium; and (e) about 1.3 mg of magnesium stearate.

In some embodiments, provided herein is a pharmaceutical composition for oral administration (e.g., capsule) comprising: (a) about 30 mg of amorphous Compound 1; (b) about 136.2 mg of pre-gelatinized starch; (c) about 136.2 mg of maanitol; (d) about 16 mg of croscarmellose sodium; and (e) about 1.6 mg of magnesium stearate.

In one embodiment, the pharmaceutical composition is an oral dosage form. In one embodiment, the oral dosage form is a capsule. In another embodiment, the oral dosage form is a tablet. In one embodiment, the capsule shell is Swedish orange or white.

5.4.1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, suitable carriers which can be employed in pharmaceutical compositions include mannitol, pre-gelatinized starch, croscarmellose sodium, magnesium stearate, and HPMC capsule shell.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as provided herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions is equal to or less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v or v/v.

In some embodiments, the concentration of one or more of the compounds as provided herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v.

In some embodiments, the concentration of one or more of the compounds as provided herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10% w/w, w/v, or v/v.

In some embodiments, the concentration of one or more of the compounds as provided herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9% w/w, w/v, or v/v.

In some embodiments, the amount of one or more of the compounds as provided herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g. In some embodiments, the amount of one or more of the compounds provided herein in the pharmaceutical compositions provided herein is about 1 mg, about 1.5 mg, about 2 mg, about 2.5 mg, about 3 mg, about 3.1 mg, about 3.2 mg, about 3.3 mg, about 3.4 mg, about 3.5 mg, about 4 mg, about 5 mg, about 6 mg, about 7 mg, about 8 mg, about 9 mg, or about 10 mg.

In some embodiments, the amount of one or more of the compounds as provided herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as provided herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

5.4.1.1 Formulations for Oral Administration

In some embodiments, provided herein are pharmaceutical compositions for oral administration containing a compound as provided herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds provided herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropyl alcohol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savory, sea buckthorn, sesame, shea butter, silicone, soybean, sunflower, tea tree, thistle, tsubaki, vetiver, walnut, and wheat germ oils. Exemplary oils also include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropyl alcoholamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

5.4.1.2 Formulations for Parenteral Administration

In some embodiments, provided herein are pharmaceutical compositions for parenteral administration containing a compound as provided herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as provided herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

5.4.1.3 Formulations for Topical Administration

In some embodiments, provided herein are pharmaceutical compositions for topical (e.g., transdermal) administration containing a compound as provided herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

5.4.1.4 Formulations for Inhalation Administration

In some embodiments, provided herein are pharmaceutical compositions for inhalation administration containing a compound as provided herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

5.4.1.5 Formulations for Ocular Administration

In some embodiments, the disclosure provides a pharmaceutical composition for treating ophthalmic disorders. The pharmaceutical composition can contain an effective amount of a compound as provided herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as provided herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, benzalkonium halide, cetalkonium halide, cetethyldimonium halide, cetylpyridinium halide, benzododecinium halide, chlorallyl methenamine halide, myristalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

5.4.1.6 Formulations for Controlled Release Administration

In some embodiments, provided herein are pharmaceutical compositions for controlled release administration containing a compound as provided herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as provided herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref. Biomed. Eng.* 14:201 (1987); Buchwald et al., *Surgery* 88:507 (1980); Saudek et al., *N Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

5.4.2 Dosages

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to about 1000 mg, or about 0.01 mg to about 500 mg per day, or about 0.1 mg to about 500 mg per day, or about 1 mg to 50 mg per day, or about 5 mg to 40 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiment, the daily dose of a compound described herein can range from about 0.0001 mg/kg to about 1000 mg/kg, about 0.001 mg/kg to about 1000 mg/kg, about 0.01 mg/kg to about 1000 mg/kg, about 0.1 mg/kg to about 1000 mg/kg, about 0.0001 mg/kg to about 500 mg/kg, about 0.001 mg/kg to about 500 mg/kg, about 0.01 mg/kg to 100 mg/kg, about 0.01 mg/kg to about 100 mg/kg, about 0.1 mg/kg to about 100 mg/kg, about 0.01 mg/kg to 50 mg/kg, about 0.05 mg/kg to 20 mg/kg, or about 0.05 mg/kg to 10 mg/kg. For example, the daily dose can be about 10 mg/kg, 5 mg/kg, 1.5 mg/kg, 0.5 mg/kg, 0.15 mg/kg, or about 0.05 mg/kg For example, the daily dose can be about 1 mg/kg, about 1.5 mg/kg, about 2 mg/kg, about 2.5 mg/kg, about 3 mg/kg, about 3.1 mg/kg, about 3.2 mg/kg, about 3.3 mg/kg, about 3.4 mg/kg, about 3.5 mg/kg, about 4 mg/kg, about 5 mg/kg, about 6 mg/kg, about 7 mg/kg, about 8 mg/kg, about 9 mg/kg, or about 10 mg/kg.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as provided herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as provided herein can continue as long as necessary. In some embodiments, an agent as provided herein is administered for more than about 1, about 2, about 3, about 4, about 5, about 6, about 7, about 14, about 21, or about 28 days. In some embodiments, an agent as provided herein is administered for less than about 28, about 21, about 14, about 7, about 6, about 5, about 4, about 3, about 2, or about 1 day. In some embodiments, an agent as provided herein is administered for about 1, about 2, about 3, about 4, about 5, about 6, about 7, about 14, about 21, or about 28 days. In some embodiments, an agent as provided herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein, is administered in a pharmaceutical composition that comprises one or more agents, and the agent has a shorter half-life than the compound provided herein unit dose forms of the agent and the compound provided herein can be adjusted accordingly.

5.4.3 Kits

In some embodiments, provided herein are kits. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . etc." Other variations of memory aids will be readily apparent. A "daily dose" can be a single tablet or capsule or several tablets or capsules to be taken on a given day.

The kit can further contain another agent. In some embodiments, the compound as provided herein and the agent are provided as separate pharmaceutical compositions in separate containers within the kit. In some embodiments, the compound as provided herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

5.5. Therapeutic Methods

Provided herein is a method for treating a PI3K mediated disorder in a subject, comprising administering a therapeutically effective amount of a solid form provided herein, or a pharmaceutical composition provided herein to said subject. In one embodiment, the PI3K mediated disorder is cancer, an inflammatory disease or an auto-immune disease. In one embodiment, the cancer is solid tumor.

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-α, β, δ), which are generally activated by receptor tyrosine kinases (RTKs); Class IB (e.g., PI3K-γ), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem.* 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal.* 23(4):603-8). Unlike PI3K-δ, PI3K-γ is not associated with a regulatory subunit of the p85 family, but rather with a regulatory subunit in the p101 or p84 families. PI3K-γ is associated with GPCRs, and is responsible for the very rapid induction of PIP3. PI3K-γ can be also activated by RAS.

In some embodiments, provided herein are methods of modulating a PI3 kinase activity (e.g., selectively modulating) by contacting the kinase with an effective amount of a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Modulation can be inhibition (e.g., reduction) or activation (e.g., enhancement) of kinase activity. In some embodiments, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest, with a compound provided herein. In some embodiments, provided herein are methods of inhibiting kinase activity in a subject by administering into the subject an effective amount of a compound as provided herein, or a pharmaceutically acceptable form thereof. In some embodiments, the kinase activity is inhibited (e.g., reduced) by more than about 25%, 30%, 40%, 50%, 60%, 70%, 80%, or 90%, when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject.

In some embodiments, the kinase is a lipid kinase or a protein kinase. In some embodiments, the kinase is selected from a PI3 kinase including different isoforms, such as PI3 kinase α, PI3 kinase β, PI3 kinase γ, PI3 kinase δ; DNA-PK; mTOR; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR); and IGFR.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound as provided herein, or a pharmaceutically acceptable form thereof, or a pharmaceutical composition as provided herein. In some embodiments, provided herein is a method of treating a PI3K-δ or PI3K-γ mediated disorder in a subject, the method comprising administering a therapeutically effective amount of a compound as provided herein, or a pharmaceutically acceptable form thereof, or a pharmaceutical composition as provided herein. In some embodiments, provided herein is a method for inhibiting at least one of PI3K-δ and PI3K-γ, the method comprising contacting a cell expressing PI3K in vitro or in vivo with an effective amount of a compound or composition provided herein. PI3Ks have been associated with a wide range of conditions, including immunity, cancer and thrombosis (reviewed in Vanhaesebroeck, B. et al. (2010) *Current Topics in Microbiology and Immunology*, DOI 10.1007/82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11):1151-62); Rommel C. et al. (2007) *Nat Rev Immunol* 7(3):191-201; Durand C A et al. (2009) *J Immunol.* 183(9):5673-84; Dil N, Marshall A J. (2009) *Mol Immunol.* 46(10):1970-8; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86).

PI3K-γ Activities

PI3K-γ is a Class 1B PI3K that associates with the p101 and p84 (p87PIKAP) adaptor proteins, and canonically signals through GPCRs. Non-canonical activation through tyrosine kinase receptors and RAS can occur. Activated PI3K-γ leads to production of PIP3, which serves as a docking site for downstream effector proteins including AKT and BTK, bringing these enzymes to the cell membrane where they may be activated. A scaffolding role for PI3K-γ has been proposed and may contribute to the activation of the RAS/MEK/ERK pathway. The interaction with the RAS pathway explains activities attributed to kinase dead PI3K-γ in cells or in animals. PI3K-γ is essential for function of a variety of immune cells and pathways. Chemokine responses (including IL-8, fMLP, and C5a), leading to neutrophil, basophil or monocyte cell migration, is dependent on PI3K-γ (HIRSCH et al., "Central Role for G Protein-Coupled Phosphoinositide 3-Kinase γ in Inflammation," *Science* 287:1049-1053 (2000); SASAKI et al., "Function of PI3Kγ in Thymocyte Development, T Cell Activation, and Neutrophil Migration," *Science* 287:1040-1046 (2000); LI et al., "Roles of PLC-β2 and -β3 and PI3Kγ in Chemoattractant-Mediated Signal Transduction," *Science* 287:1046-1049 (2000)). The requirement for PI3K-γ-dependent neutrophil migration is demonstrated by failure of arthritis development in the K/BXN serum transfer arthritis model in PI3K-γ knockout mice (Randis et al., *Eur. J. Immunol.*, 2008, 38(5), 1215-24). Similarly, the mice fail to develop cellular inflammation and airway hyper-responsiveness in the ovalbumin induced asthma model (Takeda et al., *J. Allergy Clin. Immunol.*, 2009; 123, 805-12). PI3K-γ deficient mice also have defects in T-helper cell function. T-cell cytokine production and proliferation in response to activation is reduced, and T helper dependent viral clearance is defective (Sasaki et al., *Science,* 2000, 287, 1040-46). T cell dependent inflammatory disease models including EAE also do not develop in PI3K-γ deficient mice, and both the T-cell activation defect and cellular migration defects may contribute to efficacy in this model (Comerfold, *PLOS One*, 2012, 7, e45095). The imiquimod psoriasis model has also been used to demonstrate the importance of PI3K-γ in the inflammatory response. Using PI3K-γ deficient mice in this model, the accumulation of γδ T cells in the skin is blocked, as well as dendritic cell maturation and migration (ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012)). The role of PI3K-γ in cellular trafficking can also be demonstrated in oncology models where tumor inflammation is important for growth and metastasis of cancers. In the Lewis Lung Carcinoma model, monocyte activation, migration, and differentiation in tumors are defective. This defect results in a reduction in tumor growth and extended survival in PI3K-γ deficient mice (Schmid et al., *Cancer Cell*, 2011, 19, 715-27) or upon treatment with inhibitors that target PI3K-γ. In pancreatic cancer, PI3K-γ can be inappropriately expressed, and in this solid tumor cancer or others where PI3K-γ plays a functional role, inhibition of PI3K-γ can be beneficial.

For instance, while not wishing to be bound by theory, PI3K-γ is expressed in Gr1+CD11b+myeloid cells, and directly promotes myeloid cell invasion and consequently, immunosuppression of pancreatic ductal carcinomas. Hardamon et. al., Proceedings: AACR 103rd Annual Meeting 2012, Cancer Research: Apr. 15, 2012; Volume 72, Issue 8, Supplement 1 Inhibition of PI3K-γ also shows promise for the treatment of hematologic malignancies. In a T-ALL model employing a T cell directed knockout of pten, PI3K-δ and PI3K-γ are both essential for the appropriate development of disease, as shown with genetic deletion of both genes (Subramaniam et al. *Cancer Cell* 21, 459-472, 2012). In addition, in this T-ALL model, treatment with a small molecule inhibitor of both kinases leads to extended survival of these mice. In CLL, chemokine networks support a pseudo-follicular microenvironment that includes Nurse like cells, stromal cells and T-helper cells. The roles of PI3K-γ in the normal chemokine signaling and T cell biology suggest the value of inhibiting this target in CLL (BURGER, "Inhibiting B-Cell Receptor Signaling Pathways in Chronic Lymphocytic Leukemia," *Curr. Mematol. Malig. Rep.* 7:26-33 (2012)). Accordingly, PI3K-γ inhibitors are therapeutically interesting for diseases of the immune system where cell trafficking and T cell or myeloid cell function is important. In oncology, solid tumors that are dependent on tumor inflammation, or tumors with high levels of PI3K-γ expression, can be targeted. For hematological cancers, a special role for PI3K-γ and PI3K-δ isoforms in TALL and potentially in CLL suggests targeting these PI3Ks in these diseases.

Without being limited by a particular theory, PI3K-γ has been shown to play roles in inflammation, arthritis, asthma, allergy, multiple sclerosis (MS), and cancer, among others (e.g., Ruckle et al., *Nature Rev., Drug Discovery*, 2006, 5, 903-18; Schmid et al., "Myeloid cells in tumor inflammation," *Vascular Cell*, 2012, doi:10.118612045-824X-4-14). For example, PI3K-γ functions in multiple signaling pathways involved in leukocyte activation and migration. PI3K-γ has been shown to drive priming and survival of autoreactive CD4+ T cells during experimental autoimmune encephalomyelitis (EAE), a model for MS. When administered from onset of EAE, a PI3K-γ inhibitor has been shown to cause inhibition and reversal of clinical disease, and reduction of demyelination and cellular pathology in the CNS (Comerford et al., *PLOS One*, 2012, 7, e45095). PI3K-γ also regulates thymocyte development, T cell activation, neutrophil migration, and the oxidative burst (Sasaki et al., *Science*, 2000, 287, 1040-46). In addition, it is shown that allergic airway hyper-responsiveness, inflammation, and remodeling do not develop in PI3K-γ deficient mice (Takeda et al., *J. Allergy Clin. Immunol.*, 2009; 123, 805-12). PI3K-γ is shown to be required for chemoattractant-induced production of phosphatidylinositol 3,4,5-trisphosphate and has an important role in chemoattractant-induced superoxide production and chemotaxis in mouse neutrophils and in production of T cell-independent antigen-specific antibodies composed of the immunoglobulin λ light chain (Li et al., *Science*, 2000, 287, 1046-49). PI3K-γ is reported to be a crucial signaling molecule required for macrophage accumulation in inflammation (Hirsch et al., *Science*, 2000, 287, 1049-53). In cancers, pharmacological or genetic blockade of p110γ suppresses inflammation, growth, and metastasis of implanted and spontaneous tumors, suggesting that PI3K-γ can be an important therapeutic target in oncology (Schmid et al., *Cancer Cell*, 2011, 19, 715-27). For example, it is shown that PI3K-γ has a tumor-specific high accumulation in pancreatic ductal adenocarcinoma (PDAC) in human, signifying a role of PI3K-γ in pancreatic cancer (Edling et al., *Human Cancer Biology*, 2010, 16(2), 4928-37).

In certain embodiments, provided herein are methods of treating or preventing a PI3K-gamma mediated disorder in a subject, comprising administering to the subject a therapeutically effective amount of a compound provided herein, e.g., a selective PI3K-γ inhibitor, e.g., Compound 1), or a pharmaceutically acceptable form thereof.

In one embodiment, the subject has or is at risk of having a PI3K-gamma mediated disorder selected from cancer, an inflammatory disease, or an autoimmune disease. In one embodiment, the cancer is a solid tumor. In one embodiment, the cancer is selected from one or more of: a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the cancer is a hematological cancer.

In one embodiment, the inflammatory disease is arthritis.

In one embodiment, the subject is a human. In one embodiment, the subject is identified as having or being at risk of having a PI3K-gamma mediated disorder via the use of a biomarker.

In one embodiment, the therapeutically effective dose is about 2 mg, about 1-3 mg, about 1-5 mg, about 1-10 mg, about 0.5-20 mg, about 0.1-50 mg per day, about 0.1-75 mg per day, about 0.1-100 mg per day, about 0.1-250 mg per day, about 0.1-500 mg per day, about 0.1-1000 mg per day, about 1-50 mg per day, about 1-75 mg per day, about 1-100 mg per day, about 1-250 mg per day, about 1-500 mg per day, about 1-1000 mg per day, about 10-50 mg per day, about 10-75 mg per day, about 10-100 mg per day, about 10-250 mg per day, about 10-500 mg per day, about 10-1000 mg per day, about 100-500 mg per day, or about 100-1000 mg per day. In one embodiment, the therapeutically effective dose is about 0.029 mg/kg, about 0.014-0.14 mg/kg, about 0.02-0.04 mg/kg, about 0.01-0.05 mg/kg, about 0.01-0.1, or about 0.01-0.5 mg/kg. In one embodiment, the compound is administered once every two days. In one embodiment, wherein the compound is administered once per day. In one embodiment, the compound is administered twice per day.

In one embodiment, the compound is administered at a dose such that the level of the compound in the subject is higher than the compound's IC50 of PI3K-gamma inhibition during at least 70%, 80%, 90%, 95%, 97%, 98%, or 99% of a selected time period, e.g., 6 hours, 12 hours, 24 hours, or 48 hours immediately following the administration. In one embodiment, the compound is administered at a dose such that the level of the compound in the subject is higher than the compound's IC90 of PI3K-gamma inhibition during at least 50%, 60%, 70%, 80%, 90%, 95%, 97%, 98%, or 99% of a selected time period, e.g., 6 hours, 12 hours, 24 hours, or 48 hours, immediately following the administration. In one embodiment, the compound is administered at a dose such that the level of the compound in the subject does not rise higher than the compound's IC20 or IC50 of PI3K-delta inhibition within a selected time period, e.g., 6 hours, 12 hours, 24 hours, or 48 hours, immediately following the administration. In one embodiment, the level of the compound is measured from the subject's plasma. In one embodiment, the level of the compound is measured from the subject's tissue. In one embodiment, the compound is administered at a dose such that it provides at least 50% inhibition of PI3K-gamma in the subject but less than 10% or 20% inhibition of PI3K-delta in the subject.

In one embodiment, the subject is a human and the compound has a half-life of about 10-13 hours in the subject. In one embodiment, the method further comprises administering to the subject a second therapeutic agent that is a P-gp substrate. In one embodiment, the second therapeutic agent is Norvir (ritonavir).

PI3K-δ and/or PI3K-γ Activities

PI3K-δ has roles in impairments of B-cell signaling and development, antibody production, T-cell function, Th1 and Th2 differentiation, and mast and basophil degranulation. Without being limited by a particular theory, PI3K-γ has roles in T-cell function, neutrophil and macrophage recruitment, macrophage activation, neutrophil oxidative burst, and dendritic cell migration Inhibition of PI3K-δ and/or PI3K-γ isoforms can result in efficacy against inflammation and cancer, e.g., in arthritis, asthma, multiple sclerosis (MS), and tumor models. For example, deficiency in PI3K-δ and/or PI3K-γ can result in efficacy in K/BxN arthritis model (Kyburz et al., Springer Semin. Immunopathology, 2003, 25, 79-90) or K/BxN serum transfer model of arthritis (Randis et al., Eur. J. Immunol., 2008, 38(5), 1215-24), where it is shown that recognition of the immune complexes depends on both PI3K-δ and PI3K-γ, whereas cell migration is dependent on PI3K-γ. Deficiency in PI3K-δ or PI3K-γ can also result in efficacy in murine ovalbumin (OVA) induced allergic asthma model (Lee et al., FASEB J., 2006, 20, 455-65; Takeda et al., J. Allergy Clin. Immunol., 2009; 123, 805-12), where it is shown that inhibition of either PI3K-δ or PI3K-γ inhibits ovalbumin induced lung infiltration and improves airway responsiveness. Deficiency in PI3K-δ or PI3K-γ can also result in efficacy in murine experimental autoimmune encephalomyelitis (model for MS), where it is shown that PI3K-γ deletion may provide better efficacy as compared to PI3K-δ deletion (Haylock-Jacob et al., J. Autoimmunity, 2011, 36, 278-87; Comerford et al., PLOS One, 2012, 7, e45095), including reduction in T-cell receptor induced $CD4^+$ T cell activation, leukocyte infiltration and Th1/Th17 responses, and dendritic cell migration (Comerfold, PLOS One, 2012, 7, e45095). Furthermore, inhibition of PI3K-γ can also result in decreased tumor inflammation and growth (e.g., Lewis lung carcinoma model, Schmid et al., Cancer Cell, 2011, 19(6), 715-27). PI3K-γ deletion combined with PI3K-δ deletion results in increased survival in T-cell acute lymphoblastic leukemia (T-ALL) (Subramaniam et al., Cancer Cell, 2012, 21, 459-72). Inhibitors of both PI3K-δ and PI3K-γ are also shown to be efficacious in PTEN-deleted T-ALL cell line (MOLT-4). In the absence of PTEN phosphatase tumor suppressor function, PI3K-δ or PI3K-γ alone can support the development of leukemia, whereas inactivation of both isoforms suppresses tumor formation. Thus, inhibitors of PI3K-δ and/or PI3K-γ can be useful in treating inflammation, such as arthritis, allergic asthma, and MS; and in treating cancer, for example, due to effects such as reductions in solid tumor associated inflammation, angiogenesis and tumor progression.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9 Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) J Exp Med. 196(6):753-63; Bilancio A, et al. (2006) Blood 107(2):642-50; Okkenhaug K. et al. (2002) Science 297(5583):1031-4; Al-Alwan M M et al. (2007) J Immunol. 178(4):2328-35; Zhang T T, et al. (2008) J Allergy Clin Immunol. 2008; 122(4):811-819.e2; Srinivasan L, et al. (2009) Cell 139(3):573-86).

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garçon F. et al. (2008) Blood 111(3):1464-71; Okkenhaug K et al. (2006). J Immunol. 177(8):5122-8; Soond D R, et al. (2010) Blood 115(11):2203-13; Reif K, (2004). J Immunol. 2004; 173(4):2236-40; Ji H. et al. (2007) Blood 110(8): 2940-7; Webb L M, et al. (2005) J Immunol. 175(5):2783-7; Liu D, et al. (2010) J Immunol. 184(6):3098-105; Haylock-Jacobs S, et al. (2011) J Autoimmun. 2011; 36(3-4):278-87; Jarmin S J, et al. (2008) J Clin Invest. 118(3): 1154-64).

Numerous publications support roles of PI3K-δ and PI3K-γ in the differentiation, maintenance, and activation of immune and malignant cells, as described in more detail herein.

PI3K-δ and PI3K-γ isoforms are preferentially expressed in leukocytes where they have distinct and non-overlapping roles in immune cell development and function. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); BUITENHUIS et al., "The role of the PI3K-PKB signaling module in regulation of hematopoiesis," *Cell Cycle* 8(4):560-566 (2009); HOELLENRIEGEL and BURGER, "Phosphoinositide 3'-kinase delta: turning off BCR signaling in Chronic Lymphocytic Leukemia," *Oncotarget* 2(10):737-738 (2011); HIRSCH et al., "Central Role for G Protein-Coupled Phosphoinositide 3-Kinase γ in Inflammation," *Science* 287: 1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J. Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J. Autoimmun.* 36:278-287 (2011); SOOND et al., "PI3K p110δ regulates T-cell cytokine production during primary and secondary immune responses in mice and humans," *Blood* 115(11):2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9):936-943 (2005). As key enzymes in leukocyte signaling, PI3K-δ and PI3K-γ facilitate normal B-cell, T-cell and myeloid cell functions including differentiation, activation, and migration. See, e.g., HOELLENRIEGEL and BURGER, "Phosphoinositide 3'-kinase delta: turning off BCR signaling in Chronic Lymphocytic Leukemia," *Oncotarget* 2(10):737-738 (2011); CUSHING et al., "PI3Kδ and PI3Kγ as Targets for Autoimmune and Inflammatory Diseases," *J. Med. Chem.* 55:8559-8581 (2012). PI3K-δ or PI3K-γ activity is critical for preclinical models of autoimmune and inflammatory diseases. See, e.g., HIRSCH et al., "Central Role for G Protein-Coupled Phosphoinositide 3-Kinase γ in Inflammation," *Science* 287:1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J. Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J. Autoimmun.* 36:278-287 (2011); SOOND et al., "PI3K p110δ regulates T-cell cytokine production during primary and secondary immune responses in mice and humans," *Blood* 115(11): 2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9): 936-943 (2005). Given the key role for PI3K-δ and PI3K-γ in immune function, inhibitors of the PI3K-δ and/or γ have therapeutic potential in immune-related inflammatory or neoplastic diseases.

PI3K-δ and PI3K-γ are central to the growth and survival of B- and T-cell malignancies and inhibition of these isoforms may effectively limit these diseases. See, e.g., SUBRAMANIAM et al., "Targeting Nonclassical Oncogenes for Therapy in T-ALL," *Cancer Cell* 21:459-472 (2012); LANNUTTI et al., "CAL-101 a p110δ selective phosphatidylinositol-3-kinase inhibitor for the treatment of B-cell malignancies, inhibits PI3K signaling and cellular viability," *Blood* 117(2):591-594 (2011). PI3K-δ and PI3K-γ support the growth and survival of certain B-cell malignancies by mediating intracellular BCR signaling and interactions between the tumor cells and their microenvironment. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); HOELLENRIEGEL et al., "The phosphoinositide 3'-kinase delta inhibitor, CAL-101, inhibits B-cell receptor signaling and chemokine networks in chronic lymphocytic leukemia," *Blood* 118(13): 3603-3612 (2011); BURGER, "Inhibiting B-Cell Receptor Signaling Pathways in Chronic Lymphocytic Leukemia," *Curr. Mematol. Malig. Rep.* 7:26-33 (2012). Increased BCR signaling is a central pathologic mechanism of B-cell malignancies and PI3K activation is a direct consequence of BCR pathway activation. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); DAVIS et al., "Chronic active B-cell-receptor signaling in diffuse large B-cell lymphoma," *Nature* 463:88-92 (2010); PIGHI et al., "Phospho-proteomic analysis of mantle cell lymphoma cells suggests a pro-survival role of B-cell receptor signaling," *Cell Oncol. (Dordr)* 34(2):141-153 (2011); RIZZATTI et al., "Gene expression profiling of mantle cell lymphoma cells reveals aberrant expression of genes from the PI3K-AKT, WNT and TGFβ signaling pathways," *Brit. J. Haematol.* 130:516-526 (2005); MARTINEZ et al., "The Molecular Signature of Mantle Cell Lymphoma Reveals Multiple Signals Favoring Cell Survival," *Cancer Res.* 63:8226-8232 (2003). Interactions between malignant B-cells and supporting cells (e.g., stromal cells, nurse-like cells) in the tumor microenvironment are important for tumor cell survival, proliferation, homing, and tissue retention. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); KURTOVA et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009); BURGER et al., "High-level expression of the T-cell chemokines CCL3 and CCL4 by chronic lymphocytic leukemia B cells in nurselike cell cocultures and after BCR stimulation," *Blood* 113(13) 3050-3058 (2009); QUIROGA et al., "B-cell antigen receptor signaling enhances chronic lymphocytic leukemia cell migration and survival: specific targeting with a novel spleen tyrosine kinase inhibitor, R406," *Blood* 114(5):1029-

1037 (2009) Inhibiting PI3K-δ,γ with an inhibitor in certain malignant B-cells can block the BCR-mediated intracellular survival signaling as well as key interactions with their microenvironment that are critical for their growth.

PI3K-δ and PI3K-γ also play a direct role in the survival and proliferation of certain T-cell malignancies. See, e.g., SUBRAMANIAM et al., "Targeting Nonclassical Oncogenes for Therapy in T-ALL," Cancer Cell 21:459-472 (2012). Aberrant PI3K-δ and PI3K-γ activity provides the signals necessary for the development and growth of certain T-cell malignancies. While BTK is expressed in B-cells, it is not expressed in T-cells, and therefore BTK is not a viable target for the treatment of T-cell malignancies. See, e.g., NISITANI et al., "Posttranscriptional regulation of Bruton's tyrosine kinase expression in antigen receptor-stimulated splenic B cells," PNAS 97(6):2737-2742 (2000); DE WEERS et al., "The Bruton's tyrosine kinase gene is expressed throughout B cell differentiation, from early precursor B cell stages preceding immunoglobulin gene rearrangement up to mature B cell stages," Eur. J Immunol. 23:3109-3114 (1993); SMITH et al., "Expression of Bruton's Agammaglobulinemia Tyrosine Kinase Gene, BTK, Is Selectively Down-Regulated in T Lymphocytes and Plasma Cells," J. Immunol. 152:557-565 (1994). PI3K-δ and/or γ inhibitors may have unique therapeutic potential in T-cell malignancies.

In neutrophils, PI3K-δ, along with PI3K-γ, contribute to the responses to immune complexes, FCγRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008) Eur J Immunol. 38(5):1215-24; Pinho V, (2007) J Immunol. 179 (11):7891-8; Sadhu C. et al. (2003) J Immunol. 170(5):2647-54; Condliffe A M et al. (2005) Blood 106(4):1432-40). It has been reported that in certain autoimmune diseases, preferential activation of PI3K-β may be involved (Kulkarni et al., Immunology (2011) 4(168) ra23: 1-11). It was also reported that PI3K-β-deficient mice were highly protected in an FcγR-dependent model of autoantibody-induced skin blistering and partially protected in an FcγR-dependent model of inflammatory arthritis, whereas combined deficiency of PI3K-β and PI3K-δ resulted in near complete protection in inflammatory arthritis (Id.).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCγR and C5a signaling) (Randis T M, et al. (2008) Eur J Immunol. 38(5):1215-24; Marwick J A et al. (2009) Am J Respir Crit Care Med. 179(7):542-8; Konrad S, et al. (2008) J Biol Chem. 283(48):33296-303).

Theophylline increases histone deacetylase-2 and corticosteroid sensitivity in vitro and in smoking mice in vivo by inhibiting PI3 kinase (e.g., PI3K-delta). PI3K is activated in COPD lungs and certain PI3K inhibitors have been shown to mimic the effects of theophylline in reversing corticosteroid resistance. Yasuo, T., et al., Am J Respir Crit Care Med 2010; 182:897-904. While not wishing to be bound by theory, a rationale for the use of PI3K inhibitors (e.g., compounds provided herein) to treat COPD is that a PI3K inhibitor can increase the corticosteroid sensitivity in a subject.

In mast cells, stem cell factor-(SCF) and IL3-dependent proliferation, differentiation and function are PI3K-δ dependent, as is chemotaxis. The allergen/IgE crosslinking of FCγR1 resulting in cytokine release and degranulation of the mast cells is severely inhibited by treatment with PI3K-δ inhibitors, suggesting a role for PI3K-δ in allergic disease (Ali K et al. (2004) Nature 431(7011):1007-11; Lee K S, et al. (2006) FASEB J. 20(3):455-65; Kim M S, et al. (2008) Trends Immunol. 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) J Exp Med. 205(10):2419-35; Tassi I, et al. (2007) Immunity 27(2):214-27; Saudemont A, (2009) Proc Natl Acad Sci USA. 106(14):5795-800; Kim N, et al. (2007) Blood 110(9): 3202-8).

The roles of PI3K-δ and PI3K-γ in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma, and inflammatory respiratory disease, such as COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O. et al. (2010) Chem Biol, 17(2):123-34; WO 2009/088986; WO2009/088880; WO 2011/008302; each incorporated herein by reference). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) Arthritis Rheum 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302; each incorporated herein by reference).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S. et al. (2011) J. Autoimmunity 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class 1A PI3Ks, which includes PI3K-δ. The deletion of PI3K-γ in the transgenically activated class 1A lupus model is protective, and treatment with a PI3K-γ selective inhibitor in the murine MLR//lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

PI3K-δ and/or PI3K-γ Isoforms in Certain Cancers

Class I PI3Ks, particularly PI3K-δ and PI3K-γ isoforms, are also associated with cancers (reviewed, e.g., in Vogt, P K et al. (2010) *Curr Top Microbiol Immunol.* 347:79-104; Fresno Vara, J A et al. (2004) *Cancer Treat Rev.* 30(2):193-204; Zhao, L and Vogt, PK. (2008) *Oncogene* 27(41):5486-96) Inhibitors of PI3K, e.g., PI3K-δ and/or PI3K-γ, have been shown to have anti-cancer activity (e.g., Courtney, K D et al. (2010) *J Clin Oncol.* 28(6):1075-1083); Markman, B et al. (2010) *Ann Oncol.* 21(4):683-91; Kong, D and Yamori, T (2009) *Curr Med Chem.* 16(22):2839-54; Jimeno, A et al. (2009)*J Clin Oncol.* 27:156s (suppl; abstr 3542); Flinn, I W et al. (2009) *J Clin Oncol.* 27:156s (suppl; abstr 3543); Shapiro, G et al. (2009) *J Clin Oncol.* 27:146s (suppl; abstr 3500); Wagner, A J et al. (2009) *J Clin Oncol.* 27:146s (suppl; abstr 3501); Vogt, P K et al. (2006) *Virology* 344(1): 131-8; Ward, S et al. (2003) *Chem Biol.* 10(3):207-13; WO 2011/041399; US 2010/0029693; US 2010/0305096; US 2010/0305084; each incorporated herein by reference).

In one embodiment, described herein is a method of treating cancer. In one embodiment, provided herein is a method of treating a hematological cancer comprising administering a pharmaceutically effective amount of a compound provided herein to a subject in need thereof. In one embodiment, provided herein is a method of treating a solid tumor comprising administering a pharmaceutically effective amount of a compound provided herein to a subject in need thereof. Types of cancer that can be treated with an inhibitor of PI3K (e.g., Compound 1) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) *Mol Cancer Ther.* 7:841-850); endometrial cancer (e.g., Bansal, N et al. (2009) *Cancer Control.* 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) *Cancer J.* 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and solid tumors, including prostate, breast and glioblastomas (Chen J. S. et al. (2008) *Mol Cancer Ther.* 7(4):841-50; Ikeda H. et al. (2010) *Blood* 116(9): 1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3): 1027-36; Meadows, S A, 52$^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16): 4323-7.

In one embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with hematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non-Hodgkin's lymphoma (Furman, R R, et al. 52$^{nd}$ Annual ASH Meeting and Exposition; 2010 Dec. 4-7; Orlando, Fla.; Hoellenriegel, J, et al. 52$^{nd}$ Annual ASH Meeting and Exposition; 2010 Dec. 4-7; Orlando, Fla.; Webb, H K, et al. 52$^{nd}$ Annual ASH Meeting and Exposition; 2010 Dec. 4-7; Orlando, Fla.; Meadows, et al. 52$^{nd}$ Annual ASH Meeting and Exposition; 2010 Dec. 4-7; Orlando, Fla.; Kahl, B, et al.

52$^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research 102$^{nd}$ Annual Meeting; 2011 Apr. 2-6; Orlando, Fla.). In this subset of tumors, treatment with the PI3K-δ inhibitor either alone or in combination with a cytotoxic agent can be effective.

Another mechanism for PI3K-δ inhibitors to have an effect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

Accordingly, provided herein is a method of treating or preventing a cancer or disease (including but not limited to a hematologic malignancy, or a specific type or sub-type of cancer or disease, such as a specific type or sub-type of hematologic malignancy), with a PI3K-γ selective inhibitor, wherein the adverse effects associated with administration of inhibitors for other isoform(s) of PI3K (e.g., PI3K-α and/or PI3K-β) are reduced. In one embodiment, provided herein is a method of treating or preventing the cancer or disease, with a PI3K-γ selective inhibitor, at a lower (e.g., by about 10%, by about 20%, by about 30%, by about 40%, by about 50%, by about 60%, by about 70%, or by about 80%) dose as compared to treatment with a PI3K-γ non-selective or less selective PI3K-γ inhibitor (e.g., a PI3Kpan inhibitors, e.g., inhibiting PI3K-α, β, δ, and γ).

The role of PI3K-γ pathway in promoting myeloid cell trafficking to tumors and the role of blockade of p100γ in suppression of tumor inflammation and growth in breast cancer, pancreatic cancer, and lung cancer are reported, for example, in Schmid et al. (2011) *Cancer Cell* 19, 715-727, the entirety of which is incorporated herein by reference. In one embodiment, provided herein is a method of treating or preventing pancreatic cancer with a PI3K inhibitor.

In another embodiment, provided herein is a method of treating or preventing breast cancer with a PI3K inhibitor. In yet another embodiment, provided herein is a method of treating or preventing lung cancer with a PI3K inhibitor. In one embodiment, the PI3K inhibitor is a PI3K-γ inhibitor, selective or non-selective over one or more other PI3K isoform(s). In one embodiment, the PI3K inhibitor is a PI3K-γ selective inhibitor.

While not wishing to be bound by theory, it is believed that tumor growth is influenced by two classes of immune cells in the tumor microenvironment: effector cells which include cytotoxic cells and M1 macrophages, and which have anti-tumor activity, and suppressor cells, which include M2 macrophages, MDSC (myeloid derived suppressor cell), Tregs (regulatory T cell), and regulatory dendritic cells, which have pro-tumor activity because they inhibit the effector cells. An abundance of suppressor cells can lead to tumor immune tolerance, and enhancement of tumor growth.

Certain of these cell types are briefly described. M1 denotes a pro-inflammatory (anti-tumor) phenotype of a MDSC or TAM. M2 denotes an anti-inflammatory (pro-tumor) phenotype of a MDSC or TAM.

PI3K-γ is not expressed in at least some cancer cell types. Schmid et al., 2011, Cancer Cell 19. Accordingly, in some embodiments, the PI3K-γ inhibitor reduces cancer cell growth without having a substantial direct effect on the cancer cell itself. For instance, in some embodiments, the PI3K-γ inhibitor inhibits cancer cell growth through changes in the tumor microenvironment, e.g., the immune cells in close proximity to the cancer cells.

Evidence in the literature supports the idea that a PI3K-γ inhibitor can reduce tumor associated myeloid cells. For instance, in PI3K-γ-deficient mice, tumor-associated myeloid cells are reduced. Schmid et al., 2011, Cancer Cell 19. Together, these data indicate that a large class of PI3K-γ inhibitors should reduce tumor associated myeloid cells, thereby increasing the immune response against cancer cells, and treating the cancer. While not wishing to be bound by theory, a PI3K-γ may operate through the following mechanism. PI3K-γ signaling may tilt the balance of immune cells towards pro-tumor M2 cells and away from anti-tumor M1 cells, by inducing expression of immunosuppressive, wound healing genes such as Arginase 1, TGF-beta1, PDGFBB, MMP9, and MMP13, and suppressing pro-inflammatory factors such as IL12, iNos, and interferon gamma. Blocking PI3K-γ signaling with an inhibitor tilts the balance towards anti-tumor M1 cells by stimulating a T cell activating gene expression program. Kaneda et al. PI3-kinase gamma controls the macrophage M1-M2 switch, thereby promoting tumor immunosuppression and progression. [abstract]. In: Proceedings of the 105th Annual Meeting of the American Association for Cancer Research; 2014 Apr. 5-9; San Diego, Calif. Philadelphia (Pa.): AACR; Cancer Res 2014; 74(19 Suppl):Abstract nr 3650. doi: 10.1158/1538-7445.AM2014-3650.

In some embodiments, a PI3K-γ inhibitor provided herein is administered to a patient in order to block a homeostatic down-regulation of T cell response. While not wishing to be bound by theory, this may allow the body to raise an effective immune response against the cancer cell. Exemplary agents of this type include immune checkpoint therapeutics, e.g., agents that act on CTLA-4, PD-1, or PD-L1, e.g., antibodies that bind to CTLA-4, PD-1, or PD-L1. Immune checkpoint therapeutics are described in more detail below.

In some embodiments, a PI3K-γ inhibitor provided herein is administered to a patient in order to eliminate immuno-suppressive cells in the tumor microenvironment. The immunosuppressive cell may be, e.g., a T regulatory cell (e.g., a cell that secretes mediators that induce CD8+ cytotoxic T cell death); a Tumor-associated macrophage (TAM; e.g., anM2 (pro-tumor) TAMS that blocks T cell activity and promotes angiogenesis); or a myeloid-derived suppressor cell (MDSC; e.g., a cell that secretes mediators that inhibit T cell differentiation and proliferation).

In some embodiments, a compound provided herein is administered to a patient in order to reduce the migration or differentiation of a tumor associated myeloid cell. In some embodiments, the compound is a compound that shows single agent activity in a syngeneic model system. In some embodiments, the compound is administered in combination with a second therapeutic, as discussed herein. In some embodiments, the administration results in a reduction in the level of MDSCs in the tumor microenvironment; the level of M2 TAMS in the tumor microenvironment; the level of T-regulatory cells in the tumor microenvironment, or any combination thereof. In some embodiments, the administration results in an unchanged or increased level of T-effector cells in the tumor microenvironment. In embodiments, the administration results in an increase in an immune response to the tumor, e.g., an increase in the levels or tumor-attacking activity of cytotoxic T cells, M1 inflammatory TAMs, or a combination thereof.

In some embodiments, an MDSC has one or more of the following properties: suppressing anti-tumor immune attack; inducing vascularization of the tumor; inducing ECM breakdown, e.g., which may contribute to metastasis; and supporting tumor growth. Accordingly, in some embodiments, administration of a PI3K-γ inhibitor described herein inhibits one or more of these functions in an MDSC.

TAMs (tumor-associated macrophages) can also have one or more of the following properties: suppressing anti-tumor immune attack; inducing vascularization of the tumor; inducing ECM breakdown, e.g., which may contribute to metastasis; and supporting tumor growth. Accordingly, in some embodiments, administration of a PI3K-γ inhibitor as described herein inhibits one or more of these functions in a TAM.

In embodiments, a PI3K-γ inhibitor is administered to a patient who has received chemotherapy and/or radiation therapy. While not wishing to be bound by theory, in some embodiments, chemotherapy or radiation therapy results in a wound healing response that leads to repopulation of the cancer site, e.g., tumor, with TAMs and MDSCs. Administering the PI3K-γ inhibitor, in some embodiments, reduces the levels of TAMs and MDSCs in the microenvironment, decreasing their support for tumor cell growth and/or allowing the immune system to attack the cancer cells. See Claire E. Lewis, "Imaging immune cell infiltrating tumors in zebrafish", AACR Annual Meeting (Apr. 5, 2014).

While not wishing to be bound by theory, a rationale for the use of a PI3K-gamma inhibitor as adjunct therapy to radiation is to prevent the accumulation of tumor supporting myeloid cells into the radiated tumor, thus impairing tumor regrowth following radiation therapy. This is supported by work of Kioi et al. (2010) *Clin Invest.* 120(3):694-705 showing that an inhibitor of myeloid cell migration into post-irradiated tumors (e.g., AMD3100) blocked tumor vasculogenesis and tumor regrowth.

In certain embodiments, provided herein is a method of treating a disorder or disease provided herein, comprising administering a compound provided herein, e.g., a PI3K γ selective inhibitor, a PI3K δ selective inhibitor, or a PI3K γ/δ dual inhibitor. Without being limited by a particular theory, in some embodiments, selectively inhibiting PI3K-γ isoform can provide a treatment regimen where adverse effects associated with administration of a non-selective PI3K inhibitor are minimized or reduced. Without being limited by a particular theory, in some embodiments, selectively inhibiting PI3K-δ isoform can provide a treatment regimen where adverse effects associated with administration of a non-selective PI3K inhibitor are minimized or reduced. Without being limited by a particular theory, in some embodiments, selectively inhibiting PI3K-δ and γ isoform can provide a treatment regimen where adverse effects associated with administration of a non-selective PI3K inhibitor are minimized or reduced. Without being limited by a particular theory, it is believed that the adverse effects can be reduced by avoiding the inhibition of other isoforms (e.g., α or β) of PI3K.

In one embodiment, the adverse effect is hyperglycemia. In another embodiment, the adverse effect is rash. In another embodiment, the adverse effect is impaired male fertility that may result from inhibition of β isoform of PI3K (see, e.g., Ciraolo et al., *Molecular Biology of the Cell*, 21: 704-711 (2010)). In another embodiment, the adverse effect is testicular toxicity that may result from inhibition of PI3K-β (see, e.g., Wisler et al., Amgen SOT, Abstract ID #2334 (2012)). In another embodiment, the adverse effect is embryonic lethality (see, e.g., Bi et al., *J Biol Chem*, 274: 10963-10968 (1999)). In another embodiment, the adverse effect is defective platelet aggregation (see, e.g., Kulkarni et al., *Science*, 287: 1049-1053 (2000)). In another embodiment, the adverse effect is functionally defective neutrophil (id).

In certain embodiments, provided herein is a method of treating or preventing cancer (e.g., colon cancer, melanoma, bladder cancer, renal cancer, breast, lung cancer, glioblastoma, solid tumors, and a cancer of hematopoietic origin (e.g., DLBCL, CLL, Hodgkin lymphoma, non-Hodgkin lymphomas)) comprising administering to the subject a PI3K inhibitor (e.g., a PI3K-γ inhibitor, e.g., Compound 1).

Without being bound by a particular theory, a rationale for the use of a PI3K inhibitor to treat or prevent cancer is that cells derived from tumors (e.g., from CT26 mouse tumors) can suppress anti-tumor immune cell function, including T-cell proliferation, as shown in the examples provide herein, and treatment with a compound provided herein can release the suppression. The tumor microenvironment can inhibit the activation and proliferation of immune effector cells due to the presence of suppressive myeloid cells (e.g., myeloid derived suppressor cells or MDSC and M2 macrophages). Compounds provided herein can affect the number and activity M2 macrophages in a tumor microenvironment, e.g., reduce or inhibit the level of M2, pro-tumor macrophages. The reduction or inhibition of M2 macrophages, which produce anti-inflammatory cytokines and other factors, would lead to increased anti-tumor immunity, including T cell proliferation. Therefore, a compound provided herein can treat or prevent cancer such as colon cancer, melanoma, bladder cancer, renal cancer, breast, lung cancer, glioblastoma, solid tumors, and a cancer of hematopoietic origin (e.g., lymphoma, DLBCL, CLL, Hodgkin disease, non-Hodgkin lymphomas). Further, it has also been shown in the examples provided herein that anti-PDL1 can also release suppression of T cell proliferation by blocking the interaction between PD1 on T cells and PDL1 on tumor cells and regulatory cells. The cytotoxic T cells that are induced to proliferate and survive by both anti PDL-1 and compound 1 are hypothesized to slow tumor growth. Compounds provided herein can relieve immunosuppression which can lead to T cells proliferation and activation. Compounds provided herein can treat or prevent cancer by inducing T cell mediated immunity. In one embodiment, the compound provided herein can decrease tumor volume. In one embodiment, a combination of a PI3K inhibitor such as a compound provided herein and anti-PDL1 would be effective in treating or preventing cancer by inducing T cell mediated tumor immunity. In some embodiments, the effect of a compound provided herein on T-cell function can be assessed by analyzing the pro-inflammatory cytokine levels in tumor tissues and serum, e.g., a MSD pro-inflammatory panel. In another embodiment, the pro-inflammatory cytokines are selected from IFN-γ, IL-1β, IL-10, IL-12 p70, IL-2, IL-4, IL-5, IL-6, KC/GRO, and TNF-α. In one embodiment, the effect of a compound provided herein on T cell function can be assessed by analyzing the IFN-γ level. For example, tumor tissues and serum treated with a compound provided herein, e.g., Compound 1, can be assessed by analyzing the IFN-γ level.

Treatment of Neuropsychiatric Disorders

In other embodiments, inhibition of PI3K (such as PI3K-δ and/or PI3K-γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry* 159:1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J. Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113:883-886; Garvey, M. A. et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J. Neuroimmunol.* 179: 173-179). Autoantibodies recognizing central nervous system (CNS) epitopes are also found in sera of most PANDAS subjects (Yaddanapudi, K. et al. (2010) *Mol. Psychiatry* 15:712-726). Thus, several neuropsychiatric disorders have been associated with immune and autoimmune components, making them suitable for therapies that include PI3K-δ and/or PI3K-γ inhibition.

In certain embodiments, a method of treating (e.g., reducing or ameliorating one or more symptoms of) a neuropsychiatric disorder, (e.g., an autoimmune brain disorder), using a PI3K-δ and/or PI3K-γ inhibitor is described, alone or in combination therapy. For example, one or more PI3K-δ and/or PI3K-γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or PI3K-γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD-Not Otherwise Specified (PDD-NOS). Animal models for evaluating the activity of the PI3K-δ and/or PI3K-γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

In some embodiments, provided herein is a method for treating rheumatoid arthritis or asthma in a subject, or for reducing a rheumatoid arthritis-associated symptom or an asthma-associated symptom in a subject, comprising administering an effective amount of a PI3K-γ inhibitor to a subject in need thereof, wherein one or more of the adverse effects associated with administration of inhibitors for one or more other isoforms of PI3K are reduced. In one embodiment, the one or more other isoforms of PI3K is PI3K-α, PI3K-β, and/or PI3K-δ. In one embodiment, the one or more other isoforms of PI3K is PI3K-α and/or PI3K-β. In one embodiment, the method is for treating rheumatoid arthritis in a subject, or for reducing a rheumatoid arthritis-associated symptom in a subject. In another embodiment, the method is for treating asthma in a subject, or for reducing an asthma-associated symptom in a subject.

In some embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat disease conditions, including, but not limited to, diseases associated with malfunctioning of one or more types of PI3 kinase. In one embodiment, a detailed description of conditions and disorders mediated by p110δ kinase activity is set forth in Sadu et al., WO 01/81346, which is incorporated herein by reference in its entirety for all purposes.

In some embodiments, the disclosure relates to a method of treating a hyperproliferative disorder in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Treatment of Cancers

In certain embodiments, provided herein are methods of modulating tumor microenvironment of cancer cells in a subject, comprising administering to the subject a therapeutically effective amount of a compound provided herein (e.g., a selective PI3K-γ inhibitor, e.g., Compound 1), or a pharmaceutically acceptable form thereof.

As used herein and unless otherwise specified, "tumor microenvironment" refers to the cellular and extracellular environment where the tumors are located. This location can include surrounding blood vessels, immune cells, fibroblasts, secreted signaling molecules, and the extracellular matrix. The tumor microenvironment includes non-neoplastic stromal and immune cells that provide growth and survival support to the neoplastic tumor.

As used herein and unless otherwise specified, "immunotherapy" refers to treatments that stimulate, enhance, or suppress the body's own immune system to fight a disease. Diseases that may be suitable for immunotherapy treatment include, but are not limited to, cancer, inflammatory diseases, and infectious diseases. Immunotherapy includes a variety of treatments that work in different ways. For example, some are intended to boost the immune system defenses in a general way; others help train the immune system to recognize and attack cancer cells specifically. Cancer immunotherapies include, but are not limited to, cell-based therapies (also known as cancer vaccines), antibody therapies, and cytokine therapies (e.g., interleukin-2 and interferon-α).

Many cancers are known to be susceptible to the treatment of one or more immunotherapies, including treatment targeting the effector cells in the tumor microenvironment (e.g., immune checkpoint therapy such as PD-1/PD-L1 inhibitors and CTLA-4 inhibitors), treatment targeting suppressor cells in the tumor microenvironment (e.g., CSF-1R inhibitors (affecting MDSC and TAM) and IDO/TDO inhibitors). Without being limited by a particular theory, a compound provided may affect MDSC, TAM, and other components in the tumor microenvironment. The role of TAM in tumor microenvironment is described, e.g., in Lewis and Pollard, Cancer Res. 2006; 66: (2). Jan. 15, 2006.

In one embodiment, the number of one or more pro-tumor immune cells in the tumor microenvironment is reduced, or the activity of one or more pro-tumor immune cells in the tumor microenvironment is reduced or inhibited, after administration of the compound.

In some embodiments, the pro-tumor immune cell is a T-cell, an M2 macrophage, a stromal cell, a dendritic cell, an endothelial cell, or a myeloid cell. In one embodiment, the myeloid cell is a tumor associated suppressive myeloid cell. In one embodiment, the tumor associated suppressive myeloid cell is identified by (i) CD45+, CD11b+, Ly6C+ and Ly6G+, (ii) CD45+, CD11b+, Ly6C− and Ly6G−, (iii) CD45+, CD11b+, Ly6C− and Ly6G+, or (iv) CD45+, CD11b+, Ly6C+ and Ly6G−. In one embodiment, the tumor associated suppressive myeloid cell is a tumor associated macrophage (TAM), a myeloid derived suppressor cell (MDSC), a monocytic immature myeloid cell (iMc), or a granulocytic iMc/neutrophil. In one embodiment, the TAM is identified by CD45+, CD11b+, Ly6C−, and Ly6G−. In one embodiment, the myeloid derived suppressor cell (MDSC) is identified by CD45+, CD11b+, Ly6C− and Ly6G+. In one embodiment, the monocytic immature myeloid cell (iMc) is identified by CD45+, CD11b+, Ly6C+ and Ly6G−. In one embodiment, the granulocytic iMc/neutrophil is identified by CD45+, CD11b+, Ly6C+ and Ly6G+. See e.g., Coussens L M. et al., Cancer Discov. 2011 June; 1(1):54-67.

In one embodiment, the activation of M2 macrophage in the tumor microenvironment is reduced or inhibited after administration of the compound. In one embodiment, the p-AKT level in the M2 macrophage is reduced after administration of the compound. In one embodiment, the number of M2 macrophage cells in the tumor microenvironment is reduced after administration of the compound. In one embodiment, the migration of M2 macrophage cells into the tumor microenvironment is reduced or inhibited after administration of the compound. In one embodiment, the differentiation of myeloid cells into M2 macrophage cells in the tumor microenvironment is reduced or inhibited after administration of the compound. In one embodiment, the differentiation into M2 macrophage cells is measured by Arginase-1 (ARG1) level or VEGF level, and the ARG1 level or VEGF level is reduced by at least 10%, 20%, 30%, 40%, 50%, 60%, 70%, 80%, or 90% compared to a reference value.

In one embodiment, the number of myeloid-derived suppressor cells in the tumor microenvironment is reduced after administration of the compound. In one embodiment, the differentiation of bone marrow cells into myeloid-derived suppressor cells is reduced or inhibited after administration of the compound. In one embodiment, the differentiation into myeloid-derived suppressor cells is measured by Arginase-1 (ARG1) level, VEGF level, or iNOS level, and the ARG1 level, VEGF level, or iNOS level is reduced by at least 10%, 20%, 30%, 40%, 50%, 60%, 70%, 80%, or 90% compared to a reference value.

In one embodiment, the production of proangiogenic factor is reduced or inhibited after administration of the compound. In one embodiment, the proangiogenic factor is reduced or inhibited by reduction or inhibition of macrophage or MDSC differentiation. In one embodiment, the proangiogenic factor is VEGF.

In one embodiment, the effect of the compounds provided herein (e.g., Compound 1) on MDSC (e.g., human MDSC) function is measured by expression of iNOS and arginase and production of ROS and IL-10, measured by the suppression function of the MDSC (e.g., in co-culture assays with CD8+), measured by activation of pAKT in response to a stimulant (e.g., CXCL12, IL-1b, TNF-α, or CSF1), or measured by transwell chemotaxis assays (T cells and MDSC).

In one embodiment, the effect of the compounds provided herein (e.g., Compound 1) on MDSC (e.g., murine MDSC) function and macrophage M2-polarization is measured by isolating myeloid cells from bone marrow, polarizing with IFNg or IL-4 and then testing for secretion of TNF-α, IL-12, ROS production in M1 and IL-10, IL-1b, or VEGF, or measured by methods provided herein or elsewhere.

In one embodiment, the effect of the compounds provided herein (e.g., Compound 1) on myeloid and CD8+ is measured by in vivo models (e.g., MC38 and 4T1). In one embodiment, the effect is measured by TGI, MDSC and macrophage infiltrate, CD8+, and IFN-gamma production in CD8+.

In one embodiment, the effect of the compounds provided herein (e.g., Compound 1) on myeloid and CD8+ is measured by QT-PCR or intracellular FACS of myeloid infiltrate. In one embodiment, the effect is measured by expression of functional markers (e.g., iNOS, arginase, or IL-10).

In one embodiment, the number of one or more anti-tumor immune cells in the tumor microenvironment is increased, or the activity of one or more anti-tumor immune cells in the tumor microenvironment is increased, after administration of the compound.

In one embodiment, the cancer susceptible to the treatment of one or more immunotherapies is a hematological cancer. In one embodiment, the hematological cancer is chronic lymphocytic leukemia (CLL). In one embodiment, the tumor microenvironment is a CLL proliferation center. In one embodiment, the hematological cancer is lymphoma.

In one embodiment, the cancer susceptible to the treatment of one or more immunotherapies is a solid tumor. In one embodiment, the solid tumor is lung cancer, breast cancer, colon cancer, or glioblastoma. In one embodiment, the cancer is selected from one or more of: a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma. In one embodiment, the solid tumor is melanoma, bladder cancer, head and neck cancer, lung cancer (e.g., non-small cell lung cancer), renal cell carcinoma, ovarian cancer, breast cancer (e.g., triple-negative breast cancer), colon cancer, or glioblastoma.

In one embodiment, the solid tumor is melanoma. In one embodiment, the solid tumor is lung cancer. In one embodiment, the solid tumor is non-small cell lung cancer. In one embodiment, the solid tumor is renal cell carcinoma. Melanoma, lung cancer (e.g., non-small cell lung cancer), and renal cell carcinoma are known to be sensitive to immunotherapies. Data linking a poor prognosis to high TAM cell counts have been reported in breast, prostate, endometrial, bladder, kidney, esophageal, superficial, carcinoma, melanoma, and follicular lymphoma cancers. See e.g., Lewis and Pollard, Cancer Res. 2006; 66: (2). Jan. 15, 2006. One anti-PD-1 antibody drug, nivolumab, (Opdivo—Bristol Myers Squibb), produced complete or partial responses in non-small-cell lung cancer, melanoma, and renal-cell cancer, in a clinical trial with a total of 296 patients.

In one embodiment, the solid tumor is head and neck cancer. Head and neck tumors tend to be highly immunogenic and have strong anti-PD-1/PD-L1 efficacy. In one embodiment, the solid tumor is bladder cancer. Bladder cancer also has strong anti-PD-1/PD-L1 efficacy. A high number of TAM cells has been associated with a poor prognosis and increased tumor angiogenesis in bladder cancer.

In one embodiment, the solid tumor is breast cancer. In one embodiment, the breast cancer is triple-negative breast cancer. A high number of TAM cells has been associated with a poor prognosis of breast cancer. See e.g., Lewis and Pollard, Cancer Res. 2006; 66: (2). Jan. 15, 2006. In one embodiment, the solid tumor is ovarian cancer. In one embodiment, the solid tumor is colon cancer. Breast cancer, ovarian cancer, and colon cancer are known to be sensitive to immunotherapies (e.g., bevacizumab and trastuzumab) and can also have anti-PD-1/PD-L1 efficacy.

In one embodiment, the solid tumor is glioblastoma. In one embodiment, the solid tumor is glioblastoma multiforme. It has been reported that PI3K-gamma expression is upregulated in brain microglia. Without being limited by a particular theory, PI3K-γ inhibitors provided herein (e.g., Compound 1) may have P-glycoprotein inhibitory activity and thus can cross the blood brain barrier.

In one embodiment, the anti-tumor immune attack by effector T cells is increased, vascularization of the tumor is reduced, extracellular matrix (ECM) breakdown is reduced, or tumor growth is decreased, compared to a reference value, after administration of the compound.

In one embodiment, the tumor volume of the cancer is reduced after administration of the compound. In one embodiment, the tumor volume of the cancer is reduced by at least 10%, 20%, 30%, 50%, 60%, or 60%, compared to a reference value.

In one embodiment, the level of apoptosis of the cancer cells is increased after administration of the compound. In one embodiment, the level of apoptosis of the cancer cells is increased by at least 10%, 20%, 30%, 40%, or 50%, compared to a reference value.

In some embodiments, the subject is naive to immunotherapy treatment. In some embodiments, the subject is naive to radiation therapy treatment. In some embodiments, the subject is naive to chemotherapy treatment.

In some embodiments, the subject has been pre-treated or previously treated with one or more immunotherapy treatments. In one embodiment, the subject is responsive to the pre-treatment or previous treatment with the immunotherapy. In one embodiment, the immunotherapy treatment is a checkpoint treatment such as a PD-1 or PD-L1 inhibitor. In one embodiment, the subject is a smoker. It has been reported that smoker patients may respond better to immunotherapy (e.g., a PD-L1 inhibitor MPDL3280A) than non-smoker patients in a phase I clinical study for patients with melanoma or cancers of the lung, kidney, colon, GI tract, or head and neck cancers.

In one embodiment, the cancer is melanoma, and the subject has been pre-treated or previously treated with one or more immunotherapy treatments. In one embodiment, the subject has been pre-treated or previously treated with two or more immunotherapy treatments.

In one embodiment, the cancer is head and neck cancer, lung cancer (e.g., non-small cell lung cancer), renal cell carcinoma, or bladder cancer, and the subject has been pre-treated or previously treated with one immunotherapy treatment.

In one embodiment, the cancer is breast cancer (e.g., triple-negative breast cancer), ovarian cancer, glioblastoma, or colon cancer, and the subject is naive to immunotherapy treatment.

In one embodiment, provided herein is a method of treating, preventing, or managing melanoma in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is ipilimumab (Yervoy), interleukin-2, vemurafenib, dabrafenib, or trametinib.

In one embodiment, provided herein is a method of treating, preventing, or managing lung cancer (e.g., non-small cell lung cancer) in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is bevacizumab, erlotinib, gefitinib, afatinib, or denosumab.

In one embodiment, provided herein is a method of treating, preventing, or managing renal cell carcinoma in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is bevacizumab, interleukin-2, axitinib, carfilzomib, everolimus, interferon-α, lenalidomide, pazopanib, sirolimus (rapamycin), sorafenib, sunitinib, temsirolimus, thalidomide, or tivozanib.

In one embodiment, provided herein is a method of treating, preventing, or managing bladder cancer in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is Bacillus Calmette-Guérin (BCG).

In one embodiment, provided herein is a method of treating, preventing, or managing head and neck cancer in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is cetuximab, nimotuzumab, bevacizumab, or erlotinib.

In one embodiment, provided herein is a method of treating, preventing, or managing breast cancer (e.g., triple-negative breast cancer) in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is bevacizumab or trastuzumab.

In one embodiment, provided herein is a method of treating, preventing, or managing ovarian cancer in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is bevacizumab.

In one embodiment, provided herein is a method of treating, preventing, or managing colon cancer in a subject, comprising administering to the subject a therapeutically effective amount of a compound provided herein (e.g., Compound 1), or a pharmaceutically acceptable form thereof, wherein the subject has been pre-treated or previously treated with one or more immunotherapy treatments. In one embodiment, the immunotherapy treatment is bevacizumab, cetuximab, or panitumumab.

In some embodiments, the disclosure relates to a method of treating a cancer of hematopoietic origin. In certain embodiments, the cancer of hematopoietic origin is lymphoma or leukemia. In some embodiments, the cancer of hematopoietic origin is selected from acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), Hodgkin lymphoma (HL), non-Hodgkin lymphoma (NHL), follicular lymphoma, diffuse large B-cell lymphoma (DLBCL), mantle cell lymphoma (MCL), mastocytosis (e.g., systemic mastocytosis), multiple myeloma (MM), myelodysplastic syndrome (MDS), myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), and hypereosinophilic syndrome (HES)).

In some embodiments, the disclosure relates to a method of treating a solid tumor. In some embodiments, the solid tumor is selected from ovarian cancer, colon cancer, fibrosarcoma, pancreatic cancer, lung cancer, breast cancer, lymphoma, melanoma, and glioblastoma. In some embodiment, the solid tumor is a CNS tumor. In one embodiment, the CNS tumor is glioblastoma. Compound 1 shows good permeability cross blood-brain-barrier and can achieving efficacious concentration in a CNS tumor.

In one embodiment, Compound 1 can be an inhibitor of P-gp (P-glycoprotein). P-glycoprotein impedes the entry of various drugs that are used in the treatment, for example, of central nervous system diseases. Without being bound by a particular theory, the P-gp substrate may help maintain normal levels of P-gp activity in a patient being treated with a PI3K-γ inhibitor. In some embodiments, Compound 1 may not be effluxed from a tumor and thus can maintain efficacious concentration of Compound 1 in a tumor. For example, the concentration can be maintained for about at least 6 hours, at least 10 hours, at least 12 hours, at least 24 hours, or at least 48 hours. In one embodiment, Compound 1 can be administered once daily.

In some embodiments, Compound 1 is administered to a patient in combination with a second therapeutic that is a P-gp substrate. In another embodiment, Compound 1 can inhibit the efflux of the second therapeutic such as a cancer drug that is a P-gp substrate. Therefore, Compound 1 can be efficacious in maintaining the concentration of the co-administered cancer drug in a tumor. For example, the concentration can be maintained for about at least 6 hours, at least 10 hours, at least 12 hours, at least 24 hours, or at least 48 hours. In one embodiment, Compound 1 can be administered once daily.

P-glycoprotein is a component of the blood-brain barrier and is present on the surface of the endothelial cells of the barrier. A PI3K-γ inhibitor provided herein such as Compound 1 can be a P-glycoprotein inhibitor and thus can cross the blood brain barrier. In some embodiments, a PI3K-γ inhibitor provided herein such as Compound 1 can maintain an efficacious concentration in CNS tumor or a brain tumor (e.g., glioblastoma).

As used herein "solid tumor" refers to an abnormal mass of tissue. Solid tumors may be benign or malignant. A solid tumor grows in an anatomical site outside the bloodstream (in contrast, for example, to cancers of hematopoietic origin such as leukemias) and requires the formation of small blood vessels and capillaries to supply nutrients, etc. to the growing tumor mass. Solid tumors are named for the type of cells that form them. Non-limiting examples of solid tumors are sarcomas, carcinomas (epithelial tumors), melanomas, and glioblastomas.

In some embodiments, the disclosure relates to a method of inhibiting growth of a tumor. "Inhibiting growth of a tumor" refers to slowing tumor growth and/or reducing tumor size "Inhibiting growth of a tumor" thus includes killing tumor cells as well as slowing or arresting tumor cell growth.

Exemplary solid tumors include, but are not limited to, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), cervical cancer (e.g., cervical adenocarcinoma), colorectal cancer (e.g., colon cancer, rectal cancer, colorectal adenocarcinoma), gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), pancreatic cancer (e.g., pancreatic andenocarcinoma, intraductal papillary mucinous neoplasm (IPMN)), prostate cancer (e.g., prostate adenocarcinoma), skin cancer (e.g., squamous cell carcinoma (SCC), keratoacanthoma (A), melanoma, basal cell carcinoma (BCC)) and soft tissue sarcoma (e.g., malignant fibrous histiocytoma (MFH), liposarcoma, malignant peripheral nerve sheath tumor (MPNST), chondrosarcoma, fibrosarcoma, myxosarcoma, osteosarcoma).

In some embodiments, the disclosure relates to a method of treating a cancer of hematopoietic origin comprising administering to a subject a gamma selective compound (e.g., Compound 1). In certain embodiments, the cancer of hematopoietic origin is lymphoma or leukemia. In some embodiments, the cancer of hematopoietic origin is selected from acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), Hodgkin lymphoma (HL), non-Hodgkin lymphoma (NHL), follicular lymphoma, diffuse large B-cell lymphoma (DLBCL), mantle cell lymphoma (MCL), mastocytosis (e.g., systemic mastocytosis), multiple myeloma (MM), myelodysplastic syndrome (MDS), myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), and hypereosinophilic syndrome (HES)).

In some embodiments, the disclosure relates to a method of treating a solid tumor comprising administering to a subject a gamma selective compound (e.g., Compound 1). In some embodiments, the solid tumor is selected from ovarian cancer, colon cancer, fibrosarcoma, pancreatic cancer, lung cancer, breast cancer, lymphoma, melanoma, and glioblastoma.

In some embodiments, the disclosure relates to a method of treating an inflammatory disease comprising administering to a subject a gamma selective compound (e.g., Compound 1).

In some embodiment, the gamma selective compound has a delta/gamma selectivity ratio of >1 to <10, 10 to <50, or 50 to <350 can be combined with a compound that has a gamma/delta selectivity ratio of greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000.

Patients that can be treated with a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, according to the methods as provided herein include, for example, but not limited to, patients that have been diagnosed as having psoriasis; restenosis; atherosclerosis; ischemic stroke, BPH; breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute lymphoblastic leukemia, chronic myelogenous leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Müllerian tumor; oral cavity and oropharyngeal cancers such as, hypopharyngeal cancer, laryngeal cancer, nasopharyngeal cancer, and oropharyngeal cancer; stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas, carcinoids or carcinoid tumors; rectal cancer; and colon cancer.

Patients that can be treated with compounds provided herein, or pharmaceutically acceptable salt, ester, prodrug, solvate, hydrate or derivative of said compounds, according to the methods provided herein include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrom's macroglobulinemia.

Without being limited by a particular theory, in one embodiment, the cancer or disease being treated or prevented, such as a blood disorder or hematologic malignancy, has a high expression level of one or more PI3K isoform(s) (e.g., PI3K-α, PI3K-β, PI3K-δ, or PI3K-γ or a combination thereof). In one embodiment, the cancer or disease that can be treated or prevented by methods, compositions, or kits provided herein includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, transformed CLL, Richter syndrome Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma (FL), Waldenstrom's macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS. In one embodiment, the hematologic malignancy is relapsed. In one embodiment, the hematologic malignancy is refractory. In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In exemplary embodiments, the cancer or hematologic malignancy is CLL. In exemplary embodiments, the cancer or hematologic malignancy is CLL/SLL. In exemplary embodiments, the cancer or hematologic malignancy is transformed CLL or Richter syndrome. In exemplary embodiments, the cancer or hematologic malignancy is SLL.

In one embodiment, without being limited by a particular theory, a compound provided herein (e.g., a PI3K-γ selective compound provided herein) inhibits the migration and/or activation of T-cells and myeloid cells (e.g., macrophages or polarized M2 macrophages), reducing survival and/or proliferative support provided by those cells to malignant CLL cells within the tumor microenvironment (TME). In one embodiment, without being limited by a particular theory, the migration of CD3+T cells to the CLL-associated chemokine CXCL12 is blocked by a compound provided herein (e.g., a PI3K-γ selective compound provided herein). In another embodiment, without being limited by a particular theory, a compound provided herein (e.g., a PI3K-γ selective compound provided herein) block the myeloid cell mediated re-growth of a cancer following chemotherapy through its effects on inhibiting the post-chemotherapy migration of myeloid cells into a tumor.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sézary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sézary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom's macroglobulinemia (lymphoplasmacytic lymphoma). In another embodiment, the B cell lymphoma is marginal zone lymphoma (MZL). In another embodiment, the B cell lymphoma is MCL. In another embodiment, the B cell lymphoma is HL. In another embodiment, the B cell lymphoma is iNHL. In another embodiment, the B cell lymphoma is DLBCL. In another embodiment, the B cell lymphoma is Richter's lymphoma.

In one embodiment, the cancer or hematologic malignancy is a T cell lymphoma. In a specific embodiment, provided herein is a method of treating or managing a T cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a T cell lymphoma comprising administering to a patient a therapeutically effective amount of a compound provided herein, or a pharmaceutically acceptable derivative (e.g., salt or solvate) thereof. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sézary syndrome. In a specific embodiment, provided herein is a method of treating or managing Sézary syndrome comprising administering to a patient a therapeutically effective amount of a compound provided herein, or a pharmaceutically acceptable derivative (e.g., salt or solvate) thereof. Also provided herein is a method of treating or lessening one or more of the symptoms associated with Sézary syndrome comprising administering to a patient a therapeutically effective amount of a compound provided herein, or a pharmaceutically acceptable derivative (e.g., salt or solvate) thereof. The symptoms associated with Sézary syndrome include, but are not limited to, epidermotropism by neoplastic CD4+ lymphocytes, Pautrier's microabscesses, erythroderma, lymphadenopathy, atypical T cells in the peripheral blood, and hepatosplenomegalyIn one embodiment, the therapeutically effective amount for treating or managing Sézary syndrome is from about 25 mg to 75 mg, administered twice daily. In other embodiments, the therapeutically effective amount is from about 50 mg to about 75 mg, from about 30 mg to about 65 mg, from about 45 mg to about 60 mg, from about 30 mg to about 50 mg, or from about 55 mg to about 65 mg, each of which is administered twice daily. In one embodiment, the effective amount is about 60 mg, administered twice daily.

In one embodiment, the cancer or hematologic malignancy is relapsed. In one embodiment, the cancer or hematologic malignancy is refractory. In certain embodiments, the cancer being treated or prevented is a specific sub-type of cancer described herein. In certain embodiments, the hematologic malignancy being treated or prevented is a specific sub-type of hematologic malignancy described herein. Certain classifications of type or sub-type of a cancer or hematologic malignancy provided herein is known in the art. Without being limited by a particular theory, it is believed that many of the cancers that become relapsed or refractory develop resistance to the particular prior therapy administered to treat the cancers. Thus, without being limited by a particular theory, a compound provided herein can provide a second line therapy by providing an alternative mechanism to treat cancers different from those mechanisms utilized by certain prior therapies. Accordingly, in one embodiment, provided herein is a method of treating or managing cancer or hematologic malignancy comprising administering to a patient a therapeutically effective amount of a compound provided herein, or a pharmaceutically acceptable derivative (e.g., salt or solvate) thereof, wherein the cancer or hematologic malignancy is relapsed after, or refractory to, a prior therapy.

In exemplary embodiments, the cancer or hematologic malignancy is refractory iNHL. In exemplary embodiments, the cancer or hematologic malignancy is refractory CLL. In exemplary embodiments, the cancer or hematologic malignancy is refractory SLL. In exemplary embodiments, the cancer or hematologic malignancy is refractory to rituximab therapy. In exemplary embodiments, the cancer or hematologic malignancy is refractory to chemotherapy. In exemplary embodiments, the cancer or hematologic malignancy is refractory to radioimmunotherapy (RIT). In exemplary embodiments, the cancer or hematologic malignancy is iNHL, FL, splenic marginal zone, nodal marginal zone, extranodal marginal zone, or SLL, the cancer or hematologic malignancy is refractory to rituximab therapy, chemotherapy, and/or RIT.

In another exemplary embodiment, the cancer or hematologic malignancy is lymphoma, and the cancer is relapsed after, or refractory to, the treatment by a BTK inhibitor such as, but not limited to, ibrutinib or ONO-4059. In another exemplary embodiment, the cancer or hematologic malignancy is CLL, and the cancer is relapsed after, or refractory to, the treatment by a BTK inhibitor such as, but not limited to, ibrutinib and AVL-292.

In certain embodiments, provided herein are methods of treating or preventing a solid tumor in a subject, comprising administering to the subject a therapeutically effective amount of a compound provided herein (e.g., a selective PI3K-γ inhibitor, e.g., Compound 1), or a pharmaceutically acceptable form thereof.

In one embodiment, the solid tumor is selected from one or more of: a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the compound, or a pharmaceutically acceptable form thereof, is administered at a dose sufficient to cause a decrease in tumor growth of at least 10%, 20%, 30%, 40%, or 50% compared to a reference value, after administration of the compound.

In one embodiment, the method further comprises administering an immunomodulator to the subject. In one embodiment, the immunomodulator is a PDL-1 inhibitor or an anti-PDL-1 antibody.

In one embodiment, the method further comprises administering a PI3K-delta inhibitor to the subject.

In one embodiment, the compound, or a pharmaceutically acceptable form thereof, is administered at a dose such that the level of the compound in the subject is higher than the compound's IC50 of PI3K-gamma inhibition during at least 70%, 80%, 90%, 95%, 97%, 98%, or 99% of a selected time period, e.g., 6 hours, 12 hours, 24 hours, or 48 hours, immediately following the administration. In one embodiment, the compound, or a pharmaceutically acceptable form thereof, is administered at a dose such that the level of the compound in the subject is lower than the compound's IC50 of PI3K-delta inhibition during at least 70%, 80%, 90%, 95%, 97%, 98%, or 99% of a selected time period, e.g., 6 hours, 12 hours, 24 hours, or 48 hours, immediately following the administration. In one embodiment, the level of the compound is measured from the subject's plasma. In one embodiment, the level of the compound is measured from the subject's tissue.

In one embodiment, the subject has been previously treated with cyclophosphamide, docetaxel, paclitaxel, 5-FU, or temozolomide.

In one embodiment, the anti-tumor effect of the compound is maintained for a period of time after the discontinuation of treatment with the compound. In one embodiment, the period of time is at least 1 day, 2 days, 3 days, 4 days, 5 days, or 6 days.

Treatment of an Inflammatory Disorder

In one embodiment, provided herein is a method of treating an inflammation disorder, including autoimmune diseases in a subject. The method comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of autoimmune diseases include but are not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis (e.g., inflammatory alopecia), Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatisis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, that selectively inhibits PI3K-δ and/or PI3K-γ as compared to all other type I PI3 kinases. Such selective inhibition of PI3K-δ and/or PI3K-γ can be advantageous for treating any of the diseases or conditions described herein. For example, selective inhibition of PI3K-δ and/or PI3K-γ can inhibit inflammatory responses associated with inflammatory diseases, autoimmune disease, or diseases related to an undesirable immune response including, but not limited to asthma, emphysema, allergy, dermatitis, rheumatoid arthritis, psoriasis, lupus erythematosus, anaphylaxsis, or graft versus host disease. Selective inhibition of PI3K-δ and/or PI3K-γ can further provide for a reduction in the inflammatory or undesirable immune response without a concomitant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one or more of the subject methods are effective in ameliorating symptoms associated with rheumatoid arthritis including, but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, or 60%, or about 75% to 90%. In another aspect, the subject methods are effective in reducing knee inflammation by at least about 2%, 5%, 10%, 15%, 20%, 25%, 30%, 50%, or 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, or 87%, or about 90% or more. In another aspect, the subject methods are effective in reducing ankle histopathology scores by about 5%, 10%, 15%, 20%, 25%, 30%, 40%, 50%, 60%, 75%, 80%, or 90%, or more. In still another aspect, the subject methods are effective in reducing knee histopathology scores by about 5%, 10%, 15%, 20%, 25%, 30%, 40%, 50%, 60%, 75%, 80%, or 90%, or more.

In certain embodiments, provided herein are methods of treating or preventing arthritis in a subject, comprising administering to the subject a therapeutically effective amount of a compound provided herein (e.g., a selective PI3K-γ inhibitor, e.g., Compound 1), or a pharmaceutically acceptable form thereof. In one embodiment, the treatment results in reduction of periosteal bone formation in the subject. In one embodiment, the treatment results in at least 10%, 20%, 40%, 47%, 50%, 52%, 60%, 80%, or 82% reduction of periosteal bone formation in the subject, compared to a reference value. In one embodiment, the periosteal bone formation is measured by histopathology score or periosteal bone width. In one embodiment, the treatment results in at least 10%, 20%, 27%, 30%, 36%, 40%, 45%, 50%, or 57% reduction of inflammation, at least 10%, 20%, 28%, 30%, 40%, 44%, 50%, or 60%, 70%, or 71% reduction of pannus, at least 10%, 20%, 28%, 30%, 40%, 45%, 50%, or 59% reduction of cartilage damage, or at least 10%, 20%, 25%, 30%, 40%, 44%, 50%, 60%, or 65% reduction of bone resorption in the subject, compared to a reference value. In one embodiment, wherein the treatment results in reduction of joint swelling or anti-collagen level in the subject.

In some embodiments, provided herein are methods for treating disorders or conditions in which the δ isoform of PI3K is implicated to a greater extent than other PI3K isoforms such as PI3K-α and/or PI3K-β. In some embodiments, provided herein are methods for treating disorders or conditions in which the γ isoform of PI3K is implicated to a greater extent than other PI3K isoforms such as PI3K-α and/or PI3K-β. Selective inhibition of PI3K-δ and/or PI3K-γ can provide advantages over using less selective compounds which inhibit PI3K-α and/or PI3K-β, such as an improved side effects profile or lessened reduction in the ability to reduce a bacterial, viral, and/or fungal infection.

In other embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat respiratory diseases including, but not limited to, diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein is used for the treatment of asthma. Also, a compound provided herein, or a pharmaceutically acceptable form thereof, or a pharmaceutical composition described herein, can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In certain embodiments, provided herein are methods of reducing neutrophil migration or infiltration in a subject suffering from an inflammatory disease, comprising administering to the subject a therapeutically effective amount of a compound provided herein (e.g., a selective PI3K-γ inhibitor, e.g., Compound 1), or a pharmaceutically acceptable form thereof. In one embodiment, the neutrophil migration or infiltration is reduced by at least about 10%, 20%, 40%, 60%, 80%, or 90% compared to a reference value, after administration of the compound. In one embodiment, the inflammatory disease is selected from the group consisting of COPD, arthritis, asthma, psoriasis, scleroderma, myositis, sarcoidosis, dermatomyositis, CREST syndrome, systemic lupus erythematosus, Sjorgren syndrome, encephalomyelitis, and inflammatory bowel disease (IBD). In one embodiment, the inflammatory disease is COPD or arthritis. In one embodiment, the subject is unresponsive or refractory to a PI3K-delta inhibitor treatment.

Treatment of Other Disorders or Conditions

In some embodiments, the disclosure provides a method of treating diseases related to vasculogenesis or angiogenesis in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method is for treating a disease selected from tumor angiogenesis, chronic inflammatory disease such as rheumatoid arthritis and chronic inflammatory demyelinating polyneuropathy, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of cardiovascular conditions include, but are not limited to, atherosclerosis, restenosis, vascular occlusion and carotid obstructive disease.

In some embodiments, the disclosure relates to a method of treating diabetes in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein.

In addition, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used to treat acne. In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of multiorgan failure. Also provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the prevention of blastocyte implantation in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders involving platelet aggregation or platelet adhesion, including, but not limited to, Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of a disease which is skeletal muscle atrophy, skeletal or muscle hypertrophy. In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

Additionally, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of bursitis, lupus, acute disseminated encephalomyelitis (ADEM), Addison's disease, antiphospholipid antibody syndrome (APS), amyloidosis (including systemic and localized amyloidosis; and primary and secondary amyloidosis), aplastic anemia, autoimmune hepatitis, coeliac disease, crohn's disease, diabetes mellitus (type 1), eosinophilic gastroenterides, goodpasture's syndrome, graves' disease, guillain-barré syndrome (GBS), hashimoto's disease, inflammatory bowel disease, lupus erythematosus (including cutaneous lupus erythematosus and systemic lupus erythematosus), myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, pigmented villonodular synovitis (also known as tenosynovial giant cell tumor), tendonitis, tonsillitis, uveitis (e.g., ocular uveitis), vaginitis, vasculitis, or vulvitis.

Further, the compounds provided herein may be used for the treatment of Perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, ocular lymphoma, MALT lymphoma, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressler syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other aspects, the compounds provided herein are used for the treatment of Autoimmune hepatitis, Jejunitis, Mesenteritis, Mucositis, Nonalcoholic steatohepatitis, Non-viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohn's disease, Diverticulitis, Enteritis, Enterocolitis, Enterohepatitis, Eosinophilic esophagitis, Esophagitis, Gastritis, Hemorrhagic enteritis, Hepatitis, Hepatitis virus infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Bruton's disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Nonne Milroy Meige syndrome, Spleen disease, Splenomegaly, Thymoma, Thymus disease, Perivasculitis, Phlebitis, Pleuropericarditis, Polyarteritis nodosa, Vasculitis, Takayasus arteritis, Temporal arteritis, Thromboangiitis, Thromboangiitis obliterans, Thromboendocarditis, Thrombophlebitis, or COPD.

In another aspect, provided herein are methods of disrupting the function of a leukocyte or disrupting a function of an osteoclast. The method includes contacting the leukocyte or the osteoclast with a function disrupting amount of a compound provided herein.

In another aspect, provided herein are methods for the treatment of an ophthalmic disease by administering one or more of compounds provided herein, or pharmaceutically acceptable forms thereof, or pharmaceutical compositions as provided herein, to the eye of a subject.

Methods are further provided for administering the compounds provided herein via eye drop, intraocular injection, intravitreal injection, topically, or through the use of a drug eluting device, microcapsule, implant, or microfluidic device. In some cases, the compounds provided herein are administered with a carrier or excipient that increases the intraocular penetrance of the compound such as an oil and water emulsion with colloid particles having an oily core surrounded by an interfacial film.

In certain embodiments, provided herein are methods of treating, preventing, and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: Crohn's disease; cutaneous lupus; multiple sclerosis; rheumatoid arthritis; and systemic lupus erythematosus.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: ankylosing spondylitis; chronic obstructive pulmonary disease; myasthenia gravis; ocular uveitis, psoriasis; and psoriatic arthritis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: adult-onset Still's disease; inflammatory alopecia; amyloidosis; antiphospholipid syndrome; autoimmune hepatitis; autoimmune skin disease, Behcet's disease; chronic inflammatory demyelinating polyneuropathy; eosinophilic gastroenteritis; inflammatory myopathies, pemphigus, polymyalgia rheumatica; relapsing polychondritis; Sjogren's syndrome; temporal arthritis; ulcerative colitis; vasculis; vitiligo, and Wegner's granulomatosis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: gout flare; sarcoidosis; and systemic sclerosis.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: asthma; arthritis (e.g., rheumatoid arthritis and psoriatic arthritis); psoriasis; scleroderma; myositis (e.g., dermatomyositis); lupus (e.g., cutaneous lupus erythematosus ("CLE") or systemic lupus erythematosus ("SLE")); or Sjögren's syndrome.

Efficacy of a compound provided herein in treating, preventing and/or managing the disease or disorder can be tested using various animal models known in the art. For example: efficacy in treating, preventing and/or managing asthma can be assessed using ova induced asthma model described, for example, in Lee et al. (2006) *J Allergy Clin Immunol* 118(2):403-9; efficacy in treating, preventing and/or managing arthritis (e.g., rheumatoid or psoriatic arthritis) can be assessed using autoimmune animal models described, for example, in Williams et al. (2010) *Chem Biol*, 17(2): 123-34, WO 2009/088986, WO2009/088880, and WO 2011/008302; efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke et al. (2007) *Clinics in Dermatology*, 25: 596-605; efficacy in treating, preventing and/or managing fibrosis or fibrotic condition can be assessed using the unilateral ureteral obstruction model of renal fibrosis (see Chevalier et al., *Kidney International* (2009) 75:1145-1152), the bleomycin induced model of pulmonary fibrosis (see Moore and Hogaboam, *Am. J. Physiol. Lung. Cell. Mol. Physiol.* (2008) 294:L152-L160), a variety of liver/biliary fibrosis models (see Chuang et al., *Clin Liver Dis* (2008) 12:333-347 and Omenetti, A. et al. (2007) *Laboratory Investigation* 87:499-514 (biliary duct-ligated model)), or a number of myelofibrosis mouse models (see Varicchio, L. et al. (2009) *Expert Rev. Hematol.* 2(3): 315-334); efficacy in treating, preventing and/or managing scleroderma can be assessed using mouse model induced by repeated local injections of bleomycin ("BLM") described, for example, in Yamamoto et al. (1999) *J Invest Dermatol* 112: 456-462; efficacy in treating, preventing and/or managing dermatomyositis can be assessed using myositis mouse model induced by immunization with rabbit myosin described, for example, in Phyanagi et al. (2009) *Arthritis & Rheumatism*, 60(10): 3118-3127; efficacy in treating, preventing and/or managing lupus (e.g., CLE or SLE) can be assessed using various animal models described, for example, in Ghoreishi et al. (2009) *Lupus,* 19: 1029-1035, Ohl et al. (2011) *Journal of Biomedicine and Biotechnology*, Article ID 432595 (14 pages), Xia et al. (2011) *Rheumatology,* 50:2187-2196, Pau et al. (2012) *PLoS ONE,* 7(5): e36761 (15 pages), Mustafa et al. (2011) *Toxicology,* 290: 156-168, Ichikawa et al. (2012) *Arthritis and Rheumatism,* 62(2): 493-503, Ouyang et al. (2012) *J Mol Med*, DOI 10.1007/s00109-012-0866-3 (10 pages), Rankin et al. (2012) *Journal of Immunology,* 188:1656-1667; and efficacy in treating, preventing and/or managing Sjögren's syndrome can be assessed using various mouse models described, for example, in Chiorini et al. (2009) *Journal of Autoimmunity,* 33: 190-196.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

In one embodiment, provided herein is a method of treating, preventing and/or managing arthritis. As used herein, "arthritis" encompasses all types and manifestations of arthritis. Examples include, but are not limited to, crystalline arthritis, osteoarthritis, psoriatic arthritis, gouty arthritis, reactive arthritis, rheumatoid arthritis and Reiter's arthritis. In one embodiment, the disease or disorder is rheumatoid arthritis. In another embodiment, the disease or disorder is psoriatic arthritis. Also provided herein is a method of treating, preventing and/or managing one or more symptoms associated with arthritis. Examples of the symptoms include, but are not limited to, joint pain, which progresses into joint deformation, or damages in body organs such as in blood vessels, heart, lungs, skin, and muscles.

In one embodiment, provided herein is a method of treating, preventing and/or managing psoriasis. As used herein, "psoriasis" encompasses all types and manifestations of psoriasis. Examples include, but are not limited to, plaque psoriasis (e.g., chronic plaque psoriasis, moderate plaque psoriasis and severe plaque psoriasis), guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Also provided herein is a method of treating, preventing and/or managing one or more symptoms associated with psoriasis. Examples of the symptoms include, but are not limited to: red patches of skin covered with silvery scales; small scaling spots; dry, cracked skin that may bleed; itching; burning; soreness; thickened, pitted or ridged nails; and swollen and stiff joints.

In one embodiment, provided herein is a method of treating, preventing and/or managing fibrosis and fibrotic condition. As used herein, "fibrosis" or "fibrotic condition" encompasses all types and manifestations of fibrosis or fibrotic condition. Examples include, but are not limited to, formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein;

reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus. In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods provided herein is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In one embodiment, provided herein is a method of treating, preventing and/or managing scleroderma. Scleroderma is a group of diseases that involve hardening and tightening of the skin and/or other connective tissues. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin). In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

Localized scleroderma (localized cutaneous fibrosis) includes morphea and linear scleroderma. Morphea is typically characterized by oval-shaped thickened patches of skin that are white in the middle, with a purple border. Linear scleroderma is more common in children. Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyly, and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology,* 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In one embodiment, provided herein is a method of treating, preventing and/or managing inflammatory myopathies. As used herein, "inflammatory myopathies" encompass all types and manifestations of inflammatory myopathies. Examples include, but are not limited to, muscle weakness (e.g., proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo1 antibodies), anti-signal recognition particle antibodies (anti-SRP), anti-Mi-2 antibodies, anti-p155 antibodies, anti-PM/Sci antibodies, and anti-RNP antibodies.

The inflammatory myopathy can be an acute inflammatory myopathy or a chronic inflammatory myopathy. In some embodiments, the inflammatory myopathy is a chronic inflammatory myopathy (e.g., dermatomyositis, polymyositis, or inclusion body myositis). In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

In another embodiment, provided herein is a method of treating, preventing and/or managing a skin condition (e.g., a dermatitis). In some embodiments, the methods provided herein can reduce symptoms associated with a skin condition (e.g., itchiness and/or inflammation). In some such embodiments, the compound provided herein is administered topically (e.g., as a topical cream, eye-drop, nose drop or nasal spray). In some such embodiments, the compound is a PI3K-delta inhibitor (e.g., a PI3K inhibitor that demonstrates greater inhibition of PI3K-delta than of other PI3K isoforms). In some embodiments, the PI3K-delta inhibitor prevents mast cell degranulation.

As used herein, "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritis), swelling (edema), hay fever, anaphalaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes. In some embodiments, the symptom associated with inflammatory myopathy, or the skin condition or symptom associated with the skin condition, is a skin rash or itchiness (pruritis) caused by a skin rash.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., utricaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α, TNF-α, IL-6, IL-8, IL-1, or a combination thereof. In certain embodiments, the subject exhibits an elevated level of IFN-α. In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In one embodiment, provided herein is a method of treating, preventing and/or managing myositis. As used herein, "myositis" encompasses all types and manifestations of myositis. Examples include, but are not limited to, myositis ossificans, fibromyositis, idiopathic inflammatory myopathies, dermatomyositis, juvenile dermatomyositis, polymyositis, inclusion body myositis and pyomyositis. In one embodiment, the disease or disorder is dermatomyositis. Also provided herein is a method of treating, preventing and/or managing one or more symptoms associated with myositis. Examples of the symptoms include, but are not limited to: muscle weakness; trouble lifting arms; trouble swallowing or breathing; muscle pain; muscle tenderness; fatigue; fever; lung problems; gastrointestinal ulcers; intestinal perforations; calcinosis under the skin; soreness; arthritis; weight loss; and rashes.

In one embodiment, provided herein is a method of treating, preventing and/or managing lupus. As used herein, "lupus" refers to all types and manifestations of lupus. Examples include, but are not limited to, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, hematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. In one embodiment, the lupus is systemic lupus erythematosus (SLE), cutaneous lupus erythematosus (CLE), drug-induced lupus, or neonatal lupus. In another embodiment, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is chronic discloid lupus erythematosus (CDLE) or lupus erythematosus profundus (LEP) (also known as lupus erythematosus panniculitis). Types, symptoms, and pathogenesis of CLE are described, for example, in Wenzel et al. (2010), *Lupus*, 19, 1020-1028.

In one embodiment, provided herein is a method of treating, preventing and/or managing Sjögren's syndrome. As used herein, "Sjögren's syndrome" refers to all types and manifestations of Sjögren's syndrome. Examples include, but are not limited to, primary and secondary Sjögren's syndrome. Also provided herein is a method of treating, preventing and/or managing one or more symptoms associated with Sjögren's syndrome. Examples of the symptoms include, but are not limited to: dry eyes; dry mouth; joint pain; swelling; stiffness; swollen salivary glands; skin rashes; dry skin; vaginal dryness; persistent dry cough; and prolonged fatigue.

In some embodiments, provided herein is a method of treating a bone disorder in a subject that comprises administering to said subject a therapeutically effective amount of a compound provided herein (e.g., a PI3K-γ selective compound provided herein), or a pharmaceutically acceptable form (e.g., pharmaceutically acceptable salts, hydrates, solvates, isomers, prodrugs, and isotopically labeled derivatives) thereof, or a pharmaceutical composition as provided herein. As used herein, "bone disorder" encompasses all types and manifestations of bone disorders. Exemplary bone disorders include, but are not limited to, bone cancer, bone metastases, osteoporosis, fracture repair, avascular necrosis (osteonecrosis), bone spur (osteophytes), craniosynostosis, Coffin-Lowry syndrome, fibrodysplasia ossificans progressive, fibrous dysplasia, Fong Disease (Nail-patella syndrome), Giant cell tumor of bone, Greenstick Fracture, hypophosphatasia, Klippel-Feil syndrome, metabolic bone disease, osteoarthritis, osteitis deformans (Paget's disease of bone), osteitis fibrosa cystica (osteitis fibrosa or Von Recklinghausen's disease of bone), osteitis pubis, condensing osteitis (osteitis condensas), osteochondritis dissecans, osteochondroma (bone tumor), osteogenesis imperfect, osteomalacia, osteomyelitis, osteopenia, osteopetrosis, porotic hyperostosis, primary hyperparathyroidism, renal osteodystrophy, Salter-Harris fractures, and water on the knee. In one embodiment, the bone disorder is a systemical bone disorder. In another embodiment, the bone disorder is a topical bone disorder. In one embodiment, the bone disorder is associated with excess bone formation. In another embodiment, the bone disorder is associated with excess bone resorption. In one embodiment, without being limited by a particular theory, a compound provided herein inhibits differentiation of osteoclasts from bone marrow macrophages.

In some embodiments, a symptom associated with the disease or disorder provided herein is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease is statistically significant, for example, as assessed using an appropriate parametric or non-parametric statistical comparison.

Methods of Treatment, Prevention and/or Management for Pulmonary or Respiratory Disorders Without being limited by a particular theory, it was found that administering a compound provided herein (e.g., Compound 1) by inhalation can accord various therapeutic benefits as described herein in treating, preventing and/or managing pulmonary or respiratory diseases. Accordingly, in certain embodiments, provided herein is a method of treating, preventing, and/or managing a pulmonary or respiratory disease in a subject, comprising administering to a subject in need thereof by inhalation a therapeutically or prophylactically effective amount of a compound provided herein, or an enantiomer, a mixture of enantiomers, or a mixture of two or more diastereomers thereof, or a pharmaceutically acceptable form thereof.

In addition, without being limited by a particular theory, it was found that administering a compound provided herein by inhalation results in a prolonged retainment of the compound in patient's lung. Thus, in some embodiments, provided herein is a method of eliciting prolonged anti-inflammatory effect in lung in a subject suffering from a pulmonary or respiratory disease, comprising administering to the subject by inhalation a therapeutically or prophylactically effective amount of a compound provided herein, or an enantiomer, a mixture of enantiomers, or a mixture of two or more diastereomers thereof, or a pharmaceutically acceptable form thereof, wherein the compound is retained in lung for a prolonged period (e.g., a period longer than what is provided by oral administration).

In some embodiments, the compound is retained in lung for about hour, about 3 hours, about 6 hours, about 12 hours, about 24 hours, about 48 hours, or about 72 hours longer than what is provided by oral administration.

In some embodiments, more than 80%, more than 70%, more than 60%, more than 50%, more than 40%, more than 30%, or more than 20% of the amount of the compound as initially administered to patient remains in lung at 24 hours after administration by inhalation.

In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 5 hours after the administration. In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 12 hours after the administration. In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 24 hours after the administration.

In some embodiments, the compound is administered at a dose of less than 0.01 µg/kg/day, less than 0.02 µg/kg/day, less than 0.05 µg/kg/day, less than 0.1 µg/kg/day, less than 0.2 µg/kg/day, less than 0.5 µg/kg/day, less than 1 µg/kg/day, less than 2 µg/kg/day, less than 5 µg/kg/day, less than 10 µg/kg/day, less than 20 µg/kg/day, less than 50 µg/kg/day, or less than 100 µg/kg/day. In some embodiments, the compound is administered at a dose of about 0.01 µg/kg/day, about 0.02 µg/kg/day, about 0.05 µg/kg/day, about 0.1 µg/kg/day, about 0.2 µg/kg/day, about 0.5 µg/kg/day, about 1 µg/kg/day, about 2 µg/kg/day, about 5 µg/kg/day, about 10 µg/kg/day, about 20 µg/kg/day, about 50 µg/kg/day, or about 100 µg/kg/day. In some embodiments, the compound is administered at a dose of from about 0.01 µg/kg/day to about 100 µg/kg/day, from about 0.01 µg/kg/day to about 50 µg/kg/day, from about 0.01 µg/kg/day to about 20 µg/kg/day, from about 0.01 µg/kg/day to about 10 µg/kg/day, from about 0.01 µg/kg/day to about 5 µg/kg/day, from about 0.01 µg/kg/day to about 1 µg/kg/day, from about 0.05 µg/kg/day to about 1 µg/kg/day, or from about 0.1 µg/kg/day to about 1 µg/kg/day.

In one embodiment, the compound is administered once daily (QD). In another embodiment, the compound is administered twice daily (BID). In another embodiment, the compound is administered three time daily (TID). In another embodiment, the compound is administered four times daily (QID).

In one embodiment, the subject is a mammal. In another embodiment, the subject is a human.

In one embodiment, provided herein is a method of treating, preventing, and/or managing a pulmonary or respiratory disease in a subject, comprising administering to a subject in need thereof by inhalation a therapeutically or prophylactically effective amount of a PI3Kγ inhibitor, or an enantiomer, a mixture of enantiomers, or a mixture of two or more diastereomers thereof, or a pharmaceutically acceptable form thereof. In some embodiments, the PI3Kγ inhibitor has a delta/gamma selectivity ratio of greater than about 1 to <10, greater than about 10 to <50, or greater than about 50 to <350. In some embodiments, the PI3Kγ inhibitor has a delta/gamma selectivity ratio of greater than about 1, greater than about 5, greater than about 10, greater than about 15, greater than about 20, greater than about 25, greater than about 50, greater than about 75, greater than about 100, greater than about 150, greater than about 200, greater than about 250, greater than about 300, greater than about 350, greater than about 500, or greater than about 1000.

In one embodiment, provided herein is a method of treating, preventing, and/or managing a pulmonary or respiratory disease in a subject, comprising administering to a subject in need thereof by inhalation a therapeutically or prophylactically effective amount of Compound 1, or an enantiomer, a mixture of enantiomers, or a mixture of two or more diastereomers thereof, or a pharmaceutically acceptable form thereof. In one embodiment, Compound 1 is a PI3Kγ inhibitor. In one embodiment, the compound, e.g., Compound 1 has a delta/gamma selectivity ratio of greater than about 1 to <10, greater than about 10 to <50, or greater than about 50 to <350. In one embodiment, the compound, e.g., Compound 1 has a delta/gamma selectivity ratio of greater than about 50 to <350. In one embodiment, the compound, e.g., Compound 1 has a delta/gamma selectivity ratio of greater than about 50 to <150. In one embodiment, the compound, e.g., Compound 1 has a delta/gamma selectivity ratio of greater than about 75 to <125. In one embodiment, the compound has a delta/gamma selectivity ratio of greater than about 100. In some embodiments, the compound has a delta/gamma selectivity ratio of greater than about 1, greater than about 5, greater than about 10, greater than about 15, greater than about 20, greater than about 25, greater than about 50, greater than about 75, greater than about 100, greater than about 150, greater than about 200, greater than about 250, greater than about 300, greater than about 350, greater than about 500, or greater than about 1000.

Administration by Inhalation

Many diseases of the respiratory tract are known to respond to treatment by the direct application of therapeutic agents by inhalation. Such administration can result in the better utilization of the medicament in that the drug is deposited directly at the desired site and where its action may be required. Therefore, without being limited by a particular theory, administration by inhalation can significantly reduce the dose required to achieve therapeutic efficacy, which, in turn can result in marked reduction of undesired side effects and cost of medicament. It is typically accepted in the industry that the bioavailability of the drug is optimum when the drug particles delivered to the respiratory tract are between 1 to 5 microns in size.

Various methods and devices can be used to deliver a compound provided herein by inhalation. The inhalable formulation can be administered via the mouth or nose ultimately for pulmonary delivery thereof. For example, dry powder inhalers (DPIs), which usually have a means for introducing the drug (active drug plus carrier) into a high velocity air stream, can be used to practice the methods provided herein. The high velocity air stream is used as the primary mechanism for breaking up the cluster of micronized particles or separating the drug particles from the carrier. Inhalation devices useful for dispensing powder forms of medicament such as those described in U.S. Pat. Nos. 3,507,277; 3,518,992; 3,635,219; 3,795,244; and 3,807,400, are encompassed by the current disclosure. In certain embodiments, such devices also include propeller means, which upon inhalation aid in dispensing the powder out of the capsule, so that it is not necessary to rely solely on the inhaled air to suction powder from the capsule. (See, e.g., U.S. Pat. Nos. 2,517,482; 3,831,606; 3,948,264; and 5,458, 135, all of which are incorporated herein by reference). In certain embodiments, utilization of vibration to facilitate suspension of power into an inhaled gas stream and which utilizes synthetic jetting to aerosolize drug powder from a blister pack is also provided herein. (See, e.g., U.S. Pat. Nos. 7,318,434 and 7,334,577, incorporated herein by reference). In some embodiments, controlled aliquots or doses of a medication or pre-packaged drug in a blister pack, which includes a frangible crowned top element which can be conical, conical with a rounded point, rounded, such as those described in U.S. Pat. No. 7,080,644, are also encompassed.

In certain embodiments, a compound provided herein is administered using metered dose inhalers (MDIs). MDIs typically have a pressurized canister filled with a liquid propellant. The drug is either suspended or dissolved in the propellant. The MDIs have a metering valve for metering out a known quantity of the propellant and hence the drug. When the canister is depressed against the MDI housing a known quantity of the propellant is discharged. The propellant evaporates leaving behind a fine aerosol of the drug suitable for inhalation by the patient. In certain embodiments, MDIs that contain a breath actuation mechanism a spacer are also encompassed herein.

In some embodiments, a compound provided herein is administered using nebulizers, such as the jet nebulizers. Nebulizers produce a fine aerosol mist/droplets which carry the drug either as a suspension or dissolved in the aqueous medium. The jet nebulizers use compressed air to atomize the aqueous solution. A drug can be administered to a patient with repetitive non-forced inhalation over a prolonged period of time.

Examples of devices suitable for such pulmonary delivery include, but are not limited to, air-jet, ultrasonic, or vibrating-mesh devices such as Pari LC Star, Aeroeclipse II, Prodose (HaloLite), Acorn II, T Up-draft II, Sidestream, AeroTech II, Mini heart, MisterNeb, Sonix 2000, MABIS-Mist II and other suitable aerosol systems. In some embodiments, the nebulizer is a vibrating-mesh nebulizer that could include an AERONEB PRO, AERONEB SOLO, AERONEB GO, AERONEB LAB, OMRON MICROAIR, PART EFLOW, RESPIRONICS I-NEB, or other suitable devices.

Pulmonary or Respiratory Diseases

Provided herein is a method of treating, preventing, and/or managing pulmonary or respiratory disease using a compound provided herein. Examples of pulmonary or respiratory disease include, but are not limited to, lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, post inflammatory pulmonary fibrosis, primary pulmonary hypertension, pulmonary thromboembolism, disorders of the pleura, disorders of the mediastinum, disorders of the diaphragm, disorders of the larynx, disorders of the trachea, acute lung injury, hypoventilation, hyperventilation, sleep apnea, acute respiratory distress syndrome, mesothelioma, sarcoma, graft rejection, graft versus host disease, lung cancer, allergic rhinitis, allergy, allergic bronchopulmonary aspergillosis, asbestosis, aspergilloma, aspergillosis, bronchiectasis, chronic bronchitis, emphysema, eosinophilic pneumonia, idiopathic pulmonary fibrosis, idiopathic interstitial pneumonia, non-specific interstitial pneumonia (NSIP), bronchiolitis obliterans with organizing pneumonia (BOOP, also called cryptogenic organizing pneumonia or COP), lymphocytic interstitial pneumonia (LIP), acute interstitial pneumonitis invasive pneumococcal disease, pneumococcal pneumonia, influenza, nontuberculous mycobacteria, pleural effusion, a pleural cavity disease, empyema, pleurisy, pneumoconiosis, pneumocytosis, respiratory viral infection, acute bronchitis, aspiration pneumonia, ventilator-associated pneumonia, pneumocystic jiroveci pneumonia, pneumonia, pulmonary actinomycosis, pulmonary alveolar proteinosis, pulmonary anthrax, pulmonary edema, pulmonary embolus, pulmonary embolism, acute chest syndrome, idiopathic pulmonary hemosiderosis, pulmonary hemorrhage, pulmonary hyperplasia, pulmonary inflammation, pulmonary histiocytosis X, eosinophilic granuloma, pulmonary Langerhan's cell histiocytosis, occupational lung disease, pneumopathy due to inhalation of dust, respiratory conditions due to chemical fumes and vapors, lipoid pneumonia, pulmonary hypertension, pulmonary arterial hypertension, pulmonary nocardiosis, pulmonary tuberculosis, pulmonary veno-occlusive disease, pulmonary vascular disease, rheumatoid lung disease, connective tissue disease-associated interstitial lung disease (e.g., systemic sclerosis (SSc or scleroderma)-associated interstitial lung disease, polymyositis-associated interstitial lung disease, dermatomyositis-associated interstitial lung disease, rheumatoid arthritis-associated interstitial lung disease, systemic lupus erythematosus-associated interstitial lung disease, interstitial lung disease associated with Sjögren's syndrome, mixed connective tissue disease-associated interstitial lung disease, and ankylosing spondylitis-associated interstitial lung disease), a restrictive lung disease, a respiratory tract infection (upper and lower), sarcoidosis, Wegener's granulomatosis (also known as granulomatosis with polyangiitis (GPA) or necrotizing granulomatous vasculitis (NGV)), Churg-Strauss Syndrome, microscopic polyangiitis (MPA), small cell lung carcinoma, non-small cell lung carcinoma, lymphangioleiomyomatosis (LAM), radiation-induced lung disease (also known as radiation pneumonitis), pulmonary vasculitis, viral pneumonia, pneumococcal pneumonia, bacterial pneumonia, bronchopneumonia, epithelial tumors, papillomas, adenomas, squamous cell carcinoma, small cell carcinoma, adenocarcinoma, large cell carcinoma, adenosquamous carcinoma, carcinoid tumor, carcinoma of salivary-gland type, soft tissue tumors, localized fibrous tumor, epithelioid hemangioendothelioma, pleuropulmonary blastoma, chondroma, calcifying fibrous pseudotumor of the pleura, congenital peribronchial myofibroblastic tumor, diffuse pulmonary lymphangiomatosis, desmoplastic small round cell tumor, mesothelial tumors, adenomatoid tumor, epithelioid mesothelioma, sarcomatoid mesothelioma, biphasic mesothelioma, hamartoma, sclerosing hemangioma, clear cell tumor, germ cell neoplasms, thymoma, melanoma, and secondary tumor. In certain embodiments, provided herein is a method of treating, preventing, and/or managing a lymphoproliferative disease using a compound provided herein. Examples of lymphoproliferative disease include, but are not limited to, lymphoid interstitial pneumonia, nodular lymphoid hyperplasia, and lymphomatoid granulomatosis.

In certain embodiments, the pulmonary or respiratory disease to be treated, prevented and/or managed using a compound provided herein is an obstructive lung disease or disorder. In some embodiments, the obstructive lung disease is acute respiratory distress syndrome (ARDS), asthma, bronchiectasis, bronchiolectasis, bronchiolitis, bronchitis, chronic obstructive pulmonary disease (COPD), or emphysema.

Chronic Obstructive Pulmonary Disease

In one embodiment, said obstructive lung disease or disorder is chronic obstructive pulmonary disease (COPD), e.g., as diagnosed by a forced expiratory air volume in 1 second ($FEV_1$) to forced vital capacity (FVC) ratio of less than 0.7. In another embodiment, administration of a compound provided herein results in a detectable rise in the $FEV_1$/FEC ratio above 0.7 after administration, e.g., a rise of 0.02, 0.03, 0.04, 0.05, 0.06, 0.07, 0.08, 0.09, 0.10, or more or more.

In one embodiment, provided herein is a method of reducing a COPD associated symptom in a subject, comprising administering a compound provided herein (e.g., Compound 1), or an enantiomer, a mixture of enantiomers, or a mixture of two or more diastereomers thereof, or a pharmaceutically acceptable form thereof, by inhalation in an amount sufficient to reduce the COPD associated symptom. In one embodiment, the subject is a mammalian subject, e.g., an animal model or as part of therapeutic protocol. In one embodiment, the compound is used as a single agent or in combination with another agent or therapeutic modality.

In one embodiment, provided herein is a method of treating, preventing, and/or managing COPD in a subject, comprising administering an effective amount of a compound provided herein (e.g., Compound 1), or an enantiomer, a mixture of enantiomers, or a mixture of two or more diastereomers thereof, or a pharmaceutically acceptable form thereof, to a subject in need thereof by inhalation. In one embodiment, the compound is administered as a single agent. In another embodiment, the compound is administered in combination with another agent or therapeutic modality.

As used herein, and unless otherwise specified, "COPD" or a "symptom" associated with COPD encompasses all types of manifestation of COPD as disclosed herein or as known in the art. Examples of COPD include, but are not limited to, emphysema, chronic bronchitis, and bronchiectasis. Examples of symptom of COPD include, but are not limited to, wheezing, coughing, chest tightness, shortness of breath, difficulty in breathing, coughing up mucus/phlegm, and use of accessory muscle. Symptoms are often worse at night or in the early morning, or in response to exercise or cold air. In one embodiment, the symptom of asthma is shortness of breath or difficulty in breathing.

As used herein, and unless otherwise specified, to "decrease," "ameliorate," "reduce," "inhibit," "treat" (or the like) COPD or a symptom associated with COPD includes reducing the severity and/or frequency of one or more symptoms of COPD, as well as preventing COPD and/or one or more symptoms of COPD (e.g., by reducing the severity and/or frequency of flares of symptoms).

In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have COPD or the level in samples derived from subjects who do not have COPD). In some embodiments, the decrease is statistically significant, for example, as assessed using an appropriate parametric or non-parametric statistical comparison.

In certain embodiments, the subject is an animal model of COPD, a human with COPD, or a subject (e.g., a human) at risk for developing COPD. In some embodiments, the subject is a human who has a family history of COPD, who carries a gene associated with COPD, who is positive for a biomarker associated with COPD, or a combination thereof. In some embodiments, the subject has been diagnosed with COPD. In some embodiments, the subject has one or more signs or symptoms associated with COPD. In some embodiments, the subject is at risk for developing COPD (e.g., the subject carries a gene that, individually, or in combination with other genes or environmental factors, is associated with development of COPD).

In one embodiment, the subject has been previously diagnosed of COPD or has episodic symptoms of airflow obstruction (e.g., shortness of breath, wheezing and/or chest tightness) for at least 1 week, 2 weeks, 1 month, 2 months, 3 months, 6 months, 9 months, 12 months before a compound provided herein (e.g., Compound 1), or an enantiomer, a mixture of enantiomers, or a mixture of two or more diastereomers thereof, or a pharmaceutically acceptable form thereof, is administered. In one embodiment, the subject has been previously diagnosed of COPD or has episodic symptoms of airflow obstruction (e.g., wheezing and/or chest tightness) for at least 6 months before a compound provided herein (e.g., Compound 1), or an enantiomer or a mixture of enantiomers thereof, or a pharmaceutically acceptable salt, solvate, hydrate, co-crystal, clathrate, or polymorph thereof, is administered.

In some embodiments, the subject has been previously treated for COPD. In some embodiments, the subject has been previously treated for COPD but are non-responsive to standard therapies. In one embodiment, the standard therapy is steroid, e.g., corticosteroids. In some embodiments, the subject has developed steroid resistance, e.g., from previous treatment with steroids. In some embodiments, the subject can have inherent steroid resistance that is not a result of previous treatments. Steroid resistance can be overcome by a PI3K inhibitor, e.g., a compound provided herein (e.g., Compound 1). Thus, combination therapy with a compound provided herein and a steroid can be beneficial. In one embodiment, provided herein is a method of treating, preventing, and/or managing COPD in a subject, comprising administering an effective amount of a compound provided herein (e.g., Compound 1), or an enantiomer, a mixture of enantiomers, or a mixture of two or more diastereomers thereof, or a pharmaceutically acceptable form thereof, to a subject in need thereof, wherein the subject has been previously administered a therapy for COPD.

In some embodiments, the subject has not been previously treated for COPD.

In one embodiment, without being limited by any particular theory, administering an effective amount of a compound provided herein (e.g., Compound 1), or an enantiomer, a mixture of enantiomers, or a mixture of two or more diastereomers thereof, or a pharmaceutically acceptable form thereof, does not result in, or results in reduced, one or more common side effects of COPD treatment. The common side effects of COPD treatment include, but are not limited to: allergic reactions such as rashes, hives, swelling of the face, mouth and tongue, and breathing problems; sudden breathing problems; effects on heart such as increased blood pressure, fast and irregular heartbeat, and chest pain; effects on nervous system such as tremor and nervousness; reduced adrenal function; changes in blood contents; weakened immune system and higher chance of infections; lower bone mineral density; eye problems such as glaucoma and cataracts; slowed growth in children; pneumonia; thrush in the mouth and throat; throat irritation; hoarseness and voice changes; viral respiratory infections; headache; and muscle and bone pain.

In some embodiments, the side effect is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the side effect level in the subject treated with other COPD therapies (e.g., albuterol, levalbuterol, ipratropium, tiotropium, terbutaline, theophylline, formoterol, salmeterol, flucatisone, methylprednisone, and prednisone). In some embodiments, the decrease is statistically significant, for example, as assessed using an appropriate parametric or non-parametric statistical comparison.

Asthma

In another specific embodiment, said obstructive lung disease or disorder is asthma. In some embodiments, administration of a compound provided herein results in a detectable improvement in one or more symptoms of asthma, e.g., airway obstruction, as determined by spirometry or a peak flow meter.

In one embodiment, provided herein is a method of reducing an asthma associated symptom in a subject, comprising administering a compound provided herein (e.g., Compound 1), or an enantiomer, a mixture of enantiomers, or a mixture of two or more diastereomers thereof, or a pharmaceutically acceptable form thereof, by inhalation in an amount sufficient to reduce the asthma associated symptom. In one embodiment, the subject is a mammalian subject, e.g., an animal model or as part of therapeutic protocol. In one embodiment, the compound is used as a single agent or in combination with another agent or therapeutic modality.

In one embodiment, provided herein is a method of treating, preventing, and/or managing asthma in a subject, comprising administering an effective amount of a compound provided herein (e.g., Compound 1), or an enantiomer, a mixture of enantiomers, or a mixture of two or more diastereomers thereof, or a pharmaceutically acceptable form thereof to a subject in need thereof by inhalation. In one embodiment, the compound is administered as a single agent. In another embodiment, the compound is administered in combination with another agent or therapeutic modality.

As used herein, and unless otherwise specified, "asthma" or a "symptom" associated with asthma encompasses all types of manifestation of asthma as disclosed herein or as known in the art. Examples of asthma include, but are not limited to, severe and/or refractory asthma, atopic (extrinsic) asthma, non-atopic (intrinsic) asthma, type 1 brittle asthma, type 2 brittle asthma, asthma attack, status asthmaticus, exercise-induced asthma, or occupational asthma. In one embodiment, the asthma is severe or refractory asthma. Examples of symptom of asthma include, but are not limited to, wheezing, coughing, chest tightness, shortness of breath, and use of accessory muscle. Symptoms are often worse at night or in the early morning, or in response to exercise or cold air. Asthma is clinically classified according to the frequency of symptoms, forced expiratory volume in 1 second ($FEV_1$), and peak expiratory flow rate. In one embodiment, the symptom of asthma is wheezing or chest tightness.

As used herein, and unless otherwise specified, "asthma" or a "symptom" associated with asthma also encompasses biological concomitants of asthma as disclosed herein or as known in the art. Examples include, but are not limited to, immune complexes, elevated levels of cytokines (e.g., interferons (e.g., Type I interferons, e.g., IFN-α and/or IFN-β); interleukins (e.g., IL-6, IL-8, IL-1, and IL-18) and TNF-α), elevated levels of anti-dsDNA autoantibodies, overexpression of IFN-α and/or IFN-β inducible genes, elevated levels of IP-10, elevated levels of sCD40L, reduced levels of C3-derived C3b, reduced peripheral iNKT cell frequencies, defective B cell-mediated stimulation of iNKT cells, altered CD1d expression on B cells, reduced numbers of natural regulatory T cells (Treg), altered level of C-reactive protein, overexpression of mRNA for IL-4, overexpression of mRNA for IL-21, and elevated serum anti-collagen level. In some embodiments, the symptom is overexpression of IFN-α, TNF-α, IL-6, IL-8, or IL-1. In one embodiment, the symptom is overexpression of IFN-α. In one embodiment, the symptom is overexpression of IL-6. In some embodiments, the symptom is overexpression of mRNA for IL-4 or overexpression of mRNA for IL-21. In some embodiments, the symptom is elevated serum anti-collagen level.

As used herein, and unless otherwise specified, to "decrease," "ameliorate," "reduce," "inhibit," "treat" (or the like) asthma or a symptom associated with asthma includes reducing the severity and/or frequency of one or more symptoms of asthma, as well as preventing asthma and/or one or more symptoms of asthma (e.g., by reducing the severity and/or frequency of flares of symptoms).

In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have asthma or the level in samples derived from subjects who do not have asthma). In some embodiments, the decrease is statistically significant, for example, as assessed using an appropriate parametric or non-parametric statistical comparison.

In certain embodiments, the subject is an animal model of asthma, a human with asthma, or a subject (e.g., a human) at risk for developing asthma. In some embodiments, the subject is a human who has a family history of asthma, who carries a gene associated with asthma, who is positive for a biomarker associated with asthma, or a combination thereof. In some embodiments, the subject has been diagnosed with asthma. In some embodiments, the subject has one or more signs or symptoms associated with asthma. In some embodiments, the subject is at risk for developing asthma (e.g., the subject carries a gene that, individually, or in combination with other genes or environmental factors, is associated with development of asthma).

In one embodiment, the subject has been previously diagnosed of asthma or has episodic symptoms of airflow obstruction (e.g., wheezing and/or chest tightness) for at least 1 week, 2 weeks, 1 month, 2 months, 3 months, 6 months, 9 months, 12 months before a compound provided herein (e.g., Compound 1), or an enantiomer, a mixture of enantiomers, or a mixture of two or more diastereomers thereof, or a pharmaceutically acceptable form thereof, is administered. In one embodiment, the subject has been previously diagnosed of asthma or has episodic symptoms of airflow obstruction (e.g., wheezing and/or chest tightness) for at least 6 months before a compound provided herein (e.g., Compound 1), or an enantiomer, a mixture of enantiomers, or a mixture of two or more diastereomers thereof, or a pharmaceutically acceptable form thereof, is administered.

In one embodiment, the subject has a forced expiratory volume in one second ($FEV_1$) value of at least 95%, 90%, 85%, 80%, 75%, 70%, 65%, 60%, 55%, or 50% of a control value. In one embodiment, the subject has a forced expiratory volume in one second ($FEV_1$) value of at least 70% of a control value. In one embodiment, the control value may be calculated based on American Thoracic Society (ATS)/European Respiratory Society (ERS) standards.

In one embodiment, the subject has a positive response to a skin prick test to an allergen. In one embodiment, the positive response means that the induration of skin test wheal is larger in diameter (e.g., at least 2 mm larger) than the diameter of the control wheal. The allergen can be any allergen provided herein or known in the art that can be used in the diagnosis or determining status of asthma.

In one embodiment, the subject has an early-phase asthmatic response (EAR) of at least 5%, 10%, 15%, 20%, 25%, 30%, 35%, 40%, 45%, or 50% to an inhaled allergen challenge. In one embodiment, the subject has an early-phase asthmatic response of at least 20% to an inhaled allergen challenge. In one embodiment, the EAR response is a decrease from pre-challenge in $FEV_1$ on 2 consecutive occasions within 0 to <3 hours of last allergen challenge.

In one embodiment, the subject has a late-phase asthmatic response (LAR) of at least 5%, 10%, 15%, 20%, 25%, 30%, 35%, 40%, 45%, or 50% to an inhaled allergen challenge. In one embodiment, the subject has a late-phase asthmatic response of at least 15% to an inhaled allergen challenge. In one embodiment, the LAR response is a decrease from pre-challenge in $FEV_1$ on 2 consecutive occasions within 3 to 10 hours of last allergen challenge.

In one embodiment, the subject has an early-phase asthmatic response of at least 20% and a late-phase asthmatic response of at least 15% to an inhaled allergen challenge. The inhaled allergen can be any inhaled allergen provided herein or known in the art that can be used in the diagnosis or determining status of asthma.

In one embodiment, the subject exhibits an elevated level of C-reactive protein. In one embodiment, the subject exhibits an elevated level of C-reactive protein of at least 1.0 mg/L. In one embodiment, the subject exhibits an elevated level of C-reactive protein of at least 7 mg/L.

In some embodiments, the subject exhibits elevated levels of antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies. In some embodiments, the subject exhibits elevated levels of anti-dsDNA antibodies. In some embodiments, the subject exhibits elevated levels of anti-Sm antibodies.

In some embodiments, the subject exhibits autoantibodies against one or more antigens that are known to be associated with asthma or with asthma subtypes. In some embodiments, the subject exhibits autoantibodies against Sm/anti-RNP or Ro/La autoantigens.

The levels of antibodies associated with asthma can be assessed using any suitable method, e.g., methods known in the art, e.g., indirect immunofluorescence. In some embodiments, the methods disclosed herein reduce or prevent an increase in the levels of one or more of the foregoing antibodies.

In some embodiments, the subject exhibits elevated levels of IFN-α, TNF-α, IL-6, IL-8, or IL-1. In one embodiment, the subject exhibits an elevated level of IFN-α. In another embodiment, the subject exhibits an elevated level of IL-6.

In another embodiment, the subject exhibits an elevated level of mRNA for IL-4 or IL-21.

In some embodiments, the subject has a mutation (e.g., an SNP) in a gene associated with asthma. In one embodiment, the gene is selected from STAT4, IRF5, BANK1, ITGAM, PD1, FAM167A-BLK, IRF5-TNP03, KIAA1542, TNFA1P3, XKR6, 1q25.1, PXK, ATG5, ICA1, XKR6, LYN and SCUB2 or a combination thereof. In some embodiments, the subject carries the DR3 and DQ2 variants, or the DR2 and DQ6 variants of HLA class II genes. In some embodiments, the subject has a deficiency in one or more complement proteins, e.g. a deficiency of a complement protein coded by the C4A or C2 genes on chromosome 6, or the C1r and C1s genes on chromosome 12.

In some embodiments, the subject exhibits excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac).

In some embodiments, the subject is an animal model of asthma provided herein or known in the art. Examples include, but are not limited to, the murine lipopolysaccharide (LPS) induced pulmonary inflammation model, and the murine ovalbumin-induced allergic airway inflammation model.

In some embodiments, the subject has been previously treated for asthma. In some embodiments, the subject has been previously treated for asthma but is non-responsive to standard therapies. Thus, in one embodiment, provided herein is a method of treating, preventing, and/or managing asthma in a subject, comprising administering an effective amount of a compound provided herein (e.g., Compound 1), or an enantiomer, a mixture of enantiomers, or a mixture of two or more diastereomers thereof, or a pharmaceutically acceptable form thereof, to a subject in need thereof, wherein the subject has been previously administered a therapy for asthma.

In some embodiments, the subject has not been previously treated for asthma.

In one embodiment, without being limited by any particular theory, administering an effective amount of a compound provided herein (e.g., Compound 1), or an enantiomer, a mixture of enantiomers, or a mixture of two or more diastereomers thereof, or a pharmaceutically acceptable form thereof, does not result in, or results in reduced, one or more common side effects of asthma treatment. The common side effects of asthma treatment include, but are not limited to, oral candidiasis, thrush, dysphonia (hoarseness), reflex cough, bronchospasm, poor growth, decreased bone density, disseminated varicella infection (chickenpox that spreads to organs), easy bruising, cataracts, glaucoma, adrenal gland suppression, stomach upset, headache, liver test abnormalities, skin rashes, Churg Strauss syndrome, bad taste in month, cough, itching, sore throat, sneezing, stuffy nose, shortness of breath, wheezing, viral illness, upper respiratory tract infections, sinusitis, feeling dizzy or faint, hives, changes in voice, swelling of the tongue, or difficulty in swallowing.

In some embodiments, the side effect is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the side effect level in the subject treated with other asthma therapies (e.g., Xolair, Cromolyn Sodium, Nedocromil, Montelukast, and prednisone). In some embodiments, the decrease is statistically significant, for example, as assessed using an appropriate parametric or non-parametric statistical comparison.

In one embodiment, the regression of asthma is a decrease (e.g., at least 5%, 10%, 15%, 20%, 25%, 30%, 35%, 40%, 45%, 50% decrease) in the level of maximal decrease from pre-allergen challenge in $FEV_1$ following allergen challenge. The level of maximal decrease from pre-allergen challenge in $FEV_1$ following allergen challenge can be measured in EAR or LAR.

In one embodiment, the regression of asthma is a decrease (e.g., at least 5%, 10%, 15%, 20%, 25%, 30%, 35%, 40%, 45%, 50% decrease) in area under the curve (AUC) of $FEV_1$ following allergen challenge.

In one embodiment, the regression of asthma is an increase (e.g., at least 5%, 10%, 15%, 20%, 25%, 30%, 35%, 40%, 45%, 50% increase) in the amount of methacholine that is required to induce a 20% fall in $FEV_I$ ($PC_{20}$) following allergen challenge.

In one embodiment, the regression of asthma is a decrease (e.g., at least 5%, 10%, 15%, 20%, 25%, 30%, 35%, 40%, 45%, 50% decrease) in exhaled nitric oxide level of the subject.

In one embodiment, the regression of asthma is a decrease (e.g., at least 5%, 10%, 15%, 20%, 25%, 30%, 35%, 40%, 45%, 50% decrease) in the C-reactive protein (CRP) level of the subject.

In one embodiment, the regression of asthma is a decrease (e.g., at least 5%, 10%, 15%, 20%, 25%, 30%, 35%, 40%, 45%, 50% decrease) in white blood cell count and/or differential cell count in induced sputum of the subject after allergen challenge.

5.6. Combination Therapy

In some embodiments, the compound provided herein is administered in combination with one or more other therapies. In one embodiment, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and/or radiation treatment, to provide a synergistic or additive therapeutic effect.

By "in combination with," it is not intended to imply that the other therapy and the PI3K modulator must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for cancer or hematologic malignancy, i.e., it is used in a subject who has not been previously administered another drug or therapy intended to treat cancer or hematologic malignancy or one or more symptoms thereof.

In other embodiments, the compound provided herein is a second line treatment for cancer or hematologic malignancy, i.e., it is used in a subject who has been previously administered another drug or therapy intended to treat cancer or hematologic malignancy or one or more symptoms thereof.

In other embodiments, the compound provided herein is a third or fourth line treatment for cancer or hematologic malignancy, i.e., it is used in a subject who has been previously administered two or three other drugs or therapies intended to treat cancer or hematologic malignancy or one or more symptoms thereof.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In one aspect, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can present synergistic or additive efficacy when administered in combination with agents that inhibit IgE production or activity. Such combination can reduce the undesired effect of high level of IgE associated with the use of one or more PI3K-δ inhibitors, if such effect occurs. This can be particularly useful in treatment of autoimmune and inflammatory disorders (AIID) such as rheumatoid arthritis. Additionally, the administration of PI3K-δ, PI3K-γ, or PI3K-δ/γ inhibitors as provided herein in combination with inhibitors of mTOR can also exhibit synergy through enhanced inhibition of the PI3K pathway.

In a separate but related aspect, provided herein is a combination treatment of a disease associated with PI3K-δ comprising administering to a subject in need thereof a PI3K-δ inhibitor and an agent that inhibits IgE production or activity. Other exemplary PI3K-δ inhibitors are applicable for this combination and they are described in, e.g., U.S. Pat. No. 6,800,620, incorporated herein by reference. Such combination treatment is particularly useful for treating autoimmune and inflammatory diseases (AIID) including, but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2.

Agents that inhibit IgE activity include, for example, anti-IgE antibodies such as for example Omalizumab and TNX-901.

For treatment of autoimmune diseases, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with commonly prescribed drugs including, but not limited to, Enbrel®, Remicade®, Humira®, Avonex®, and Rebif®. For treatment of respiratory diseases, the subject compounds, or pharmaceutically acceptable forms thereof, or pharmaceutical compositions, can be administered in combination with commonly prescribed drugs including, but not limited to, Xolair®, Advair®, Singulair®, and Spiriva®.

The compounds as provided herein, or pharmaceutically acceptable forms (e.g., pharmaceutically acceptable salts, hydrates, solvates, isomers, prodrugs, and isotopically labeled derivatives) thereof, or pharmaceutical compositions as provided herein, can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein is a pharmaceutical composition for inhibiting abnormal cell growth in a subject which comprises an amount of a compound provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent or a biotherapeutic agent). Many chemotherapeutics are presently known in the art and can be used in combination with a compound provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade® (bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; BTK inhibitors such as ibrutinib (PCI-32765), AVL-292, Dasatinib, LFM-AI3, ONO-WG-307, and GDC-0834; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; EZH2 inhibitors such as, but not limited to, EPZ-6438 (N-(4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide), GSK-126 ((S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-(6-methyl-2-oxo-4-propyl-1,2-dihydropyridin-3-yl)methyl)-6-(2-(4-methylpiperazin-1-yl)pyridine-4-yl)-1H-indazole-4-carboxamide), E11, 3-deazaneplanocin A (DNNep, 5R-(4-amino-1H-imidazo[4,5-c]pyridin-1-yl)-3-(hydroxymethyl)-3-cyclopentene-1S,2R-diol), small interfering RNA (siRNA) duplexes targeted against EZH2 (S. M. Elbashir et al., Nature 411:494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843, all of which are incorporated herein by reference; JAK/STAT inhibitors such as lestaurtinib, tofacitinib, ruxolitinib, pacritinib, CYT387, baricitinib, GLPG0636, TG101348, INCB16562, CP-690550, and AZD1480; PKC-β inhibitor such as Enzastaurin; SYK inhibitors such as, but not limited to, GS-9973, PRT 062607, R406, (S)-2-(2-((3,5-dimethylphenyl)amino)pyrimidin-4-yl)-N-(1-hydroxypropan-2-yl)-4-methylthiazole-5-carboxamide, R112, GSK143, BAY61-3606, PP2, PRT 060318, R348, and those provided in, for example, U.S. Publication Nos. 2003/0113828, 2003/0158195, 2003/0229090, 2005/0075306, 2005/0232969, 2005/0267059, 2006/0205731, 2006/0247262, 2007/0219152, 2007/0219195, 2008/0114024, 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073, 2012/0142671, 2012/0184526, 2012/0220582, 2012/0277192, 2012/0309735, 2013/0040984, 2013/0090309, 2013/0116260, and 2013/0165431, all of which are incorporated herein by reference; SYK inhibitor such as R788 (fostamatinib); SYK/JAK dual inhibitor such as PRT2070; nitrogen mustards such as bendamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2''-trichlorotriethyla-mine; urethan; vindesine; dacarbazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle nonspecific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354, each incorporated herein by reference. Additional examples of hedgehog inhibitors include, but are not limited to, GDC-0449 (also known as RG3616 or vismodegib) described in, e.g., Von Hoff D. et al., *N Engl. J. Med.* 2009; 361(12):1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.,* 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other hormonal therapy and chemotherapeutic agents include, but are not limited to, anti-estrogens (e.g. tamoxifen, raloxifene, and megestrol acetate), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids or taxanes (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C, cytosine arabinoside), and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracyclines (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immuno-stimulants and/or immuno-modulatory agents (e.g., IL-1, 2, 4, 6, 7, 12, 15, or 21), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab), or Perjeta (pertuzumab)).

In some embodiments, the biotherapeutic agent is an immunotherapeutic agent, e.g., a cancer vaccine e.g., a tumor vaccine. Exemplary cancer vaccines include Aduro (GVAX); Advaxis (ADXS11-001, ADXS31-001, ADXS31-164, ADXS31-142 (ADXS-PSA)); ALVAC-CEA vaccine; Avax Technologies (AC Vaccine); Amgen (talimogene laherparepvec); Biovest International (BiovaxID in phase III); Bavarian Nordic (PROSTVAC); Celldex Therapeutics (CDX110, CDX1307 and CDX1401); The Center of Molecular Immunology (CimaVax-EGF); CureVac develops mRNA-based cancer immunotherapies; CV9104; Dendreon Corp (Neuvenge); Galena Biopharma (NeuVax); Antigen Express (Ae-37); Geron Corporation (GRNVAC1); GlobeImmune (Tarmogens, GI-4000, GI-6207, GI-6301); Heat Biologics (ImPACT Therapy); Immatics biotechnologies (IMA901); Merck (Stimuvax); Panacela Labs, Inc. (MOBILAN Adenovirus-based treatment); Prima BioMed (Cvac); Scancell Holdings (SCIB 1).

In embodiments, the biotherapeutic agent is a cellular therapy, e.g., dendritic cell therapy or a chimeric T cell therapy such as CART. Dendritic cell therapy can comprise loading dendritic cells with an antigen obtained from a patient's tumor, then administering the dendritic cells to the patient in order to sensitize the patient's own T cells to the tumor antigens. Chimeric antigen receptors (CARs) are engineered receptors that can be used to confer tumor specificity to a T cell. CARS have been generated with specificity for α-folate receptor, CAIX, CD19, CD20, CD22, CD30, CD33, CD44v7/8, CEA, EGP-2, EGP-40, erb-B2, erb-B 2,3,4, FBP, Fetal acetylcholine receptor, FD2, Her2/neu, IL13R-a2, KDR, k-light chain, LeY, L1 cell adhesion molecule, MAGE-A1, mesothelin, CMV-infected cells, MUC1, NKG2D ligands, oncofetal antigen h5T4, PSCA, PSMA, TAA, TAG-72, and VEGF-R2.

In one embodiment, the biotherapeutic agent is an anti-CD37 antibody such as, but not limited to, IMGN529, K7153A and TRU-016. In another embodiment, the biotherapeutic agent is an anti-CD20 antibody such as, but not limited to, $^{131}$I tositumomab, $^{90}$Y ibritumomab, $^{111}$I ibritumomab, obinutuzumab (GAZYVA), and ofatumumab. In another embodiment, the biotherapeutic agent is an anti-CD52 antibody such as, but not limited to, alemtuzumab.

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiment, the PI3K inhibitor is an inhibitor of delta isoform of PI3K. In some embodiment, the PI3K inhibitor is an inhibitor of gamma isoform of PI3K. In some embodiments, the PI3K inhibitor is an inhibitor of alpha isoform of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165, each incorporated herein by reference. Additional PI3K inhibitors that can be used in combination with the pharmaceutical compositions, include but are not limited to, RP-6530, TG 100-115, RV1729, AMG-319, GSK 2126458, GDC-0980, GDC-0941, Sanofi XL147, XL499, XL756, XL147, PF-4691502, BKM 120, CAL-101 (GS-1101), CAL 263, SF1126, PX-886, and a dual PI3K inhibitor (e.g., Novartis BEZ235). In one embodiment, the PI3K inhibitor is an isoquinolinone. In one embodiment, the PI3K inhibitor is RP-6530, which has the chemical name: (S)-2-(1-((9H-purin-6-yl)amino)propyl)-3-(3-fluorophenyl)-4H-chromen-4-one. In one embodiment, the PI3K inhibitor is TG 100-115, which has the chemical name: 6,7-Bis(3-hydroxyphenyl)pteridine-2,4-diamine. In one embodiment, the PI3K inhibitor is RV1729, which has the chemical name: 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide.

Without being bound by any particular theory, it is believed that the role of each PI3K isoform is critically dependent on cell type and upstream initiating signals, and therefore pharmacologic inhibition of specific isoforms can lead to different physiologic outcomes. PI3K is a lipid kinase existing in multiple isoforms that have central roles in the regulation of important cellular processes, including cell growth and survival. Puri et al., Frontiers in Immunology. 2012, 3: 256. PI3K-δ and PI3K-γ are both expressed in CLL and NHL tumor cells. Signaling through PI3K is critical for supporting the growth and survival of these malignancies as they mediate intracellular BCR signaling and promote interactions between the tumor cells and their microenvironment. Puri et al., Frontiers in Immunology. 2012, 3: 256.

The specific functions of PI3K-δ in malignant B cells support the rationale for it to be a therapeutic target to control these diseases. PI3K-δ inhibition disrupts malignant cell interaction with the stromal microenvironment, thereby short-circuiting chemokine-mediated stimulation of CLL and other B-cell malignancies, priming cells for apoptosis by pharmacologic or natural stimuli. Pharmacologic inhibition of PI3K-δ reduces disease activity in various models of B-cell-derived malignancies, including CLL and B-cell lymphomas. PI3K-δ inhibition improves the therapeutic potential of other antitumor agents in various preclinical models of B-cell malignancy, including CLL. Lannutti et al., Blood. 2011, 117, 591-594.

The role of PI3K-γ in cells that maintain the malignant B-cell microenvironment creates potential for therapeutic inhibition of PI3K-γ to control these diseases. PI3K-γ plays a role in T-cell activation and migration and GPCR-associated chemokine signaling. Reif et al. J Immunol. 2004; 173:2236-2240. PI3K-γ also mediates adhesion and trafficking of tumor-associated macrophages (TAMs). Reif et al. J Immunol. 2004; 173:2236-2240. Hasan et al., Int Immunopharmacology. 2010, 10, 1017-1021; Laffargue et al., Immunity. 2002, 16, 441-451. There is dynamic interplay or "cross-talk" between PI3K-δ and PI3K-γ in essential cellular activities in malignant cells. In certain tumor types, PI3K-γ can promote tumorigenesis in the absence of PI3K-δ. Subramaniam et al., Cancer Cell. 2012, 21, 459-472.

In certain tumor types, dual isoform inhibition may be necessary for optimal tumor growth inhibition in preclinical models. Subramaniam et al., Cancer Cell. 2012, 21, 459-472. As shown in the examples, in some cell lines (e.g., NHL (e.g., follicular lymphoma), DLBCL, mantle cell, multiple myeloma, T-cell lymphoma), combined inhibition of PI3K-δ and PI3K-γ shows greater growth inhibition than inhibition of either isoform alone.

In one embodiment, the PI3K-delta selective compound is GSK-2269557 (2-(6-(1H-indol-4-yl)-1H-indazol-4-yl)-5-((4-isopropylpiperazin-1-yl)methyl)oxazole), GS9820 (CAL-120, (S)-2-(1-((9H-purin-6-yl)amino)ethyl)-6-fluoro-3-phenylquinazolin-4(3H)-one), GS-1101 (5-fluoro-3-phenyl-2-([S)]-1-[9H-purin-6-ylamino]-propyl)-3H-quinazolin-4-one), AMG319, or TGR-1202 ((S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one), or a mixture thereof. In one embodiment, the PI3K-delta selective compound is GS1101.

In one embodiment, the PI3K-delta selective compound is a PI3K-delta inhibitor as described in WO 2005/113556, the entirety of which is incorporated herein by reference. In one embodiment, the PI3K-delta selective compound is Compound No. 113 or 107 as described in 2005/113556.

In one embodiment, the PI3K-delta selective compound is a PI3K-delta compound as described in WO2014/006572, the entirety of which is incorporated herein by reference. In one embodiment, the PI3K-delta selective compound is a PI3K-delta inhibitor has an alpha/delta selectivity ratio of greater than about 100, greater than about 250, greater than about 500, greater than about 750, or greater than about 1000. In one embodiment, the PI3K-delta selective compound is a PI3K-delta inhibitor has a beta/delta selectivity ratio of greater than about 10, greater than about 20, greater than about 30, greater than about 40, or greater than about 50. In one embodiment, the PI3K-delta selective compound is a PI3K-delta inhibitor has a gamma/delta selectivity ratio of greater than about 1, greater than about 10, greater than about 25, greater than about 30, or greater than about 50. In one embodiment, the PI3K-delta selective compound is Compound Nos. A1, A2, B, B1 or B2 as described in WO2014/006572. In one embodiment, the PI3K-delta selective compound is Compound No. B1 as described in WO2014/006572.

In one embodiment, the PI3K-delta selective compound is a PI3K-delta compound as described in WO 2013/032591, the entirety of which is incorporated herein by reference. In one embodiment, the PI3K-delta selective compound is a compound of Formula (I) as described in WO 2013/032591. In one embodiment, the PI3K-delta selective compound is a compound described in WO 2013/032591 with a IC$_{50}$ (nM) for the PI3K-delta isoform of less than 100 nM and a IC$_{50}$ (nM) for the PI3K-alpha, beta, or gamma of greater than about 100 nM, greater than about 1 µM, or greater than about 10 µM. In one embodiment, the PI3K-delta selective compound has an alpha/delta selectivity ratio, a beta/delta selectivity ratio, or a gamma/delta selectivity ratio of greater than 1, greater than about 10, or greater than about 100. In one embodiment, the PI3K-delta selective compound is Compound Nos. 13, 30, 41, 55, 57, 124, 167, 183, 185, 187, 191, 196, 226, 230, 232, 234, 235, 326, 327, 328, 333, 334, 336, 337, 338, 356, 359, 378, 439, 440, 443, or 455, as described in WO 2013/032591. In one embodiment, the PI3K-delta selective compound is Compound Nos. 183, 230, 234, 235, 326, 333, 336, 337, 338, or 359, as described in WO 2013/032591. In one embodiment, the PI3K-delta selective compound is Compound No. 359 as described in WO 2013/032591.

In one embodiment, provided herein are pharmaceutical compositions comprising a compound of Formula (I'), (A'), (I), or (A), or a pharmaceutically acceptable form thereof, and a PI3K-delta selective compound, wherein the PI3K-delta selective compound is GSK-2269557, GS-9820, GS-1101 (Cal-101 or idelalisib), AMG319, or TGR-1202, or a mixture thereof. In one embodiment, the PI3K-delta selective compound is GS1101. In one embodiment, the composition is synergistic in treating or preventing a PI3K mediated disorder. In one embodiment, the PI3K-delta selective compound is a compound described in WO2011/146882, the entirety of which is incorporated herein by reference. In one embodiment, the PI3K-delta selective compound is a compound described in WO2011/146882 with a IC$_{50}$ (nM) for the PI3K-delta isoform of less than 100 nM and a IC$_{50}$ (nM) for the PI3K-alpha, beta, or gamma of greater than about 100 nM, greater than about 1 µM, or greater than about 10 µM. In one embodiment, the PI3K-delta selective compound has an alpha/delta selectivity ratio, a beta/delta selectivity ratio, or a gamma/delta selectivity ratio of greater than 1, greater than about 10, or greater than about 100. In one embodiment, the PI3K-delta selective compound is Compound No. 69 as described in WO2011/146882.

In one embodiment, the PI3K-delta selective compound is a compound described in WO2013/012915, the entirety of which is incorporated herein by reference. In one embodiment, the PI3K-delta selective compound is a compound described in WO2013/012915 with a IC$_{50}$ (nM) for the PI3K-delta isoform of less than 100 nM and a IC$_{50}$ (nM) for the PI3K-alpha, beta, or gamma of greater than about 100 nM, greater than about 1 µM, or greater than about 10 µM. In one embodiment, the PI3K-delta selective compound has an alpha/delta selectivity ratio, a beta/delta selectivity ratio, or a gamma/delta selectivity ratio of greater than 1, greater than about 10, or greater than about 100. In one embodiment, the PI3K-delta selective compound is Compound No. I-41 or I-106 as described in WO2013/012915.

In one embodiment, the PI3K-delta selective compound is a compound described in WO2013/012918, the entirety of which is incorporated herein by reference. In one embodiment, the PI3K-delta selective compound is a compound described in WO2013/012918 with a IC$_{50}$ (nM) for the PI3K-delta isoform of less than 100 nM and a IC$_{50}$ (nM) for the PI3K-alpha, beta, or gamma of greater than about 100 nM, greater than about 1 µM, or greater than about 10 µM. In one embodiment, the PI3K-delta selective compound has an alpha/delta selectivity ratio, a beta/delta selectivity ratio, or a gamma/delta selectivity ratio of greater than 1, greater than about 10, or greater than about 100. In one embodiment, the PI3K-delta selective compound is Compound No. 19, 28, 37, 38, 51, 59, 60, 89, 92, 103, 106, 107, 108, or 109 as described in WO2013/012918. In one embodiment, the PI3K-delta selective compound is Compound No. 103 or 106 as described in WO2013/012918.

In one embodiment, provided herein are methods of treating or preventing a PI3K mediated disorder in a subject, comprising administering to the subject a therapeutically effective amount of a compound of Formula (I'), (A'), (I), or (A), or a pharmaceutically acceptable form thereof, in combination with a PI3K-delta selective compound, wherein the PI3K-delta selective compound is GSK-2269557, GS-9820, GS-1101 (Cal-101), AMG319, or TGR-1202, or a mixture thereof. In one embodiment, provided herein are methods of enhancing a PI3K-delta selective compound treatment of a PI3K mediated disorder in a subject comprising administering a compound of Formula (I'), (A'), (I), or (A), or a pharmaceutically acceptable form thereof, in combination with the PI3K selective delta compound, wherein the PI3K-delta selective compound is GSK-2269557, GS9-820, GS-1101 (Cal-101), AMG319, or TGR-1202, or a mixture thereof. In one embodiment, the PI3K- delta selective compound is GS1101. In one embodiment, the administering a compound of Formula (I'), (A'), (I), or (A), or a pharmaceutically acceptable form thereof, in combination with the PI3K-delta selective compound provides synergistic effect.

Also provided herein are methods of inhibiting growth of a cell comprising contacting the cell with a compound of Formula (I'), (A'), (I), or (A), or a pharmaceutically acceptable form thereof, in combination with a PI3K-delta selective compound, wherein the PI3K-delta selective compound is GSK-2269557, GS-9820, GS-1101 (Cal-101), AMG319, or TGR-1202, or a mixture thereof. In one embodiment, the PI3K-delta selective compound is GS1101. In one embodiment, the cell is a cancer cell. In another embodiment, the cell is in a subject. In one embodiment, the subject is afflicted with a proliferative disease, cancer, autoimmune disease, or inflammatory disease.

In one embodiment, the PI3K-delta selective compound is a compound selected from US Patent Publication Nos. 20140058103, 20140051699, 20140045825, 20140011819, 20130231356, 20130225557, 20120245144, 20100305084, 20100256167, 20100168139, 20100152211, and 20100029693. In one embodiment, the PI3K-delta selective compound is a compound selected from U.S. Pat. Nos. 8,653,077, 8,637,533, 8,623,881, 8,586,597, 8,569,296, 8,563,540, 8,492,389, 8,440,651, 8,138,195, 7,932,260, and 6,949,535.

For example, a compound provided herein with a delta/gamma selectivity ratio of greater than 150 can be combined with a compound that has a gamma/delta selectivity ratio of 1000 at various amounts (e.g., a ratio of 10:1 or 40:1 of a gamma selective compound and a delta selective compound) to provide synergistic effect in cell lines (e.g., diffuse large B-cell lymphoma cell lines such as SU-DHL-4, TMD-8 and Farage).

The PI3K-gamma selective compound and PI3K-delta selective compound composition or combination therapy can provide synergistic effect in treating or preventing a PI3K mediated disorder. In one embodiment, the disorder is a cancer. In one embodiment, the cancer is diffuse large B-cell lymphoma (e.g., TMD-8 and Farage cell lines), B-cell lymphoma (e.g., karpas-422 cell line), T-cell lymphoma, non-Hodgkin's lymphoma, Hodgkin lymphoma, or anaplastic large cell lymphoma (e.g., HH cell line).

In some embodiments, the synergistic effect can be characterized by an isobologram. Potency shifting is usually shown using an isobologram which shows how much less a compound is required in combination to achieve a desired effect level, when compared to the single agent doses needed to reach that effect. The choice of effect level for the isobologram display and combination index calculations can either be manually or automatically selected in the Chalice Analyzer. Potency shifting is scored as the combination index (CI). Chou et al., Adv Enzyme Regul 1984; 22: 27-55. The CI is a rough estimate of how much a compound was needed in combination relative to the single agent doses required to achieve the chosen effect level, and a value of 0.1 means that only a tenth of equivalent amounts of the single agents were needed for the combination to reach the same effect level. Additive effect is CI=1.0. Synergistic effect is CI<1. Antagonistic effect is CI>1.0.

In some embodiment, the synergistic effect is characterized by Synergy Score.

Different stimuli can be used to preferentially induce T-cell or CLL-cell migration. For example, CCL19 and CCL21 stimuli selectively induce migration of both CLL and T-cells. CXCL13 is CLL-cell specific, whereas CXCL12 is T-cell specific. As such, stimuli CXCL13 and CXCL12 can be used to induce CLL-cell and T-cell migrations, respectively. The PI3K-gamma selective compounds provided herein can inhibit cancer-promoting cell migration, e.g., CXCL 12-induced T-cell migration. In some embodiments, elevated pAKT levels indicate that the CXCL12-induced migration machinery is activated. Consequently, in some embodiments, the PI3K-gamma selective compound, e.g., Compound 1, interferes with AKT signaling and/or reduces pAKT levels in the T-cells. In one embodiment, the PI3K-gamma selective compound is a compound that has a delta/gamma selectivity ratio of greater than about 50, such as Compound 1. In another embodiment, the PI3K-delta selective compound is a compound that has a gamma/delta selectivity ratio of greater than about 50. The gamma selective compound can be more potent than a delta selective compound at inhibiting cancer-promoting cell migration, e.g., CXCL12-induced T cell migration in CLL PBMCs. The ability to inhibit the migration of cancer-promoting cells can stop the growth of cancers by blocking the migration of cells that promote cancer growth to the cancer cell niche. In another embodiment, gamma or delta selective compounds can inhibit the migration of cancer cells themselves and limit cancer cell dissemination. As such, the gamma selective compounds provided herein can be used to treat and/or prevent cancer, or slow down the progression of cancer or metastasis. Treatment with a combination of gamma and delta selective compounds can have an earlier response time compared to a delta selective compound alone, for example in B cell meditated cancers.

In one embodiment, a compound provided herein (e.g., Compound 1), or a pharmaceutically acceptable form thereof, is administered in combination with a chemotherapy (e.g., temozolomide) for the treatment of a cancer. In one embodiment, the cancer is glioblastoma (e.g., glioblastoma multiforme). In one embodiment, provided herein is a method of treating glioblastoma in a subject, comprising administering to the subject a therapeutically effective amount of Compound 1, or a pharmaceutically acceptable form thereof, in combination with a chemotherapy. In one embodiment, the compound is administered subsequent to the chemotherapy. In one embodiment, the compound is administered concurrently to the chemotherapy. In one embodiment, the compound is administered prior to the chemotherapy.

In some embodiments, provided herein is a method for using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of a compound provided herein in this combination therapy can be determined as described herein.

In certain embodiments, provided herein are methods of treating a solid tumor in a subject, comprising administering to the subject a therapeutically effective amount of a compound provided herein (e.g., Compound 1), or a pharmaceutically acceptable form thereof, in combination with a radiation therapy.

In one embodiment, the solid tumor is selected from one or more of: a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer (e.g., triple negative breast cancer), a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the compound, or a pharmaceutically acceptable form thereof, is administered after the radiation therapy is administered. In one embodiment, the compound, or a pharmaceutically acceptable form thereof, is administered at the same time that radiation therapy is administered. In one embodiment, the compound, or a pharmaceutically acceptable form thereof, is administered alone after discontinuing the radiation therapy.

Radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound provided herein, or a pharmaceutically acceptable form (e.g., pharmaceutically acceptable salts, hydrates, solvates, isomers, prodrugs, and isotopically labeled derivatives) thereof, which amount is effective in sensitizing abnormal cells to treatment with radiation. The amount of the compound used in this method can be determined according to the means for ascertaining effective amounts of such compounds described herein.

In one embodiment, a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with an amount of one or more substances selected from anti-angiogenesis agents, signal transduction inhibitors, and antiproliferative agents, glycolysis inhibitors, or autophagy inhibitors.

Other therapeutic agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound provided herein, or a pharmaceutically acceptable form thereof, or a pharmaceutical composition described herein. Such therapeutic agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNAs that inhibit expression of proteins including, but not limited to ATG5 (which are implicated in autophagy), can also be used.

In some embodiments, provided herein is a method of and/or a pharmaceutical composition for treating a cardiovascular disease in a subject which comprises an amount of a compound provided herein, or a pharmaceutically acceptable form (e.g., pharmaceutically acceptable salts, hydrates, solvates, isomers, prodrugs, and isotopically labeled derivatives) thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetylsalicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

In one embodiment, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with a compound provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, e.g., codeine, dihydromorphine, ergotamine, fentanyl or morphine; anginal preparations, e.g., diltiazem; antiallergics, e.g. cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α[[[6[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, β-Lactam antibiotics, an agent containing an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a compound provided herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immuno-modulation, such as immuno-modulators, immuno-suppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and anti-platelet drugs are also contemplated by the methods herein.

In exemplary embodiments, for treating renal carcinoma, one can combine a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, with sorafenib and/or avastin. For treating an endometrial disorder, one can combine a compound provided herein with doxorubincin, taxotere (taxol), and/or cisplatin (carboplatin). For treating ovarian cancer, one can combine a compound provided herein with cisplatin, carboplatin, docetaxel, doxorubincin, topotecan, and/or tamoxifen. For treating breast cancer, one can combine a compound provided herein with paclitaxel or docetaxel, gemcitabine, capecitabine, tamoxifen, letrozole, erlotinib, lapatinib, PD0325901, bevacizumab, trastuzumab, OSI-906, and/or OSI-930. For treating lung cancer, one can combine a compound as provided herein with paclitaxel, docetaxel, gemcitabine, cisplatin, pemetrexed, erlotinib, PD0325901, and/or bevacizumab.

In some embodiments, the disorder to be treated, prevented and/or managed is a hematological cancer, e.g., lymphoma (e.g., T-cell lymphoma; NHL), myeloma (e.g., multiple myeloma), and leukemia (e.g., CLL), and a compound provided herein is used in combination with: HDAC inhibitors such as vorinostat, romidepsin and ACY-1215; mTOR inhibitors such as everolimus; anti-folates such as pralatrexate; nitrogen mustard such as bendamustine; gemcitabine, optionally in further combination with oxaliplatin; rituximab-cyclophosphamide combination; PI3K inhibitors such as RP-6530, TG 100-115, RV1729, GS-1101, XL 499, GDC-0941, and AMG-319; angiogenesis inhibitors such as pomalidomide or BTK inhibitors such as ibrutinib, AVL-292, Dasatinib, LFM-AI3, ONO-WG-307, and GDC-0834. In some embodiments, the disorder to be treated, prevented and/or managed is DLBCL, and a compound provided herein (e.g., compound 1), or a pharmaceutically acceptable derivative (e.g., salt or solvate) thereof, is used in combination with HDAC inhibitors provided herein. In one particular embodiment, the HDAC inhibitor is ACY-1215.

In some embodiments, the disorder to be treated, prevented and/or managed is DLBCL, and a compound provided herein (e.g., compound 1), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is DLBCL, and a compound provided herein (e.g., compound 1), or a pharmaceutically acceptable derivative (e.g., salt or solvate) thereof, is used in combination with IRAK inhibitors provided herein. In one particular embodiment, the IRAK4 inhibitor is ND-2110 or ND-2158.

In some embodiments, the disorder to be treated, prevented and/or managed is WM, and a compound provided herein (e.g., compound 1), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is WM, and a compound provided herein (e.g., compound 1), or a pharmaceutically acceptable derivative (e.g., salt or solvate) thereof, is used in combination with IRAK4 inhibitors provided herein. In one particular embodiment, the IRAK4 inhibitor is ND-2110 or ND-2158.

In some embodiments, the disorder to be treated, prevented and/or managed is T-ALL, the subject/patient has a PTEN deficiency, and a compound provided herein (e.g., compound 1), or a pharmaceutically acceptable derivative (e.g., salt or solvate) thereof, is used in combination with doxorubicin and/or vincristine.

In certain embodiments, wherein inflammation (e.g., arthritis, asthma) is treated, prevented and/or managed, a compound provided herein can be combined with, for example: PI3K inhibitors such as RP-6530, TG 100-115, RV1729, GS-1101, XL 499, GDC-0941, and AMG-319; BTK inhibitors such as ibrutinib and AVL-292; JAK inhibitors such as tofacitinib and GLPG0636; SYK inhibitors such as fostamatinib.

In certain embodiments wherein asthma is treated, prevented and/or managed, a compound provided herein can be combined with, for example: beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate; corticosteroids such as, but not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®); mast cell stabilizers such as cromolyn sodium (e.g., Intal® or Nasalcrom®) and nedocromil (e.g., Tilade®); xanthine derivatives such as, but not limited to, theophylline (e.g., Aminophyllin®, Theo-24® or Theolair®); leukotriene receptor antagonists such as, but are not limited to, zafirlukast (Accolate®), montelukast (Singulair®), and zileuton (Zyflo®); and adrenergic agonists such as, but are not limited to, epinephrine (Adrenalin®, Bronitin®, EpiPen® or Primatene Mist®).

In certain embodiments wherein arthritis is treated, prevented and/or managed, a compound provided herein can be combined with, for example: TNF antagonist (e.g., a TNF antibody or fragment, a soluble TNF receptor or fragment, fusion proteins thereof, or a small molecule TNF antagonist); other biologic antirhheumatics (e.g., IL-6 antagonists, IL-1 antagonists, costimulatory modulators); an antirheumatic (e.g., methotrexate, auranofin, aurothioglucose, azathioprine, etanercept, gold sodium thiomalate, chrloroquine, hydroxychloroquine sulfate, leflunomide, sulfasalzine, penicillamine); a muscle relaxant; a narcotic; a non-steroid anti-inflammatory drug (NSAID); an analgesic; an anesthetic; a sedative; a local anesthetic; a neuromuscular blocker; an antimicrobial (e.g., an aminoglycoside, an antifungal, an antiparasitic, an antiviral, a carbapenem, cephalosporin, a fluoroquinolone, a macrolide, a penicillin, a sulfonamide, a tetracycline, another antimicrobial); an antipsoriatic; a corticosteroid; an anabolic steroid; a cytokine or a cytokine antagonist; a calcineurin inhibitor (e.g., cyclosporine, tacrolimus).

In some embodiments, a compound provided herein (e.g., compound 1), or an enantiomer or a mixture of enantiomers thereof, or a pharmaceutically acceptable salt, solvate, hydrate, co-crystal, clathrate, or polymorph thereof) is administered in combination with an agent for the treatment of rheumatoid arthritis. Examples of agents for the treatment of rheumatoid arthritis include, but are not limited to, various NSAIDs, corticosteroids, sulfasalazine, auranofin, methotrexate, azathioprine, penicillamine, cyclosporine, Arava (leflunomide), TNF inhibitors (e.g., Enbrel (etanercept), Remicade (infliximab), Humira (adalimumab), Simponi (golimumab), and Cimzia (certolizumab)), IL-1 inhibitors (e.g., Kineret (anakinra)), T-cell costimulatory modulators (e.g., Orencia (abatacept)), Anti-CD20 (e.g., Rituxan (rituximab)), and IL-6 inhibitors (e.g., Actemra (tocilizumab)). In one embodiment, the agent is Cimzia (certolizumab). In another embodiment, the agent is Actemra (tocilizumab).

In some embodiments, a compound provided herein (e.g., compound 1), or an enantiomer or a mixture of enantiomers thereof, or a pharmaceutically acceptable salt, solvate, hydrate, co-crystal, clathrate, or polymorph thereof) is administered in combination with an agent for rheumatology. Examples of agents for rheumatology include, but are not limited to, Rayos (prednisone), Stendra (avanafil), Actemra (tocilizumab), Duexis (ibuprofen and famotidine), Actemra (tocilizumab), Krystexxa (pegloticase), Vimovo (naproxen+esomeprazole), Cimzia (certolizumab pegol), Colcrys (colchicine), Pennsaid (diclofenac sodium topical solution), Simponi (golimumab), Uloric (febuxostat), Orencia (abatacept), Elaprase (idursulfase), Orencia (abatacept), Vioxx (rofecoxib), Enbrel (etanercept), Humira (adalimumab), Remicade (infliximab), Bextra, Kineret, Remicade (infliximab), Supartz, Mobic (meloxicam), Vivelle (estradiol transdermal system), Lodine XL (etodolac), Arava, Salagen, Arthrotec, Etodolac, Ketoprofen, Synvisc, Tolmetin Sodium, Azulfidine EN-tabs Tablets (sulfasalazine delayed release tablets, USP), and Naprelan (naproxen sodium).

In some embodiments, the second agent is selected from belimumab, AGS-009, rontalizumab, vitamin D3, sifalimumab, AMG 811, IFNα Kinoid, CEP33457, epratuzumab, LY2127399, Ocrelizumab, Atacicept, A-623, SBI-087, AMG557, laquinimod, rapamycin, cyclophosphamide, azathioprine, mycophenolate, leflunomide, methotrexate, CNTO 136, tamibarotene, N-acetylcysteine, CDP7657, hydroxychloroquine, rituximab, carfilzomib, bortezomib, ONX 0914, IMO-3100, DV1179, sulfasalazine, and chloroquine. In one embodiment, the second agent is methotrexate, sulfasalazine, chloroquine, or hydroxychloroquine. In one embodiment, the second agent is methotrexate.

In certain embodiments wherein psoriasis is treated, prevented and/or managed, a compound provided herein can be combined with, for example: budesonide, epidermal growth factor, corticosteroids, cyclosporine, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13 and TGFβ.

In certain embodiments wherein fibrosis or fibrotic condition of the bone marrow is treated, prevented and/or managed, a compound provided herein can be combined with, for example, a Jak2 inhibitor (including, but not limited to, INCB018424, XL019, TG101348, or TG101209), an immuno-modulator, e.g., an IMID® (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In certain embodiments wherein fibrosis or fibrotic condition of the heart is treated, prevented and/or managed, a compound provided herein can be combined with, for example, eplerenone, furosemide, pycnogenol, spironolactone, TcNC100692, torasemide (e.g., prolonged release form of torasemide), or combinations thereof.

In certain embodiments wherein fibrosis or fibrotic condition of the kidney is treated, prevented and/or managed, a compound provided herein can be combined with, for example, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or combinations thereof.

In certain embodiments wherein fibrosis or fibrotic condition of the skin is treated, prevented and/or managed, a compound provided herein can be combined with, for example, Bosentan (Tracleer), p144, pentoxifylline; pirfenidone; pravastatin, STI571, Vitamin E, or combinations thereof.

In certain embodiments wherein fibrosis or fibrotic condition of the gastrointestinal system is treated, prevented and/or managed, a compound provided herein can be combined with, for example, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLEC™, triheptadecanoin (THA), ULTRASE MT20, ursodiol, or combinations thereof.

In certain embodiments wherein fibrosis or fibrotic condition of the lung is treated, prevented and/or managed, a compound provided herein can be combined with, for example, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, anti-pseudomonas IgY gargle, ARIKACE™, AUREXIS® (tefibazumab), AZAPRED, azathioprine, azithromycin, azithromycin, AZLI, aztreonam lysine, BIBF1120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Moli1901, MP-376 (levofloxacin solution for inhalation), mucoid exopolysaccharide *P. aeruginosa* immune globulin IV, mycophenolate mofetil, n-acetylcysteine, N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB656933, SB-656933-AAA, sildenafil, tamoxifen, technetium [Tc-99m] sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, or combinations thereof.

In certain embodiments wherein fibrosis or fibrotic condition of the liver is treated, prevented and/or managed, a compound provided herein can be combined with, for example, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, or combinations thereof.

In certain embodiments wherein cystic fibrosis is treated, prevented and/or managed, a compound provided herein can be combined with, for example, 552-02, 5-methyltetrahydrofolate and vitamin B12, Ad5-CB-CFTR, Adeno-associated virus-CFTR vector, albuterol, alendronate, alpha tocopherol plus ascorbic acid, amiloride HCl, aquADEK™, ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl) trimethylammonium salt 1:1, VX-770, VX-809, Zinc acetate, or combinations thereof.

In some embodiments, a compound provided herein is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments wherein scleroderma is treated, prevented and/or managed, a compound provided herein can be combined with, for example: an immunosuppressant (e.g., methotrexate, azathioprine (Imuran®), cyclosporine, mycophenolate mofetil (Cellcept®), and cyclophosphamide (Cytoxan®)); T-cell-directed therapy (e.g., halofuginone, basiliximab, alemtuzumab, abatacept, rapamycin); B-cell directed therapy (e.g., rituximab); autologous hematopoietic stem cell transplantation; a chemokine ligand receptor antagonist (e.g., an agent that targets the CXCL12/CSCR4 axis (e.g., AMD3100)); a DNA methylation inhibitor (e.g., 5-azacytidine); a histone deacetylase inhibitor (e.g., trichostatin A); a statin (e.g., atorvastatin, simvastatin, pravastatin); an endothelin receptor antagonist (e.g., Bosentan®); a phosphodiesterase type V inhibitor (e.g., Sildenafil®); a prostacyclin analog (e.g., trepostinil); an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)); corticosteroids; nonsteroidal anti-inflammatory drugs; light therapy; and blood pressure medications (e.g., ACE inhibitors).

In certain embodiments wherein inflammatory myopathies are treated, prevented and/or managed, a compound provided herein can be combined with, for example: topical creams or ointments (e.g., topical corticosteroids, tacrolimus, pimecrolimus); cyclosporine (e.g., topical cyclosporine); an anti-interferon therapy, e.g., AGS-009, Rontalizumab (rhuMAb IFNalpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid; corticosteroids such as prednisone (e.g., oral prednisone); immunosuppressive therapies such as methotrexate (Trexall®, Methotrexate®, Rheumatrex®), azathioprine (Azasan®, Imuran®), intravenous immunoglobulin, tacrolimus (Prograf®), pimecrolimus, cyclophosphamide (Cytoxan®), and cyclosporine (Gengraf®, Neoral®, Sandimmune®); anti-malarial agents such as hydroxychloroquine (Plaquenil®) and chloroquine (Aralen®); total body irradiation; rituximab (Rituxan®); TNF inhibitors (e.g., etanercept (Enbrel®), infliximab (Remicade®)); AGS-009; Rontalizumab (rhuMAb IFNalpha); Vitamin D3; Sifalimumab (MEDI-545); AMG 811; IFNα Kinoid; CEP33457; agents that inhibit IgE production such as TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2; agents that inhibit IgE activity such as anti-IgE antibodies (e.g., Omalizumab and TNX-90); and additional therapies such as physical therapy, exercise, rest, speech therapy, sun avoidance, heat therapy, and surgery.

In certain embodiments wherein myositis (e.g., dermatomysitis) is treated, prevented and/or managed, a compound provided herein can be combined with, for example: corticosteroids; corticosteroid sparing agents such as, but not limited to, azathioprine and methotrexate; intravenous immunoglobulin; immunosuppressive agents such as, but not limited to, tacrolimus, cyclophosphamide and cyclosporine; rituximab; TNFα inhibitors such as, but not limited to, etanercept and infliximab; growth hormone; growth hormone secretagogues such as, but not limited to, MK-0677, L-162752, L-163022, NN703 ipamorelin, hexarelin, GPA-748 (KP102, GHRP-2), and LY444711 (Eli Lilly); other growth hormone release stimulators such as, but not limited to, Geref, GHRH (1-44), Somatorelin (GRF 1-44), ThGRF genotropin, L-DOPA, glucagon, and vasopressin; and insulin-like growth factor.

In certain embodiments wherein Sjögren's syndrome is treated, prevented and/or managed, a compound provided herein can be combined with, for example: pilocarpine; cevimeline; nonsteroidal anti-inflammatory drugs; arthritis medications; antifungal agents; cyclosporine; hydroxychloroquine; prednisone; azathioprine; and cyclophamide.

Administration of a compound provided herein, or a pharmaceutically acceptable form thereof, can be effected by any method that enables delivery of the compound to the site of action. An effective amount of a compound provided herein, or a pharmaceutically acceptable form thereof, can be administered in either single or multiple doses by any of the accepted modes of administration of agents having similar utilities, including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound provided herein, or a pharmaceutically acceptable form thereof, is administered in a pharmaceutical composition that comprises one or more agents, and the agent has a shorter half-life than the compound provided herein, unit dose forms of the agent and the compound as provided herein can be adjusted accordingly.

In some embodiments, the compound provided herein and the second agent are administered as separate compositions, e.g., pharmaceutical compositions. In some embodiments, the PI3K modulator and the agent are administered separately, but via the same route (e.g., both orally or both intravenously). In other embodiments, the PI3K modulator and the agent are administered in the same composition, e.g., pharmaceutical composition.

In some embodiments, a compound provided herein (e.g., compound 1), or an enantiomer or a mixture of enantiomers thereof, or a pharmaceutically acceptable salt, solvate, hydrate, co-crystal, clathrate, or polymorph thereof) is administered in combination with an agent for pulmonary or respiratory diseases. Examples of agents for pulmonary or respiratory diseases include, but are not limited to, Dymista (azelastine hydrochloride and fluticasone propionate), Kalydeco (ivacaftor), Qnasl (beclomethasone dipropionate) nasal aerosol, Rayos (prednisone) delayed-release tablets, Surfaxin (lucinactant), Tudorza Pressair (aclidinium bromide inhalation powder), Arcapta (indacaterol maleate inhalation powder), Daliresp (roflumilast), Xalkori (crizotinib), Cayston (aztreonam for inhalation solution), Dulera (mometasone furoate+formoterol fumarate dihydrate), Teflaro (ceftaroline fosamil), Adcirca (tadalafil), Tyvaso (treprostinil), Alvesco (ciclesonide), Patanase (olopatadine hydrochloride), Letairis (ambrisentan), Xyzal (levocetirizine dihydrochloride), Brovana (arformoterol tartrate), Tygacil (tigecycline), Ketek (telithromycin), Spiriva HandiHaler (tiotropium bromide), Aldurazyme (laronidase), Iressa (gefitinib), Xolair (omalizumab), Zemaira (alphal-proteinase inhibitor), Clarinex, Qvar (beclomethasone dipropionate), Remodulin (treprostinil), Xopenex, Avelox I.V. (moxifloxacin hydrochloride), DuoNeb (albuterol sulfate and ipratropium bromide), Foradil Aerolizer (formoterol fumarate inhalation powder), Invanz, NasalCrom Nasal Spray, Tavist (clemastine fumarate), Tracleer (bosentan), Ventolin HFA (albuterol sulfate inhalation aerosol), Biaxin XL (clarithromycin extended-release tablets), Cefazolin and Dextrose USP, Tri-Nasal Spray (triamcinolone acetonide spray), Accolate, Cafcit Injection, Proventil HFA Inhalation Aerosol, Rhinocort Aqua Nasal Spray, Tequin, Tikosyn Capsules, Allegra-D, Clemastine fumarate syrup, Curosurf, Dynabac, Infasurf, Priftin, Pulmozyme (dornase alfa), Sclerosol Intrapleural Aerosol, Singulair, Synagis, Ceftin (cefuroxime axetil), Cipro (ciprofloxacin HCl), Claritin RediTabs (10 mg loratadine rapidly-disintegrating tablet), Flonase Nasal Spray, Flovent Rotadisk, Metaprotereol Sulfate Inhalation Solution (5%), Nasacort AQ (triamcinolone acetonide) Nasal Spray, Omnicef, Raxar (grepafloxacin), Serevent, Tilade (nedocromil sodium), Tobi, Vanceril 84 mcg Double Strength (beclomethasone dipropionate, 84 mcg) Inhalation Aerosol, Zagam (sparfloxacin) tablets, Zyflo (Zileuton), Accolate, Allegra (fexofenadine hydrochloride), Astelin nasal spray, Atrovent (ipratropium bromide), Augmentin (amoxicillin/clavulanate), Azmacort (triamcinolone acetonide) Inhalation Aerosol, Breathe Right, Claritin Syrup (loratadine), Claritin-D 24 Hour Extended Release Tablets (10 mg loratadine, 240 mg pseudoephedrine sulfate), Covera-HS (verapamil), Nasacort AQ (triamcinolone acetonide) Nasal Spray, OcuHist, Pulmozyme (dornase alfa), RespiGam (Respiratory Syncitial Virus Immune Globulin Intravenous), Tavist (clemastine fumarate), Tripedia (Diptheria and Tetanus Toxoids and Acellular Pertussis Vaccine Absorbed), Vancenase AQ 84 mcg Double Strength, Visipaque (iodixanol), Zosyn (sterile piperacillin sodium/tazobactam sodium), Cedax (ceftibuten), and Zyrtec (cetirizine HCl). In one embodiment, the agent for pulmonary or respiratory diseases is Arcapta, Daliresp, Dulera, Alvesco, Brovana, Spiriva HandiHaler, Xolair, Qvar, Xopenex, DuoNeb, Foradil Aerolizer, Accolate, Singulair, Flovent Rotadisk, Tilade, Vanceril, Zyflo, or Azmacort Inhalation Aerosol. In one embodiment, the agent for pulmonary or respiratory diseases is Spiriva HandiHaler.

In some embodiments, a compound provided herein (e.g., compound 1), or an enantiomer or a mixture of enantiomers thereof, or a pharmaceutically acceptable salt, solvate, hydrate, co-crystal, clathrate, or polymorph thereof) is administered in combination with an agent for immunology or infectious diseases. Examples of agents for immunology or infectious diseases include, but are not limited to, Horizant (gabapentin enacarbil), Qnasl (beclomethasone dipropionate) nasal aerosol, Rayos (prednisone) delayed-release tablets, Stribild (elvitegravir, cobicistat, emtricitabine, tenofovir disoproxil fumarate), Tudorza Pressair (aclidinium bromide inhalation powder), Arcapta (indacaterol maleate inhalation powder), Benlysta (belimumab), Complera (emtricitabine/rilpivirine/tenofovir disoproxil fumarate), Daliresp (roflumilast), Dificid (fidaxomicin), Edurant (rilpivirine), Firazyr (icatibant), Gralise (gabapentin), Incivek (telaprevir), Nulojix (belatacept), Victrelis (boceprevir), Cayston (aztreonam for inhalation solution), Egrifta (tesamorelin for injection), Menveo (meningitis vaccine), Oravig (miconazole), Prevnar 13 (Pneumococcal 13-valent Conjugate Vaccine), Teflaro (ceftaroline fosamil), Zortress (everolimus), Zymaxid (gatifloxacin ophthalmic solution), Bepreve (bepotastine besilate ophthalmic solution), Berinert (C1 Esterase Inhibitor (Human)), Besivance (besifloxacin ophthalmic suspension), Cervarix [Human Papillomavirus Bivalent (Types 16 and 18) Vaccine, Recombinant], Coartem (artemether/lumefantrine), Hiberix (Haemophilus b Conjugate Vaccine; Tetanus Toxoid Conjugate), Ilaris (canakinumab), Ixiaro (Japanese Encephalitis Vaccine, Inactivated, Adsorbed), Kalbitor (ecallantide), Qutenza (capsaicin), Vibativ (telavancin), Zirgan (ganciclovir ophthalmic gel), Aptivus (tipranavir), Astepro (azelastine hydrochloride nasal spray), Cinryze (C1 Inhibitor (Human)), Intelence (etravirine), Moxatag (amoxicillin), Rotarix (Rotavirus Vaccine, Live, Oral), Tysabri (natalizumab), Viread (tenofovir disoproxil fumarate), Altabax (retapamulin), AzaSite (azithromycin), Doribax (doripenem), Extina (ketoconazole), Isentress (raltegravir), Selzentry (maraviroc), Veramyst (fluticasone furoate), Xyzal (levocetirizine dihydrochloride), Eraxis (anidulafungin), Gardasil (quadrivalent human papillomavirus (types 6, 11, 16, 18) recombinant vaccine), Noxafil (posaconazole), Prezista (darunavir), Rotateq (rotavirus vaccine, live oral pentavalent), Tyzeka (telbivudine), Veregen (kunecatechins), Aptivus (tipranavir), Baraclude (entecavir), Tygacil (tigecycline), Ketek (telithromycin), Tindamax, tinidazole, Xifaxan (rifaximin), Amevive (alefacept), FluMist (Influenza Virus Vaccine), Fuzeon (enfuvirtide), Lexiva (fosamprenavir calcium), Reyataz (atazanavir sulfate), Alinia (nitazoxanide), Clarinex, Daptacel, Fluzone Preservative-free, Hepsera (adefovir dipivoxil), Pediarix Vaccine, Pegasys (peginterferon alfa-2a), Restasis (cyclosporine ophthalmic emulsion), Sustiva, Vfend (voriconazole), Avelox I.V. (moxifloxacin hydrochloride), Cancidas, Peg-Intron (peginterferon alfa-2b), Rebetol (ribavirin), Spectracef, Twinrix, Valcyte (valganciclovir HCl), Viread (tenofovir disoproxil fumarate), Xigris (drotrecogin alfa [activated]), ABREVA (docosanol), Biaxin XL (clarithromycin extended-release tablets), Cefazolin and Dextrose USP, Children's Motrin Cold, Evoxac, Kaletra Capsules and Oral Solution, Lamisil (terbinafine hydrochloride) Solution (1%), Lotrisone (clotrimazole/betamethasone diproprionate) lotion, Malarone (atovaquone; proguanil hydrochloride) Tablet, Rapamune (sirolimus) Tablets, Rid Mousse, Tri-Nasal Spray (triamcinolone acetonide spray), Trivagizole 3 (clotrimazole) Vaginal Cream, Trizivir (abacavir sulfate; lamivudine; zidovudine AZT) Tablet, Agenerase (amprenavir), Cleocin (clindamycin phosphate), Famvir (famciclovir), Norvir (ritonavir), Panretin Gel, Rapamune (sirolimus) oral solution, Relenza, Synercid I.V., Tamiflu capsule, Vistide (cidofovir), Allegra-D, CellCept, Clemastine fumarate syrup, Cleocin (clindamycin phosphate), Dynabac, REBETRON™ Combination Therapy, Simulect, Timentin, Viroptic, INFANRIX (Diphtheria and Tetanus Toxoids and Acellular Pertussis Vaccine Adsorbed), Acyclovir Capsules, Aldara (imiquimod), Aphthasol, Combivir, Condylox Gel 0.5% (pokofilox), Famvir (famciclovir), Flagyl ER, Flonase Nasal Spray, Fortovase, INFERGEN (interferon alfacon-1), Intron A (interferon alfa-2b, recombinant), Norvir (ritonavir), Rescriptor Tablets (delavirdine mesylate tablets), SPORANOX (itraconazole), Stromectol (ivermectin), Taxol, Trovan, VIRACEPT (nelfinavir mesylate), Zerit (stavudine), Albenza (albendazole), Apthasol (Amlexanox), Carrington patch, Confide, Crixivan (Indinavir sulfate), Gastrocrom Oral Concentrate (cromolyn sodium), Havrix, Lamisil (terbinafine hydrochloride) Tablets, Leukine (sargramostim), Oral Cytovene, RespiGam (Respiratory Syncitial Virus Immune Globulin Intravenous), Videx (didanosine), Viramune (nevirapine), Vistide (cidofovir), Vitrasert Implant, Zithromax (azithromycin), Cedax (ceftibuten), Clarithromycin (Biaxin), Epivir (lamivudine), Intron A (Interferon alfa-2b, recombinant), Invirase (saquinavir), Valtrex (valacyclovir HCl), Western blot confirmatory device, Zerit (stavudine), and Zyrtec (cetirizine HCl).

In some embodiments, the second agent is an HDAC inhibitor, such as, e.g., belinostat, vorinostat, panobinostat, ACY-1215, or romidepsin.

In some embodiments, the second agent is an mTOR inhibitor, such as, e.g., everolimus (RAD 001).

In some embodiments, the second agent is a proteasome inhibitor, such as, e.g., bortezomib or carfilzomib.

In some embodiments, the second agent is a PKC-β inhibitor, such as, e.g., Enzastaurin (LY317615).

In some embodiments, the second agent is a JAK/STAT inhibitor, such as, e.g., INCB16562 or AZD1480.

In some embodiments, the second agent is an anti-folate, such as, e.g., pralatrexate.

In some embodiments, the second agent is a farnesyl transferase inhibitor, such as, e.g., tipifarnib.

In some embodiments, the second agent is an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein (e.g., compound 1), or a pharmaceutically acceptable derivative (e.g., salt or solvate) thereof, is used in combination bendamustine and one additional active agent. In one embodiment, the cancer or hematological malignancy is iNHL.

In some embodiments, a compound provided herein (e.g., compound 1), or a pharmaceutically acceptable derivative (e.g., salt or solvate) thereof, is used in combination rituximab and one additional active agent. In one embodiment, the cancer or hematological malignancy is iNHL.

In some embodiments, a compound provided herein (e.g., compound 1), or a pharmaceutically acceptable derivative (e.g., salt or solvate) thereof, is used in combination bendamustine and rituximab. In one embodiment, the cancer or hematological malignancy is iNHL.

In some embodiments, a compound provided herein (e.g., compound 1), or a pharmaceutically acceptable derivative (e.g., salt or solvate) thereof, is used in combination fludarabine, cyclophosphamide, and rituximab. In one embodiment, the cancer or hematological malignancy is CLL.

In some embodiments, a compound provided herein (e.g., compound 1), or a pharmaceutically acceptable derivative (e.g., salt or solvate) thereof, is used in combination with an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein (e.g., compound 1), or a pharmaceutically acceptable derivative (e.g., salt or solvate) thereof, is used in combination with an antibody-drug conjugate, such as, e.g., inotuzumab ozogamicin, or brentuximab vedotin.

In some embodiments, a compound provided herein (e.g., compound 1), or a pharmaceutically acceptable derivative (e.g., salt or solvate) thereof, is used in combination with a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, a compound provided herein (e.g., compound 1), or a pharmaceutically acceptable derivative (e.g., salt or solvate) thereof, is used in combination with one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide, Doxorubicin or Hydroxydaunomycin, Vincristine or Oncovin, Prednisone).

In some embodiments, a compound provided herein (e.g., compound 1), or a pharmaceutically acceptable derivative (e.g., salt or solvate) thereof, is used in combination with an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K-delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein (e.g., compound 1), or a pharmaceutically acceptable derivative (e.g., salt or solvate) thereof, and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors, SYK inhibitors, and/or PI3K-delta inhibitors).

Further without being limited by a particular theory, it was found that a compound provided herein (e.g., compound 1) does not affect BTK or MEK pathway. Accordingly, in some embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is iNHL. In another embodiment, the cancer or hematological malignancy is CLL.

In other embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a MEK inhibitor. In one embodiment, the MEK inhibitor is trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)-N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2-yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with an EZH2 inhibitor. In one embodiment, the EZH2 inhibitor is EPZ-6438, GSK-126, GSK-343, E11, or 3-deazaneplanocin A (DNNep). In one embodiment, the cancer or hematological malignancy is DLBCL. In another embodiment, the cancer or hematological malignancy is iNHL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a bcl-2 inhibitor. In one embodiment, the BCL2 inhibitor is ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[((2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3 ((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), or G3139 (Oblimersen). In one embodiment, the cancer or hematological malignancy is DLBCL. In another embodiment, the cancer or hematological malignancy is iNHL. In another embodiment, the cancer or hematological malignancy is CLL. In another embodiment, the cancer or hematological malignancy is ALL. In another embodiment, the cancer or hematological malignancy is CTCL.

In other embodiments, provided herein is a method of treating or managing iNHL comprising administering to a patient a therapeutically effective amount of a compound provided herein (e.g., compound 1), or a pharmaceutically acceptable derivative (e.g., salt or solvate) thereof, in combination with rituximab. In one embodiment, the patient is an elderly patient. In another embodiment, iNHL is relapsed or refractory.

In other embodiments, provided herein is a method of treating or managing iNHL comprising administering to a patient a therapeutically effective amount of a compound provided herein (e.g., compound 1), or a pharmaceutically acceptable derivative (e.g., salt or solvate) thereof, in combination with bendamustine. In one embodiment, iNHL is relapsed or refractory.

In other embodiments, provided herein is a method of treating or managing iNHL comprising administering to a patient a therapeutically effective amount of a compound provided herein (e.g., compound 1), or a pharmaceutically acceptable derivative (e.g., salt or solvate) thereof, in combination with rituximab, and in further combination with bendamustine. In one embodiment, iNHL is relapsed or refractory.

In other embodiments, provided herein is a method of treating or managing iNHL comprising administering to a patient a therapeutically effective amount of a compound provided herein (e.g., compound 1), or a pharmaceutically acceptable derivative (e.g., salt or solvate) thereof, in combination with lenalidomide. In one embodiment, iNHL is relapsed or refractory.

In other embodiments, provided herein is a method of treating or managing CLL comprising administering to a patient a therapeutically effective amount of a compound provided herein (e.g., compound 1), or a pharmaceutically acceptable derivative (e.g., salt or solvate) thereof, in combination with rituximab. In one embodiment, the patient is an elderly patient. In another embodiment, CLL is relapsed or refractory.

In other embodiments, provided herein is a method of treating or managing CLL comprising administering to a patient a therapeutically effective amount of a compound provided herein (e.g., compound 1), or a pharmaceutically acceptable derivative (e.g., salt or solvate) thereof, in combination with bendamustine. In one embodiment, CLL is relapsed or refractory.

In other embodiments, provided herein is a method of treating or managing CLL comprising administering to a patient a therapeutically effective amount of a compound provided herein (e.g., compound 1), or a pharmaceutically acceptable derivative (e.g., salt or solvate) thereof, in combination with rituximab, and in further combination with bendamustine. In one embodiment, CLL is relapsed or refractory.

In other embodiments, provided herein is a method of treating or managing CLL comprising administering to a patient a therapeutically effective amount of a compound provided herein (e.g., compound 1), or a pharmaceutically acceptable derivative (e.g., salt or solvate) thereof, in combination with lenalidomide. In one embodiment, CLL is relapsed or refractory.

In other embodiments, provided herein is a method of treating or managing DLBCL comprising administering to a patient a therapeutically effective amount of a compound provided herein (e.g., compound 1), or a pharmaceutically acceptable derivative (e.g., salt or solvate) thereof, in combination with rituximab. In one embodiment, the patient is an elderly patient. In another embodiment, DLBCL is relapsed or refractory.

In other embodiments, provided herein is a method of treating or managing DLBCL comprising administering to a patient a therapeutically effective amount of a compound provided herein (e.g., compound 1), or a pharmaceutically acceptable derivative (e.g., salt or solvate) thereof, in combination with bendamustine. In one embodiment, DLBCL is relapsed or refractory.

In other embodiments, provided herein is a method of treating or managing DLBCL comprising administering to a patient a therapeutically effective amount of a compound provided herein (e.g., compound 1), or a pharmaceutically acceptable derivative (e.g., salt or solvate) thereof, in combination with rituximab, and in further combination with bendamustine. In one embodiment, DLBCL is relapsed or refractory.

In other embodiments, provided herein is a method of treating or managing DLBCL comprising administering to a patient a therapeutically effective amount of a compound provided herein (e.g., compound 1), or a pharmaceutically acceptable derivative (e.g., salt or solvate) thereof, in combination with R-GDP (rituximab, cyclophosphamide, vincristine and prednisone). In one embodiment, DLBCL is relapsed or refractory. In another embodiment, the treatment is done subsequent to treatment by R-CHOP.

In other embodiments, provided herein is a method of treating or managing DLBCL comprising administering to a patient a therapeutically effective amount of a compound provided herein (e.g., compound 1), or a pharmaceutically acceptable derivative (e.g., salt or solvate) thereof, in combination with ibrutinib. In one embodiment, DLBCL is relapsed or refractory.

In other embodiments, provided herein is a method of treating or managing T-cell lymphoma (PTCL or CTCL) comprising administering to a patient a therapeutically effective amount of a compound provided herein (e.g., compound 1), or a pharmaceutically acceptable derivative (e.g., salt or solvate) thereof, in combination with rituximab. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compound 1), or a pharmaceutically acceptable derivative (e.g., salt or solvate) thereof, in combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compound 1), or a pharmaceutically acceptable derivative (e.g., salt or solvate) thereof, in combination with rituximab, and in further combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compound 1), or a pharmaceutically acceptable derivative (e.g., salt or solvate) thereof, in combination with romidepsin. In one embodiment, T-cell lymphoma is relapsed or refractory.

In other embodiments, provided herein is a method of treating or managing mantle cell lymphoma comprising administering to a patient a therapeutically effective amount of a compound provided herein (e.g., compound 1), or a pharmaceutically acceptable derivative (e.g., salt or solvate)

thereof, in combination with rituximab. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compound 1), or a pharmaceutically acceptable derivative (e.g., salt or solvate) thereof, in combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compound 1), or a pharmaceutically acceptable derivative (e.g., salt or solvate) thereof, in combination with rituximab, and in further combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compound 1), or a pharmaceutically acceptable derivative (e.g., salt or solvate) thereof, in combination with ibrutinib. In one embodiment, mantle cell lymphoma is relapsed or refractory.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a AraC. In one embodiment, the cancer or hematological malignancy is AML.

In specific embodiments, compound 1 or a pharmaceutically acceptable form thereof, is used in combination with one or more second agent or second therapy provided herein.

In some embodiments, the second agent is an antibody-drug conjugate, such as, e.g., inotuzumab ozogamicin, or brentuximab vedotin.

In some embodiments, the second agent is a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, the second agent is one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide, Doxorubicin or Hydroxydaunomycin, Vincristine or Oncovin, Prednisone).

In some embodiments, the second agent is an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K-delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein (e.g., compound 1) and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors, SYK inhibitors, and/or PI3K-delta inhibitors).

Further without being limited by a particular theory, it was found that a compound provided herein (e.g., compound 1) does not affect BTK or MEK pathway. Accordingly, in some embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is CLL.

In other embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a MEK inhibitor. In one embodiment, the MEK inhibitor is trametinib, selumetinob, AS703026/MSC1935369, XL-518/GDC-0973, BAY869766/RDEA119, GSK1120212 (trametinib), pimasertib, refametinib, PD-0325901, TAK733, MEK162/ARRY438162, RO5126766, WX-554, RO4987655/CH4987655 or AZD8330. In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a bcl-2 inhibitor. In one embodiment, the BCL2 inhibitor is ABT-199, ABT-737, ABT-263, GX15-070 (obatoclax mesylate) or G3139 (Genasense). In one embodiment, the cancer or hematological malignancy is DLBCL. In another embodiment, the cancer or hematological malignancy is ALL. In another embodiment, the cancer or hematological malignancy is CTCL.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein (e.g., compound 1), or a pharmaceutically acceptable derivative (e.g., salt or solvate) thereof, in combination with a AraC. In one embodiment, the cancer or hematological malignancy is AML.

In specific embodiments, compound 1 or a pharmaceutically acceptable form thereof, is used in combination with one or more second agent or second therapy provided herein.

In certain embodiments, provided herein are pharmaceutical composition comprising a therapeutically effective amount of a compound provided herein (e.g., compound 1), or a pharmaceutically acceptable form thereof, and a PI3K-delta inhibitor.

In one embodiment, the PI3K-delta inhibitor is a PI3K-delta selective inhibitor. In one embodiment, the PI3K-delta inhibitor is GS-1101 (Cal-101), GSK-2269557, GS-9820, AMG319, or TGR-1202, or a mixture thereof. In one embodiment, the PI3K-delta inhibitor is of the formula:

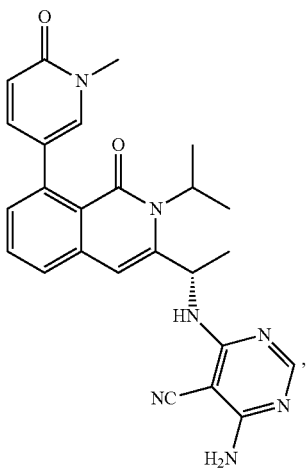 [SMILES: CC(C)n1c([C@H](C)Nc2ncnc(N)c2C#N)cc2cccc(-c3ccc(=O)n(C)c3)c2c1=O]

or a pharmaceutically acceptable form thereof.

In one embodiment, the molar ratio of the compound, or a pharmaceutically acceptable form thereof, to the PI3K-delta inhibitor is in the range of from about 10000:1 to about 1:10000. In one embodiment, the molar ratio of the compound, or a pharmaceutically acceptable form thereof, to the PI3K-delta inhibitor is in the range of from about 10:1 to about 1:10. In one embodiment, the composition comprises the compound, or a pharmaceutically acceptable form thereof, at an amount of in the range of from about 0.01 mg to about 75 mg and the PI3K-delta inhibitor at an amount of in the range of from about 0.01 mg to about 1100 mg. In one embodiment, the compound, or a pharmaceutically acceptable form thereof, and the PI3K-delta inhibitor are the only therapeutically active ingredients.

In one embodiment, the compound, or pharmaceutically acceptable form thereof, and the PI3K-delta inhibitor are in a single dosage form. In one embodiment, the compound, or pharmaceutically acceptable form thereof, and the PI3K-delta inhibitor are in separate dosage forms. In one embodiment, the composition further comprising a pharmaceutically acceptable excipient.

In one embodiment, the composition is synergistic in treating a cancer, inflammatory disease, or autoimmune disease.

In one embodiment, provided herein is a method of treating a PI3K-mediated disorder in a subject, comprising administering to the subject a therapeutically effective amount of the composition.

In certain embodiments, provided herein are methods treating a PI3K-mediated disorder in a subject, comprising administering to the subject a therapeutically effective amount of a compound provided herein (e.g., compound 1), or a pharmaceutically acceptable form thereof, in combination with a PI3K-delta inhibitor.

In one embodiment, the compound, or a pharmaceutically acceptable form thereof, is administered concurrently with the PI3K-delta inhibitor. In one embodiment, the compound, or a pharmaceutically acceptable form thereof, is administered subsequent to the PI3K-delta inhibitor. In one embodiment, the compound, or a pharmaceutically acceptable form thereof, is administered prior to the PI3K-delta inhibitor. In one embodiment, the compound, or a pharmaceutically acceptable form thereof, is administered alone after discontinuing the administration of the PI3K-delta inhibitor.

In one embodiment, the PI3K-mediated disorder is a cancer, autoimmune disease, or inflammatory disease. In one embodiment, the cancer is of hematopoietic origin. In one embodiment, the cancer is a leukemia or lymphoma. In one embodiment, the leukemia or lymphoma is a B-cell lymphoma, T-cell lymphoma, non-Hodgkin lymphoma, Hodgkin lymphoma, or anaplastic large cell lymphoma.

In one embodiment, the cancer is a solid tumor. In one embodiment, the cancer is selected from one or more of: a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the PI3K-delta inhibitor is a PI3K-delta selective inhibitor. In one embodiment, the PI3K-delta inhibitor is of the formula:

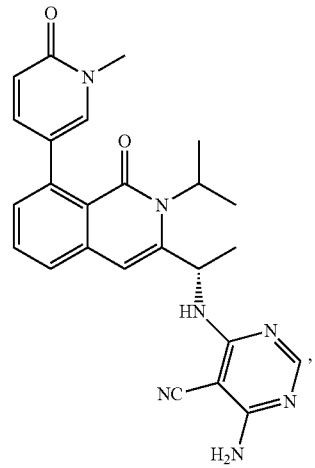 [SMILES: CC(C)n1c([C@H](C)Nc2ncnc(N)c2C#N)cc2cccc(-c3ccc(=O)n(C)c3)c2c1=O]

or a pharmaceutically acceptable form thereof.

In one embodiment, the compound, or a pharmaceutically acceptable form thereof, and the PI3K-delta inhibitor are in a single dosage form. In one embodiment, the compound, or a pharmaceutically acceptable form thereof, and the PI3K-delta inhibitor are in separate dosage forms.

In one embodiment, the concentration of the compound that is required to achieve 50% inhibition is at least 20%, 30%, 40%, or 50% lower when the compound is administered in combination with the PI3K-delta inhibitor than when the compound is administered individually. In one embodiment, the concentration of the PI3K-delta inhibitor that is required to achieve 50% inhibition is at least 20%, 30%, 40%, or 50% lower when the PI3K-delta inhibitor is administered in combination with the compound than when the PI3K-delta inhibitor is administered individually. In one embodiment, the dose of the compound that is required to achieve 50% inhibition is at least 20%, 30%, 40%, or 50% lower when the compound is administered in combination with the PI3K-delta inhibitor than when the compound is administered individually. In one embodiment, the dose of the PI3K-delta inhibitor that is required to achieve 50% inhibition is at least 20%, 30%, 40%, or 50% lower when the PI3K-delta inhibitor is administered in combination with the compound than when the PI3K-delta inhibitor is administered individually.

In one embodiment, the combination is synergistic as indicated by a combination index value that is less than 0.7, 0.5, or 0.1 for the combination of the compound and the PI3K-delta inhibitor. In one embodiment, the combination index value is assessed at 50% inhibition. In one embodiment, the combination index value is assessed at 50% growth inhibition. In one embodiment, the combination is synergistic as indicated by a Synergy Score that is greater than 1, 2, or 3 for the combination of the Compound 1 and the PI3K-delta inhibitor. In one embodiment, the combination is synergistic as indicated by a Synergy Score that is greater than 1, 2, or 3, for the combination of the compound and the PI3K-delta inhibitor for inhibition or growth inhibition.

In one embodiment, the PI3K-mediated disorder is cancer, and the anti-cancer effect provided by the combination is at least 2 fold greater, at least 3 fold greater, at least 5 fold greater, or at least 10 fold greater than the anti-cancer effect provided by Compound 1, or pharmaceutically acceptable form thereof, alone. In one embodiment, the PI3K-mediated disorder is cancer, and the anti-cancer effect provided by the combination is at least 2 fold greater, at least 3 fold greater, at least 5 fold greater, or at least 10 fold greater than the anti-cancer effect provided by the PI3K-delta inhibitor alone.

In one embodiment, wherein one or more side effects associated with administration of the compound, or a pharmaceutically acceptable form thereof, alone is reduced when the combination is administered at a dose that achieves the same therapeutic effect. In one embodiment, one or more side effects associated with administration of the PI3K-delta inhibitor alone is reduced when the combination is administered at a dose that achieves the same therapeutic effect.

Combinations with Immune Modulators

While not wishing to be bound by theory, it is believed that tumor growth is influenced by at least two classes of immune cells in the tumor microenvironment: effector cells (including cytotoxic cells and M1 macrophages) which have anti-tumor activity, and tumor associated suppressor cells (including M2 macrophages, MDSC, Tregs, and regulatory dendritic cells) which have pro-tumor activity because they inhibit the effector cells or provide direct growth stimulation to the tumor cells or tumor vasculature. An abundance of suppressor cells can lead to tumor immune tolerance, and enhancement of tumor growth. A combination cancer therapy can be designed taking this mechanism into consideration.

For example, in embodiments, a PI3K-γ inhibitor as described herein (or a compound provided herein (e.g., compound 1) is administered in combination with a second therapeutic that blocks homeostatic down-regulation of a T cell response in an effector T cell. This second agent may be an immune checkpoint therapy as described below. As another example, in embodiments, a PI3K-γ inhibitor as described herein is administered in combination with a second therapeutic that reduces or eliminates suppressive cells in the tumor microenvironment, e.g., may deplete MDSCs, TAMs or M2 macrophages, or any combination thereof. This agent could comprise, e.g., a CSF1R inhibitor, a CCL2 inhibitor, a CXCR4 inhibitor, a MEK inhibitor, or an MTOR inhibitor, or any combination thereof. In some embodiments, the second agent is an immunotherapy such as a tumor vaccine, e.g., a tumor vaccine described herein. In some embodiments, the second agent is a cell therapy, e.g., a dendritic cell or a chimeric T cell, e.g., as described herein. In some embodiments, the second agent is an interleukin, e.g., IL7, IL12, IL15, or IL21. According to non-limiting theory, some interleukins exert an anti-cancer effect by stimulating the growth of immune cell populations.

In another embodiment, a compound provided herein (e.g., compound 1) is administered in combination with a vaccine, e.g., a cancer vaccine, (e.g., a dendritic cell renal carcinoma (DC-RCC) vaccine). In certain embodiments, the combination of compound and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In some embodiments, a compound provided herein, or a pharmaceutically acceptable derivative (e.g., salt or solvate) thereof, is administered in combination with one or more immune checkpoint therapies. In some embodiments, provided herein is a method of treating a cancer in a subject, comprising administering to the subject a PI3K-gamma inhibitor or a compound as described herein (e.g., compound 1) in combination with one or more immune checkpoint therapies (e.g., PD-1 or PD-L1 inhibitors). In some embodiments, provided herein is a method of treating a solid cancer in a subject, comprising administering to the subject Compound 1, or a pharmaceutically acceptable form thereof, in combination with one or more of PD-1 or PD-L1 inhibitors. In one embodiment, the cancer is melanoma, bladder cancer, head and neck cancer, lung cancer (e.g., non-small cell lung cancer), or renal cell carcinoma. In one embodiment, the cancer is melanoma. In one embodiment, the cancer is bladder cancer. In one embodiment, the cancer is lung cancer. In one embodiment, the cancer is non-small cell lung cancer. In one embodiment, the cancer is renal cell carcinoma. In one embodiment, the cancer is head and neck cancer. In one embodiment, the cancer is breast cancer. In one embodiment, the cancer is triple-negative breast cancer. In one embodiment, the cancer is colon cancer. In one embodiment, the cancer is glioblastoma. In one embodiment, the cancer is ovarian cancer.

In some embodiments, the subject is naive to immunotherapy treatment. In some embodiments, the subject is naive to radiation therapy treatment. In some embodiments, the subject is naive to chemotherapy treatment.

In some embodiments, the subject has been pre-treated or previously treated with one or more immunotherapy treatments. In one embodiment, the subject is responsive to the pre-treatment or previous treatment with the immunotherapy. In one embodiment, the immunotherapy treatment is a checkpoint treatment such as a PD-1 or PD-L1 inhibitor. In one embodiment, the subject is a smoker.

In one embodiment, the cancer is melanoma, and the subject has been pre-treated or previously treated with one or more immunotherapy treatments. In one embodiment, the subject has been pre-treated or previously treated with two or more immunotherapy treatments.

In one embodiment, the cancer is head and neck cancer, lung cancer (e.g., non-small cell lung cancer), renal cell carcinoma, or bladder cancer, and the subject has been pre-treated or previously treated with one immunotherapy treatment.

In one embodiment, the cancer is breast cancer (e.g., triple-negative breast cancer), ovarian cancer, glioblastoma, or colon cancer, and the subject is naive to immunotherapy treatment.

In some embodiments, the immune checkpoint therapy inhibits CTLA-4, PD-1, or PD-L1, or any combination thereof. The immune checkpoint therapy may be, e.g., a small molecule or an antibody. In some embodiments, the immune checkpoint therapy is an antibody that inhibits programmed cell death 1 (also known as PD-1). In another embodiment, the immune checkpoint therapy is nivolumab (also known as Opdivo). In some embodiments, the immune checkpoint therapy is anti-PD-L1 (programmed cell death ligand 1, also known as cluster of differentiation 274 (CD274)), anti-PDL2, or anti-CTLA-4 (cytotoxic T-lymphocyte antigen 4, also known as cluster of differentiation (CD152)) antibody. Certain anti-PD-1, anti-PD-L1, and anti-CTLA-4 antibodies have activity in preclinical and clinical tumor models. Cancer Res; 73(12) Jun. 15, 2013; Curran M A et al. PNAS 2010; 107:4275-4280; Topalian et al. N Engl J Med 2012; 366:2443-2454; Wolchok et al., 2013. NEJM 369.

There are two main types of immune checkpoint therapies: an activator of a costimulatory molecule, and an inhibitor of an immune checkpoint molecule.

When the immune checkpoint therapy is an activator of a costimulatory molecule, it may be, e.g., chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. In certain embodiments, the immune checkpoint therapy is an inhibitor of OX40 or anti-OX40 ab.

In the second situation, the immune checkpoint therapy is an inhibitor of an immune checkpoint molecule, for instance, an inhibitor of PD-1, PD-L1, PD-L2, CTLA4, TIM3, LAG3, VISTA, BTLA, TIGIT, LAIR1, CD160, 2B4 and/or TGFR beta. For instance, the inhibitor of an immune checkpoint molecule may inhibit PD-1, PD-L1, LAG-3, TIM-3 or CTLA4, or any combination thereof.

Inhibition of an inhibitory molecule can be performed at the DNA, RNA or protein level. For example, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

The antibody molecule may be, e.g., a full antibody or fragment thereof (e.g., a Fab, F(ab')$_2$, Fv, or a single chain Fv fragment (scFv)). The antibody molecule may be, e.g., in the form of a bispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In certain embodiments, the antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

In certain embodiments, the immune checkpoint therapy is an inhibitor of PD-1, e.g., human PD-1. In another embodiment, the immune checkpoint therapy is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immune checkpoint therapies, e.g., in combination with an inhibitor of LAG-3, TIM-3 or CTLA4. In some embodiments, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Also provided herein are other combinations of immune checkpoint therapies with a PD-1 inhibitor (e.g., one or more of PD-L2, CTLA4, TIM3, LAG3, VISTA, BTLA, TIGIT, LAIR1, CD160, 2B4 and/or TGFR). Any of the PI3K inhibitor molecules known in the art or disclosed herein can be used in the aforesaid combinations of inhibitors of checkpoint molecule.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 inhibitor is AMP-224. In some embodiments, a PI3K inhibitor, e.g., a PI3K-γ inhibitor as described herein (e.g., Compound 1), is administered together with an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the combination therapy is used in a method of treating a cancer, as described herein.

In some embodiments, the PD-L1 inhibitor is anti-PD-L1 antibody. In some embodiments, the anti-PD-L1 inhibitor is chosen from YW243.55.570, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO2007/005874.

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).

In one embodiment, the LAG-3 inhibitor is an anti-LAG-3 antibody molecule. In one embodiment, the LAG-3 inhibitor is BMS-986016.

In some embodiments, the anti-PD-L1 binding antagonist is chosen from YW243.55.570, MPDL3280A, MEDI-4736, MSB-0010718C, or MDX-1105. MDX-1105, also known as BMS-936559, is an anti-PD-L1 antibody described in WO2007/005874. Antibody YW243.55.570 (heavy and light chain variable region sequences shown in SEQ ID Nos. 20 and 21, respectively) is an anti-PD-L1 described in WO 2010/077634.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335.

Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174.

MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No.: 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the inhibitor is a soluble ligand (e.g., a CTLA-4-Ig), or an antibody or antibody fragment that binds to PD-L1, PD-L2 or CTLA4. For example, a compound disclosed herein, e.g., Compound 1, can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, Yervoy, CAS No. 477202-00-9). In some embodiments, a compound provided herein is administered in combination with an anti-PD-L1 inhibitor (e.g., nivolumab) and a CTLA-4 antibody (e.g., ipilimumab). In some embodiments, a compound provided herein is administered in combination with nivolumab and ipilimumab.

In some embodiments, a compound provided herein, or a pharmaceutically acceptable derivative (e.g., salt or solvate) thereof, is administered in combination with an anti-PD-L1 or anti-CTLA-4 antibody. In some embodiments, a compound provided herein, or a pharmaceutically acceptable derivative (e.g., salt or solvate) thereof, is administered in combination with an anti-PD-L1 antibody. In another embodiment, a compound provided herein, or a pharmaceutically acceptable derivative (e.g., salt or solvate) thereof, is administered in combination with anti-CTLA-4 antibody. In some embodiments, the anti-PD-L1 antibody is selected from BMS-936559, MPDL3280A, and MDX-1105. In some embodiments, the anti-CTLA-4 antibody is selected from ipilimumab and tremelimumab.

In some embodiments, provided herein is a method of treating breast cancer, colon cancer, pancreatic cancer, melanoma, glioblastoma, or lung cancer comprising administering to a patient a therapeutically effective amount of a compound provided herein (e.g., compound 1), or a pharmaceutically acceptable derivative (e.g., salt or solvate) thereof, in combination with an anti-PD-L1 or an anti-CTLA-4 antibody. In another embodiment, the cancer is chosen form a carcinoma (e.g., advanced or metastatic carcinoma), melanoma or a lung carcinoma, e.g., a non-small cell lung carcinoma. In one embodiment, the cancer is a lung cancer, e.g., a non-small cell lung cancer. In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600E mutation). In another embodiment, the cancer is a hepatocarcinoma, e.g., an advanced hepatocarcinoma, with or without a viral infection, e.g., a chronic viral hepatitis. In another embodiment, the cancer is a prostate cancer, e.g., an advanced prostate cancer. In yet another embodiment, the cancer is a myeloma, e.g., multiple myeloma. In yet another embodiment, the cancer is a renal cancer, e.g., a renal cell carcinoma (RCC) (e.g., a metastatic RCC or clear cell renal cell carcinoma (CCRCC)).

For example, a compound provided herein (e.g., compound 1) can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, a compound provided herein (e.g., compound 1) is administered after treatment with an anti-CTLA4 antibody (e.g., ipilimumab) with or without a BRAF inhibitor (e.g., vemurafenib or dabrafenib).

In some embodiments, the immune checkpoint therapy is a costimulatory ligand. In some embodiments, the costimulatory ligand is OX40L, 41BBL, CD153, ICOSL, or CD40L.

In some embodiments, the immune checkpoint therapy is a MCSF/CSF-1R inhibitor. An anti-CSF-1R can deplete TAMs, resulting in tumor growth inhibition. Cancer Cell 25, 1-14, Jun. 16, 2014. In some embodiments, the CSF-1R inhibitor is BLZ945, GW2850, R05509554, or PLX3397. In some embodiments, the CSF-1R inhibitor is BLZ945 or GW2850. In some embodiments, the CSF-1R inhibitor is PLX3397.

In some embodiments, the immune checkpoint therapy is an immunostimulant. In some embodiments, the immunostimulant is GMCSF, TLR ligands, 41BBL, or ICOSL.

In some embodiments, the immune checkpoint therapy is a CXCR4/CXCL12 inhibitor. In some embodiments, the CXCR4/CXCL12 inhibitor is AMD3100, AMD11070, AMD12118, AMD11814, or AMD13073. In some embodiments, the CXCR4/CXCL12 inhibitor is AMD3100.

In some embodiments, the immunotherapy is a CCL2 and/or CCR2 antagonist. In some embodiments, the antagonist of CCL2 and/or CCR2 is an anti-CCL2 or CCR2 antibody. CCL2 is a chemokine and CCR2 is a chemokine receptor. CCL2 and CCR2, according to non-limiting theory, play a role in MDSC migration.

In some embodiments, a PI3K-γ inhibitor disclosed herein, e.g., Compound 1, is administered in combination with a BTK inhibitor. In one embodiment, the BTK inhibitor is BTK inhibitors such as ibrutinib, AVL-292, Dasatinib, LFM-AI3, ONO-WG-307, and GDC-0834.

In some embodiments, a PI3K-γ inhibitor disclosed herein, e.g., Compound 1, is administered in combination with an IDO (indoleamine 2,3-dioxygenase) inhibitor or an TDO (tryptophan 2,3-dioxygenase) inhibitor. In one embodiment, the IDO inhibitor is indoximod, NLG919, INCB024360, F001287, norharmane, rosmarinic acid, or alpha-methyl-tryptophan Although IDO inhibitors act within the TME, they do not specifically target MDSCs. The overexpression of IDO by dendritic cells creates an immunosuppressive tumor microenvironment.

In some embodiments, a PI3K-γ inhibitor disclosed herein, e.g., Compound 1, is administered in combination with an inhibitor of one or more members of TAM family, a receptor tyrosine kinase (RTK) subfamily comprising Tyro-3 (also called Sky), Ax1 and Mer. In one embodiment, the TAM inhibitor is BGB324 (R428), S49076, TP0903, CEP-40783, ONO-9330547, bosutinib (SKI606, PF5208763), cabozantinib (XL184), sunitinib (SU11248), foretinib (XL880, GSK1363089), MGCD265, BMS777607 (ASLAN002), LY2801653, SGI7079, amuvatinib (SGI-0470-02, MP470), SNS314, PF-02341066, diaminopyrimidine, spiroindoline, UNC569, UNC1062, UNC1666, UNC2025, or LDC1267. Additional TAM inhibitors include those described in Mollard et al., Med. Chem. Lett. 2011, 2, 907-912 and Feneyrolles et al., Mol. Cancer Ther. 13(9), Published OnlineFirst Aug. 19, 2014, the entireties of which are incorporated by reference herein.

In some embodiment, a PI3K-γ inhibitor disclosed herein, e.g., Compound 1, is administered to a subject concurrent or prior to the administration of immune checkpoint therapy. In some embodiment, an immunostimulant is administered to a subject concurrent or prior to the administration of immune checkpoint therapy. In some embodiment, chemotherapy (e.g., carboplatin, oxaliplatin, or radiation) is administered to a subject concurrent or prior to the administration of immune checkpoint therapy.

In some embodiments, a PI3K-γ inhibitor disclosed herein, e.g., Compound 1, is administered in combination with an ARG1 inhibitor. While not wishing to be bound by theory, it has been reported that tumor associated myeloid cells establish an immunosuppressive microenvironment in tumors through the expression of Arginase-1, which depletes the tumor microenvironment of arginine, thereby the death or inhibition of anti-tumor immune cells. Schmid et al., Proceedings: AACR 103rd Annual Meeting 2012, Cancer Research: Apr. 15, 2012; Volume 72, Issue 8, Supplement 1. It has been reported that suppression of PI3K-gamma or Arginase-1 expression blocked myeloid cell induced death of T cells in vitro. Id. According to the non-limiting theory, PI3K-gamma inhibition blocks Arginase-1 expression, thereby increasing the number of CD8+T cells in tumors, stimulating T cell-mediated cytotoxicity of tumor cells, and suppressing growth and metastasis of tumors. Combination therapies can be designed in accordance with this mechanism.

For instance, in some embodiments, a PI3K-γ inhibitor disclosed herein, e.g., Compound 1, is administered in combination with an ARG1 inhibitor. The ARG1 inhibitor may be, e.g., an inhibitory nucleic acid such as a siRNA, an inhibitory anti-ARG-1 antibody, or an analog of arginine. Other exemplary inhibitors of ARG1 include N-hydroxy-guanidinium or N-hydroxy-nor-1-arginine, and boronic acid derivatives, such as, 2(S)-amino-6-boronohexanoic acid, and S-(2-boronoethyl)-1-cysteine, α-α-disubstituted amino acid based arginase inhibitors [such as (R)-2-amino-6-borono-2-(2-(piperidin-1-yl)ethyl)hexanoic acid], and piceatannol-3'-O-β-d-glucopyranoside (PG). Steppan et al., "Development of novel arginase inhibitors for therapy of endothelial dysfunction.", Front Immunol. 2013 Sep. 17; 4:278. doi: 10.3389/fimmu.2013.00278.

The PI3K-γ inhibitors disclosed herein can have minimal effects on T-cell activation when compared to the suppressive effect of a PI3K δ inhibitor on T-cell activation. Lewis lung carcinoma tumor growth can be reduced in PI3K-γ knockout mice and can have decreased tumor associated suppressive myeloid cell infiltrates. Tumor associated suppressive myeloid cells can include e.g., myeloid derived suppressor cells (MDSCs) and tumor associated macrophages (TAMs). PI3K-γ knockout mice have TAMs where the M2 phenotype is lost. M2 cells are immunosuppressive and support tumor growth. PI3K inhibitors provided herein can block M2 phenotype (e.g., in an in vitro differentiation system), and thus can slow tumor growth.

For example, the effect of PI3K-γ inhibitors and PI3K δ inhibitors on T cell activation as measured by inhibition of IFN-γ in response to ConA has shown that PI3K-δ is plays a role in mediating T cell activation, while PI3K-γ has minimal effects on T-cell activation. The $IC_{50}$ for a PI3K-δ inhibitor in this assay is 3 nM, and the $IC_{50}$ for a PI3K-γ inhibitor is 2500 nM. Administration of PI3K-γ inhibitors can lead to impaired. T-cell migration but may have reduced effects on T-cell proliferation or activation.

In some embodiments, the PI3K-γ inhibitors disclosed herein can have potent effects on tumor associated suppressive myeloid cells without inhibiting the effector T-cell. The PI3K-γ inhibitors disclosed herein can have potent effects on tumor associated suppressive myeloid cells without blocking anti-tumor T-cell effects and thus can increase T cell activity. In one embodiment, this effect can be enhanced by administering CTLA4 antagonists and/or PD-1 and PDL1 antagonists. The PI3K-γ inhibitors disclosed herein can increase T cell activation and proliferation. In some embodiments, provided herein is a method of blocking tumor associated suppressive myeloid cells without inhibiting the effects on anti-tumor T-cells comprising administering an effective amount of a PI3K-γ inhibitor disclosed herein or a pharmaceutically acceptable salt thereof to a subject. In some embodiments, provided herein is a method of blocking tumor associated suppressive myeloid cells without inhibiting the effects on anti-tumor T-cells comprising administering an effective amount of a compound disclosed herein or a pharmaceutically acceptable salt thereof to a subject. In some embodiments, the subject has lung cancer, breast cancer, glioblastoma, or lymphoma (e.g., non-Hodgkin's lymphoma).

Further provided herein are methods of modulating kinase activity by contacting a kinase with an amount of a compound provided herein sufficient to modulate the activity of the kinase. Modulate can be inhibiting or activating kinase activity. In some embodiments, provided herein are methods of inhibiting kinase activity by contacting a kinase with an amount of a compound provided herein sufficient to inhibit the activity of the kinase. In some embodiments, provided herein are methods of inhibiting kinase activity in a solution by contacting said solution with an amount of a compound provided herein sufficient to inhibit the activity of the kinase in said solution. In some embodiments, provided herein are methods of inhibiting kinase activity in a cell by contacting said cell with an amount of a compound provided herein sufficient to inhibit the activity of the kinase in said cell. In some embodiments, provided herein are methods of inhibiting kinase activity in a tissue by contacting said tissue with an amount of a compound provided herein sufficient to inhibit the activity of the kinase in said tissue. In some embodiments, provided herein are methods of inhibiting kinase activity in an organism by contacting said organism with an amount of a compound provided herein sufficient to inhibit the activity of the kinase in said organism. In some embodiments, provided herein are methods of inhibiting kinase activity in an animal by contacting said animal with an amount of a compound provided herein sufficient to inhibit the activity of the kinase in said animal. In some embodiments, provided herein are methods of inhibiting kinase activity in a mammal by contacting said mammal with an amount of a compound provided herein sufficient to inhibit the activity of the kinase in said mammal. In some embodiments, provided herein are methods of inhibiting kinase activity in a human by contacting said human with an amount of a compound provided herein sufficient to inhibit the activity of the kinase in said human. In some embodiments, the % of kinase activity after contacting a kinase with a compound provided herein is less than 1, 5, 10, 20, 30, 40, 50, 60, 70, 80 90, 95, or 99% of the kinase activity in the absence of said contacting step.

In certain embodiments, provided herein are pharmaceutical composition comprising a therapeutically effective amount of a compound provided herein (e.g., compound 1), or a pharmaceutically acceptable form thereof, and an immunomodulator.

In one embodiment, the immunomodulator is an inhibitor of PD-1, PD-L1, LD-L2, CTLA-4, TIM3, LAG3, VISTA, BTLA, TIGIT, LAIR1, CD160, 2B4, TGFR-beta, or IDO/TDO, or a combination thereof. In one embodiment, the immunomodulator is an inhibitor of PD-L1. In one embodiment, the immunomodulator is an antibody or fragment thereof, an inhibitory nucleic acid, a soluble ligand, or a fusion of a PD-1 ligand with a Fc region of an immunoglobulin. In one embodiment, the immunomodulator is a costimulatory ligand, a MCSF/CSF-1R inhibitor, an immunostimulant, a CXCR4/CXCL12 inhibitor, a CCL2 inhibitor, or a CCR2 inhibitor. In one embodiment, the immunomodulator is cyclophosphamide, docetaxel, paclitaxel, 5-FU, or temozolomide.

In one embodiment, provided herein is a method of treating a PI3K-mediated disorder in a subject, comprising administering to the subject a therapeutically effective amount of the composition.

Combination Therapy for Pulmonary and Respiratory Diseases

In some embodiments, the compound provided herein is administered in combination with one or more other therapies. Such therapies include therapeutic agents as well as other medical interventions, behavioral therapies (e.g., avoidance of sunlight), and the like.

By "in combination with," it is not intended to imply that the other therapy and the compound provided herein must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for a pulmonary or respiratory disease, i.e., it is used in a subject who has not been previously administered another drug intended to treat a pulmonary or respiratory disease, or one or more symptoms of the disease.

In some embodiments, the compound provided herein is a second line treatment for a pulmonary or respiratory disease, i.e., it is used in a subject who has been previously administered another drug intended to treat a pulmonary or respiratory disease, or one or more symptoms of the disease.

In some embodiments, the compound provided herein is a third or fourth line treatment for a pulmonary or respiratory disease, i.e., it is used in a subject who has been previously administered two or three other drugs intended to treat a pulmonary or respiratory disease, or one or more symptoms of the disease.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In some embodiments, the compound provided herein and the second agent are administered as separate compositions, e.g., pharmaceutical compositions. In some embodiments, the compound provided herein and the agent are administered separately, but via the same route (e.g., both by inhalation). In some embodiments, the compound provided herein and the agent are administered in the same composition, e.g., pharmaceutical composition.

In some embodiments, the compound provided herein (e.g., PI3K-δ inhibitor or PI3K-γ inhibitor) is administered in combination with an agent that inhibits IgE production or activity. In some embodiments, the compound provided herein (e.g., PI3K-δ inhibitor or PI3K-γ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments, wherein inflammation (e.g., COPD, asthma) is treated, prevented and/or managed, a compound provided herein can be combined with, for example: PI3K inhibitors such as RP-6530, TG 100-115, RV1729, GS-1101, XL 499, GDC-0941, and AMG-319; BTK inhibitors such as ibrutinib and AVL-292; JAK inhibitors such as tofacitinib and GLPG0636; SYK inhibitors such as fostamatinib.

In some embodiments, a compound provided herein can be combined with other agents that act to relieve the symptoms of inflammatory conditions, such as COPD, asthma, and the other diseases described herein. These agents include, but are not limited to, non-steroidal anti-inflammatory drugs (NSAIDs), e.g., acetylsalicylic acid; ibuprofen; naproxen; indomethacin; nabumetone; and tolmetin. In some embodiments, corticosteroids are used to reduce inflammation and suppress activity of the immune system.

In some embodiments, a compound provided herein (e.g., Compound 1), or an enantiomer, a mixture of enantiomers, or a mixture of two or more diastereomers thereof, or a pharmaceutically acceptable form thereof, is administered in combination with an agent for pulmonary or respiratory diseases. Examples of agents for pulmonary or respiratory diseases include, but are not limited to, Abraxane (paclitaxel protein-bound particles for injectable suspension), Adempas (riociguat), Anoro Ellipta (umeclidinium and vilanterol inhalation powder), Breo Ellipta (fluticasone furoate and vilanterol inhalation powder), Opsumit (macitentan), Qnasl (beclomethasone dipropionate) nasal aerosol, Sirturo (bedaquiline), Dymista (azelastine hydrochloride and fluticasone propionate), Kalydeco (ivacaftor), Qnasl (beclomethasone dipropionate) nasal aerosol, Rayos (prednisone) delayed-release tablets, Surfaxin (lucinactant), Tudorza Pressair (aclidinium bromide inhalation powder), Arcapta (indacaterol maleate inhalation powder), Daliresp (roflumilast), Xalkori (crizotinib), Cayston (aztreonam for inhalation solution), Dulera (mometasone furoate+formoterol fumarate dihydrate), Teflaro (ceftaroline fosamil), Adcirca (tadalafil), Tyvaso (treprostinil), Alvesco (ciclesonide), Patanase (olopatadine hydrochloride), Letairis (ambrisentan), Xyzal (levocetirizine dihydrochloride), Brovana (arformoterol tartrate), Tygacil (tigecycline), Ketek (telithromycin), Spiriva HandiHaler (tiotropium bromide), Aldurazyme (laronidase), Iressa (gefitinib), Xolair (omalizumab), Zemaira (alpha1- proteinase inhibitor), Clarinex, Qvar (beclomethasone dipropionate), Remodulin (treprostinil), Xopenex (levalbuterol), Avelox I.V. (moxifloxacin hydrochloride), DuoNeb (albuterol sulfate and ipratropium bromide), Foradil Aerolizer (formoterol fumarate inhalation powder), Invanz, NasalCrom Nasal Spray, Tavist (clemastine fumarate), Tracleer (bosentan), Ventolin HFA (albuterol sulfate inhalation aerosol), Biaxin XL (clarithromycin extended-release tablets), Cefazolin and Dextrose USP, Tri-Nasal Spray (triamcinolone acetonide spray), Accolate (zafirlukast), Cafcit Injection, Proventil HFA Inhalation Aerosol, Rhinocort Aqua Nasal Spray, Tequin, Tikosyn Capsules, Allegra-D, Clemastine fumarate syrup, Curosurf, Dynabac, Infasurf, Priftin, Pulmozyme (dornase alfa), Sclerosol Intrapleural Aerosol, Singulair (montelukast sodium), Synagis, Ceftin (cefuroxime axetil), Cipro (ciprofloxacin HCl), Claritin RediTabs (10 mg loratadine rapidly-disintegrating tablet), Flonase Nasal Spray, Flovent Rotadisk, Metaprotereol Sulfate Inhalation Solution (5%), Nasacort AQ (triamcinolone acetonide) Nasal Spray, Omnicef, Raxar (grepafloxacin), Serevent, Tilade (nedocromil sodium), Tobi, Vanceril 84 mcg Double Strength (beclomethasone dipropionate, 84 mcg) Inhalation Aerosol, Zagam (sparfloxacin) tablets, Zyflo (Zileuton), Allegra (fexofenadine hydrochloride), Astelin nasal spray, Atrovent (ipratropium bromide), Augmentin (amoxicillin/clavulanate), Azmacort (triamcinolone acetonide) Inhalation Aerosol, Breathe Right, Claritin Syrup (loratadine), Claritin-D 24 Hour Extended Release Tablets (10 mg loratadine, 240 mg pseudoephedrine sulfate), Covera-HS (verapamil), OcuHist, RespiGam (Respiratory Syncitial Virus Immune Globulin Intravenous), Tripedia (Diptheria and Tetanus Toxoids and Acellular Pertussis Vaccine Absorbed), Vancenase AQ 84 mcg Double Strength, Visipaque (iodixanol), Zosyn (sterile piperacillin sodium/tazobactam sodium), Cedax (ceftibuten), and Zyrtec (cetirizine HCl). In one embodiment, the agent for pulmonary or respiratory diseases is Arcapta (indacaterol maleate inhalation powder), Daliresp (roflumilast), Dulera (mometasone furoate+formoterol fumarate dihydrate), Alvesco (ciclesonide), Brovana (arformoterol tartrate), Spiriva HandiHaler (tiotropium bromide), Xolair (omalizumab), Qvar (beclomethasone dipropionate), Xopenex (levalbuterol), DuoNeb (albuterol sulfate and ipratropium bromide), Foradil Aerolizer (formoterol fumarate inhalation powder), Accolate (zafirlukast), Singulair (montelukast sodium), Flovent Rotadisk (fluticasone propionate inhalation powder), Tilade (nedocromil sodium), Vanceril (beclomethasone dipropionate, 84 mcg), Zyflo (Zileuton), and Azmacort (triamcinolone acetonide) Inhalation Aerosol. In one embodiment, the agent for pulmonary or respiratory diseases is Spiriva HandiHaler (tiotropium bromide).

Examples of agents for pulmonary or respiratory diseases include, but are not limited to, acetylcysteine (mucomyst) selected from Tudorza Pressair (aclidinium bromide), Atrovent (ipratropium), and Spiriva (tiotropium).

Examples of agents for pulmonary or respiratory diseases include, but are not limited to, beta2 agonists selected from short-acting beta2 agonists and long acting beta2 agonists. Short acting beta2 agonists include, but are not limited to, Proventil (albuterol), Tomalate (bitolterol), Xopenex (levalbuterol), Maxair (pirbuterol), and Alupent (metaproterenol). Long acting beta2 agonists include, but are not limited to, Brovana (arformoterol tartrate), Foradil (formoterol), Arcapta Neohaler (indacaterol maleate), and Serevent (salmeterol).

Examples of agents for pulmonary or respiratory diseases include, but are not limited to, combination of two agents. In one embodiment, the combination is administered through inhalation. The combination of two agents includes, but is not limited to a beta2 agonist and an anticholinergi selected from Combivent (albuterol and ipratropium) and Anoro Ellipta (umeclidinium and vilanterol inhalation powder). The combination of two agents include, but are not limited to a beta2 agonist and a corticosteroid selected from Advair (fluticasone and salmeterol), Breo Ellipta (fluticasone furoate and vilanterol inhalation powder), Dulera (mometasone furoate and formoterol fumarate, and Symbicort (budesonide and formoterol).

Examples of agents for pulmonary or respiratory diseases include, but are not limited to, corticosteroids selected from Vanceril Beclovent (beclomethasone), Pulmicort (budesonide), Alvesco (ciclesonide), Aerobid (flunisolide), Flovent (fluticasone), Asmanex (mometasone furoate), and Azmacort (triamcinolone).

Examples of agents for pulmonary or respiratory diseases include, but are not limited to, leukotriene inhibitors selected from Singulair (montelukast), Accolate (zafirlukast), and Zyflo (zileuton).

Examples of agents for pulmonary or respiratory diseases include, but are not limited to, mast cell stablizers selected from Intal (cromolyn sodium) and Tilade (nedocromil).

Examples of agents for pulmonary or respiratory diseases include, but are not limited to, phosphodiesterase 4 (PDE4) inhibitors selected from Daliresp (roflumilast).

In some embodiments, a compound provided herein (e.g., Compound 1), or an enantiomer, a mixture of enantiomers, or a mixture of two or more diastereomers thereof, or a pharmaceutically acceptable form thereof, is administered in combination with an agent for immunology or infectious diseases. Examples of agents for immunology or infectious diseases include, but are not limited to, Kineret (anakinra), Lovenox (enoxaparin sodium) Injection, Makena (hydroxyprogesterone caproate injection), Myalept (metreleptin for injection), Qnasl (beclomethasone dipropionate) nasal aerosol, Simponi (golimumab), Sitavig (acyclovir) buccal tablets, Tecfidera (dimethyl fumarate), Tivicay (dolutegravir), VariZIG, Varicella Zoster Immune Globulin (Human), Flublok (seasonal influenza vaccine), Flucelvax (influenza virus vaccine), Fulyzaq (crofelemer), Horizant (gabapentin enacarbil), Qnasl (beclomethasone dipropionate) nasal aerosol, Rayos (prednisone) delayed-release tablets, Stribild (elvitegravir, cobicistat, emtricitabine, tenofovir disoproxil fumarate), Tudorza Pressair (aclidinium bromide inhalation powder), Arcapta (indacaterol maleate inhalation powder), Benlysta (belimumab), Complera (emtricitabine/rilpivirine/tenofovir disoproxil fumarate), Daliresp (roflumilast), Dificid (fidaxomicin), Edurant (rilpivirine), Firazyr (icatibant), Gralise (gabapentin), Incivek (telaprevir), Nulojix (belatacept), Victrelis (boceprevir), Cayston (aztreonam for inhalation solution), Egrifta (tesamorelin for injection), Menveo (meningitis vaccine), Oravig (miconazole), Prevnar 13 (Pneumococcal 13-valent Conjugate Vaccine), Teflaro (ceftaroline fosamil), Zortress (everolimus), Zymaxid (gatifloxacin ophthalmic solution), Bepreve (bepotastine besilate ophthalmic solution), Berinert (C1 Esterase Inhibitor (Human)), Besivance (besifloxacin ophthalmic suspension), Cervarix [Human Papillomavirus Bivalent (Types 16 and 18) Vaccine, Recombinant], Coartem (artemether/lumefantrine), Hiberix (Haemophilus b Conjugate Vaccine; Tetanus Toxoid Conjugate), Ilaris (canakinumab), Ixiaro (Japanese Encephalitis Vaccine, Inactivated, Adsorbed), Kalbitor (ecallantide), Qutenza (capsaicin), Vibativ (telavancin), Zirgan (ganciclovir ophthalmic gel), Aptivus (tipranavir), Astepro (azelastine hydrochloride nasal spray), Cinryze (C1

Inhibitor (Human)), Intelence (etravirine), Moxatag (amoxicillin), Rotarix (Rotavirus Vaccine, Live, Oral), Tysabri (natalizumab), Viread (tenofovir disoproxil fumarate), Altabax (retapamulin), AzaSite (azithromycin), Doribax (doripenem), Extina (ketoconazole), Isentress (raltegravir), Selzentry (maraviroc), Veramyst (fluticasone furoate), Xyzal (levocetirizine dihydrochloride), Eraxis (anidulafungin), Gardasil (quadrivalent human papillomavirus (types 6, 11, 16, 18) recombinant vaccine), Noxafil (posaconazole), Prezista (darunavir), Rotateq (rotavirus vaccine, live oral pentavalent), Tyzeka (telbivudine), Veregen (kunecatechins), Baraclude (entecavir), Tygacil (tigecycline), Ketek (telithromycin), Tindamax, tinidazole, Xifaxan (rifaximin), Amevive (alefacept), FluMist (Influenza Virus Vaccine), Fuzeon (enfuvirtide), Lexiva (fosamprenavir calcium), Reyataz (atazanavir sulfate), Alinia (nitazoxanide), Clarinex, Daptacel, Fluzone Preservative-free, Hepsera (adefovir dipivoxil), Pediarix Vaccine, Pegasys (peginterferon alfa-2a), Restasis (cyclosporine ophthalmic emulsion), Sustiva, Vfend (voriconazole), Avelox I.V. (moxifloxacin hydrochloride), Cancidas, Peg-Intron (peginterferon alfa-2b), Rebetol (ribavirin), Spectracef, Twinrix, Valcyte (valganciclovir HCl), Xigris (drotrecogin alfa [activated]), ABREVA (docosanol), Biaxin XL (clarithromycin extended-release tablets), Cefazolin and Dextrose USP, Children's Motrin Cold, Evoxac, Kaletra Capsules and Oral Solution, Lamisil (terbinafine hydrochloride) Solution (1%), Lotrisone (clotrimazole/betamethasone diproprionate) lotion, Malarone (atovaquone; proguanil hydrochloride) Tablet, Rapamune (sirolimus) Tablets, Rid Mousse, Tri-Nasal Spray (triamcinolone acetonide spray), Trivagizole 3 (clotrimazole) Vaginal Cream, Trizivir (abacavir sulfate; lamivudine; zidovudine AZT) Tablet, Agenerase (amprenavir), Cleocin (clindamycin phosphate), Famvir (famciclovir), Norvir (ritonavir), Panretin Gel, Rapamune (sirolimus) oral solution, Relenza, Synercid I.V., Tamiflu capsule, Vistide (cidofovir), Allegra-D, CellCept, Clemastine fumarate syrup, Dynabac, REBETRON™ Combination Therapy, Simulect, Timentin, Viroptic, INFANRIX (Diphtheria and Tetanus Toxoids and Acellular Pertussis Vaccine Adsorbed), Acyclovir Capsules, Aldara (imiquimod), Aphthasol, Combivir, Condylox Gel 0.5% (pokofilox), Flagyl ER, Flonase Nasal Spray, Fortovase, INFERGEN (interferon alfacon-1), Intron A (interferon alfa-2b, recombinant), Rescriptor Tablets (delavirdine mesylate tablets), SPORANOX (itraconazole), Stromectol (ivermectin), Taxol, Trovan, VIRACEPT (nelfinavir mesylate), Zerit (stavudine), Albenza (albendazole), Apthasol (Amlexanox), Carrington patch, Confide, Crixivan (Indinavir sulfate), Gastrocrom Oral Concentrate (cromolyn sodium), Havrix, Lamisil (terbinafine hydrochloride) Tablets, Leukine (sargramostim), Oral Cytovene, RespiGam (Respiratory Syncitial Virus Immune Globulin Intravenous), Videx (didanosine), Viramune (nevirapine), Vitrasert Implant, Zithromax (azithromycin), Cedax (ceftibuten), Clarithromycin (Biaxin), Epivir (lamivudine), Invirase (saquinavir), Valtrex (valacyclovir HCl), and Zyrtec (cetirizine HCl).

Further therapeutic agents that can be combined with a subject compound can be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents provided herein or other suitable agents, depending on the condition being treated. Hence, in some embodiments, the compounds as provided herein will be co-administered with other agents as described above.

When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as provided herein and any of the agents described above can be simultaneously administered, wherein both the agents are present in separate formulations. In another alternative, a compound as provided herein can be administered just followed by and any of the agents described above, or vice versa. In the separate administration protocol, a compound as provided herein and any of the agents described above can be administered a few minutes apart, or a few hours apart, or a few days apart.

Administration of the compounds as provided herein can be effected by any method that enables delivery of the compounds to the site of action. An effective amount of a compound as provided herein can be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as provided herein is administered in a pharmaceutical composition that comprises one or more agents, and the agent has a shorter half-life than the compound as provided herein, unit dose forms of the agent and the compound as provided herein can be adjusted accordingly.

6. EXAMPLES

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

| Abbreviations/Acronyms | Full Name/Description |
|---|---|
| ACN or MeCN | acetonitrile |
| DCM | dichloromethane |
| DMF | dimethylformamide |
| EtOAc | ethyl acetate |
| IPA | isopropyl alcohol |
| IPAc | isopropyl acetate |
| MEK | methyl ethyl ketone |
| 2-MeTHF | 2-methyltetrahydroruran |
| MIBK | methyl iso-butyl ketone |
| MTBE or TBME | tert-butyl methyl ether |
| THF | tetrahydrofuran |
| DIPEA | diisopropylethylamine |
| DIPA | Diisopropanolamine |
| EDCI | 3-(3-Dimethylaminopropyl)-1-ethyl-carbodiimide hydrochloride |

Example 1

Preparation of Compound 1

A. Method 1

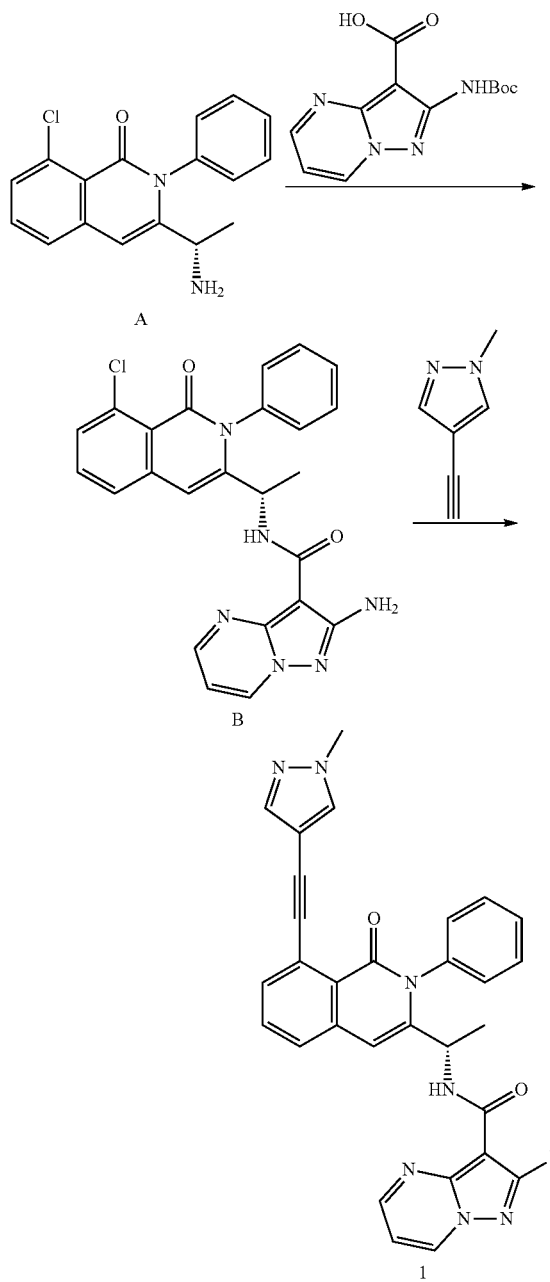

Compound 1 was prepared in 3 steps from compound A according to the following procedures: Compound A was coupled to 2-((tert-butoxycarbonyl)amino)pyrazolo[1,5-a]pyrimidine-3-carboxylic acid according to the following procedure: Compound A (27.4 mmol, 1.0 equiv), HOBt hydrate (1.2 equiv), 2-((tert-butoxycarbonyl)amino)pyrazolo[1,5-a]pyrimidine-3-carboxylic acid (1.05 equiv) and EDCI (1.25 equiv) were added to a 200 mL round bottomed flask with a stir bar. N,N-Dimethylformamide (50 mL) was added and the suspension was stirred at RT for 2 min. Hunig's base (4.0 equiv) was added and after which the suspension became homogeneous and was stirred for 22 h resulting in the formation of a solid cake in the reaction flask. The solid mixture was added to water (600 mL) and stirred for 3 h. The resulting cream colored solid was filtered and washed with water (2×100 mL) and dried. The solid was then dissolved in methylene chloride (40 mL) after which trifluoroacetic acid (10 equiv, 20 mL) was added and the reaction was stirred for 30 min at RT after which there is no more starting material by LC/MS analysis. The solution was then concentrated and coevaporated with a mixture of methylene chloride/ethanol (1:1 v/v) and then dried under high vacuum overnight. The resulting solid was triturated with 60 mL of ethanol for 1 h and then collected via vacuum filtration. The beige solid was then neutralized with sodium carbonate solution (100 mL) and then transferred to a separatory funnel with methylene chloride (350 mL). The water layer was extracted with an additional 100 mL of methylene chloride. The combined organic layers were dried over sodium sulfate, filtered and concentrated under vacuum to provide a pale yellow solid that was purified using flash silica gel chromatography (Combiflash, 24 g column, gradient of 0-5% methanol/methylene chloride) to provide amide B. ESI-MS m/z: 459.4 [M+H]+.

Amide B was placed in a sealed tube (0.67 mmol, 1.0 equiv) followed by dichlorobis(acetonitrile)palladium (15 mol %), X-Phos (45 mol %), and cesium carbonate (3.0 equiv) Propionitrile (5 mL) was added and the mixture was bubbled with Ar for 1 min. 4-Ethynyl-1-methyl-1H-pyrazole (1.24 equiv) was added and the resulting orange mixture was sealed and stirred in an oil bath at 85° C. for 1.5 h. The resulting brownish-black mixture was allowed to cool at which point there was no more SM by LC/MS analysis. The mixture was then filtered through a short plug of cotton using acetonitrile and methylene chloride. The combined filtrates were concentrated onto silica gel and purified using flash silica gel chromatography (Combiflash, 4 g column, gradient of 0-5% methylene chloride/methanol). The resulting material was further purified by reverse phase HPLC (15-90% acetonitrile with 0.1% formic acid/water with 0.1% formic water) to provide desired Compound 1. The solution containing Compound 1 was lyophilized to give amorphous Compound 1. ESI-MS m/z: 529.5 [M+H]+.

B. Method 2

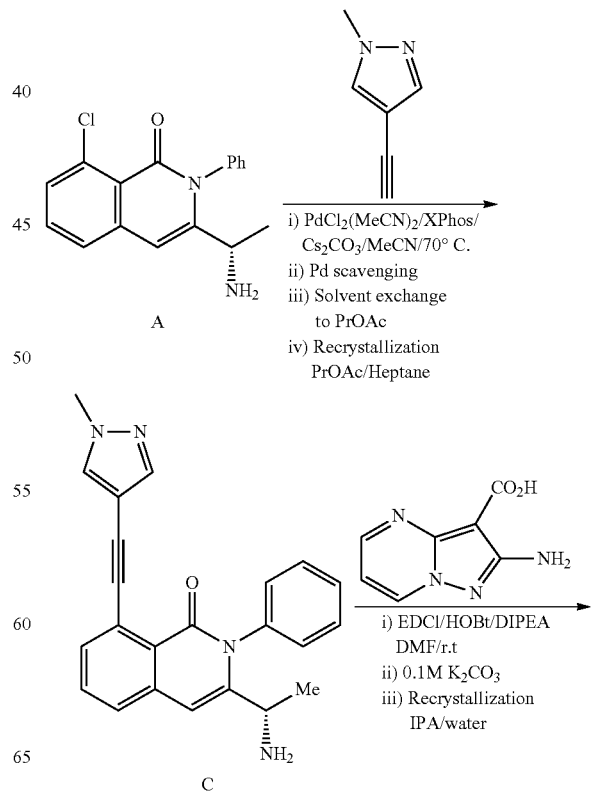

-continued

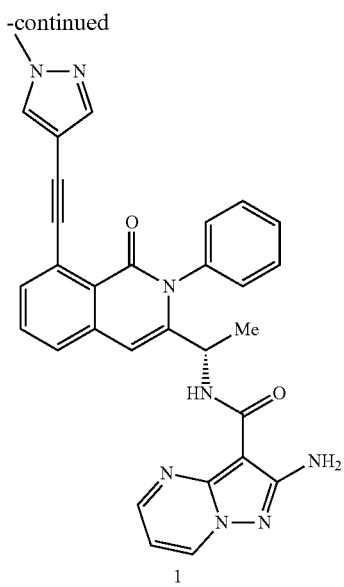

1

The first step started with palladium-catalyzed cross-coupling of Compound A with 4-ethynyl-1-methyl-1H-pyrazole in acetonitrile to form Compound C. The allowable temperature range for this coupling was 70±5° C. Once the cross-coupling reaction was complete, the reaction mixture was cooled to room temperature and filtered to remove insoluble inorganic salts. The resulting solution was first treated with a functionalized silica gel followed by regular silica gel. Crude Compound C was collected by filtration and washing of the silica gel with a 30% propyl acetate/acetonitrile solution. Crystallization of Compound C was achieved by solvent exchange into n-PrOAc and crystals were isolated by filtration and drying to within specification limits. Typical chemical purity is >98% area. Typical yields are 70-80%.

More specifically, acetonitrile (ACS grade, MeCN) was degassed with nitrogen for at least 30 minutes. Degassed acetonitrile (2 volumes) under nitrogen was charged to the reaction vessel. Compound A (1 wt, 1 equ.), dichlorobis(acetonitrile)palladium (II) (0.05 equ.), dicyclohexyl[2-(2,4,6-triisopropylphenyl)phenyl]phosphane (XPhos) (0.1025 equ.) and cesium carbonate (1.2 equ.) under nitrogen were also charged to the reaction vessel. The reaction mixture was agitated. 4-ethynyl-1-methyl-1H-pyrazole (1.2 equ. corrected for assay content) was charged into the reaction vessel. Heat the reaction mixture to 70±2° C. (internal temperature).

The reaction was monitored by HPLC after 3 hours. Once the reaction was determined complete the heat was turned off and the reaction mixture cooled to room temperature (22±3° C.) over a minimum of 2 hours and held at r.t. for ≥2 hours. The suspension was filtered and the cake washed with acetonitrile (2×2 volumes). The washes were combined with the filtrate (product layer). The filtrate (product layer) was transferred back into the reaction vessel. The vessel was flushed with nitrogen for at least 2 minutes and agitation re-started. 2-mercaptoethyl ethyl sulfide Silica [PhosphonicS SEM26] (0.5 wt % with respect to Compound A) was charged at room temperature (22±3° C.). The mixture was stirred for ≥4 hours at r.t. The resin was filtered off and washed with acetonitrile (2×2 volumes). The washes were combined with the filtrate (product layer).

The acetonitrile solution (product layer) was pumped through a pre-packed silica cartridge (flow rate≈50 mL/min) and collected the filtrate in a clean vessel. The silica column was washed with 30% propyl acetate in acetonitrile (5×4 volumes). The washes were combined with the previous filtrate. The acetonitrile/propyl acetate solution was transferred into a clean distillation vessel. The volume was reduced to 10 volumes under vacuum (200 Torr, 45° C.). Propyl acetate (10 volumes) was charged to the distillation vessel. The reaction volume was reduced to 10 volumes under vacuum (140 Torr, 50° C.). The vacuum was released and propyl acetate (10 volumes) was charged to the distillation vessel. The reaction volume was reduced to 10 volumes under vacuum (100 Torr, 50° C.).

The PrOAc solution/mixture was heated to reflux (Target 102° C.) with stirring, under nitrogen, and was held for ≥30 minutes. The heat was turned off and the mixture was cooled to r.t. (22±3° C.) over 4 hours. Heptane (10 volumes, ACS grade) was charged to the suspension at r.t. (22±3° C.) over 30 minutes. The mixture was aged for ≥1 hour at r.t. (22±3° C.). The solid was filtered off and washed with heptane (2×5 volumes). The solid was deliquored under vacuum for ≥2 hours. The solid was transferred to drying trays and placed in a vacuum oven and dried at 40° C. under vacuum, with a nitrogen bleed, until constant weight was achieved.

The second step is an amide coupling reaction between Compound C and the carboxylic acid employing EDCI and HOBt at 30° C. Compound C was treated with the carboxylic acid, HOBt, EDCI and DIPEA in DMF and stirred at 30° C. under nitrogen until judged complete by HPLC. The reaction mixture was polish filtered and pumped slowly into a 0.1M potassium carbonate aq. solution. After ageing, the resulting suspension was filtered. The crude Compound 1 was subsequently purified by recrystallization. The solid was dissolved in a mixture of hot IPA/water (1:1) and treated with water. On cooling Compound 1 precipitated from solution. The crystals were isolated by filtration, washed with water and dried. Typical chemical purity is >98% area. Typical yields are 60-70%.

Specifically, the reaction vessel was charged with Compound C (1 wt, 1 equ.), 2-aminopyrazolo[1,5-a]pyrimidinecarboxylic acid (1.05 equ), 1-hydroxybenzotriazole hydrate (0.1 equ.), 1-ethyl-(3-dimethylaminopropyl)carbodiimide hydrochloride, anhydrous (1.2 equ.), N,N-dimethylformamide, ACS grade (10 volumes), and N,N-diisopropylethylamine, ReagentPlus (3 equ.) at r.t. (22±3° C.) with under nitrogen at r.t. The reaction mixture was heated at 30±5° C. under nitrogen. The reaction was stirred at 30±5° C. (Target 30° C.). The reaction was monitored by HPLC after 16 hours. This reaction could also be conducted without the base, N-diisopropylethylamine.

The reaction mixture was quenched as follows. A 0.1M solution of potassium carbonate in water was prepared. The quench vessel was charged with potassium carbonate (3.2 equ) followed by water (80 volumes). The mixture was stirred at r.t. until fully dissolved. The DMF reaction solution (product layer) was polish filtered. The reaction vessel was rinsed with a small amount of DMF (0.5 volumes). The DMF rinse was passed through the polish filter. The DMF solution (product layer) was slowly transferred into the potassium carbonate solution over ≥2 hours at r.t (22±3° C.). The suspension was aged for ≥1 hour at r.t. (22±3° C.). The solid was filtered off under house vacuum (table top filter), de-liquored and washed with water (2×10 volumes). It was deliquored under vacuum at r.t. until constant weight was achieved.

A vessel was charged with crude Compound 1, isopropyl alcohol (10 volumes) followed by water (10 volumes). The mixture was agitated. The suspension was heated to 80±3° C. (Target 80° C.). The mixture was aged for ≥15 minutes. Water (10 volumes) was charged to the vessel at such a rate to maintain the internal temperature between 80±5° C. (Target 80° C.). The internal temperature was adjusted to 80° C. and held for ≥20 minutes before proceeding to the next step. The suspension was cooled to r.t. (22±3° C.) over 4 hours. The suspension was aged at r.t. for ≥4 hours. The solid was filtered under vacuum. The solid was washed with 20% isopropyl alcohol in water (2×5 volumes). The solid was deliquored under vacuum for ≥1 hour. The solid was transferred to drying trays and placed in a vacuum oven and dry at 40° C. under vacuum, with a nitrogen bleed, until constant weight was achieved. Characterization of the solid showed it was Form 1.

C. Method 3

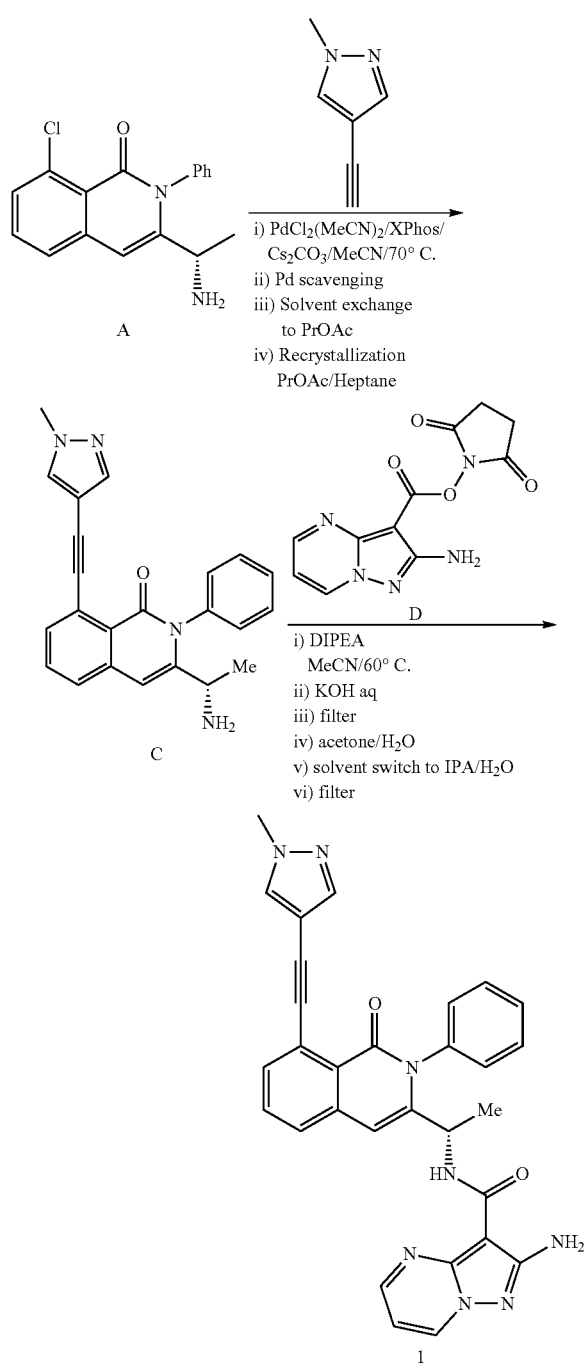

The first step is palladium-catalyzed cross-coupling of Compound A with 4-ethynyl-1-methyl-1H-pyrazole in acetonitrile to form Compound C. The same procedures from Method 2 above can be used to produce compound C. Compound C was coupled with compound D to form Compound 1.

Compound D was prepared by converting the carboxylic acid to its NHS activated ester.

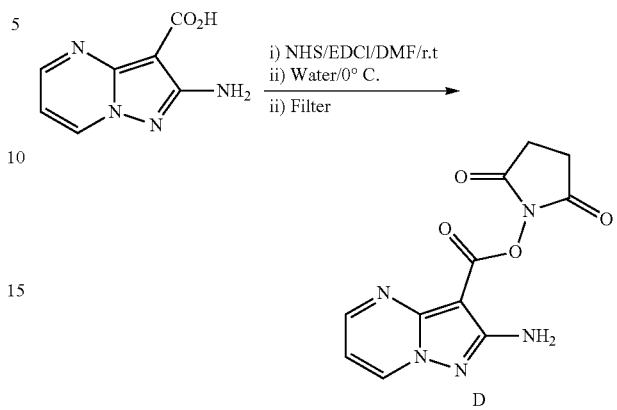

The reaction vessel was flushed with nitrogen for ≥15 minutes. DMF (2 volumes) was charged to the vessel. The jacket temperature was set to 23° C. N-Hydroxysuccinimide (HOSu or NHS) (1.3 equ.) was charged to the reaction vessel, followed by 2-aminopyrazolo[1,5-a]pyrimidinecarboxylic acid (1 wt, 1 equ.) and EDCI (1.3 equ.) and DMF (13 volumes) at 23° C. under nitrogen.

The reaction mixture was stirred at 23° C. under nitrogen. The reaction was monitored by HPLC. Once judged complete the reaction contents were cooled to 0±5° C. Water (20 volumes) was added over ≥4 hours to the reaction mixture via peristaltic pump) under nitrogen at such a rate to maintain the internal temperature at 0±5° C. The suspension was aged for 1 hour at 0±5° C. The solid was filtered off under vacuum and washed with water (2×5 volumes). The solid was deliquored for ≥1 hour then transferred into a vacuum oven and dried at 40° C., under vacuum, with a slight nitrogen purge until constant weight was achieved. In an alternative example, the reaction was ran without DIPEA.

The coupling of compound C with compound D was carried out as follows. The reaction vessel was evacuated and purged with nitrogen for ≥15 minutes. Compound C (1 wt, 1 equ.), Compound D (1.05 equ.) and acetonitrile (15 volumes), were charged to the reaction vessel at 22±3° C., under nitrogen. The reaction vessel was evacuated and back filled with nitrogen. The mixture was agitated. N,N-Diisopropylethylamine (DIPEA) (1.1 equ.) at 22±3° C. was charged to the reaction vessel under nitrogen. The reaction mixture was heated to 60±2° C. and stirred under nitrogen. The reaction was monitored by HPLC.

Once the reaction was judged complete by HPLC a 1M solution of potassium hydroxide (0.5 equ., 1.21 volumes) was charged to the reaction vessel at such a rate to maintain an internal temperature between 52-60° C. The suspension was aged at 60±2° C. for 2 hours, then cooled to 22±3° C. over 1 hour. The solid was filtered off under vacuum then washed with acetonitrile (2×2.5 volumes) followed by 4:1/water: acetonitrile (2×2.5 volumes). It was deliquored under vacuum at r.t. for ≥12 hours.

Water (8 volumes), crude compound 1 (1 wt) from and acetone (32 volumes) were charged to the recrystallization vessel. The mixture was agitated and heated to 55±5° C. The solution was aged at 55±5° C. (Target 50° C.) for 10 minutes and then cooled the solution to 23±3° C. The reaction solution was transferred into a holding drum. The recrystallization vessel was rinsed with acetone (twice). The reflux condenser was exchanged for a short path distillation setup on the recrystallization vessel and flushed with nitrogen for a minimum of 15 minutes. The reaction solution was transferred through an inline polish filter (media PTFE, pore size 1 μm) back into the recrystallization vessel. Acetone (2 volumes) was charged into the holding drum and the rinses were transferred into the recrystallization vessel through the inline filter. The mixture was agitated and the jacket temperature was set to 45° C.

The solvent volume was reduced to 20 volumes under reduced pressure maintaining an internal temperature at ≥30° C. (Target 35° C.). The vacuum was released and a mixture of 3:2/isopropyl alcohol:water (20 volumes) was charged to the recrystallization vessel. The solvent volume was reduced to 20 volumes under reduced pressure maintaining an internal temperature at ≥30° C. (Target 35° C.). The vacuum was released and a mixture of 3:2/isopropyl alcohol:water (20 volumes) was charged to the recrystallization vessel. The solvent volume was reduced to 20 volumes under reduced pressure maintaining an internal temperature at ≥30° C. (Target 35° C.). The vacuum was released and a mixture of 3:2/isopropyl alcohol:water (10 volumes) was charged to the recrystallization vessel. The short path distillation head was replaced with a reflux condenser.

The reactor was purged with nitrogen for at least 15 minutes. The stirred suspension was heated to 60±2° C. (Target 60° C.). The suspension was aged at 60±2° C. (Target 60° C.) for 14±2 hours and was then cooled to 23±3° C. over ≥1 hour. A small sample was taken to confirm conversion to Form 1 was complete. The suspension was aged for ≥3 hours. The solid was filtered off under vacuum and washed the solid with 20% isopropyl alcohol in water (2×5 volumes). The solid was deliquored under vacuum for ≥1 hour, transferred to drying trays, placed in a vacuum oven and dried at 40° C. under vacuum, with a nitrogen bleed, until constant weight was achieved. Characterization of the solid showed it was Form 1.

The typical yield for Method 3 is about 75-85%.

Example 2

Polymorph Screen

A. Solubility Screen

Amorphous Compound 1 (30 mg) was weighed out and 100 μl (~3 vols) solvent was added at room temperature. Many samples initially dissolved but precipitated back out again after stirring for a few minutes. It was assumed that these samples had crystallized, so additional portions of solvent were added to determine the solubility of the crystalline material. See Table 1 for solubility assessment of amorphous Compound 1.

Samples were stirred at 50° C. for 1 hour then cooled to 5° C. using a linear cooling rate of 0.1° C./min. Samples were stirred at 5° C. for ~9 hours then observations were made and small portions of the samples containing solids were filtered, air dried and analyzed by XRPD.

Crystalline samples were filtered and dried in a vacuum oven for 3 days at RT prior to characterization. Amorphous samples were matured (shaken in cycles of 4 hours at RT/4 hours at 50° C.) and were analyzed by XRPD after 32 days. Solutions were stored in the freezer, and then left to evaporate at ambient if no precipitate formed at −20° C. Solids produced by evaporation were analyzed by XRPD.

B. Maturation Screen

This screen was carried out using all the solvents from the solubility screen except DMF (as it was too soluble to make a slurry) and those solvents that were very poorly soluble (as suspension in these solvents from the solubility screen were already maturing). Anisole was added as an additional solvent for this screen.

Amorphous Compound 1 (30 mg) was prepared in glass vials and 500 μl (~17 vols) solvent was added at 25° C. The samples were shaken in the maturation chamber (cycles of 4 hours at RT/4 hours at 50° C.) for 3 days. Small aliquots of samples containing solids were filtered and analyzed by XRPD. Samples containing crystals were analyzed by optical microscopy to assess suitability for SXRD determination prior to XRPD analysis. Solutions were left to evaporate at ambient conditions then any resulting solids were analyzed by XRPD. Selected solids were filtered and dried in a vacuum oven for 2 days prior to characterization.

C. Low Temperature Screen

This screen was carried out with the same set of solvents as were used in the solubility screen and one additional solvent (anisole).

Amorphous Compound 1 (30 mg) was prepared in glass vials and cooled to 5° C. Solvent (either 500 μl (~17 vols) or 250 μl (~8 vols) based on the results from solubility screen) was added and samples were stirred at 5° C. overnight. Small aliquots of samples containing solids were filtered and analyzed by XRPD. Solutions were left to evaporate at ambient conditions then any resulting solids were analyzed by XRPD. Selected solids were filtered and dried in a vacuum oven for 2 days prior to characterization. Samples containing poorly crystalline solids were left to stir at 5° C. for a total of 40 days and then were re-analyzed by XRPD.

D. Maturation Screen—Mixed Solvents

Amorphous Compound 1 (30 mg) was prepared in glass vials and 500 μl (~17 vols) of mixed solvents (pre-mixed using 50/50 v/v) was added at room temperature. Samples were matured (shaken in cycles of 4 hours at 25° C./4 hours at 50° C.) for 2 days. Small aliquots of samples containing solids were filtered and analyzed by XRPD. Solutions were left to evaporate at ambient conditions then any resulting solids were analyzed by XRPD.

E. Results

Table 1 summarizes the solubility assessment of amorphous Compound 1. During the initial solubility assessment of the amorphous material it was observed that many samples initially dissolved but precipitated back out again after stirring for a few minutes. It was assumed that these had precipitated as a crystalline form of the free base. Further solvent was added to assess the solubility of the crystalline form, which was found to be much less soluble than the amorphous material.

The results of the polymorph screen are summarized in Table 2. The results of the maturation screen in mixed solvents are summarized in Table 3. The polymorph screens showed a total of six distinct forms of the free base. Forms 1, 2, 3 and 4 were crystallized from a range of solvents. Forms 5 and 6 were made by maturing in anisole and by slurrying at low temperatures in nitromethane, respectively. All samples that displayed good crystallinity were filtered and dried before being analyzed by high resolution XRPD.

Table 4 provides the results of the damp and dried samples of various samples. Table 5 provides further characterization results of the various forms of Compound 1.

Figure 21:
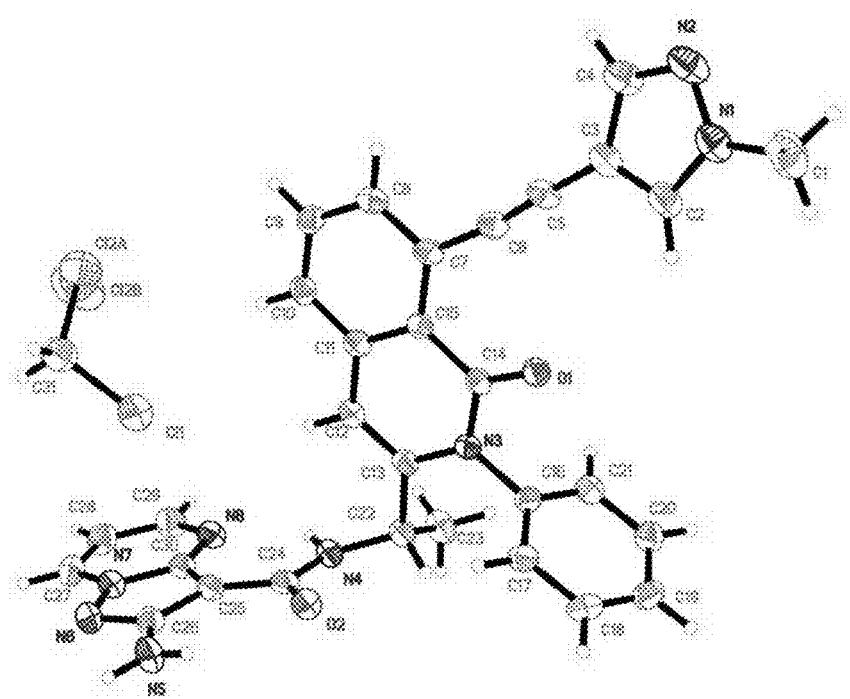
FIG. 21 is a representative ORTEP plot of Form 2 of Compound 1.

Forms 2, 3 and 4 were found to be a set of pseudo-isostructural solvates. The XRPD diffractograms are grouped into Forms 2, 3 and 4 but within each group there are small differences in the diffractograms, indicating some variation in the crystal lattice due to the inclusion of different sized solvent molecules. A representative ORTEP (Oak Ridge Thermal Ellipsoid Plot) plot of crystal structure of Form 2 is shown in FIG. 21, which shows that there is one molecule of solvent for each molecule of Compound 1. The same relationship may apply to all samples of Forms 2, 3 and 4, e.g., that they are all mono-solvates, which partially de-solvate on drying. This is borne out by the residual solvent levels seen in the $^1$H NMR data (not shown), which are mostly slightly less than 1 mole of solvent.

Most of the samples analyzed after drying were the same form as the damp sample, although some had reduced crystallinity. Where most of the solvent was removed by drying, the samples showed a conversion to Form 7 (a partially crystalline, partially solvated form).

The thermal behavior of all of these samples shows events relating to the loss of solvent in the TGA and DSC followed by a melt, then a re-crystallisation event. The re-crystallized sample was consistent with Form 1, showing that these solvates all convert to Form 1, once the solvent has been removed by heating.

Form 5 was a meta-stable anisole solvate that converted to Form 1 on drying in a vacuum oven. The characterization data for this dried sample was consistent with Form 1.

Form 6 was made in the polymorph screen (from nitromethane) and was also made by sonication in the cocrystal experiments provided herein (from ACN/water 50/50 v/v). The sample showed no presence of acetonitrile or conformer. This form is a hydrated form of Compound 1. Using the weight loss seen in the TGA experiment this form is a tri-hydrate form of the free base.

Representative XRPD, TGA, DSC, and GVS characterizations of Forms 1-7 are shown in FIGS. 1-19.

TABLE 1

Solubility assessment of amorphous Compound 1

| Solvent | Solubility |
| --- | --- |
| n-Heptane | <17 mg/ml |
| Ethyl acetate | <17 mg/ml |
| Isopropyl acetate | <17 mg/ml |
| MIBK | <17 mg/ml |
| 2-Propanol | <17 mg/ml |
| MEK | <17 mg/ml |
| 1-Propanol | <17 mg/ml |
| Acetone | <17 mg/ml |
| Ethanol | <17 mg/ml |
| Dimethyl sulfoxide | >=333 mg/ml |
| Water | <17 mg/ml |
| tert-Butylmethyl ether | <17 mg/ml |
| 2-Methyl-1-propanol | <17 mg/ml |
| Cyclohexane | <17 mg/ml |
| 1,4-Dioxane | <17 mg/ml |
| Toluene | <17 mg/ml |
| Chloroform | <17 mg/ml |
| 1,2-Dimethoxyethane | <17 mg/ml |
| Tetrahydrofuran | <17 mg/ml |
| Dichloromethane | 17-20 mg/ml |
| 2-Methoxyethanol | >=333 mg/ml |
| Methanol | <17 mg/ml |
| N,N-Dimethylformamide | >=333 mg/ml |
| Acetonitrile | <17 mg/ml |
| Ethyleneglycol | <17 mg/ml |
| Nitromethane | 25-33 mg/ml |
| THF/Water (95/5 v/v) | <17 mg/ml |
| IPA/Water (95/5 v/v) | <17 mg/ml |

TABLE 2

Summary of results from the polymorph screens

| | Solubility screen | | Maturation screen | Low temperature screen |
| --- | --- | --- | --- | --- |
| Solvent | initial result | after maturation (mat) or evaporation (evap) | after evaporation (evap) | after evaporation (evap) |
| n-Heptane | amorphous | crystalline, Form 1 (mat) | n/a | amorphous |
| Ethyl acetate | partially crystalline, Form 1 | partially crystalline, Form 1 (mat) | n/a | crystalline Form 1 |
| Isopropyl acetate | partially crystalline, Form 1 | amorphous (mat) | n/a | crystalline Form 1 |
| MIBK | crystalline, Form 1 | n/a | crystalline, Form 1 | crystalline Form 1 |
| 2-Propanol | crystalline | crystalline Form 4 (mat) | crystalline, Form 4 | crystalline Form 4 |
| MEK | crystalline Form 3 | n/a | crystalline, Form 3 | crystalline Form 3 |
| 1-Propanol | crystalline Form 3 + extra peaks | n/a | crystalline, Form 2 | crystalline Form 4 |
| Acetone | crystalline, similar to Form 3 | n/a | crystalline, Form 2 | crystalline Form 4 |
| Ethanol | crystalline, Form 1 | n/a | partially crystalline, Form 1 | partially crystalline Form 1 |
| Dimethyl sulfoxide | crystalline Form 4 | n/a | crystalline, Form 4 (evap) | crystalline Form 3 |
| Water | amorphous | crystalline, Form 1 (mat) | n/a | amorphous |
| tert-Butylmethyl ether | crystalline, Form 3 | n/a | crystalline, Form 3 | crystalline Form 3 |
| 2-Methyl-1-propanol | crystalline, Form 3 | crystalline Form 4 (mat) | crystalline, Form 3 | crystalline Form 4 |
| Cyclohexane | amorphous | crystalline, Form 1 (mat) | n/a | amorphous |
| 1,4-Dioxane | partially crystalline, Form 4 | solution (mat), oil (evap) | crystalline, Form 4 | crystalline Form 4 |
| Toluene | crystalline, Form 1 | n/a | crystalline, Form 1 | crystalline Form 1 |
| Chloroform | crystalline, Form 2 | n/a | crystalline, Form 4 | partially crystalline Form 4 |

TABLE 2-continued

Summary of results from the polymorph screens

| Solvent | Solubility screen initial result | Solubility screen after maturation (mat) or evaporation (evap) | Maturation screen after evaporation (evap) | Low temperature screen after evaporation (evap) |
|---|---|---|---|---|
| 1,2-Dimethoxyethane | crystalline, Form 1 | n/a | crystalline, Form 1 | crystalline Form 1 |
| Tetrahydrofuran | crystalline, Form 4 | n/a | crystalline, Form 4 | crystalline Form 4 |
| Dichloromethane | solution | crystalline, Form 2 (evap) | crystalline, Form 2 (evap) | crystalline Form 2 |
| 2-Methoxyethanol | crystalline, Form 1 | n/a | weakly crystalline, Form 1 (evap) | crystalline Form 4 |
| Methanol | crystalline, Form 1 | n/a | crystalline, Form 1 | partially crystalline Form 1 |
| N,N-Dimethylformamide | crystalline, Form 1 + extra peak | n/a | n/a | crystalline, Form 1 (evap) |
| Acetonitrile | crystalline, Form 1 | n/a | crystalline, Form 1 | crystalline Form 1 |
| Ethyleneglycol | crystalline | crystalline, Form 1 (mat) | weakly crystalline, Form 1 | crystalline Form 1 |
| Nitromethane | solution | crystalline, Form 1 (evap) | weakly crystalline, Form 1 (evap) | crystalline Form 6 |
| THF/Water (95/5 v/v) | crystalline, Form 4 | n/a | crystalline, Form 4 | crystalline Form 4 |
| IPA/Water (95/5 v/v) | partially crystalline, Form 4 | crystalline Form 4 (mat) | crystalline, Form 4 | crystalline Form 4 |
| Anisole | n/a | n/a | crystalline, Form 5 | partially crystalline Form 1 |

TABLE 3

Summary of results from polymorph screen with mixed solvents

| Solvent mixture (mixtures are 50/50 v/v) | XRPD results |
|---|---|
| 2-Methyl THF | crystalline Form 3 |
| 2-Methyl THF/IPA | crystalline Form 3 |
| 2-Methyl THF/Ethanol | crystalline Form 3 + extra peak |
| 2-Methyl THF/Toluene | crystalline Form 3 |
| Anisole/IPA | crystalline Form 1 |
| Anisole/Ethanol | crystalline Form 1 |
| Anisole/Toluene | crystalline Form 1 |
| Anisole/THF | crystalline Form 4 |
| Acetonitrile/Water | crystalline Form 1 |
| Toluene/THF | crystalline Form 4 |
| Toluene/Ethanol | crystalline Form 1 |
| Toluene/IPA | crystalline Form 4 |
| DCM/Acetone | crystalline Form 2 |

TABLE 4

Damp and dry screening samples of Compound 1

| Method | Solvent | XRPD of damp sample | XRPD of dried sample |
|---|---|---|---|
| maturation | 1-propanol | Form 2 | Form 2 |
| solubility screen | chloroform | Form 2 | Form 2 |
| solubility screen | DCM | Form 2 | Form 2 |
| maturation | 2-methyl-1-propanol | Form 3 | Form 3 |
| high temperature | MEK | Form 3 | partially crystalline new phase Form 7 |
| solubility screen | 1-propanol | Form 3 | weakly crystalline Form 7 |
| solubility screen | acetone | Form 3 | weakly crystalline Form 7 |
| solubility screen | TBME | Form 3 | partially crystalline Form 7 |
| maturation | 2-propanol | Form 4 | Form 4 |
| maturation | IPA/water 95/5 v/v | Form 4 | Form 4 |
| solubility screen | DMSO | Form 4 | Form 4 |
| solubility screen | THF | Form 4 | weakly crystalline Form 4 |
| solubility screen | THF/water 95/5 v/v | Form 4 | weakly crystalline Form 4 |
| maturation | chloroform | Form 4 | partially crystalline Form 4 |
| maturation | THF/water 95/5 v/v | Form 4 | some changes, similar to Form 2 |
| low temperature | 1-propanol | Form 4 | partially crystalline Form 4 |
| low temperature | acetone | Form 4 | weakly crystalline Form 7 |
| low temperature | 2-methyl-1-propanol | Form 4 | weakly crystalline Form 4 |
| low temperature | 1,4-dioxane | Form 4 | weakly crystalline Form 4 |
| low temperature | 2-methoxyethanol | Form 4 | almost amorphous (insufficient sample) |
| maturation | anisole | Form 5 | changes to Form 1 |
| low temperature | nitromethane | Form 6 | inconclusive - insufficient sample |
| sonication in cocrystal screen | ACN/water 50/50 v/v | Form 6 | crystalline, Form 6 |

TABLE 5

Characterization of crystalline forms of Compound 1

| Method | Solvent | XRPD of damp sample | XRPD of dried sample | NMR | Purity by HPLC | TGA | DSC | Static Stability 40° C./75% RH |
|---|---|---|---|---|---|---|---|---|
| maturation | 1-propanol | Form 2 | Form 2 | 0.85 mole eq 1-propanol (8.7 wt %) | 99.3 area % | 0.9 wt % loss 25-75° C. 8.5 wt % loss 75-250° C. | broad endotherm onset 25° C. (5.4 J/g) sharp endotherm onset 151° C. (57.9 J/g) broad exotherm onset 179° C. (29.7 J/g) sharp endotherm onset 244° C. (75.5 J/g) | amorphous after 7 and 36 days |
| maturation | 2-methyl-1-propanol | Form 3 | Form 3 | 0.79 mole eq 2-methyl-1-propanol (10.0 wt %) | 99.2 area % | 0.8 wt % loss 25-75° C. 10.4 wt % loss 75-300° C. | broad endotherm onset 29° C. (11.8 J/g) small endotherm onset 126° C. (0.9 J/g) sharp endotherm onset 148° C. (54.5 J/g) broad exotherm onset 181° C. (26.9 J/g) sharp endotherm onset 246° C. (42.8 J/g) | remains Form 3 but loss of crystallinity after 7 days and further loss after 36 days |
| high temperature | MEK | Form 3 | partially crystalline Form 7 | 0.25 mole eq MEK (3.3 wt %) | 99.5 area % | 2.0 wt % loss 25-80° C. 3.4 wt % loss 80-175° C. | broad endotherm onset 30° C. (21.6 J/g) sharp endotherm onset 127° C. (2.7 J/g) sharp endotherm onset 137° C. (7.2 J/g) broad exotherm onset 169° C. (3.2 J/g) sharp endotherm onset 207° C. (1.3 J/g) broad endotherm onset 250° C. (7.7 J/g) | remains Form 7 but loss of crystallinity after 7 days and further loss after 36 days |
| maturation | 2-propanol | Form 4 | Form 4 | 0.9 mole eq IPA (9.3 wt %) | 99.0 area % | 0.7 wt % loss 25-75° C. 9.3 wt % loss 75-225° C. | broad endotherm onset 30° C. (5.2 J/g) sharp endotherm onset 156° C. (69.0 J/g) broad exotherm onset 190° C. (28.0 J/g) sharp endotherm onset 245° C. (43.7 J/g) | remains Form 4 but loss of crystallinity after 7 days and further loss after 36 days |
| maturation | IPA/water 95/5 v/v | Form 4 | Form 4 | 0.83 mole eq IPA (8.6 wt %) | 99.2 area % | 0.8 wt % loss 25-75° C. 8.6 wt % loss 75-250° C. | broad endotherm onset 28° C. (13.3 J/g) sharp endotherm onset 156° C. (68.3 J/g) broad exotherm onset 201° C. (17.2 J/g) sharp endotherm onset 247° C. (29.1 J/g) | remains Form 4 but loss of crystallinity after 7 days and further loss after 36 days |
| maturation | anisole | Form 5 | changes to Form 1 | 0.12 mole eq anisole (2.4 wt %) | 99.0 area % | no low temperature weight loss 2.1 wt % loss 175-300° C. | small endotherm onset 126° C. (2.7 J/g) sharp endotherm onset 254° C. (79.1 J/g) | no change after 7 and 36 days |
| sonication | ACN/water 50/50 v/v | Form 6 | Form 6 | large water peak but no ACN or coformer | n/a | 10.3% wt loss 30-100° C. (3.3 mole eq water) | broad endotherm (onset 46° C., 274.0 J/g) small endotherm (onset 154° C., 21.6 J/g) small endotherm (onset 243° C., 4.9 J/g) | n/a |

Example 3

Preparation of Compound 1 Form 1 and Form 6

A. Preparation of Compound 1 Form 1

Exemplary methods to prepare Form 1 are described in Method 2 and Method 3 of Example 1.

Another method to prepare Form 1 is described below. Form 1 was scaled-up using ethanol Ethanol was chosen as a suitable ICH Class 3 solvent. Amorphous Compound 1 (1 g) was prepared in a large glass vial and warmed to 50 C. Ethanol (17 ml, 17 vols) was added at 50° C. and the sample was stirred at 500 rpm. Initially the sample formed a gum but after stirring for a few minutes, the gum converted to a bright yellow suspension. The sample was stirred at 50° C. for 1 hour then an aliquot of the solid was filtered, air dried and analyzed by XRPD. The sample was matured (shaken in cycles of 4 hours at 25° C./4 hours at 50° C.) for 2 days then another aliquot was filtered and analyzed by XRPD.

The remaining sample was allowed to cool to room temperature and was filtered through a 0.45 μm PTFE filter. The sample was air dried under vacuum for 1 hour and was dried in a vacuum oven overnight at 30° C. The resulting solid, 930 mg (93 wt %), was analyzed by XRPD, $^1$H NMR and by HPLC for purity. This method successfully produced crystalline Form 1 material in a 93 wt % yield.

Another method to prepare Form 1 is described below. IPA-water (2 ml-2 ml IPA-water) was mixed with amorphous Compound 1 (106 mg). Heat was applied to the sample until all Compound 1 is dissolved. The sample was left at room temperature overnight. Solid was collected and dried in vacuum over at 45° C. for 2 hours. The XRPD shows that the material is Form 1.

B. Preparation of Compound 1 Form 6

Small-scale preparations of Form 6 were carried. Amorphous Compound 1 (30 mg) was prepared in glass vials and cooled to 5° C. Solvent 1 was added (solvent and volume depend on the experiment, see Table 6) and observations were made. Sample was stirred at 5° C. for a few seconds then Solvent 2 was added (solvent and volume depend on the experiment, see Table 6) and further observations were made. Samples were stirred at 5° C. for ~10 minutes then aliquots of the sample were filtered, air dried and analyzed by XRPD. Samples were left to stir at 5° C. for a further 2 hours then another set of aliquots were filtered, air dried and analyzed by XRPD. All experiments were carried out at 5° C.

TABLE 6

Summary of small scale experiments to identify a method to make Form 6

| Solvent 1 | Vols | Obs. in solvent 1 | solvent 2 | Vols | Obs. On addition of solvent 2 | Obs after 10 mins stirring at 5° C. | XRPD | Obs after 2 hours stirring at 5° C. | XRPD |
|---|---|---|---|---|---|---|---|---|---|
| 2-methoxyethanol | 3 vol | solution | water | 20 vol | suspension/gum | suspension/gum | amorphous | suspension (less gum) | amorphous |
| nitromethane | 3 vol | solution | water | 20 vol | emulsion/gum | gummy solid | crystalline Form 6 | gummy solid (more solid less gum) | crystalline Form 6 |
| ACN | 3 vol | gum/solution | water | 20 vol | suspension/gum | suspension/gum | amorphous | suspension/gum | amorphous |
| ACN | 10 vol | gum/solution | water | 20 vol | suspension/gum | gummy solid | partially crystalline Form 6 | suspension | weakly crystalline Form 6 |
| water | 17 vol | dry solid (floating) | ACN | 17 vol | suspension | suspension | crystalline Form 6 | suspension | partially crystalline Form 6 |

Obs.—observation

Form 6 material was successfully prepared in three of the five experiments; the remaining experiments produced amorphous material. The best crystallinity was obtained from the experiments in nitromethane and water/ACN (50/50 v/v). Results show that all the samples except the water/ACN experiment formed gums (some of which converted to solids with stirring). Adding the water before the acetonitrile seems to prevent the formation of the gum, although the sample in water required vigorous shaking to wet the particles effectively. In addition, the crystallinity seemed to be worse after extended stirring. The best method for scale-up is the water/ACN (50/50 v/v) method with a short stir time before isolation.

A large scale-up to prepare Form 6 was carried out. Amorphous Compound 1 (1 g) was prepared in a large glass vial and cooled to 5° C. Water (11.8 ml, 12 vols) was added at 5° C. and the sample was shaken vigorously to wet the particles. The sample was stirred at 500 rpm for a few minutes to form a suspension. Acetonitrile (7.2 ml, 7 vols) was added, initially forming a yellow gum. The sample was stirred for ~5 minutes at 5° C. after which time the gum had converted to a powdery solid. The sample can be seeded with a few milligrams of Form 6. An aliquot of the sample was filtered, air dried and analyzed by XRPD. The sample was filtered through a 0.45 µm Nylon filter.

During filtration, a large lump of hard solid was found in the suspension (from the gum). This solid was broken up with a spatula to produce a powdery suspension and left to stir at 5° C. for a further 10 minutes. An aliquot was taken and analyzed by XRPD. The remaining sample was filtered through the same filter (added to the first crop) and the whole sample was air dried under vacuum for 2.5 hours and was dried in a vacuum oven at RT for 1 hour. The resulting solid, 796 mg (80 wt %), was analyzed by XRPD. This method successfully produced crystalline Form 6 material in an 80 wt % yield. This method was repeated and Form 6 was obtained in 87 wt % yield.

A comparison of the results for Forms 1 and 6 is shown in Table 7. The Form 6 sample was found to be a hydrated form of the free base. The water content of the sample varied depending on the analysis and time. Two slightly different XRPD diffractograms were recorded approximately 24 hours apart, between which the sample had been stored at ambient conditions.

The weight loss in the TGA and the water content by Karl Fischer do not agree exactly. These results can be explained by the GVS data. The isotherm plot shows a large weight change, i.e. a large uptake/release of water between 20 and 60% RH. This means that at ambient conditions the water content of the sample will be very sensitive to the ambient humidity. It seems that the water content is approximately 1-1.5 moles water at ambient conditions (approximately 40% RH) but this is not a fixed amount. The GVS results show a total change of approximately five moles of water between 0 and 90% RH; however, there are no plateaus in the isotherm plot, which would indicate a zone of stability for any particular water content. Therefore, the water content is not stable with respect to humidity. The varying water content also causes subtle changes in the XRPD diffractogram.

TABLE 7

Characterization of Forms 1 and 6 of Compound 1

| Sample | Form 1 reference | Form 1 | Form 6 |
|---|---|---|---|
| Appearance | white powder | pale yellow powder | pale yellow powder |
| XRPD | crystalline, Form 1 | crystalline, Form 1 | crystalline, Form 6 |
| ¹H NMR | consistent with structure, contains 0.05 mole IPA | consistent with structure, contains 0.29 mole ethanol | consistent with structure, contains no residual solvent but some water |
| Purity by HPLC | 98.3 area % | 99.1 area % | 98.8 area % |
| Optical microscopy | tiny irregular particles in agglomerates (approximately 1-5 µm) | n/a | mixture of fused agglomerates and primary particles. Particles are laths or irregular plates and are from <1 µm up to ~40 µm, average ~20 µm |

TABLE 7-continued

Characterization of Forms 1 and 6 of Compound 1

| Sample | Form 1 reference | Form 1 | Form 6 |
|---|---|---|---|
| Karl Fischer | n/a | n/a | 4.9 wt % water (1.5 moles) |
| TGA | 0.6 wt % loss 230-310° C. degradation after ~375° C. | n/a | 4.1 wt % loss 25-90° C. (1.25 moles water) degradation after ~375° C. |
| DSC | sharp endotherm onset 255° C. (−85.7 J/g) signs of degradation after 325° C. | n/a | broad endotherm (2 peaks) onset 38° C. (−163.9 J/g), consistent with weight loss broad endotherm onset 156° C. (−24.4 J/g) signs of degradation after 350° C. |
| GVS | total weight change 0-90% RH ~0.5 wt %, non-hygroscopic. Steady adsorption/desorption with no hysteresis. XRPD analysis of the residue showed no change in form | n/a | total weight change 0-90% RH 15.0 wt % (5.2 moles water), hygroscopic. Large steps 40-60% RH on adsorption and 40-20% RH on desorption with significant hysteresis. XRPD analysis of the residue showed small changes |
| Static Stability at 40° C./75% RH | no change after 7 days, after 63 days no change in form but loss of crystallinity | n/a | subtle changes in XRPD after 7 days, still Form 6 no further changes after 26 days |
| Static Stability at 25° C./96% RH | no change after 7 days, after 63 days no change in form but loss of crystallinity | n/a | no change in XRPD after 26 days |

Example 4

Preparation of Compound 1 Form 8

A method of preparing Form 8 is described below. On heating, Form 6 loses the water at relatively low temperatures and changes form to Form 8. Form 8 is not consistent with the non-solvated Form 1 or with any of the other forms seen in the polymorph screens. It is likely to be another non-solvated form of Compound 1. Further heating of Form 8 shows a melt endotherm in the DSC (onset 156° C., confirmed as a melt by VTX, data not shown). On cooling, the material remains amorphous. A representative XRPD of Form B is shown in FIG. 20.

Example 5

Competitive Slurry/Water Activity Experiments with Forms 1 and 6

IPA/water and ACN/water were selected as suitable solvents for the competitive slurry/water activity experiments. These solvent mixtures were selected to have some solubility of the Compound 1 free base and to be able to obtain a wide range of water activities by varying the water content. IPA/water was selected as this solvent often formed solvated forms of the free base and ACN/water was selected as this solvent produced only Form 1 of the free base during the polymorph screening experiments.

Results for the preparation of the saturated solutions are given in Table 8 and show that the amorphous material slurried in IPA/water mixtures crystallized to give the solvated Form 4. The ACN/water mixtures also showed that the amorphous material crystallized as Form 1 in all conditions. There was one exception to this—the IPA/water sample at 50° C. and at a water activity of 0.8 gave Form 1 rather than Form 4. The results of the competitive slurry experiments are given in Table 9.

TABLE 8

Experimental details and XRPD results from the preparation of saturated solutions

| Solvent | Volume IPA/ACN (μl) | Volume water (μl) | Water activity | Temperature (° C.) | Observation | XRPD result |
|---|---|---|---|---|---|---|
| IPA/water | 980 | 20 | 0.2 | 5 | suspension | crystalline Form 4 |
| IPA/water | 980 | 20 | 0.2 | 25 | suspension | crystalline Form 4 |
| IPA/water | 980 | 20 | 0.2 | 50 | suspension | crystalline Form 4 |
| IPA/water | 960 | 40 | 0.4 | 5 | suspension | crystalline Form 4 |
| IPA/water | 960 | 40 | 0.4 | 25 | suspension | crystalline Form 4 |
| IPA/water | 960 | 40 | 0.4 | 50 | suspension | crystalline Form 4 |
| IPA/water | 920 | 80 | 0.6 | 5 | suspension | crystalline Form 4 |
| IPA/water | 920 | 80 | 0.6 | 25 | suspension | crystalline Form 4 |
| IPA/water | 920 | 80 | 0.6 | 50 | suspension | crystalline Form 4 |
| IPA/water | 840 | 160 | 0.8 | 5 | suspension | crystalline Form 4 |
| IPA/water | 840 | 160 | 0.8 | 25 | suspension | crystalline Form 4 |
| IPA/water | 840 | 160 | 0.8 | 50 | suspension | crystalline Form 1 |
| ACN/water | 990 | 10 | 0.2 | 5 | suspension | crystalline Form 1 |
| ACN/water | 990 | 10 | 0.2 | 25 | suspension | crystalline Form 1 |

TABLE 8-continued

Experimental details and XRPD results from the preparation of saturated solutions

| Solvent | Volume IPA/ ACN (µl) | Volume water (µl) | Water activity | Temperature (° C.) | Observation | XRPD result |
|---|---|---|---|---|---|---|
| ACN/water | 990 | 10 | 0.2 | 50 | suspension | crystalline Form 1 |
| ACN/water | 980 | 20 | 0.4 | 5 | suspension | crystalline Form 1 |
| ACN/water | 980 | 20 | 0.4 | 25 | suspension | crystalline Form 1 |
| ACN/water | 980 | 20 | 0.4 | 50 | suspension | crystalline Form 1 |
| ACN/water | 950 | 50 | 0.6 | 5 | suspension* | n/a - no solid |
| ACN/water | 950 | 50 | 0.6 | 25 | suspension | crystalline Form 1 |
| ACN/water | 950 | 50 | 0.6 | 50 | suspension | crystalline Form 1 |
| ACN/water | 850 | 150 | 0.8 | 5 | suspension* | n/a - no solid |
| ACN/water | 850 | 150 | 0.8 | 25 | suspension | crystalline Form 1 |
| ACN/water | 850 | 150 | 0.8 | 50 | suspension | crystalline Form 1 |

*re-dissolved on filtering

TABLE 9

XRPD results from the competitive slurry/water activity experiments

| Solvent | Volume IPA/ACN (µl) | Volume water (µl) | Water activity | Temperature (° C.) | Observation after stirring for 4 days | XRPD result |
|---|---|---|---|---|---|---|
| IPA/water | 980 | 20 | 0.2 | 5 | suspension | crystalline, Form 1 |
| IPA/water | 980 | 20 | 0.2 | 25 | suspension | partially crystalline, Form 1 |
| IPA/water | 980 | 20 | 0.2 | 50 | suspension | partially crystalline, Form 1 |
| IPA/water | 960 | 40 | 0.4 | 5 | suspension | crystalline, Form 1 |
| IPA/water | 960 | 40 | 0.4 | 25 | suspension | crystalline, Form 1 |
| IPA/water | 960 | 40 | 0.4 | 50 | suspension | crystalline, Form 1 |
| IPA/water | 920 | 80 | 0.6 | 5 | suspension | crystalline, Form 1 |
| IPA/water | 920 | 80 | 0.6 | 25 | suspension | crystalline, Form 1 |
| IPA/water | 920 | 80 | 0.6 | 50 | suspension | crystalline, Form 1 |
| IPA/water | 840 | 160 | 0.8 | 5 | suspension | crystalline, Form 1 |
| IPA/water | 840 | 160 | 0.8 | 25 | suspension | crystalline, Form 1 |
| IPA/water | 840 | 160 | 0.8 | 50 | suspension | crystalline, Form 1 |
| ACN/water | 990 | 10 | 0.2 | 5 | suspension | crystalline, Form 1 |
| ACN/water | 990 | 10 | 0.2 | 25 | suspension | crystalline, Form 1 |
| ACN/water | 990 | 10 | 0.2 | 50 | suspension | crystalline, Form 1 |
| ACN/water | 980 | 20 | 0.4 | 5 | suspension | crystalline, Form 1 |
| ACN/water | 980 | 20 | 0.4 | 25 | suspension | crystalline, Form 1 |
| ACN/water | 980 | 20 | 0.4 | 50 | suspension | partially crystalline, Form 1 |
| ACN/water | 950 | 50 | 0.6 | 5 | suspension | crystalline, Form 1 |
| ACN/water | 950 | 50 | 0.6 | 25 | suspension | crystalline, Form 1 |
| ACN/water | 950 | 50 | 0.6 | 50 | solid on walls | crystalline, Form 1 |
| ACN/water | 850 | 150 | 0.8 | 5 | suspension | crystalline, Form 6 |
| ACN/water | 850 | 150 | 0.8 | 25 | suspension | crystalline, Form 1 |
| ACN/water | 850 | 150 | 0.8 | 50 | suspension | crystalline, Form 3 |

Results show that Form 1 is more stable than Form 6 in all the IPA/water experiments regardless of the temperature or water activity. No evidence of any remaining Form 6 material was seen in any of the IPA/water experiments after slurrying for 4 days.

Form 1 is also the most stable form in all the ACN/water experiments except at 50° C. with a water activity of 0.8 (where Form 3 was made) and at 5° C. for a water activity of 0.8 (where Form 6 was made). The experiment that gave Form 3 material visually looked as though the solid has completely dissolved at some point as the material was stuck to the walls of the vial and there was no solid in the liquors. This may explain why the unexpected solvated form was produced in this experiment.

Therefore, the only conditions where Form 6 is more stable than Form 1 is at 5° C. in ACN/water with a water activity of 0.8 (15 vol % water), i.e. at cold temperatures and very high water activities. Thus, if a crystallisation solvent with a low water activity is chosen, if the solvent is wet, Form 6 may not be produced. The water activity (and therefore the water content) depends on the solvent, alcohols have a much lower water activity for a given water content than acetates, acetonitrile or acetone.

Example 6

Single Crystal Experiments

A full crystal structure of Form 2 was collected and solved. A summary of structural data for Compound 1 Form 2 is provided in Table 10. Form 2 crystallizes in the orthorhombic system, space group $P2_12_12_1$ with the final R1 $[I>2\sigma(I)]=4.93\%$.

TABLE 10

Sample details and crystal data for Compound 1 Form 2

| Parameter | Value |
|---|---|
| Crystallisation solvents | DCM/acetone |
| Crystallisation method | As supplied from column |

TABLE 10-continued

Sample details and crystal data for Compound 1 Form 2

| Parameter | Value | |
|---|---|---|
| Empirical formula | $C_{31}H_{26}Cl_2N_8O_2$ | |
| Formula weight | 613.50 | |
| Temperature | 100(2) K | |
| Wavelength | 1.54178 Å | |
| Crystal size | 0.500 × 0.100 × 0.050 mm | |
| Crystal habit | Colorless Prism | |
| Crystal system | Orthorhombic | |
| Space group | $P2_12_12_1$ | |
| Unit cell dimensions | a = 8.7289(3) Å | α = 90° |
| | b = 13.2219(4) Å | β = 90° |
| | c = 25.9554(7) Å | γ = 90° |
| Volume | 2995.59(15) Å$^3$ | |
| Z | 4 | |
| Density (calculated) | 1.360 Mg/m$^3$ | |
| Absorption coefficient | 2.307 mm$^{-1}$ | |
| F(000) | 1272 | |

The asymmetric unit of Form 2 contains one fully ordered molecule of Compound 1 and one molecule of dichloromethane See FIG. 21. Anisotropic atomic displacement ellipsoids for the non-hydrogen atoms are shown at the 50% probability level. Hydrogen atoms are displayed with an arbitrarily small radius.

The absolute configuration of Compound 1 has been determined as depicted below with the Flack parameter=0.005(9). See Parsons, S and Flack, H., *Acta Cryst.* 2004, A60, s61. The chiral center has an S configuration.

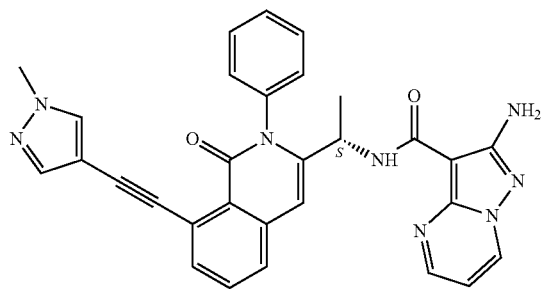

The DCM molecules sit in voids in the structure and are not bonded to the API molecules. Without being bound to a particular theory, this may explain why some of the solvent can be removed on drying without disrupting the crystal lattice and also why the same crystalline form can be made from a range of solvents.

Table 11 provides the details on data collection and structure refinement.

TABLE 11

Data collection and structure refinement for Compound 1 Form 2

| Parameter | Value |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 9.084 to 74.474° |
| Index ranges | −8 ≤ h ≤ 10, −16 ≤ k ≤ 16, −32 ≤ l ≤ 31 |
| Reflections collected | 31797 |
| Independent reflections | 6103 [R(int) = 0.0516] |
| Coverage of independent reflections | 99.4% |

TABLE 11-continued

Data collection and structure refinement for Compound 1 Form 2

| Parameter | Value |
|---|---|
| Variation in check reflections | n/a |
| Absorption correction | Semi-empirical from equivalents |
| Max. and min. transmission | 1.00000 and 0.63134 |
| Structure solution technique | Direct methods |
| Structure solution program | SHELXTL (Sheldrick, 2013) |
| Refinement technique | Full-matrix least-squares on F$^2$ |
| Refinement program | SHELXTL (Sheldrick, 2013) |
| Function minimized | $\Sigma\ w(F_o^2 - F_c^2)^2$ |
| Data/restraints/parameters | 6103/0/412 |
| Goodness-of-fit on F$^2$ | 1.039 |
| Δ/σmax | 0.002 |
| Final R indices | |
| 5464 data; I > 2σ(I) | R1 = 0.0493, wR2 = 0.1335 |
| all data | R1 = 0.0561, wR2 = 0.1428 |
| Weighting scheme | w = 1/[σ$^2$ (F$_o^2$) + (0.0956P)$^2$ + 0.7150P] where P = (F$_o^2$ + 2F$_c^2$)/3 |
| Absolute structure parameter | 0.005(9) |
| Extinction coefficient | n/a |
| Largest diff. peak and hole | 0.404 and −0.445 eÅ$^{-3}$ |

| Refinement summary: | |
|---|---|
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atom |
| H atoms (on heteroatoms), XYZ | Freely refining |
| H atoms (on heteroatoms), U | Isotropic |
| Disordered atoms, OCC | 2 part model constrained to unity |
| Disordered atoms, XYZ | freely refining |
| Disordered atoms, U | anisotropic |

Example 7

Cocrystal Screening

Materials

A diverse set of 28 pharmaceutically acceptable coformers was selected based on the potential bonding motifs of Compound 1. Compound 1 used in this example is amorphous unless stated otherwise. The list of conformers used for the cocrystal screen are: citric acid, L-malic acid, L-tartaric acid, fumaric acid, succinic acid, maleic acid, sorbic acid, ketoglutaric acid, salicylic acid, benzoic acid, 3-hydroxybenzoic acid, 2,4-dihydroxybenzoic acid, 4-aminobenzoic acid, orotic acid, urea, nicotinic acid, isonicotinic acid, nicotinamide, isonicotinamide, saccharin, L-lactic acid, L-serine, L-proline, glycine, maltol, succinimide, sulfacetamide, and p-toluenesulfonic acid monohydrate.

Solvent Drop Grinding

A 1:1 stoichiometric mixture of Compound 1 and the coformer was weighed to produce a total of 50 mg in a 2 ml stainless steel grinding jar with one 7 mm grinding ball. The materials were wetted with solvent (10 μl of nitromethane) and ground for 30 min at 30 Hz using a Retsch Mixer Miller MM300. Solids obtained after grinding were initially analyzed by XRPD. Sticky solids or liquids obtained after grinding were left to dry for 1 day and any solids obtained were initially analyzed by XRPD. A control experiment with no conformer present was also performed following the same procedure.

Dry Grinding

A 1:1 stoichiometric mixture of Compound 1 and the coformer was weighed to produce a total of 50 mg in a 2 ml stainless steel grinding jar with one 7 mm grinding ball. The materials were ground for 30 min at 30 Hz using a Retsch Mixer Miller MM300. Solids obtained after grinding were initially analyzed by XRPD. A control experiment with no conformer present was also performed following the same procedure.

Sonication

A 1:1 stoichiometric mixture of Compound 1 (25 mg) and the coformer was placed in 2 ml HPLC vials and suspended in MeCN:water 1:1 (1 ml). Ultrasound was then applied in a cup horn at 50% power for 10 min with pulses of 30 s on and 1 min off. Solids obtained after sonication were filtered and dried under suction for 10 min and the residues were initially analyzed by XRPD. Solutions obtained after sonication were placed at 5 and −20° C. for a day and any solids obtained were filtered and analyzed by XRPD. If no solids were obtained after cooling, samples were allowed to evaporate at RT and any solids obtained were analyzed by XRPD.

An initial control experiment with no coformer showed that Compound 1 is not wettable in water alone. MeCN was added to produce a suspension, showing that MeCN:water 1:1 mixture produces a suspension.

The results of the experiments are provided below in Table 12.

TABLE 12

Cocrystal screen results

| Coformer | Procedure | Solvent | Isolation | Observation | XRPD |
| --- | --- | --- | --- | --- | --- |
| None | Solvent drop grinding | Nitromethane | Grinding | Yellow solid | Form 1 |
| Citric acid | Solvent drop grinding | Nitromethane | Grinding | Yellow sticky solid | Amorphous |
| L-Malic acid | Solvent drop grinding | Nitromethane | Grinding | Yellow wet solid | Form 1 |
| L-Tartaric acid | Solvent drop grinding | Nitromethane | Grinding | Yellow solid | Form P1C3 |
| Fumaric acid | Solvent drop grinding | Nitromethane | Grinding | Yellow solid | Form 1 + Coformer |
| Succinic Acid | Solvent drop grinding | Nitromethane | Grinding | Yellow wet solid | Amorphous + Coformer + Poor Form 1 |
| Maleic Acid | Solvent drop grinding | Nitromethane | Grinding | Yellow sticky solid | Amorphous |
| Sorbic acid | Solvent drop grinding | Nitromethane | Grinding | Yellow solid | Form 1 + Coformer |
| Ketoglutaric acid | Solvent drop grinding | Nitromethane | Grinding | Yellow sticky solid | Amorphous + 1 peak |
| Salicylic acid | Solvent drop grinding | Nitromethane | Grinding | Yellow sticky solid | Amorphous |
| Benzoic acid | Solvent drop grinding | Nitromethane | Grinding | Yellow sticky solid | Form 1 |
| 3-Hydroxybenzoic acid | Solvent drop grinding | Nitromethane | Grinding | Yellow sticky solid | — |
| 2,4-Dihydroxybenzoic acid | Solvent drop grinding | Nitromethane | Grinding | Yellow sticky solid | — |
| 4-Aminobenzoic acid | Solvent drop grinding | Nitromethane | Grinding | Yellow sticky solid | Amorphous + Coformer |
| Orotic acid | Solvent drop grinding | Nitromethane | Grinding | Yellow solid | Form 1 + Coformer |
| Urea | Solvent drop grinding | Nitromethane | Grinding | Yellow solid | Form 1 + Coformer |
| Nicotinic acid | Solvent drop grinding | Nitromethane | Grinding | Yellow solid | Form 1 + Coformer |
| Isonicotinic acid | Solvent drop grinding | Nitromethane | Grinding | Yellow solid | Form 1 + Coformer |
| Nicotinamide | Solvent drop grinding | Nitromethane | Grinding | Yellow solid | Form 1 |
| Isonicotinamide | Solvent drop grinding | Nitromethane | Grinding | Yellow solid | Form 1 |
| Saccharin | Solvent drop grinding | Nitromethane | Grinding | Yellow solid | Form 1 + Coformer |
| L-Lactic acid | Solvent drop grinding | Nitromethane | Grinding | Yellow solid | Similar to Form 3 + Coformer |
| L-Serine | Solvent drop grinding | Nitromethane | Grinding | Yellow solid | Form 1 + Coformer |
| Nicotinic acid | Solvent drop grinding | Nitromethane | Grinding | Yellow solid | Form 1 + Coformer |
| Isonicotinic acid | Solvent drop grinding | Nitromethane | Grinding | Yellow solid | Form 1 + Coformer |
| Nicotinamide | Solvent drop grinding | Nitromethane | Grinding | Yellow solid | Form 1 |
| Isonicotinamide | Solvent drop grinding | Nitromethane | Grinding | Yellow solid | Form 1 |

TABLE 12-continued

Cocrystal screen results

| Coformer | Procedure | Solvent | Isolation | Observation | XRPD |
|---|---|---|---|---|---|
| Saccharin | Solvent drop grinding | Nitromethane | Grinding | Yellow solid | Form 1 + Coformer |
| L-Lactic acid | Solvent drop grinding | Nitromethane | Grinding | Yellow solid | Similar to Form 3 + Coformer |
| L-Serine | Solvent drop grinding | Nitromethane | Grinding | Yellow solid | Form 1 + Coformer |
| L-Proline | Solvent drop grinding | Nitromethane | Grinding | Yellow solid | Form 1 + Coformer |
| Glycine | Solvent drop grinding | Nitromethane | Grinding | Yellow solid | Form 1 + Coformer |
| Maltol | Solvent drop grinding | Nitromethane | Grinding | Yellow solid | Form 1 + Coformer |
| Succinimide | Solvent drop grinding | Nitromethane | Grinding | Yellow solid | Form 1 |
| Sulfacetamide | Solvent drop grinding | Nitromethane | Grinding | Yellow solid | Form 1 + Coformer |
| p-Toluenesulfonic acid-H$_2$O | Solvent drop grinding | Nitromethane | Grinding | Yellow liquid | — |
| None | Sonication | 1:1 MeCN:Water | Filtering | Yellow solid | Form 1 |
| Citric acid | Sonication | 1:1 MeCN:Water | Filtering | Yellow solid | Similar to Form 6 |
| L-Malic acid | Sonication | 1:1 MeCN:Water | Filtering | Yellow solid | Similar to Form 6 |
| L-Tartaric acid | Sonication | 1:1 MeCN:Water | Filtering | Yellow solid | Similar to Form 6 |
| Fumaric acid | Sonication + Evaporation | 1:1 MeCN:Water | Evaporation | Yellow solid | Form 1 + Coformer |
| Succinic Acid | Sonication | 1:1 MeCN:Water | Filtering | Yellow solid | Form 1 |
| Maleic Acid | Sonication | 1:1 MeCN:Water | Filtering | Yellow solid | Form 1 |
| Sorbic acid | Sonication | 1:1 MeCN:Water | Filtering | Yellow solid | Similar to Form 6 |
| Ketoglutaric acid | Sonication | 1:1 MeCN:Water | Filtering | Yellow solid | Similar to Form 6 + 5 new peaks |
| Salicylic acid | Sonication | 1:1 MeCN:Water | Filtering | Yellow solid | Form P1C9 |
| Benzoic acid | Sonication | 1:1 MeCN:Water | Filtering | Yellow solid | Form 1 |
| 3-Hydroxybenzoic acid | Sonication | 1:1 MeCN:Water | Filtering | Yellow solid | Form 1 |
| 2,4-Dihydroxybenzoic acid | Sonication | 1:1 MeCN:Water | Filtering | Yellow solid | Form 1 |
| 4-Aminobenzoic acid | Sonication | 1:1 MeCN:Water | Filtering | Yellow solid | Form 1 |
| Orotic acid | Sonication | 1:1 MeCN:Water | Filtering | Yellow solid | Similar to Form 6 + Coformer |
| Urea | Sonication | 1:1 MeCN:Water | Filtering | Yellow solid | Similar to Form 6 |
| Nicotinic acid | Sonication | 1:1 MeCN:Water | Filtering | Yellow solid | Similar to Form 6 |
| Isonicotinic acid | Sonication | 1:1 MeCN:Water | Filtering | Yellow solid | Form 1 + Coformer |
| Nicotinamide | Sonication | 1:1 MeCN:Water | Filtering | Yellow solid | Similar to Form 6 |
| Isonicotinamide | Sonication | 1:1 MeCN:Water | Filtering | Yellow solid | Form 1 |
| Saccharin | Sonication | 1:1 MeCN:Water | Filtering | Yellow solid | Form 1 |
| L-Lactic acid | Sonication | 1:1 MeCN:Water | Filtering | Yellow solid | Form 1 |
| L-Serine | Sonication | 1:1 MeCN:Water | Filtering | Yellow solid | Form 1 |
| L-Proline | Sonication | 1:1 MeCN:Water | Filtering | Yellow solid | Form 1 |
| Glycine | Sonication | 1:1 MeCN:Water | Filtering | Yellow solid | Form 1 |
| Maltol | Sonication | 1:1 MeCN:Water | Filtering | Yellow solid | Similar to Form 6 |
| Succinimide | Sonication | 1:1 MeCN:Water | Filtering | Yellow solid | Similar to Form 6 |

TABLE 12-continued

Cocrystal screen results

| Coformer | Procedure | Solvent | Isolation | Observation | XRPD |
|---|---|---|---|---|---|
| Sulfacetamide | Sonication | 1:1 MeCN:Water | Filtering | Yellow solid | Form 1 |
| p-Toluenesulfonic acid-H2O | Sonication | 1:1 MeCN:Water | Filtering | Yellowish solid | Form 1 |
| None | Dry grinding | None | Grinding | Yellow solid | Amorphous |
| L-Tartaric acid | Dry grinding | None | Grinding | Yellow solid | Amorphous |

—: not performed,

TABLE 13

Preliminary characterization of the cocrystal screen sample

| Coformer | XRPD High resolution | $^1$H-NMR | TGA | DSC | XRPD after 7 d 40° C. 75% RH 25° C. 97% RH |
|---|---|---|---|---|---|
| L-Tartaric acid | Form P1C3 | Consistent with structure. 1.1 Eq. of acid. Water peak present. | 0.5% weight loss between 30-100° C. 1.9% weight loss between 100-160° C. 15.9% weight loss between 170-260° C., followed by degradation. | Small broad endotherm (onset 33.5° C., peak 57.8° C., 5.27 J/g). Endotherm (onset 129.2° C., peak 148.9° C., 78.48 J/g). | No change for both. |
| L-Tartaric acid | Form 6 | Consistent with structure. No peaks of the acid. Water peak present. | 10.3% weight loss between 30-100° C. No other weight loss until sample degrades at ~240° C. | Large broad endotherm (onset 46.4° C., 274.0 J/g). Small endotherm (onset 154.1° C., 21.6 J/g). Small endotherm (onset 242.9° C., 4.9 J/g). | — |
| Salicylic acid | Form P1C9 | Consistent with structure. 0.5 Eq. of acid Water peak present. | — | Large broad endotherm (onset 42.8° C., 149.6 J/g). Small endotherm (onset 120.3° C., 16.7 J/g). | — |

— = Not performed.

Solvent-drop grinding experiments and dry grinding experiments resulted in mostly amorphous pattern, Form 1 or mixtures of Form 1 and Form 3 with the coformer. Few experiments only produced sticky solids or liquids that were not suitable for XRPD analyses. One of the solvent drop grinding experiments (L-tartaric acid) resulted in a new crystalline pattern (Form P1C3) that did not correspond to any of the known crystalline forms of the Compound 1 or the coformer. XRPD, TGA and DSC characterizations of Form P1C3 are shown in FIGS. 22-23. GVS analysis of Form P1C3 is shown in FIG. 28.

The sonication experiments performed resulted in mostly Form 1, Form 6 or mixtures of Form 1 and Form 6 with the coformer. One of the experiments (salicylic acid) resulted in a new crystalline pattern (Form P1C9) that did not correspond to any of the known crystalline forms of the Compound 1 or the coformer. XRPD, TGA and DSC characterizations of Form P1C9 are shown in FIGS. 24-25.

Both samples displaying the new crystalline Forms P1C3 and P1C9 were characterized further. As the initial amount of Form 6 obtained in the polymorphism screen was very limited, one of the samples that displayed Form 6 was also further characterized. The results are summarized in Table 13.

High resolution XRPD analysis of the potential cocrystal Form P1C3 was consistent with the low resolution XRPD, showing no presence of the staring materials. $^1$H-NMR showed that material was consistent with the structure of Compound 1 with no evidence of degradation. The $^1$H-NMR also showed the presence of 1.1 eq. of the coformer and of water. Thermal analyses of Form P1C3 show a DSC with a small broad endothermic event between ~RT and ~100° C., which correlates with a 0.45% weight loss in the TGA and a second large endothermic event (onset 129.2° C.), which correlates with 1.9% weight loss in the TGA. The thermal data of Form P1C3 is consistent with a cocrystal solvate with 1 equivalent of water. Preliminary stability studies were carried out at 40° C./75% RH and 25° C./97% RH for Form P1C3 and no changes in the XRPD patterns were observed after a week.

High resolution XRPD analysis of the potential cocrystal Form P1C9 was consistent with the low resolution XRPD, showing no presence of the staring materials. $^1$H-NMR showed that material was consistent with the structure of Compound 1 with no evidence of degradation. The $^1$H-NMR also showed the presence of 0.5 eq. of the coformer and of water. Thermal analyses of Form P1C9 by DSC (no sample available for TGA analyses) showed clear differences to the starting materials, showing a broad endothermic event between ~30 and 100° C., which indicate that these could be a solvated form.

High resolution XRPD analysis of the free base Form 6 was consistent with the low resolution XRPD, showing no presence of the coformer or any other forms of the free base. $^1$H-NMR showed that material was consistent with the structure of Compound 1 with no evidence of degradation and no presence of the coformer. The $^1$H-NMR also shows a large water peak. The DSC analyses of Form 6 show a broad endothermic event between ~30 and 100° C., which indicate that this could be solvated form. The TGA of Form 6 is also consistent with a solvate, showing a weight loss between ~30 and 100° C. that is consistent with 3 eq. of water.

In order to investigate the potential cocrystals for potential development the forms obtained from L-tartaric (Form P1C3) and salicylic acids (Form P1C9) were selected for scale up and further studies.

Example 8

Scale Up Preparation of Cocrystals

Compound 1 used in this example is amorphous unless stated otherwise.

Slow Cooling

A 1:1 stoichiometric mixture of Compound 1 (40 or 400 mg) and the coformer (L-tartaric acid or salicylic acid) was placed in 4 ml vials and the appropriate solvent amounts were added to the vial. Samples were placed in a multireactor and were left at 40° C. (for DCM experiments) and 50° C. for other solvents. Samples were checked after 10 to 30 min of heating and if no dissolution was observed more solvent was added until complete dissolution was reached. Dissolution was observed in all cases except for one experiment, which showed some coformer crystals in solution. For this experiment ethanol was added until complete dissolution of the coformer was reached. The samples were then cooled down to 5° C. at 0.1° C./min and 0.25° C./min. The resulting suspensions or solutions were left at 5° C. for ca. 24 h. Any solids obtained were filtered and analyzed by XRPD. Solutions obtained were placed at −20° C. for 2 h and any solids obtained were filtered and analyzed by XRPD. If no solids were obtained after cooling, samples were allowed to evaporate at RT and any solids obtained were analyzed by XRPD. The details and the results of the scale-up experiments are summarized in tables below.

Sonication

A 1:1 stoichiometric mixture of Compound 1 at 25, 50, 250 or 500 mg and the coformer (salicylic acid) was placed in a glass vial and suspended in a MeCN-water or an ethanol-water mixture. Ultrasound was then applied in a cup horn at 50% or 100% power for 10 min with pulses of 30 s on and 1 min off. Solids obtained after sonication were allowed to stand at RT for between 30 and 120 min and then filtered and dried under suction for 10 min and the residues were analyzed by XRPD. The details and the results of the experiments are summarized in tables below.

Characterization of Cocrystals

Certain scaled up cocrystal samples were characterized by: high resolution XRPD, VT-XRPD, DSC, TGA, $^1$H-NMR, stability after 7 days at 40° C./75% RH and at 25° C./97% RH, microscopy (PLM and SEM), GVS, Karl Fischer, HPLC purity and kinetic solubility after 30 min in water and in 0.1M HCl. See tables below for the summarized results.

Results

The results of the scale up and further characterization on selected cocrystals are summarized in the following tables.

TABLE 14

Cocrystal scale up results (1/3)

| Coformer | Procedure | amount (mg) | Solvent | Solvent amount (ml) | Isolated after | Final result | XRPD |
|---|---|---|---|---|---|---|---|
| L-Tartaric acid | Slow cooling | 40 | DMSO | 0.150 | Cooling to 5° C. | Suspension in a yellow solution | Similar to Form 2 and Form 4 |
| L-Tartaric acid | Slow cooling | 40 | 2-Methoxyethanol | 0.150 | Cooling to 5° C. | Suspension in a yellow solution | Form 1 + hints of Form 2 |
| L-Tartaric acid | Slow cooling | 40 | Nitromethane (Bottle H02937) | 2.00 | Cooling to 5° C. | Suspension in a brown solution | Coformer |
| L-Tartaric acid | Slow cooling + evaporation | 40 | Dichloromethane-40% ethanol | 5.00 | Evaporation | Crystals in a yellow solution | Form 2 |
| L-Tartaric acid | Slow cooling + evaporation | 40 | Nitromethane (Bottle H02937)-5% water | 2.00 | Evaporation | Suspension in a brown solution | Form P1C3 |
| Salicylic acid | Slow cooling | 40 | DMSO | 0.150 | Cooling to 5° C. | Suspension in a yellow solution | Similar to Form 2 and Form 4 |
| Salicylic acid | Slow cooling | 40 | 2-Methoxyethanol | 0.150 | Cooling to 5° C. | Suspension in a yellow solution | Form 1 + hints of Form 2 |
| Salicylic acid | Slow cooling + evaporation | 40 | Nitromethane (Bottle H02937) | 2.00 | Evaporation | Resin | — |
| Salicylic acid | Slow cooling + evaporation | 40 | Dichloromethane | 3.00 | Evaporation | Resin | — |
| Salicylic acid | Slow cooling | 40 | Nitromethane (Bottle H02937)-5% water | 2.00 | Cooling to −20° C. | Needles in a brown solution | Similar to Form 6 |
| Salicylic acid | Slow cooling + evaporation | 40 | MeCN-50% water | 2.00 | Evaporation | Suspension in a yellow solution | Form 1 |

— = Not performed

TABLE 15

Cocrystal scale up results (2/3)

| Coformer | Procedure | amount (mg) | Solvent | Solvent amount (ml) | Sonication amplitude (%) | Result after sonication | Time at RT after sonication (min) | XRPD |
|---|---|---|---|---|---|---|---|---|
| Salicylic acid | Sonication | 25 | MeCN-50% Water | 1.00 | 50 | Suspension | 30 min | Form 1 |
| Salicylic acid | Sonication | 50 | MeCN-50% Water | 1.00 | 50 | Suspension | 30 min | Form P1C9 |
| Salicylic acid | Sonication | 25 | MeCN-50% Water | 1.00 | 50 | Suspension | >120 min | Form P2C9 + Form 1 |
| Salicylic acid | Sonication | 50 | MeCN-50% Water | 1.00 | 50 | Suspension | >120 min | Form P2C9 |
| Salicylic acid | Sonication | 50 | MeCN-50% Water | 1.00 | 50 | Suspension | >60 min | P1C9 + 1 new peak |
| Salicylic acid | Sonication | 50 | MeCN-25% Water | 1.00 | 50 | Suspension | >60 min | Form P1C9 |
| Salicylic acid | Sonication | 50 | MeCN-5% Water | 1.00 | 50 | Suspension | >60 min | Form 1 |
| Salicylic acid | Sonication | 50 | Ethanol-50% Water | 1.00 | 50 | Suspension | >60 min | Form 1 |
| Salicylic acid | Sonication | 50 | Ethanol-25% Water | 1.00 | 50 | Suspension | >60 min | Form 1 |
| Salicylic acid | Sonication | 50 | Ethanol-5% Water | 1.00 | 50 | Suspension | >60 min | Form 1 |
| Salicylic acid | Sonication | 500 | MeCN-50% water | 20.00 | 50 | Suspension | 60 min | Form 1 |
| Salicylic acid | Sonication | 500 | MeCN-50% water | 10.00 | 50 | Suspension | 60 min | Form 1 |
| Salicylic acid | Sonication | 250 | MeCN-50% water | 5.00 | 50 | Suspension | 60 min | Form 1 |
| Salicylic acid | Sonication | 250 | MeCN-50% water | 5.00 | 100 | Suspension | >120 min | Form 1 |

— = Not performed

TABLE 16

Cocrystal scale up results (3/3)

| Coformer | Procedure | amount (mg) | Solvent | Solvent amount (ml) | Isolated after | Final result | Final amount (mg) | XRPD |
|---|---|---|---|---|---|---|---|---|
| L-Tartaric acid | Slow cooling + evaporation | 40 | Nitromethane (Bottle H03010)-5% Water | 2.00 | Cooling to 5° C. + 1 day evaporation | Suspension in a yellow solution | 28.39 | Form P1C9 |
| L-Tartaric acid | Slow cooling + evaporation | 400 | Nitromethane (Bottle H02937)-5% Water | 20.00 | Cooling to 5° C. + 4 day evaporation | Brown-black resin | — | — |
| L-Tartaric acid | Slow cooling + evaporation | 400 | Nitromethane (Bottle H03010)-5% Water | 20.00 | Cooling to 5° C. + 4 day evaporation | Suspension in a yellow solution | 369.39 | Form P1C9 |

— = Not performed

TABLE 17

Characterization of selected cocrystal samples

| Form | Coformer | High Res. XRPD | DSC | TGA | ¹H-NMR | XRPD and HPLC after 7 d 40° C. 75% RH 25° C. 97% RH | KF |
|---|---|---|---|---|---|---|---|
| Form P1C3 | L-tartaric Acid | Form P1C3 | 1st broad endotherm onset | 1.2% weight loss corresponding | Consistent with structure. | XRPD: no change | |

TABLE 17-continued

Characterization of selected cocrystal samples

| Form | Coformer | Form | DSC | TGA | XRPD/NMR | Other | |
|---|---|---|---|---|---|---|---|
| | | | ~30° C. (11.95 J/g). 2nd endothermic large peak onset at 120.94° C. (65.86 J/g). | to the first DSC event. 2.8% weight loss corresponding to the second DSC event. | 1.15 eq. of coformer. | for both. | |
| Form 6 | Salicylic Acid | — | — | — | Consistent with structure. No coformer present. | — | |
| Form P1C9 | Salicylic Acid | — | — | 10.15% weight loss from RT up to ~100° C. | — | — | |
| Form P2C9 | Salicylic Acid | Form P2C9 | 1 large broad endotherm onset ~30° C. and peak at 96.2° C. (ΔH = 116.8 J/g). | 5.64% weight loss corresponding to the DSC endothermic event. | Consistent with structure. 1.2 eq. of coformer. 0.48 eq. of MeCN | — | |
| Form P1C3 | L-tartaric Acid | Form P1C3 | 1st broad endotherm onset ~30° C. (6.907 J/g). 2nd endothermic large peak onset at 124.64° C. (67.93 J/g). | 0.4% weight loss corresponding to the first DSC event. 2.8% weight loss corresponding to the second DSC event. | Consistent with the structure. 1.35 eq. of coformer 0.08 eq. of MeNO$_2$. Other peaks observed. | XRPD: no change for both. HPLC: shows a purity change of less than 3% for both. | 3.5% Water |

| Form | GVS | Microscopy | HPLC Purity (%, AUC) | 30 min Kinetic solubility (pH) |
|---|---|---|---|---|
| Form P1C3 | — | Crystals of lath and plate-like morphology of typically less than 300 μm, most around 100 μm. | 98.4% | — |
| Form 6 | — | Crystals of acicular morphology of typically less than 700 μm, most around 300 μm. | — | — |
| Form P1C9 | — | — | — | — |
| Form P2C9 | — | — | — | — |
| Form P1C3 | 3.67% weight gain from 0-90% RH, cycle 2. No hysteresis observed. XRPD after analysis | Lath shaped crystals of sizes between ~5 to 750 μm long. | Consistent with microscopy results showing lath shaped crystals with | 88.4% (sample 1) 96.5% (sample 2) | Solubility determined in duplicate as 0.04 and 0.05 mg/ml (pH | Solubility determined in duplicate as 0.02 and 0.02 mg/ml (pH |

TABLE 17-continued

Characterization of selected cocrystal samples

| shows no change. | smooth flat surfaces and sharp edges. | 2.9, 3.0) | 1.3) |

— = not performed,
* = free base Compound 1 solubility determined as 0.01 and 0.01 mg/ml (pH 7.1 and 6.8),
** = free base Compound 1 solubility determined as 0.01 and 0.01 mg/ml (pH 1.5 and 1.3).

Scale Up of L-tartaric Acid Cocrystal Form P1C3

Preliminary slow cooling experiments with L-tartaric acid showed that while four of the solvents used resulted in crystallization of the free base or of the coformer, the experiment performed using $MeNO_2$-5% water resulted in a solution that after 1 day evaporation produced the cocrystal Form P1C3.

Following the small scale investigations further slow cooling and evaporation experiments were carried out at 500 mg scale using $MeNO_2$-5% water in order to produce the L-tartaric acid cocrystal Form P1C9. All the preliminary small scale experiments performed with $MeNO_2$ showed a brown solution which were related to some potential contamination or degradation of the $MeNO_2$.

Characterization of the sample obtained from L-tartaric acid showed that the XRPD was consistent with the Form P1C3 previously obtained in the cocrystal screen with no evidence of coformer or free base forms present. Thermal analysis showed a DSC with a first small broad endothermic event between ~RT and ~100° C., which correlates with a 0.45% weight loss in the TGA. A second large endothermic event in the DSC with onset at 124.6° C. correlates with 2.8% weight loss in the TGA. These two thermal events indicate some initial residual solvent loss before 100° C., followed by solvent loss corresponding to c.a. 1 equivalent of water (calculated 2.5% water for a 1:1:1 Compound 1: L-tartaric acid: water cocrystal). The Karl Fischer analyses showed 3.5% water content, which is also consistent with a cocrystal hydrate. VT-XRPD showed no change until 140° C., where the sample shows an amorphous pattern, which does not change after cooling the sample to 30° C. $^1$H-NMR shows that the material is consistent with the structure of Compound 1 and it also shows peaks corresponding to the coformer that integrate as 1.35 eq. (note that there is only one diagnostic peak of the coformer). GVS analyses show that the material is moderately hygroscopic with 3.67% weight gain from 0-90% RH. No hysteresis is observed and the XRPD post GVS shows no change Analysis by PLM and SEM show only one type of crystal habit with the same lath morphology and of sizes ranging between 5 and 750 µm. Stability under different temperature and RH conditions showed no significant change in the purity or in the XRPD after a week at 25° C./96% RH and at 40° C./75% RH. Kinetic solubility determined after 30 min in water and 0.1M HCl showed values very similar to the free base solubility for the 0.1M HCl experiments, but a slightly higher solubility values were obtained for the water experiments. The XRPD of the solubility residues showed no change with respect to the staring materials.

Scale Up of Salicylic Acid Cocrystal Forms P1C9 and P2C9

Preliminary slow cooling experiments with salicylic acid only produced crystallization of polymorphic forms of the free base or the formation of gums.

Preliminary sonication experiments were performed following the same procedure that initially produced the salicylic acid cocrystal Form P1C9, but the materials were allowed to settle for longer times before filtering to potentially increase the yield. However, these experiments showed that if the sample was allowed to settle for more than 120 min a new pattern described as P2C9 that did not correspond to the known free base forms or to the coformer was obtained. Also the experiments showed that even when the sample was allowed to settle only for 30 min the cocrystal Form P1C9 was not consistently obtained, producing the cocrystal Form P1C9 for the 50 mg scale experiment and free base Form 1 for the 25 mg scale.

Characterization of the sample obtained from salicylic acid showed that the XRPD was consistent with the Form P1C9. The TGA analyses showed a 10.15% weight loss before 100° C. that correlates with the first endothermic event observed in the DSC of Form P1C9. This together with the previous data obtained for Form P1C9 is consistent with a cocrystal hydrate with ~4 eq. of water.

Characterization of the sample obtained from salicylic acid showed a new potential cocrystal Form P2C9. XRPD, TGA and DSC characterizations of Form P2C9 are shown in FIGS. 26-27. Thermal analysis showed a DSC with a large broad endothermic event between RT and ~110° C., which correlates with a 5.64% weight loss in the TGA. $^1$H-NMR shows that the material is consistent with the structure of Compound 1 and it also shows peaks that integrate as 1.2 eq. of the coformer, as well as the MeCN peak that integrates as 0.48 eq. of MeCN. Thermal data together with the $^1$H-NMR data indicate that P2C9 is a salicylic acid cocrystal solvate with MeCN (calculated 5.6% MeCN for a 1:1:1 Compound 1: salicylic acid: MeCN cocrystal).

A cocrystal screen was carried out on Compound 1 using 28 coformers. Sonication and solvent-drop grinding methodologies were used for the cocrystal screen.

Two different cocrystals were identified in the screen from 2 different coformers: cocrystal Form P1C3 obtained from L-tartaric and cocrystal Form P1C9 obtained from salicylic acid. These potential cocrystals showed diffractograms that did not correspond to any of the known crystalline forms of the Compound 1 or the coformers. Further $^1$H-NMR characterization on cocrystal Forms P1C3 and P1C9 confirmed the presence of the coformer, with 1.1 and 0.5 eq. of acid respectively. Thermal DSC and TGA analyses also indicated cocrystal formation in both cases showing clear differences with respect to the starting materials.

Both cocrystal Forms P1C3 and P1C9 obtained from L-tartaric and salicylic acids were selected for scale up and further investigations.

The L-tartaric acid cocrystal Form P1C3 was successfully scaled up to c. a. 500 mg from slow cooling and evaporation and fully characterized, which confirmed that Form P1C3 is a 1:1:1 Compound 1:L-tartaric acid: water cocrystal hydrate.

Kinetic solubility studies on the cocrystal Form P1C3 showed a slight improve in solubility with respect to the free base. Attempts to produce the salicylic acid cocrystal Form P1C9 from slow cooling and evaporation experiments were unsuccessful, even in a small scale. Preliminary smaller scale attempts to produce Form P1C9 from sonication resulted in the formation of Form P1C9 in some instances, however some of these experiments also produced a new potential cocrystal Form P2C9. Further $^1$H-NMR and thermal characterization of this new Form P2C9 indicated that the material was potentially an acetonitrile cocrystal solvate, so no further scale up was attempted. Attempts to produce Form P1C9 on a 500 mg scale from sonication experiments only produced the free base Form 1. Further characterization on the available Form P1C9 indicated that the material is likely to be a 1:0.5:4 Compound 1:salicylic acid: water cocrystal hydrate.

Example 9

Solid Form Characterization

X-Ray Powder Diffraction (XRPD)

Bruker AXS C2 GADDS: X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample was exposed to the X-ray beam for 120 seconds. The software used for data collection was GADDS for XP/2000 4.1.43 and the data were analyzed and presented using Diffrac Plus EVA v15.0.0.0. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 10° C./min and subsequently held isothermally for 1 minute before data collection was initiated.

Bruker AXS D8 Advance:

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v15.0.0.0.

Single Crystal X-Ray Diffraction (SCXRD)

Data were collected on an Oxford Diffraction Supernova Dual Source, Cu at Zero, Atlas CCD diffractometer equipped with an Oxford Cryosystems Cobra cooling device. The data was collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Nuclear Magnetic Resonance (NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2012.

Differential Scanning Calorimetry (DSC)

TA Instruments Q2000: DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 375° C. A purge of dry nitrogen at 50 ml/min was maintained over the sample. Modulated temperature DSC was carried out using an underlying heating rate of 2° C./min and temperature modulation parameters of ±0.64° C. (amplitude) every 60 seconds (period). The instrument control software was Advantage for Q Series v2.8.0.394 and Thermal Advantage v5.5.3 and the data were analyzed using Universal Analysis v4.5A.

Mettler DSC 823e: DSC data were collected on a Mettler DSC 823E equipped with a 34 position auto-sampler. The instrument was calibrated for energy and temperature using certified indium. Typically 0.5-3 mg of each sample, in a pin-holed aluminium pan, was heated at 10° C./min from 25° C. to 375° C. A nitrogen purge at 50 ml/min was maintained over the sample. The instrument control and data analysis software was STARe v12.1.

Thermo-Gravimetric Analysis (TGA)

TA Instruments Q500: TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminium DSC pan and heated at 10° C./min from ambient temperature to 450° C. A nitrogen purge at 60 ml/min was maintained over the sample. The instrument control software was Advantage for Q Series v2.5.0.256 and Thermal Advantage v5.5.3 and the data were analyzed using Universal Analysis v4.5A.

Mettler TGA/SDTA 851e:

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 10° C./min from ambient temperature to 450° C. A nitrogen purge at 50 ml/min was maintained over the sample. The instrument control and data analysis software was STARe v12.1.

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

Gravimetric Vapour Sorption (GVS)

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

Example 10

Micronized Compound 1 Form 1

Micronized Compound 1 Form 1 was prepared using a Fluid Energy Jet-O-Mizer 00 Jet Mill with a 2" loop. Approximately 9 g of Compound 1 Form 1 was passed through the jet-mill twice with parameters outlined below.

| Supply Air Pressure (psi) | Grinding Nozzle Pressure (psi) | Pusher Nozzle Pressure (psi) | Feeder Speed |
|---|---|---|---|
| 114 | 90 | 80 | 3 |

Approximately 7.3 g of micronized Compound 1 Form 1 was collected (81% yield). The particle size distribution after each pass is measured by the wet dispersion method (using water as dispersant) on a Malvern Mastersizer 2000 and the results are provided in the table below.

| Sample | Particle Size (μm) | | |
|---|---|---|---|
| | $D_{10}$ | $D_{50}$ | $D_{90}$ |
| Unmilled* | 2.7 | 12.0 | 40.0 |
| 1$^{st}$ Pass | 0.3 | 2.1 | 6.4 |
| 2$^{nd}$ Pass | 0.2 | 1.4 | 5.3 |

Example 11

Synthesis and Recrystallization of Compound 1

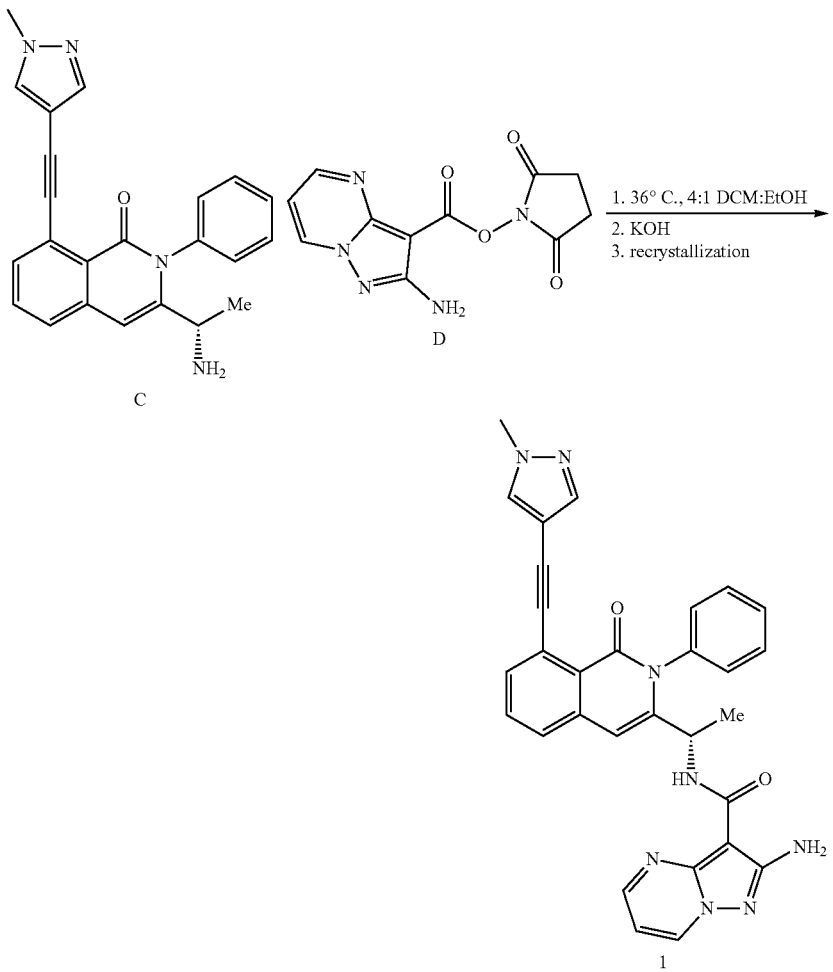

In a 50 L jacketed reactor equipped with an overhead stirrer, thermocouple and condenser was placed Compound C (1000 g, 2714 mmol) and Compound D (747 g, 2714 mmol) in 28.7 L (28.7 vol relative to Compound C, 20 vol relative to the product Compound 1) 4:1 DCM:EtOH. The suspension was stirred 36° C. for 21 h and the reaction conversion was monitored by HPLC.

After the reaction was stopped, 1M KOH (152 g, 2714 mmol) in EtOH was charged to the reaction. The mixture was stirred at 36° C. for 2 h, and then the temperature was adjusted to 20° C. over 1 h. 7.2 L DI water was charged and stirred for 15 min. The phases were allowed to separate. The bottom organic layer was drained to 3 carboys. The aqueous layer was drained and saved. The reactor was cleaned with DI water and EtOH. The organic layer and another 7.2 L DI water were charged back to the reactor. The carboys were rinsed with 3.6 L 4:1 DCM:EtOH (2.5 vol relative to product Compound 1) and the rinse was combined with the rest of the organic phase. The mixture was stirred for 15 min. The bottom organic layer was drained to the carboys and kept overnight at rt. The aqueous layer was drained and saved. The reactor was disassembled completely and cleaned with acetone, DI water and EtOH and purged overnight with nitrogen.

The distillation setup was assembled onto the reactor. The organic layer was pumped through a capsule filter (polycap, PTFE, 1 μm, cat#2603T) back into the clean reactor using a pump (KNF lab liquiport). The flask was rinsed with 3.6 L 4:1 DCM:EtOH (2.5 vol relative to product Compound 1) and the rinse was pumped through the capsule filter to be combined with the rest of the organic layer.

Distillation was started with stirring (controller set to 30). Jacket temperature was to 45° C. during the distillation. Pot temperature was about 23-27° C. during the distillation. Highest vacuum was about 400 torr. The volume of solution was reduced to about 14.4 L (10 vol). The solution remained clear at the end of the distillation. Some solid formed on the wall of the reactor above the solution. The solution was stirred (controller set at 20) overnight. Jacket temperature was set to 25° C.

28.8 L (20 vol) EtOH was charged. The distillation was restarted. Jacket temperature was set to 55° C. Pot temperature was about 44-47° C. Highest vacuum was about 250 torr. The volume of solution was reduced to about 1.5 L (15 vol). Solid formed during the distillation.

A mixture of 750 ml (7.5 vol) EtOH and 750 ml (7.5 vol) DI water was charged to the suspension. The internal temperature was adjusted to 60° C. The solids redissolved as the temperature increased. No solid was left when temperature reached 60° C. 1 g of Compound 1 (1 wt %) was charged as seed. Not all the seeds dissolved. The mixture was stirred at 60° C. for a total of 6 h, cooled to 20° C. over 10 h, and then stirred at 20° C. for 6 h. The solid was collected by filtration through a Buchner funnel equipped with a filter paper. The filter cake was washed with 2×500 ml 1:4 EtOH:water (2×5 vol). The solid was dried in the Buchner funnel with house vac for 2 d. The cake was then dried in a vacuum oven at 40° C. with a nitrogen bleed overnight for 18 h. The product Compound 1 was isolated as an off white solid. HPLC (~0.3 mg/ml in 1:1 acetonitrile:water), NMR and DSC of the isolated solid was obtained. The DSC indicates the solid is Form 1. NMR indicates very low level of residual EtOH is present in the solid.

Compared to Method 3 of Example 1, comparable chemical and chiral purity were obtained. Reaction was telescoped to polish filtration and recrystallization. Isolation of crude Compound 1 was eliminated. Less number of solvents were used. The process was slower, and the product contained residual ethanol.

In order to reduce the residual ethanol content in the product, various modifications to the recrystallization conditions were investigated. The results are listed in the table below.

| Conditions | Purity (area %) | DCM content (GC) | Ethanol content (GC) | Ethanol content (NMR mole ratio) | Yield (%) |
|---|---|---|---|---|---|
| Chase with EtOH | 99.5 | 445 ppm | 10590 ppm | 0.10 | 90 |
| Chase with 80% EtOH/H$_2$O | 99.6 | — | — | 0.06 | 80 |
| Chase with 60% EtOH/H$_2$O | 99.6 | ND | 9623 ppm | 0.07 | 82 |
| Chase with 40% EtOH/H$_2$O | 99.5 | 252 ppm | 25315 ppm | 0.18 | 85 |
| Chase with 80% EtOH/H$_2$O | 98.6* | ND | 6926 ppm | 0.05 | 77 |
| Chase with EtOH to 15 vol, add 5 vol H$_2$O, then seed | 99.6 | 196 ppm | 6981 ppm | 0.05 | 80 |
| Chase with EtOH to 15 vol, add 5 vol H$_2$O, then seed, 4 heat/cool cycles (3 h at 60° C., cool to rt in 2 h) | 99.6** | — | — | 0.03 | 75 |
| Chase with EtOH to 15 vol, add 5 vol H$_2$O, then seed, 3 heat/cool cycles (3 h at 50° C., cool to rt in 2 h) | 99.8 | — | — | 0.05 | 78 |
| Chase with EtOH to 15 vol, add 5 vol H$_2$O, then seed, 2x final volume | 99.8 | — | — | 0.03 | 72 |

Figure 29:
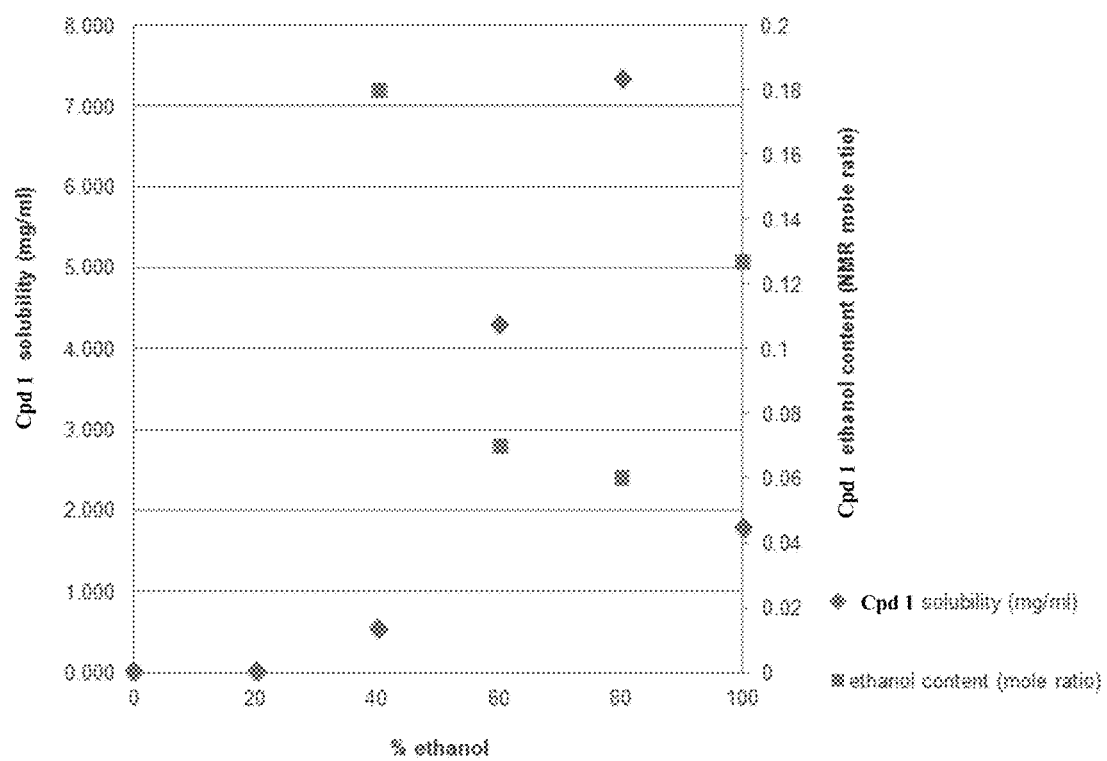
FIG. 29 shows Compound 1 solubility in ethanol/water and corresponding ethanol content in isolated Compound 1.

*containing Compound D. Compound D can be removed by quenching with KOH in ethanol.
**containing 0.11% area of impurity FIG. 29 shows Compound 1 solubility in ethanol/water and corresponding ethanol content in isolated Compound 1. The results show that using solvent mixture with higher Compound 1 solubility during chase results lower residual ethanol content in isolated Compound 1. Prolonged drying did not affect residual ethanol content (data not shown).

Figure 30:
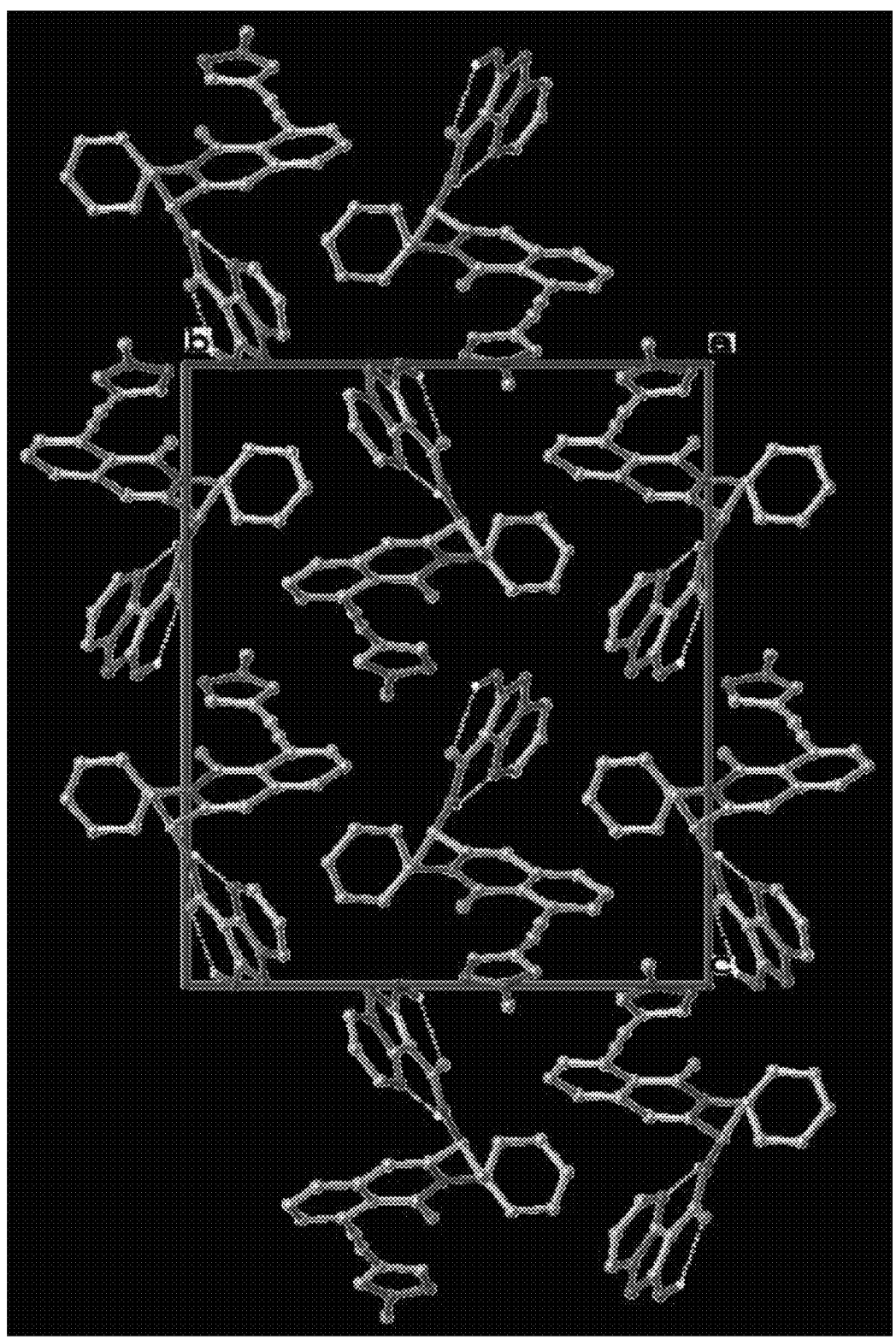
FIG. 30 is a representative crystal structure of Form 1 of Compound 1 obtained by heating 13.5 mg/ml Compound 1 in 80% ethanol/water to 60° C. then cool to room temperature.

A crystal structure of Form 1 was collected and solved. FIG. 30 shows the crystal structure of Form 1 of Compound 1 obtained by heating 13.5 mg/ml Compound 1 in 80% ethanol/water to 60° C. then cool to rt. There is no ethanol in unit cell. A summary of structural data for Compound 1

Form 1 is provided in the table below. Form 1 crystallizes in the orthorhombic system, space group $P2_12_12_1$.

| Parameter | Value |
| --- | --- |
| Formula | $C_{25}H_{31}NO_6$ |
| $D_{calc}/g\ cm^{-3}$ | 1.279 |
| $\mu/mm^{-1}$ | 0.744 |
| Formula Weight | 441.51 |
| Color | colorless |
| Shape | chunk |
| Max Size/mm | 0.30 |
| Mid Size/mm | 0.15 |
| Min Size/mm | 0.15 |
| T/K | 173(2) |
| Crystal System | orthorhombic |
| Flack Parameter | −0.03(8) |
| Hooft Parameter | 0.01(8) |
| Space Group | P212121 |
| a/Å | 11.14000(10) |
| b/Å | 12.75790(10) |
| c/Å | 16.1306(2) |
| $\alpha/°$ | 90 |
| $\beta/°$ | 90 |
| $\gamma/°$ | 90 |
| V/Å³ | 2292.53(4) |
| Z | 4 |
| Z' | 1 |
| $\Theta_{min}/°$ | 4.418 |
| $\Theta_{max}/°$ | 72.157 |
| Measured Refl. | 14293 |
| Independent Refl. | 4454 |
| Reflections Used | 4179 |
| $R_{int}$ | 0.0301 |
| Parameters | 294 |
| Restraints | 0 |
| Largest Peak | 0.172 |
| Deepest Hole | −0.237 |
| GooF | 1.041 |
| $wR_2$ (all data) | 0.0928 |
| $wR_2$ | 0.0904 |
| $R_1$ (all data) | 0.0393 |
| $R_1$ | 0.0364 |

Example 12

Screening Reaction Conditions for Preparation of Compound A by Amide Coupling of Compound C and Compound G

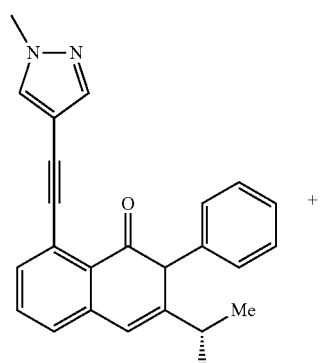

C

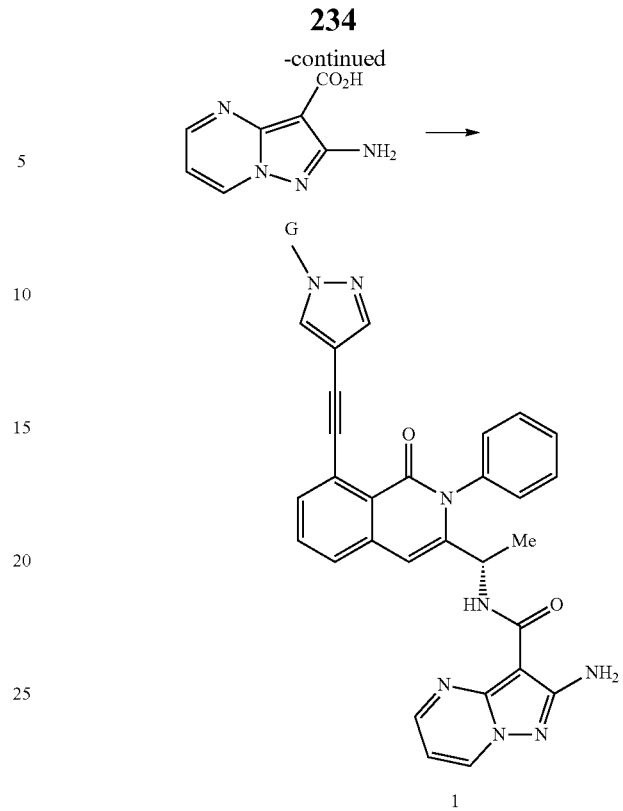

Different coupling reagents were investigated for the preparation of Compound 1 through direct amide coupling of Compound C and Compound G. These reagents include: DECP, HDMA, HBTU, COMU, PyBOP, HATU, DEPC, DPPA, and BOPC1.

EDCI coupling reactions with various activators were also investigated using the following condition: EDCI (1.15 eq), $Et_3N$ (1.1 eq), 4:1 $MeCN/H_2O$ (20 vol), 21° C. The results are listed in the Table below.

| EDCI + Activator | Activator Equiv | HPLC purity (time) |
| --- | --- | --- |
| HOBt | 1.1 | 94% (16 h) |
| HOBt | 0.2 | 74% (91 h) |
| HBTriazinone | 1.1 | 75% |
| Oxyma | 1.1 | 58% |
| Oxyma | 1.5 | 56% |
| Oxyma | 1.1 | 35% |
| NHS | 1.1 | 33% |
| Oxyma | 2.0 | 31% |
| No activator | 0 | 20% |
| K-Oxyma | 1.1 | 16% |

The following phosphorus-based coupling reagents were also investigated: DEPBT (59.5% IPC purity after 51 hours), BrOP (30.4% IPC purity after 51 hours), $(EtO)_2P(O)$—Cl (3-10% IPC purity), $(EtO)_2P(O)$-Oxyma (62.2% IPC purity, 96% purity after isolation), and T3P (72.0% IPC purity after 48 hours, base: pyridine, Temp: 40° C., solvent: MeCN (20 vol)). A scale up run was carried out with T3P (3.0 eq.) and pyridine (5.1 eq.) at 40° C. for 2 days (63.8% IPC purity).

The following mixed anhydride coupling reagents were also investigated: pivaloyl chloride (15.8% IPC purity), and iso-butyl chloroformate (34.9% IPC purity in MeCN, 14.0% IPC purity in 4:1 $MeCN:H_2O$).

The following triazine-based coupling reagents were also investigated: CDMT and DMTMM.

An example reaction of DMTMM coupling was carried out as the follows. To 1.15 eq DMTMM, 1.1 eq $Et_3N$ (or DIPEA), 1.05 eq Compound G was charged 4:1 MeCN:$H_2O$. The reaction mixture was stirred and activated overnight. 1.0 eq Compound C was then added in one bolus as a solid. The reaction gave 84% HPLC purity after 21 hours.

The reaction mixture was warmed to 40° C. Water (10.5 vol) was added over 2 h. The mixture was cooled to 21° C. over 2 h, then filtered, rinsed with 2:1 $H_2O$:MeCN (2×5 vol), and dried to provide granule product. Crude yield (79.6-84.4%), purity (97.2-97.5%).

The crude product was further purified by polish filtration in 4:1 DCM:EtOH, followed up recrystallization from 3:1 EtOH:$H_2O$ (30 vol). Overall yield (56-62%), final purity (99.5-99.6%).

Further screenings for DMTMM coupling conditions were also carried out for solvent (3:1 EtOH:$H_2O$, 14.4:4.8:1 EtOH:$H_2O$:DCM, 4:1 acetone:$H_2O$, 4:1 DCM/MeOH, 4:1 DCM/EtOH, and 100% DCM); reaction volumes (5, 7.5, 10, 15, and 20); reaction temperature (5, 20, and 40° C.); base ($Et_3N$, $iPr_2NEt$, pyridine, NMM, DBU, NaOH, and DMAP); base equivalents (3.0, 1.1, and 0.2); DMTMM equivalents (1.15, 1.10, 1.05, and 1.00); Compound C addition (as a solid one bolus, and in solution over time); and addition of water after reaction reaches completion.

Example 13

Controlled Crystallization and Recrystallization of Compound 1

Controlled crystallization and recrystallization of Compound 1 from a solvent of a mixture of acetonitrile and water were studied.

Controlled Crystallization Procedure

A reaction mixture was produced following Method 3 of Example 1 (after quench of the reaction), consisting of Compound 1 at ~124 mg/ml concentration (~8.06 L/kg volume), in a 90/10 v/v acetonitrile/water mixture.

An appropriate amount of acetonitrile/water were added to bring the solution to 80/20 v/v acetonitrile/water at 20 L/kg of Compound 1. The slurry was agitated and heated to 75° C. until all the Compound 1 was dissolved. The clear solution was polished filtered with a Zapcap filter (0.45 µm). The solution was put back into the reactor and cool down to 65° C. Form 1 of Compound 1 was used to seed with 10 wt % of the estimated amount of Compound 1 in the slurry (check that the seeds did not dissolve). The mixture was cooled down to 22° C. over 16 hours (solubility was brought from ~50 mg/ml to ~18 mg/ml at a rate of 2 mg/ml/hr) with agitation, and held under agitation for 2 hours after completion of cooling step.

20 L/kg of water was added to bring the solution to 40/60 v/v acetonitrile/water (total volume of 40 L/kg of Compound 1) over 4 hours (solubility is brought from ~18 mg/ml to ~3 mg/ml) with a syringe pump. The mixture was held under agitation at 22° C. for 2 hrs after the end of water addition.

The slurry was filtered with a Buchner funnel, the cake was washed twice with a 40/60 v/v acetonitrile/water mixture. The Buchner funnel was placed into oven at 60° C. under vacuum with nitrogen bleed to dry residual solvents and provide Form 1 of Compound 1. In one exemplary run, the yield was 75%, and the purity was 99.7 area %.

The controlled crystallization procedure was also carried out on a reaction mixture produced following the DMTMM coupling in Example 12. In one exemplary run, the yield was about 90%, and the purity was 97.6 area %.

Controlled Recrystallization Procedure

Compound 1 was synthesized following Method 3 of Example 1 (after isolation from acetonitrile/water).

20 L/kg of 80/20 v/v acetonitrile/water was added to Compound 1 solid charged into a reactor. The slurry was agitated and heated to 75° C. until all Compound 1 was dissolved. The clear solution was polish filtered with a Zapcap filter (0.45 µm). The solution was put back into the reactor and cooled down to 65° C. Form 1 of Compound 1 was used to seed with 10 wt % of the estimated amount of Compound 1 in the slurry (check that the seeds did not dissolve). The mixture was cooled down to 22° C. over 16 hours (solubility was brought from ~50 mg/ml to ~18 mg/ml at a rate of 2 mg/ml/hr) with agitation, and held under agitation for 2 hours after completion of cooling step.

20 L/kg of water was added to bring the solution to 40/60 v/v acetonitrile/water (total volume of 40 L/kg of Compound 1) over 4 hrs (solubility was brought from ~18 mg/ml to ~3 mg/ml) with a syringe pump. The mixture was held under agitation at 22° C. for 2 hrs after the end of water addition.

The slurry was filtered with a Buchner funnel. The cake was washed twice with a 40/60 v/v acetonitrile/water mixture. The Buchner funnel was placed into oven at 60° C. under vacuum with nitrogen bleed to dry residual solvents and provide Form 1 of Compound 1. In one exemplary run, the purity was 99.7 area %.

The controlled crystallization procedure was also carried out on a reaction mixture produced following the DMTMM coupling in Example 12. In one exemplary run, the yield was about 75%, and the purity was 99.4 area %.

Example 14

Preparation of Amorphous Compound 1

Amorphous compound 1 can be prepared by dissolving a crystalline solid or a mixture of crystalline solids and amorphous sample in one or more solvents and preforming lyophilisation on the solution. Amorphous compound 1 can also be prepared by preforming lyophilisation on a solution of the material obtained after purification through column chromatography. Other methods of preparing amorphous compound include spray drying.

Examples of spray solutions are described below with their respective compositions:

| Component | Spray Solution #1 (100% Compound 1) | Spray Solution #2 (2:1 Compound 1:PVP/VA 64) | Spray Solution #3 (2:1 Compound 1:HPMC-AS) |
|---|---|---|---|
| Compound 1 | 8.14 g | 6.33 g | 6.33 g |
| Polymer | — | 3.15 g | 3.15 g |
| DCM | 48 mL (63.84 g) | 56 mL (74.48 g) | 56 mL (74.48 g) |
| MeOH | 12 mL (9.50 g) | 14 mL (11.09 g) | 14 mL (11.09 g) |
| % Solids Content (w/w) | 10% | 10% | 10% |

The DCM and MeOH were added to a glass jar and mixed. If needed, the polymer was added to the solvent matrix while stirring and the solution was allowed to stir until all solids dissolved. Compound 1 was then added to the solution while stirring. All three spray solutions were mixed for an hour prior to spray drying. Spray drying was done using the Buchi B-290 mini lab-scale spray dryer and the spray parameters are provided below:

| Aspirator Rate (%) | Inlet Temp (° C.) | Outlet Temp. (° C.) | Nozzle Pressure (psi) | Pump Speed (%) | Spray Rate (g/min)* |
|---|---|---|---|---|---|
| 100 | 95 | 63-65 | 30 | 20 | 10 |

*pump was calibrated using 80:20 DCM:MeOH and might not be representative of the spray rate of the spray solutions with polymer due to the difference in viscosity The spray dried products were dried in a vacuum oven at 25° C. for ~22 hours. The post-drying products were analyzed on TGA and DSC and the results are provided in the table below.

Thermograms for Compound 1 Spray Dried SDDs-t=0

Figure 31:
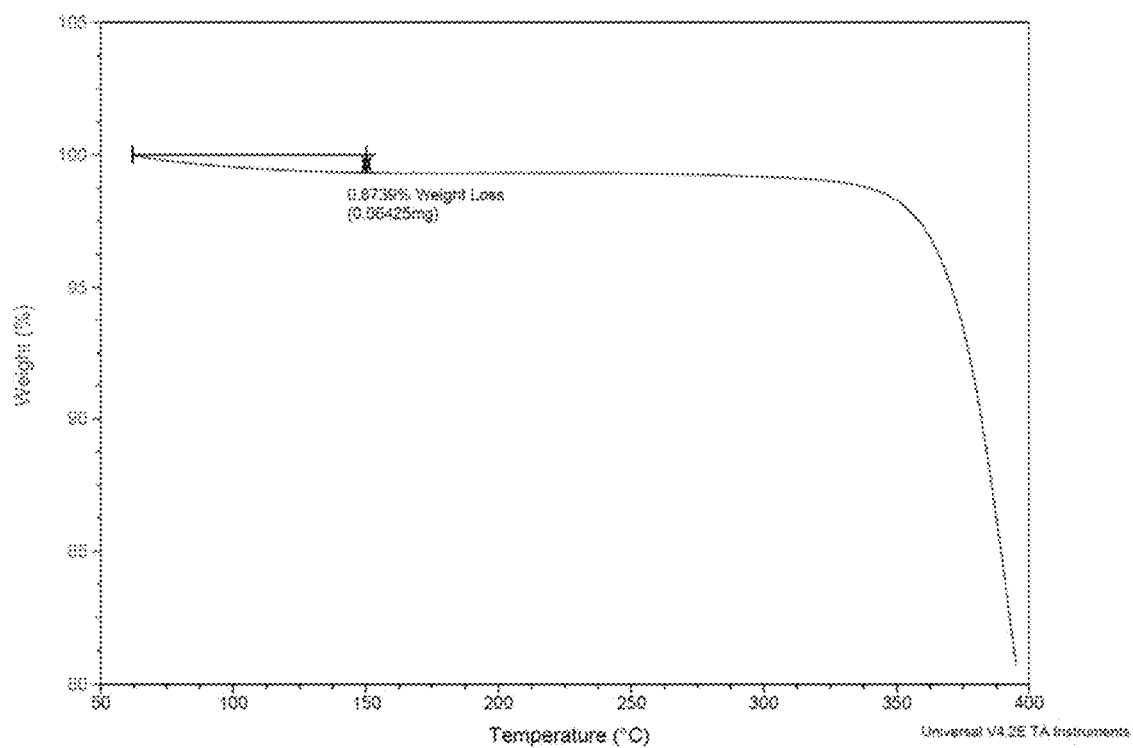
FIG. 31 is a representative TGA analysis of spray dried Compound 1.
Figure 32:
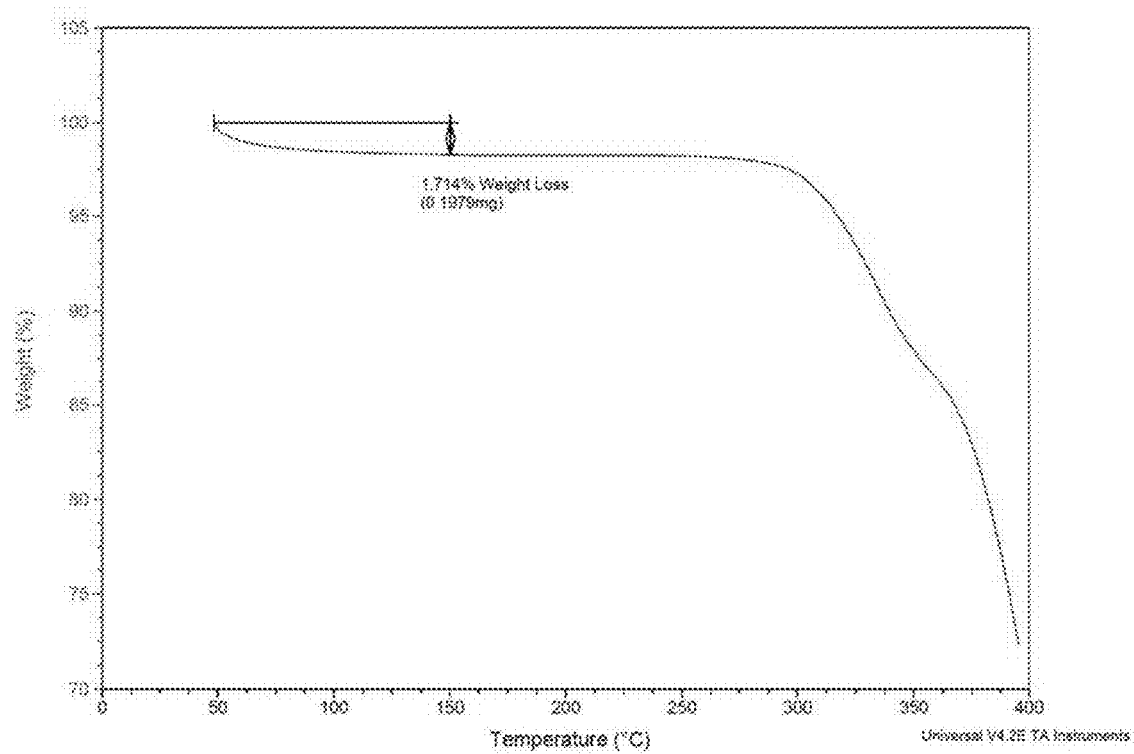
FIG. 32 is a representative TGA analysis of spray dried Compound 1 and PVP/VA 64.
Figure 33:
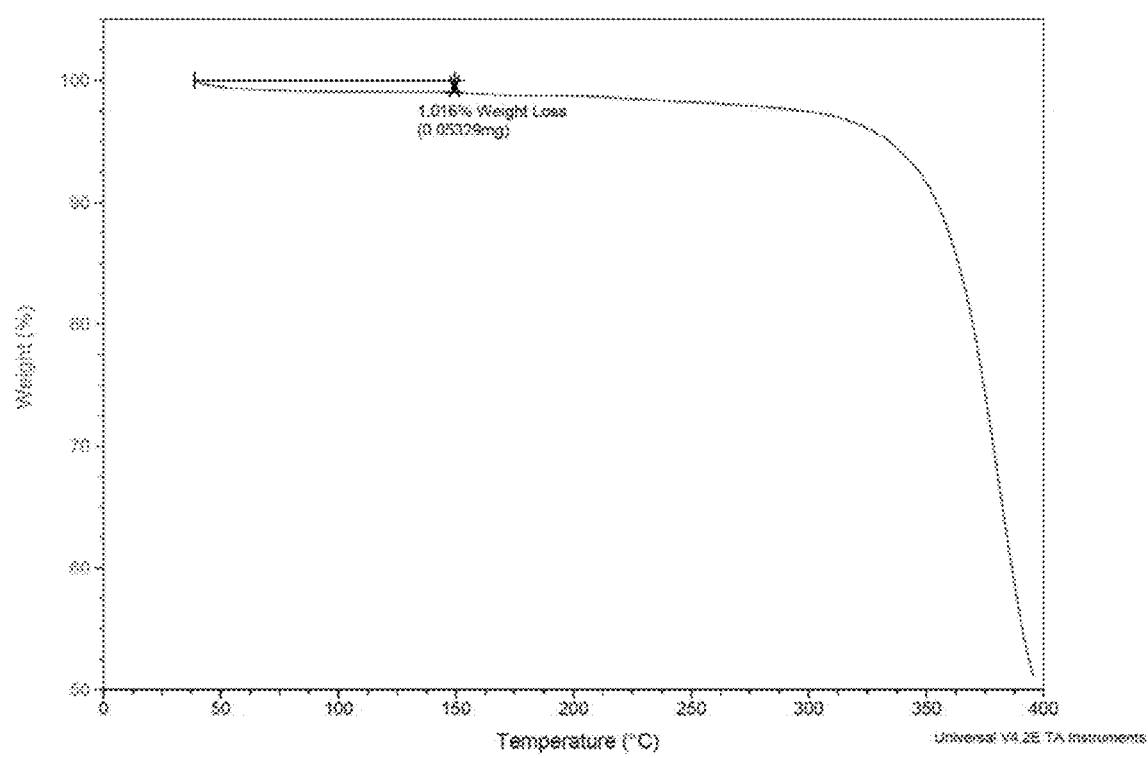

| Sample | TGA | Comments |
|---|---|---|
| Spray Dried Compound 1 | FIG. 31 | Expected $T_g$: 147° C. Observed $T_g$: 146° C. |
| 2:1 Compound 1:PVP/VA 64 | FIG. 32 | Predicted $T_g$: 132° C. Observed $T_g$: 136° C. |
| 2:1 Compound 1:HPMC-AS | FIG. 33 | Predicted $T_g$: 143° C. Observed $T_g$: 133° C. |

Example 15

Formulation of Compound 1

Compound 1 was spray dried according to the methods described herein. The sample was blended with excipients, which was then encapsulated, polished and packaged. Below is a table of the formulation for 5 mg capsule and 30 mg capsule.

| | 5 mg capsule | | 30 mg capsule | |
|---|---|---|---|---|
| Component | % w/w | mg | % w/w | mg |
| Compound 1 spray dried (Neat Amorphous API) | 1.92% | 5.00 | 9.38% | 30.00 |
| Starch 1500 (Pre-gelatinized Starch) | 46.29% | 120.35 | 42.56% | 136.20 |
| Parteck M100 (Mannitol) | 46.29% | 120.35 | 42.56% | 136.20 |
| Ac-Di-Sol (Croscarmellose Sodium) | 5.00% | 13.00 | 5.00% | 16.00 |
| Magnesium Stearate | 0.50% | 1.30 | 0.50% | 1.60 |
| TOTAL | 100% | 260.00 | 100% | 320.00 |
| HPMC Capsule Shell | Size 2, Swedish Orange | | Size 1, White | |

Example 16

Screening Reaction Conditions for Preparation of Compound C

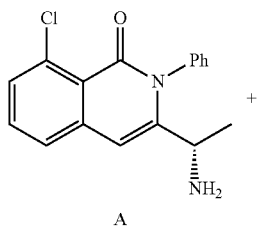

A

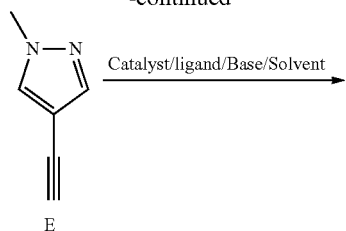

E

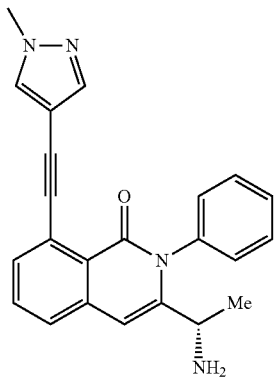

C

Metal and Pd Source Screen

Different metal sources with XPhos and alternative bases were investigated. Pd catalysts generally work better than Ni catalyst (NiCl$_2$(PPh$_3$)$_2$). Cu catalyst (CuI) was also explored as a co-catalyst to the Pd catalyst or Ni catalyst.

Xphos-Pd-G3 and Pd$_2$(dba)$_3$/Xphos (1:1 L:M) worked as well as control reaction but without observed delay. Pd$_2$(dba)$_3$: Xphos (1:1 L:M) worked well with K$_2$CO$_3$ and K$_3$PO$_4$. PdCl$_2$(MeCN)$_2$: XPhos (2:1 L:M) worked well with K$_2$CO$_3$ and K$_3$PO$_4$. Pd(OAc)$_2$: XPhos worked better with 2:1 L:M ratio than 1:1 ratio. Pd(PPh$_3$)$_4$ and PdCl$_2$(PPh$_3$)$_2$ also worked. The relative rates of reaction (from fast to slow) are: Pd(OAc)$_2$>Pd$_2$(dba)$_3$>PdCl$_2$(CH$_3$CN)$_2$. Pd(OAc)$_2$ and Pd$_2$(dba)$_3$ achieved near 100% conversion at 5 hours. PdCl$_2$(CH$_3$CN)$_2$ achieved >80% conversion at 5 hours and near 100% conversion at 24 hours. Pd$_2$(dba)$_3$ (1 mol %) achieved >60% conversion at 24 hours.

The stabilities of the alkyne starting material and the product were also investigated under reaction conditions. The product appeared stable when PdCl$_2$(MeCN)$_2$, Pd$_2$(dba)$_3$, or Pd(OAc)$_2$ were used as the catalyst. The alkyne starting material appeared stable when PdCl$_2$(MeCN)$_2$, or Pd$_2$(dba)$_3$ were used as the catalyst, while degradation of the alkyne starting material was observed when Pd(OAc)$_2$ was used.

Base Screen

The effect of the base was studied using K$_2$CO$_3$, K$_3$PO$_4$ and DIPEA with two different metal sources PdCl$_2$(MeCN)$_2$ and Pd$_2$(dba)$_3$. All experiments were conducted at 70° C. using acetonitrile as the solvent. The experiments using K$_2$CO$_3$ and K$_3$PO$_4$ as the base showed faster and better conversions than DIPEA.

Ligand Screen

Various ligands were screened using the following reaction conditions: Pd(OAc)$_2$ 5 mol %, 2:1 L:M ratio for monodentate ligands and 1:1 L:M ratio for bidentate ligands, 1.2 eq. alkyne, 1.2 eq K$_2$CO$_3$, MeCN (30 rv), 70° C. XPhos was used as control reaction. The results are listed in the Table below. The ligands MePhos and cBRIDP were also tested. cBRIDP provided the highest conversion other than the XPhos control.

| Phosphine Ligand | Conversion (21 h) | Phosphine Ligand | Conversion (21 h) | BisPhosphine Ligand | Conversion (21 h) |
|---|---|---|---|---|---|
| PCy$_3$ | 50.5 | DavePhos | 80.7 | dppp | 30.5 |
| PCy$_2$Ph | 39.4 | $^t$Bu Triplecage | 4.9 | dppe | 23.1 |
| P$^i$Pr$_3$ | 20.8 | P$^t$Bu$_2$Cy | 2.5 | dppb | 43.5 |
| PCy$_2$$^t$Bu | 55.9 | P$^t$Bu$_3$ | 61.8 | BINAP | 52.5 |
| CataCXium A | 72.5 | CataCXium PICy | 87.9 | DPEPhos | 65.6 |
| P(MeOC$_6$H$_4$)$_3$ | 53.2 | P$^t$Bu$_2$(PhNMe$_2$) | 52.0 | dppf | 67.0 |
| PPh$_2$(C$_6$H$_4$CO$_2$H) | 10.3 | PPh$_3$ | 41.3 | dbpf | 80.8 |
| PPh$_2$(C$_6$H$_4$SO$_3$H) | 24.2 | No ligand | 0 | XantPhos | 58.4 |
| SPhos | 65.6 | Control reaction | 100 | N—$^t$Bu$_2$P azetine | 65.9 |
| JohnPhos | 89.2 | | | | |

Solvent Screen

Five water immiscible solvents were screened using the following reaction conditions: Pd$_2$(dba)$_3$ 5 mol %, 2:1 L:M ratio for monodentate ligands and 1:1 L:M ratio for bidentate ligands, 1.5 eq. alkyne, 1.2 eq. K$_2$CO$_3$, solvent (30 rv), 70° C. The results showed that all screened solvents worked, and the relative rates of reaction are (from fast to slow): MeCN (control)>$^i$PrOAc>2-MeTHF>EtCN, MEK>>toluene. All screened solvents (except toluene) achieved >90% conversion at 5 hours and the performances were close to MeCN control. Toluene achieved >90% conversion at 24 hours. Water immiscible solvents may be advantageous in work up to remove Pd residues.

Further studies were carried out to screen for the overall reaction conditions. Three ligands (XPhos, cBRIDP, and CataCXiumPICy), two bases (K$_3$PO$_4$ and K$_2$CO$_3$), three solvents (MeCN, 2-Me-THF, and toluene), Pd$_2$(dba)$_3$ as Pd source with Pd load from 1 to 5 mol % were studied. Based on the results, the condition of Pd$_2$(dba)$_3$ (1 mol %), XPhos (2 mol %), K$_3$PO$_4$ as the base in MeCN was selected for further studies.

Example 17

Scale Up of Compound C

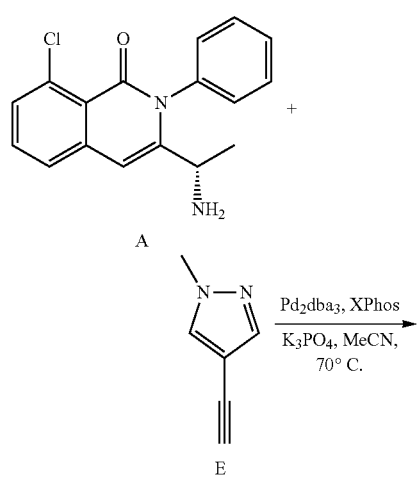

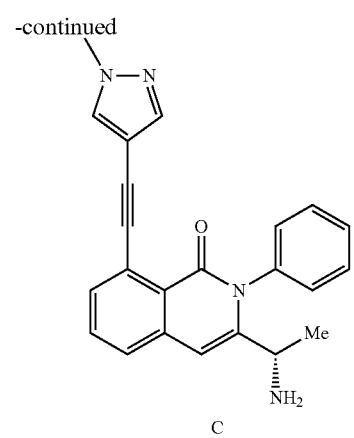

-continued

C

A 1 L jacketed reaction vessel, equipped with an overhead stirrer, temperature probe, condenser and stirrer was purged with nitrogen for a minimum of 1 hour. Potassium phosphate tribasic (1.2 equ, 42.65 g), 4-ethynyl-1-methyl-1H-pyrazole (1.2 equ, 21.34 g) and Compound A (1 wt, 1 equ. 50.05 g) were charged to the reaction vessel. Acetonitrile (14 volumes, 700 mL) was charged to the reaction vessel. A small amount was used to rinse out the bottles used for solid charging. Agitation was started. Agitation was set at 470 rpm, as found to be sufficient to suspend all the solids. Reaction mixture was heated to 40±2° C. (internal temperature).

To a second vessel (100 ml round bottom flask) was charged, in a nitrogen inerted glovebox, tris(dibenzylideneacetone)dipalladium(0) (0.01 equ. 1.533 g), 2-dicyclohexylphosphino-2',4',6'-triisopropylbiphenyl (XPhos) (0.02 equ. 1.595 g) and acetonitrile (1 volume, 50 mL). Catalyst/ligand solution was stirred at 40° C. for 40 mins.

The first reaction vessel was purged with nitrogen for a further 30 minutes before catalyst solution was transferred to the reaction vessel. The catalyst solution was transferred using a needle and syringe to minimise air/moisture exposure. Reaction mixture was heated to 70° C. (internal temperature). Reaction was monitored by HPLC. Reaction was complete when sampled at 20.5 hours. Heat was turned off and the reaction mixture was allowed to cool to 25° C. for 2.5 hours.

The suspension was filtered using a glass sinter funnel and the residue was washed with acetonitrile (1×2 volumes, 100 mL). The wash was combined with the filtrate (product layer). The filtrate (product layer) was transferred back into the reaction vessel. Reaction vessel was placed under a nitrogen purge. 2-Mercaptoethyl ethyl sulfide Silica [PhosphonicS SEM26] (50 wt % wrt Compound A, 25 g) was charged to the vessel. Scavenger was stirred for 6 hours at 28° C. Scavenger was filtered off and washed with acetonitrile (1×2 volumes, 100 mL). The wash was combined with the filtrate (product layer). Solution was transferred to a clean distillation vessel. Reaction volume was reduced to 5 volumes at atmospheric pressure (jacket temperature of 95-100° C.). Vessel was cooled to 50° C. (internal temperature) over 75 minutes. MTBE was added slowly (50 mL aliquots) keeping the batch temperature above 45° C. MTBE addition was held for 15 minutes once crystallization began. Remaining MTBE added slowly until total of 15 volumes (750 mL) added. Held for 1 hour. Reaction mixture was cooled back to 25° C. over 2 hours and held overnight. Additional MTBE 5 volumes (250 mL) added over 5 minutes. Held for 1 hour. Product was filtered off and washed with acetonitrile (2×2 volumes, 2×100 mL). The wash was combined with the mother liquors. Solid was deliquored under vacuum for 15 minutes. Solid was transferred to crystallization dish and placed in a vacuum oven and dried at 40° C. under vacuum, with an air bleed for 40 hours. Recovered solid=52.88 g, Yield=85.8%.

Example 18

Preparation of Compound E

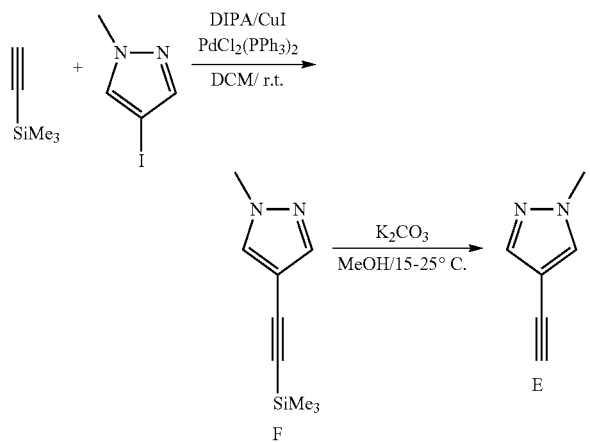

Step 1: i) DIPA (1.3 equ.)/CuI (0.02 equ.)/PdCl$_2$(PPh$_3$)$_2$ (0.01 equ.)/TMSacetylene (1.2 equ.)/CH$_2$Cl$_2$ (10 vol)/r.t.–40° C./2 hrs; ii) Cool to r.t. and filter; iii) Wash with 2M HCl (1.3 equ.); iv) Treat SiliaMetS Diamine at r.t.; v) Fitler and reduce CH$_2$Cl$_2$ to 5 vol. under reduced pressure; vi) Solvent switch to Hexane (5 vol) under reduced pressure; vii) Cool to r.t.; and viii) Filter, wash and dry.

Step 2: Compound F was taken directly into step 2 (crude product); Dissolved in MeOH and treated with K$_2$CO$_3$ at r.t.; When the reaction was complete the base was filtered off; Solvent evaporated to dryness; Oil dissolved in MTBE and passed through a plug of Silica; Filtrate concentrated to dryness; Product isolated by vacuum distillation (2-3 times). Yield=68%.

Example 19

Screening Reaction Conditions for Preparation of Compound F

Step 1 of Example 18 used 0.01 eq. of PdCl$_2$(PPh$_3$)$_2$ and 0.02 eq. of CuI. 20 experiments were conducted to investigate whether the amount of catalysts can be reduced to avoid or reduce the scavenging needed to remove Palladium/color. The experiments were performed on 2 g scale, with 5 loadings of PdCl$_2$(PPh$_3$)$_2$ (0.001, 0.002, 0.004, 0.0055, and 0.01 eq.) and 4 loadings of CuI (0.001, 0.005, 0.0125, and 0.02 eq.). IPC of the reaction mixture at different time points: 4 min, 30 min, 1 hr, 2 hrs, 4 hrs, 6 hrs, 8 hrs and 24 hrs. Samples analyzed by HPLC to determine evolution of conversion and % area of SM and impurities (particularly the homocoupling diyne side-product

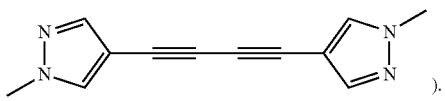).

FIG. 34A shows the reaction conversion at 2 hours (% area); FIG. 34B shows the reaction conversion at 24 hours (% area); FIG. 34C shows the product/diyne ratio (% area) at 24 hours; and FIG. 34D shows the diyne content at 24 hours (% area). The results show that the reaction conversion is affected by both Pd and Cu content, but the diyne formation is primarily affected by Pd content. Copper has a bigger impact when the Pd content is low. Reaction can reach completion with lower levels of Pd. Reducing the amount of Pd can reduce the formation of the diyne impurity. Based on the results, 0.003 eq. of Pd catalyst and 0.0175 eq. of CuI may be an optimal condition.

An exemplary study using 0.003 eq. of Pd catalyst and 0.0175 eq. of CuI was conducted as follows. 4-iodo-1-methylpyrazole (250 g, 1190 mmol), copper iodide (3.99 g, 20.82 mmol, 0.0175 eq.), and bis(triphenylphosphine)palladium(II) chloride (2.53 g, 3.57 mmol, 0.003 eq) were charged to a reactor at r.t under nitrogen. DIPA (219 mL, 1547 mmol) was charged to the reactor under nitrogen at 22° C. via syringe in a single portion. ACS grade DCM (2500 mL) was charged. The reactor was flushed with nitrogen for ≥5 minutes and the temperature was set to 15° C. Trimethylsilylacetylene (205 mL, 1428 mmol) was charged via syringe pump over 30 minutes (or 82 mL/hr or 1.4 ml/min) at 15° C. 10 mL of toluene was added in the flask at the end of the addition to rinse the vessel. The reaction was monitored by HPLC after 24 hours (reaction completed between 8-24 hours).

HCl (1785 mL, 3570 mmol) was charged at 15±3° C. and the mixture was stirred vigorously for ≥15 minutes. The mixture was then allowed to settle and the layers were separated over ≥10 minutes. The upper layer was clear yellow and the lower was clear orange. The layers were split, and the upper layer was discarded. 10 volumes (2500 mL) of 20% wt sodium thiosulfate was charged to the lower layer to scavenge palladium and copper. The mixture was stirred for overnight under nitrogen at r.t. The phases were allowed to separate over ≥10 minutes. The layers were separated.

The organic layer was transferred back into the cleaned reactor, and distilled down to 5 volumes (1250 mL). 5 volumes of hexanes (1250 mL) was added and distilled down to 5 volumes. 5 volumes of hexanes (1250 mL) was added again and distilled down to 5 volumes. Another 5 volumes of hexanes (1250 mL) was added and heated to reflux during 1 hour, and then cooled down to r.t. The mixture was filtered with a Whatman filter paper to remove the alkyne dimer side-product. The mother liquor the crystals formed in it were transferred back to a clean reactor. The solvent was distilled down to 5 volumes (1250 mL), cooled down to 24° C. over an hour, then cooled down to 0° C., and aged for an hour. The crystal product was filtered, washed with 2×1 volume of cold hexanes, dried, and collected.

Example 20

Screening Reaction Conditions for Preparation of Compound E

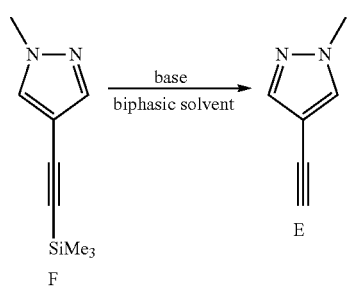

The deprotection of Compound F in biphasic solvent system (mixture of aqueous base solution and a water immiscible solvent) was investigated. The results are summarized in the table below. The experiments were performed on 100 mg scale. Using heat and a phase transfer catalyst did not improve the yield.

|  | MTBE | | | DCM | | | Ethyl Acetate | | |
| --- | --- | --- | --- | --- | --- | --- | --- | --- | --- |
|  | 2 hrs | 15 hrs | 24 hrs | 2 hrs | 15 hrs | 24 hrs | 2 hrs | 15 hrs | 24 hrs |
| KOH | 92% | 100% | X | 17.87% | 93.20% | 98.39% | 0% | 0% | 0% |
| NaOH | 6.90% | 67.90% | 85.28% | 4.28% | 18.90% | 26.70% | 0% | 0% | 0% |
| NaHCO$_3$ | 0% | 2.64% | 2.74% | 0.00% | 0% | 0% | 0% | 0% | 0% |
| K$_3$PO$_4$ | 5.78% | 96.46% | 100.00% | 5.21% | 37.79% | 54.62% | 3.81% | 4.22% | 4.96% |
| K$_2$CO$_3$ | 9.98% | 62.22% | 78.96% | 1.04% | 10.48% | 14.54% | 1.05% | 2.88% | 3.68% |

Example 21

Scale Up of Compound E

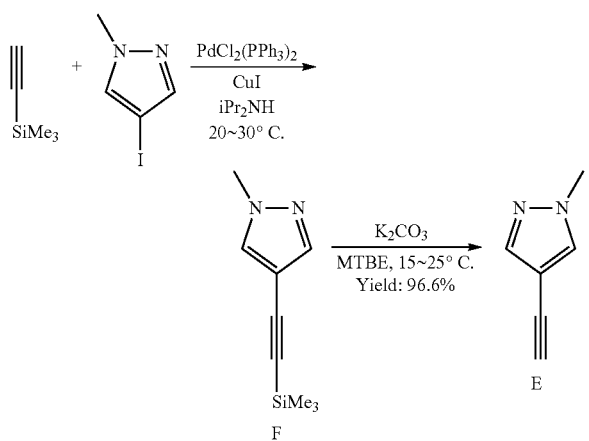

Step 1:

A clean and dry 500 L glass-lined reactor A was evacuated to −0.08−−0.05 MPa and filled with nitrogen to normal pressure. It was repeated for 3 times. The reactors were sampled for oxygen content to ensure it was ≤3%.

Diisopropylamine (106.0 kg) and 1-methyl-4-iodo-1H-pyrazole (24.3 kg, 23.6 kg corrected) were added to the reactor A at 15-25° C. Cuprous iodide (0.37 kg) was added to reactor A under the protection of nitrogen at 15-25° C. Bis(triphenylphosphine)palladium(II) chloride (1.09 kg) was added to the mixture under the protection of nitrogen at 15-25° C. The mixture was stirred for 20-30 min. Trimethylsilylacetylene (22.2 kg, 14.0 kg corrected) was added to the mixture in portions with 4-5 kg and an interval of 20-30 min for each portion at 15-30° C. The mixture was allowed to react at 20-30° C. After 2 h, the mixture was sampled every 1-2 h for purity analysis by HPLC until area % of 1-methyl-4-iodo-1H-pyrazole was ≤0.5%.

After reaction completion, the mixture was filtered with a stainless steel centrifuge. The filter cake was rinsed twice with methyl tert-butyl ether (9.2 kg×2). The filtrate was transferred to reactor A and concentrated under reduced pressure (P≤−0.08 MPa) at T≤45° C. until 40-60 was left. Methyl tert-butyl ether (92.5 kg) was added to the mixture and concentration was continued until 40-60 L was left. Methyl tert-butyl ether (92.2 kg) was added to concentrated mixture and the mixture was sampled for diisopropylamine residual analysis to ensure it was ≤1%. Active carbon (4.9 kg) was added to the mixture at 15-25° C. and the mixture was maintained for 6-8 h under stirring. The mixture was filtered with stainless steel nutsche filter at 15-25° C. The filter cake was rinsed twice with methyl tert-butyl ether (9.2 kg×2). A solution of citric acid monohydrate (6.1 kg) in purified water (121.6 kg) was added to the filtrate at 15-25° C. The mixture was stirred for 20-30 min and settled for 20-30 min before separation. The emulsion layer was separated to aqueous phase. The aqueous phase was sampled for pH analysis and wt % analysis to ensure pH was ≤7. Active carbon (4.9 kg) was added to the mixture at 15-25° C. and the mixture was maintained for 6-8 h under stirring. The mixture was filtered with stainless steel nutsche filter at 15-25° C. The filter cake was rinsed twice with methyl tert-butyl ether (9.2 kg×2). The filtrate was checked to ensure it was yellow solution.

The filtrate was transferred to reactor B and concentrated under reduced pressure (P≤−0.08 MPa) at T≤35° C. until 30-40 L was left. Anhydrous ethanol (96.3 kg) was added to the mixture and concentration was continued at T≤45° C. until 30-40 L was left. The mixture was sampled for methyl tert-butyl ether residual analysis to ensure it was ≤0.5%. The mixture was cooled to 15-25° C. Purified water (121.3 kg) was added to the mixture through peristaltic pump at 15-25° C. at a reference rate of 25-50 kg/h. Brown yellow solid precipitated.

The mixture was allowed to crystallize at 15-25° C. After 2 h, the mixture was sampled every 1-2 h for mother liquor wt % analysis until it was ≤0.5% or the difference between the two samples was ≤0.3%. The mixture was filtered with a stainless steel nutsche filter. The filter cake was rinsed twice with purified water (12.1 kg×2). The filter cake was swept in the stainless steel nutsche filter. After 12 h, the solid was sampled every 6-8 h for ethanol residual until it was ≤1%. The product was packaged in one plastic bag. Product weight=12.0 kg, Yield=52.3%, Purity (HPLC)=98.9%.

Step 2:

A clean and dry 1000 L glass-lined reactor A and a glass-lined reactor 500 L reactor B were evacuated to −0.08--0.05 MPa and filled with nitrogen to normal pressure. It was repeated for 3 times. The reactors were sampled for oxygen content to ensure it was no more than 3%.

Methyl tert-butyl ether (88.8 kg) and Compound F (12.0 kg crude from Step 1, 10.5 kg adjusted) were added to the reactor A at 15-25° C. The stirrer was started. Then a solution of potassium hydroxide (12.0 kg) in purified water (108.0 kg) was added to the mixture at 15-25° C. The mixture was allowed to react at 15-25° C. After 4 h, the mixture was sampled every 2-4 h for purity analysis by HPLC until area % of Compound F was no more than 1.0%.

Active carbon (1.2 kg) was added to the mixture at 15-25° C. The mixture was stirred for 2-3 h. The mixture was filtered with a stainless steel nutsche filter at 15-25° C. The filter cake was rinsed twice with methyl tert-butyl ether (22.2 kg×2). The filtrate was stirred for 20-30 min and settled for 20-30 min at 15-25° C. before separation. The mother liquor of step 1 (354.9 kg) and methyl tert-butyl ether (205.6 kg) were added to reactor B. The mixture was stirred for 30-40 min and settled for 20-30 min at 15-25° C. before separation. Active carbon (1.2 kg) was added to the organic phase at 15-25° C. The mixture was stirred for 2-3 h. The mixture was filtered with a stainless steel nutsche filter at 15-25° C. The filter cake was rinsed twice with methyl tert-butyl ether (22.2 kg×2). The organic phases and the filtrate were combined into reactor B and concentrated under reduced pressure at T≤25° C. until 160-190 L was left. The mixture was transferred to 200 L iron drum. Methyl tert-butyl ether (24.2 kg) was added to reactor B to rinse reactor wall and the rinsing liquor was combined with the mixture.

A clean and dry 80 L glass reactor C was evacuated to −0.08--0.05 MPa and filled with nitrogen to normal pressure. It was repeated for 3 times. The reactor was sampled for oxygen content to ensure it was ≤3%. The mixture was transferred to reactor C in portions and concentrated under reduced pressure at T≤25° C. (until 25 L was left.

n-Heptane (16.3 kg) was added to the mixture at 15-25° C. and the mixture was sampled for methyl tert-butyl ether residual analysis. The mixture was heated to 55-60° C. under stirring. Then the mixture was cooled to −10-0° C. at a reference rate of 10-15° C./h. The mixture was stirred at −10-0° C. for crystallization. After 1-2 h, the mixture was sampled every 2-3 h for wt % analysis of mother liquor until it was ≤3 wt %. The mixture was filtered with a filter flask and the filter cake was rinsed twice with pre-cooled n-heptane (8.1 kg total, −10-0° C.). The filter cake and methyl tert-butyl ether (8.9 kg) were added to 20 L flask at 15-25° C. The mixture was stirred until all solid was dissolved completely by visual check.

The mixture was transferred to reactor C and methyl tert-butyl ether (35.5 kg) was added to the mixture through in-line filter at 15-25° C. The mixture was concentrated under reduced pressure at T≤25° C. until 10-15 L was left. Methyl tert-butyl ether (~26.6 kg×2) was added to the mixture and the concentration was continued. Methyl tert-butyl ether (26.7 kg) was added to the mixture and the mixture was sampled for KF analysis to ensure it was ≤0.4%. The mixture was concentrated under reduced pressure at T≤25° C. until no distillate was observed (~10 L was left). The mixture was transferred to 10 L flask E and evacuated under reduced pressure with oil pump until solid was formed. The product was heated to 25-30° C. and then transferred to six liquid pails. Inner package: bagged with pharmaceutical grade HDPE liquid pail. Outer package: pharmaceutical grade LDPE bag with food grade security seal. Product weight 6.1 kg, Yield=94.4%, Purity (HPLC)= 98.9%.

Example 22

Preparation of Compound E

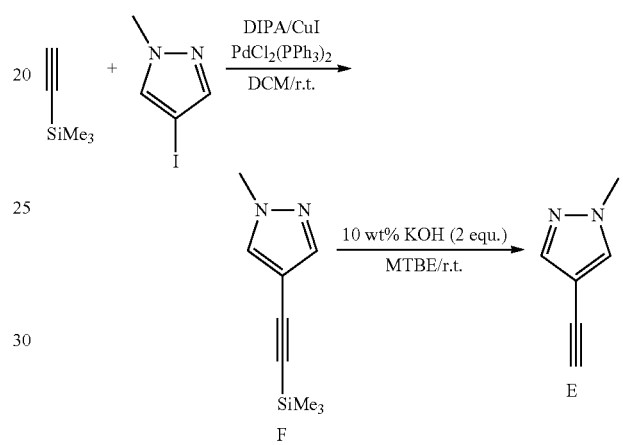

Step 1 was conducted according to the procedure as Step 1 of Example 18.

Step 2: At the end of the reaction the organic layer was separated off. The solvent was distilled off under vacuum followed by Compound E. Yield=85-88% as a colorless crystalline solid.

When Compound F crude product was telescoped into Step 2 without further purification, the overall yield of the two step was about 57%. The phase split was difficult because both layers had dark brown and solid material was present. A carbon treatment may be necessary to remove some of the color. The distilled Compound E was provided as a yellow oil.

Alternatively, Compound F was recrystallized after Step 1 before being used in Step 2. The recrystallization yield was about 71-78%, and about 25% of Compound F was lost to the mother liquid. The overall yield of the two step was about 85-88%. Only a phase split and single distillation was required to afford Compound E as a colorless crystal. The brine wash and carbon treatment from the telescope approach can be avoided.

Example 23

Preparation of Compound M

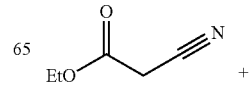

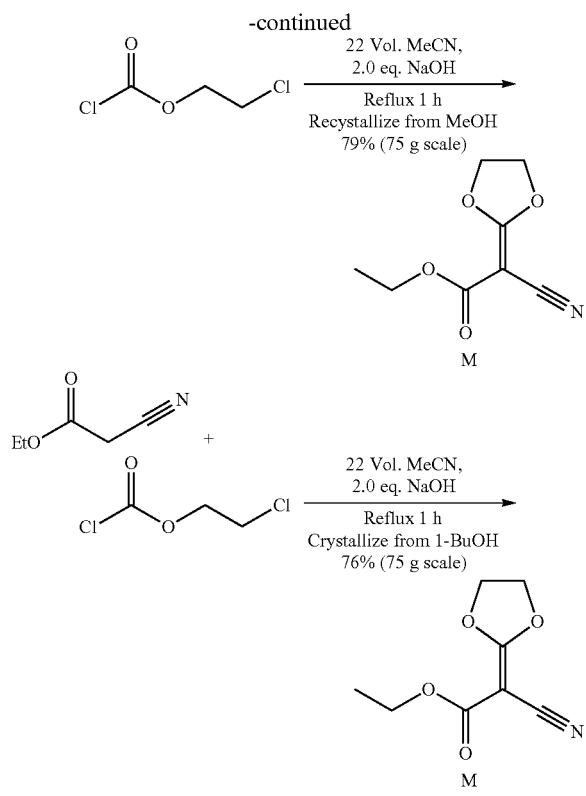

Recrystallization from MeOH led to relatively high loss due to moderate solubility.

Re-slurry with 1-propanol was less effective on larger scale or when clumps were present.

An exemplary study where 1-butanol was used for crystallization was carried out as follow. The solvent of 1-BuOH is convenient as it is also the solvent for the next reaction.

MeCN (15 volumes) and NaOH (2 equivalents) were charged to an appropriately sized jacketed reactor. Mixing was started and the jacket was set to maintain an internal temperature of 15° C. Ethyl cyanoacetate was charged to the reactor over a period of 20 to 30 minutes, adjusting the jacket to maintain temperature as necessary. Once the charge was complete, the jacket was set to maintain 20° C. and stirring was continued for 2 h. The exotherm from the deprotonation was mild and was easy to control even at larger scales. After two hours, the jacket was set to maintain an internal temperature of 10° C. A solution of 2-chloroethyl chloroformate (1 equivalent) in MeCN (2 volumes) was charged to the reactor over the course of at least 1 hour. The jacket was adjusted as necessary to maintain the internal temperature at 10-15° C. Once the charge was completed the solution was refluxed for 1 hour. Following reflux, the reactor contents were cooled to room temperature and the NaCl generated was removed by filtration. The solution can be held overnight at this point if required.

The solution was charged back to the cleaned reactor and distilled under vacuum to remove MeCN until 5 volumes remained. Once at five volumes, the vacuum was broke and 5 volumes of 1-BuOH was charged to the reactor. The distillation was restarted and continued to 5 volumes. During the course of this distillation the material started to precipitate. Once at five volumes, the vacuum was broke and a sample of the mother liquor was taken for analysis by NMR or GC. A passing IPC (in-process control) at this point required <5 mol % MeCN in 1-BuOH. If the IPC failed, distillation was continued and re-sampled at a later time point, the IPC would eventually pass. Once a passing IPC was obtained, the slurry was cooled to room temperature and held overnight if necessary.

The slurry was filtered using a Buchner funnel and the cake was slurry washed once with 1.33 volumes 1-BuOH and displacement washed once with 1.33 volumes of 1-BuOH. The cake was dried in a vacuum oven until reaching constant weight. The typical yield of this step is 75-80% and the reaction had been carried out on 225 g scale.

Example 24

Preparation of Compound J

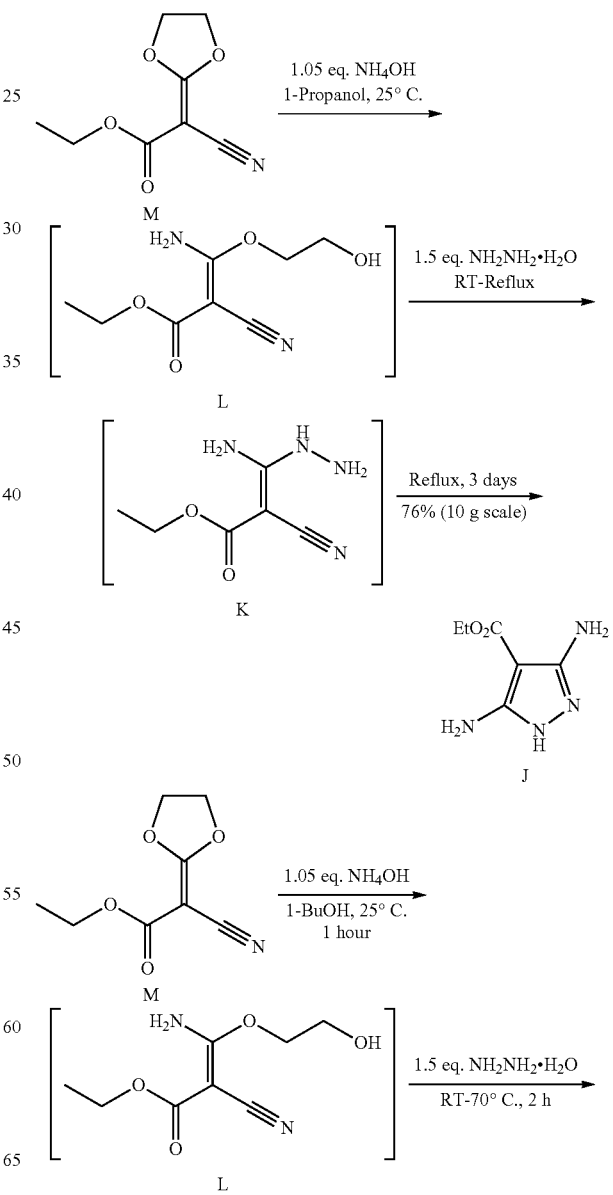

249

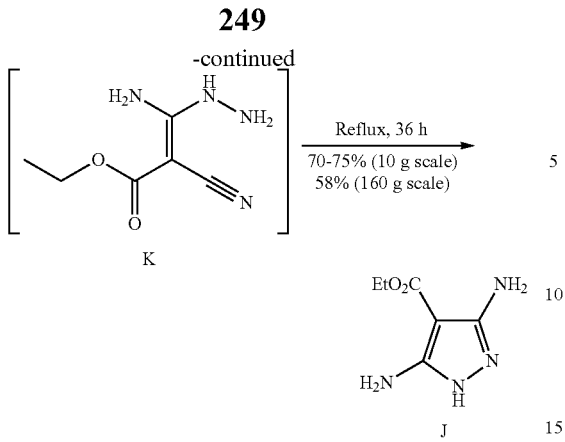

An exemplary study where 1-butanol was used as solvent was carried out as follow.

Compound M and 1-BuOH (6.5 volumes) were charged to an appropriately sized jacketed reactor. Mixing was started and the jacket was set to maintain an internal temperature of 25° C. Aqueous ammonia (1.1 equivalents) was charged to the reactor. There was an initial endotherm from the dissolution of the ammonia and then a very mild exotherm as the reaction begins. An IPC sample should be taken following a minimum of 1.5 hours and the passing criteria is <1 area % remaining starting material. Once a passing IPC was obtained, hydrazine monohydrate (1.5 equivalents) was charged to the reactor and the jacket was set to maintain an internal temperature of 70° C. After 2 hours an IPC sample can be taken and a passing test has <1 area % remaining intermediate (Compound L). Once this passing IPC occurred, the jacket was set to maintain an internal temperature of 105-110° C. (reflux). The reaction was then allowed to proceed for about 40 hours.

The solution was then cooled to 80° C. and an IPC sample was taken. The reaction was then re-heated to reflux at this time. The passing criteria was <1 area % remaining intermediate (Compound K). Once this passing IPC was obtained, the solution was cooled over 2 hours to 20° C. and the slurry was held for 2 h once that temperature was reached. The slurry was filtered using a Buchner funnel and the cake slurry was washed twice with 2 volumes of 1-BuOH and displacement washed once with 1 volume of 1-BuOH. The cake was dried in a vacuum oven to constant weight. This procedure had been carried out on 200 g scale.

Example 25

Preparation of Compound G

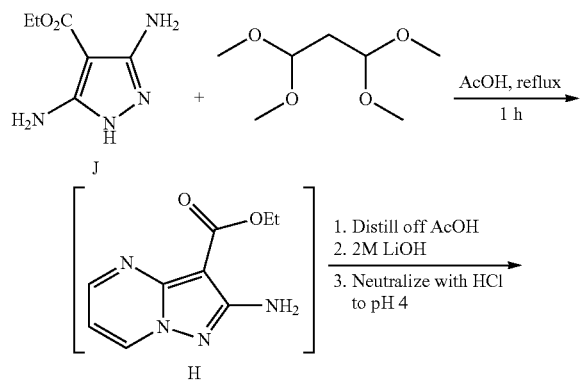

250

In an exemplary study, 3 volumes of AcOH were used. AcOH is distilled off under mild vacuum at elevated temperature to keep in solution. Once distillation ended, LiOH solution was added directly. Overall purity was about 95%.

Another exemplary study was carried out as follow: Compound J and AcOH (7.5 volumes) were charged to an appropriately sized jacketed reactor. Mixing was started and the jacket was set to maintain an internal temperature of 25° C. Tetramethoxypropane (1.01 equivalents) was charged to the reactor and the jacket was set to maintain an internal temperature of 95° C. Once at temperature, the reaction continued mixing for 1.5 hours and then an IPC sample was taken. The passing criteria for this IPC was <1 area % remaining Compound J. If necessary, a further addition of 0.05 equivalents of tetramethoxypropane may be added to push the reaction to completion. Once a passing IPC was obtained, the solution was concentrated to 3 volumes by vacuum distillation maintaining a solution temperature >60° C. to prevent premature precipitation. Once the target volume was reached the jacket was set to maintain an internal temperature of 50° C. A 4 M solution of NaOH was then charged to the reactor via cannula to neutralize the remaining AcOH. This typically required approximately 10 volumes of the base solution. The neutralization was monitored by pH probe. Solids began to precipitate during the course of the charge.

Once neutralized, the slurry was cooled to 20° C. and held at that temperature for 1 hour prior to isolation via Buchner funnel. The cake was washed twice with 2 volumes of water and once with 2 volumes of MeOH. The solids were then dried to constant weight in a vacuum oven to provide Compound H. This procedure had been performed on 110 g scale to produce a granular light brown solid.

Compound H and MeOH (3.6 volumes) were charged to an appropriately sized jacketed reactor. Mixing was started and the jacket was set to maintain an internal temperature of 25° C. A solution of LiOH (4.4 equivalents) in water (12 volumes) was charged to the reactor slowly over several minutes. There was a small exotherm upon charging, but it was small and easily managed. Once the charge was complete, the slurry was heated to 50° C. for a minimum of 2 hours. After this time an IPC sample was taken with a targeted passing specification of <1 area % Compound H. Once a passing IPC was obtained, the jacket was set to maintain the slurry at 10° C. pH was adjusted to 4 using 6 M and 1 M HCl transferred via cannula. The 6 M HCl was used for the initial adjustment and the 1 M HCl was used for the end of the titration. The slurry was held overnight at this point if necessary.

The slurry was filtered with a Buchner funnel and the cake was washed twice with 3 volumes of water and once with 3 volumes of MeOH. The cake was then dried to constant weight in a vacuum oven to provide Compound G. This procedure had been performed on 122 g scale to produce a pale yellow solid.

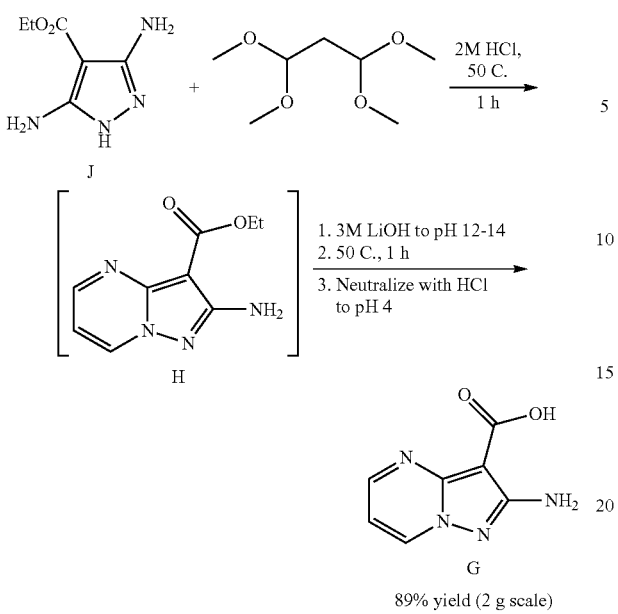

In an alternative example, the reaction was carried out using HCl as the acid instead of AcOH.

The overall average yield in three steps (preparation of Compound M, preparation of Compound J, and preparation of Compound G) was about 40-45%, and the product was obtained in off white color.

While exemplary embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the subject matter of the disclosure. All such equivalents are considered to be within the scope of the claimed subject matter and are encompassed by the appended claims.

What is claimed is:

1. A solid form of a compound of Formula (I), of a solvate of a compound of Formula (I), or of a cocrystal of a compound of Formula (I):

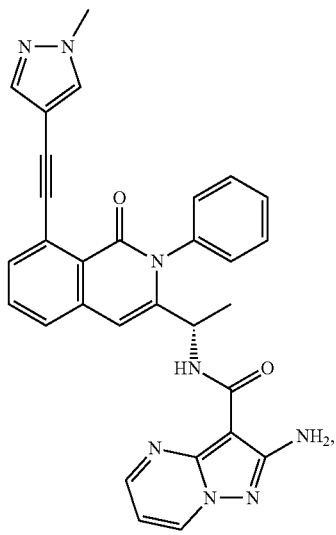

(I)

wherein the solid form is:
Form 1 of a compound of formula (I), having an X-ray powder diffraction (XRPD) pattern comprising peaks at 16.8, 23.6, and 25.6 degrees 2θ, plus or minus 0.2;
Form 2 of a 1-propanol, acetone, chloroform, or dichloromethane solvate of a compound of formula (I), having an XRPD pattern comprising peaks at 13.6, 14.9, and 21.0 degrees 2θ, plus or minus 0.2;
Form 3 of a MEK, 1-propanol, acetone, dimethyl sulfoxide, tert-butylmethyl ether, 2-methyl-1-propanol, or 2-methyl THF solvate of a compound of formula (I), having an XRPD pattern comprising peaks at 17.9, 20.6, and 25.8 degrees 2θ, plus or minus 0.2;
Form 4 of a 2-propanol, 1-propanol, dimethyl sulfoxide, 2-methyl-1-propanol, 1,4-dioxane, chloroform, THF, 2-methoxyethanol, or acetone solvate of a compound of formula (I), having an XRPD pattern comprising peaks at 7.4, 18.0, and 20.7 degrees 2θ, plus or minus 0.2;
Form 5 of an anisole solvate of a compound of formula (I), having an XRPD pattern comprising peaks at 21.0, 22.1, and 25.2 degrees 2θ, plus or minus 0.2;
Form 6 of a hydrate of a compound of formula (I), having an XRPD pattern comprising peaks at 4.8, 19.9, and 26.7 degrees 2θ, plus or minus 0.2;
Form 7 of a MEK, 1-propanol, acetone, or tert-butylmethyl ether solvate of a compound of formula (I), having an XRPD pattern comprising peaks at 7.5, 12.3, and 20.7 degrees 2θ, plus or minus 0.2;
Form 8 of a compound of formula (I), having an XRPD pattern comprising peaks at 18.8, 20.8, and 24.5 degrees 2θ, plus or minus 0.2;
Form P1C3 of a cocrystal of a compound of Formula (I) and L-tartaric acid, having an XRPD pattern comprising peaks at 11.2, 17.4, and 17.7 degrees 2θ, plus or minus 0.2;
Form P1C9 of a cocrystal of a compound of Formula (I) and salicylic acid, having an XRPD pattern comprising peaks at 6.9, 10.1, and 12.0 degrees 2θ, plus or minus 0.2; or
Form P2C9 of a cocrystal of a compound of Formula (I) and salicylic acid, having an XRPD pattern comprising peaks at 11.4, 13.4, and 24.0 degrees 2θ, plus or minus 0.2.

2. The solid form of claim 1, wherein the solid form is Form 1 of a compound of formula (I), having an X-ray powder diffraction (XRPD) pattern comprising peaks at 16.8, 23.6, and 25.6 degrees 2θ, plus or minus 0.2.

3. The solid form of claim 2, having an XRPD pattern further comprising at least one peak selected from 14.6 and 21.2 degrees 2θ, plus or minus 0.2.

4. The solid form of claim 2, having an XRPD pattern substantially as shown in FIG. 1.

5. The solid form of claim 2, which exhibits an endothermic event, as characterized by DSC, with an onset temperature at about 255° C. and/or a peak temperature at about 257° C.

6. The solid form of claim 2, which exhibits a weight loss of about 0.6% upon heating from about 230° C. to about 310° C.

7. The solid form of claim 2, which exhibits a weight increase of about 0.5% when subjected to an increase in relative humidity from about 0 to about 90% relative humidity.

8. The solid form of claim 2, having approximately unit cell dimensions of: a=11.1 Å, b=12.8 Å, c=16.1 Å, α=90°, β=90°, and γ=90°.

9. The solid form of claim 2, which is anhydrous.

10. The solid form of claim 2, which is non-hygroscopic.

11. The solid form of claim 1, wherein the solid form is Form 2 of a 1-propanol, acetone, chloroform, or dichloromethane solvate of a compound of formula (I), having an XRPD pattern comprising peaks at 13.6, 14.9, and 21.0 degrees 2θ, plus or minus 0.2.

12. The solid form of claim 11, having an XRPD pattern further comprising at least one peak selected from 7.4 and 16.7 degrees 2θ, plus or minus 0.2.

13. The solid form of claim 11, having an XRPD pattern substantially as shown in FIG. 4.

14. The solid form of claim 11, having approximately unit cell dimensions of: a=8.7 Å, b=13.2 Å, c=26.0 Å, α=90°, β=90°, and γ=90°.

15. The solid form of claim 1, wherein the solid form is Form 3 of a MEK, 1-propanol, acetone, dimethyl sulfoxide, tert-butylmethyl ether, 2-methyl-1-propanol, or 2-methyl THF solvate of a compound of formula (I), having an XRPD pattern comprising peaks at 17.9, 20.6, and 25.8 degrees 2θ, plus or minus 0.2.

16. The solid form of claim 15, having an XRPD pattern further comprising at least one peak selected from 11.7 and 23.5 degrees 2θ, plus or minus 0.2.

17. The solid form of claim 15, having an XRPD pattern substantially as shown in FIG. 9.

18. The solid form of claim 1, wherein the solid form is Form 4 of a 2-propanol, 1-propanol, dimethyl sulfoxide, 2-methyl-1-propanol, 1,4-dioxane, chloroform, THF, 2-methoxyethanol, or acetone solvate of a compound of formula (I), having an XRPD pattern comprising peaks at 7.4, 18.0, and 20.7 degrees 2θ, plus or minus 0.2.

19. The solid form of claim 18, having an XRPD pattern further comprising at least one peak selected from 11.9 and 13.6 degrees 2θ, plus or minus 0.2.

20. The solid form of claim 18, having an XRPD pattern substantially as shown in FIG. 11.

21. The solid form of claim 1, wherein the solid form is Form 5 of an anisole solvate of a compound of formula (I), having an XRPD pattern comprising peaks at 21.0, 22.1, and 25.2 degrees 2θ, plus or minus 0.2.

22. The solid form of claim 21, having an XRPD pattern further comprising at least one peak selected from 14.5 and 19.2 degrees 2θ, plus or minus 0.2.

23. The solid form of claim 21, having an XRPD pattern substantially as shown in FIG. 13.

24. The solid form of claim 1, wherein the solid form is Form 6 of a hydrate of a compound of formula (I), having an XRPD pattern comprising peaks at 4.8, 19.9, and 26.7 degrees 2θ, plus or minus 0.2.

25. The solid form of claim 24, having an XRPD pattern further comprising at least one peak selected from 11.9 and 24.8 degrees 2θ, plus or minus 0.2.

26. The solid form of claim 24, having an XRPD pattern substantially as shown in FIG. 15.

27. The solid form of claim 1, wherein the solid form is Form 7 of a MEK, 1-propanol, acetone, or tert-butylmethyl ether solvate of a compound of formula (I), having an XRPD pattern comprising peaks at 7.5, 12.3, and 20.7 degrees 2θ, plus or minus 0.2.

28. The solid form of claim 27, having an XRPD pattern further comprising at least one peak selected from 13.7 and 17.2 degrees 2θ, plus or minus 0.2.

29. The solid form of claim 27, having an XRPD pattern substantially as shown in FIG. 18.

30. The solid form of claim 1, wherein the solid form is Form 8 of a compound of formula (I), having an XRPD pattern comprising peaks at 18.8, 20.8, and 24.5 degrees 2θ, plus or minus 0.2.

31. The solid form of claim 30, having an XRPD pattern further comprising at least one peak selected from 16.0 and 17.9 degrees 2θ, plus or minus 0.2.

32. The solid form of claim 30, having an XRPD pattern substantially as shown in FIG. 20.

33. The solid form of claim 1, wherein the solid form is Form P1C3 of a cocrystal of a compound of Formula (I) and L-tartaric acid, having an XRPD pattern comprising peaks at 11.2, 17.4, and 17.7 degrees 2θ, plus or minus 0.2.

34. The solid form of claim 33, having an XRPD pattern further comprising at least one peak selected from 21.2 and 22.5 degrees 2θ, plus or minus 0.2.

35. The solid form of claim 33, having an XRPD pattern substantially as shown in FIG. 22.

36. The solid form of claim 1, wherein the solid form is Form P1C9 of a cocrystal of a compound of Formula (I) and salicylic acid, having an XRPD pattern comprising peaks at 6.9, 10.1, and 12.0 degrees 2θ, plus or minus 0.2.

37. The solid form of claim 36, having an XRPD pattern further comprising at least one peak selected from 17.8 and 20.0 degrees 2θ, plus or minus 0.2.

38. The solid form of claim 36, having an XRPD pattern substantially as shown in FIG. 24.

39. The solid form of claim 1, wherein the solid form is Form P2C9 of a cocrystal of a compound of Formula (I) and salicylic acid, having an XRPD pattern comprising peaks at 11.4, 13.4, and 24.0 degrees 2θ, plus or minus 0.2.

40. The solid form of claim 39, having an XRPD pattern further comprising at least one peak selected from 25.1 and 26.9 degrees 2θ, plus or minus 0.2.

41. The solid form of claim 39, having an XRPD pattern substantially as shown in FIG. 26.

42. A pharmaceutical composition comprising a solid form of claim 1 and a pharmaceutical acceptable excipient thereof.

43. A pharmaceutical composition consisting essentially of the solid form of claim 1.

* * * * *